US010662426B2

(12) United States Patent
Lynch et al.

(10) Patent No.: US 10,662,426 B2
(45) Date of Patent: May 26, 2020

(54) COMPOSITIONS AND METHODS FOR RAPID AND DYNAMIC FLUX CONTROL USING SYNTHETIC METABOLIC VALVES

(71) Applicant: Duke University, Durham, NC (US)

(72) Inventors: Michael David Lynch, Durham, NC (US); Ashley Delanie Trahan, Hillsborough, NC (US); Daniel Rodriguez, Durham, NC (US); Zhixia Ye, Raleigh, NC (US); Charles Bridwell Cooper, Durham, NC (US); Ahmet Bozdag, Raleigh, NC (US)

(73) Assignee: DUKE UNIVERSITY, Durham, NC (US)

( * ) Notice: Subject to any disclaimer, the term of this patent is extended or adjusted under 35 U.S.C. 154(b) by 195 days.

(21) Appl. No.: 15/317,768

(22) PCT Filed: Jun. 11, 2015

(86) PCT No.: PCT/US2015/035306
§ 371 (c)(1),
(2) Date: Dec. 9, 2016

(87) PCT Pub. No.: WO2016/053397
PCT Pub. Date: Apr. 7, 2016

(65) Prior Publication Data

US 2017/0121707 A1 May 4, 2017

Related U.S. Application Data

(60) Provisional application No. 62/010,574, filed on Jun. 11, 2014.

(51) Int. Cl.
*C12N 15/11* (2006.01)
*C12N 15/63* (2006.01)
(Continued)

(52) U.S. Cl.
CPC ........ *C12N 15/111* (2013.01); *C12N 15/1137* (2013.01); *C12N 15/63* (2013.01);
(Continued)

(58) Field of Classification Search
None
See application file for complete search history.

(56) References Cited

U.S. PATENT DOCUMENTS 8,916,358 B2 12/2014 Swartz
10,036,001 B2 7/2018 Swartz
(Continued)

FOREIGN PATENT DOCUMENTS

EP 2562249 A1 2/2013
EP 2842542 A1 3/2015
(Continued)

OTHER PUBLICATIONS

International Search Report and Written Opinion dated Apr. 27, 2016 from related International Application No. PCT/US2015/035306.

(Continued)

*Primary Examiner* — Nancy A Treptow
(74) *Attorney, Agent, or Firm* — Benesch, Friedlander, Coplan & Aronoff LLP

(57) ABSTRACT

This invention relates to metabolically engineered microorganisms, such as bacterial and or fungal strains, and bioprocesses utilizing such strains. These strains enable the dynamic control of metabolic pathways, which can be used to optimize production. Dynamic control over metabolism is accomplished via a combination of methodologies including but not limited to transcriptional silencing and controlled enzyme proteolysis. These microbial strains are utilized in a multi-stage bioprocess encompassing at least two stages, the first stage in which microorganisms are grown and metabo-
(Continued)

Growth
Production
Biomass
Limiting Nutrient
Product
Time
Growth Gene
Production Gene
Growth
Production lism can be optimized for microbial growth and at least one other stage in which growth can be slowed or stopped, and dynamic changes can be made to metabolism to improve the production of desired product, such as a chemical or fuel.

18 Claims, 15 Drawing Sheets

Specification includes a Sequence Listing.

(51) Int. Cl.
*C12N 15/113* (2010.01)
*C12N 15/70* (2006.01)

(52) U.S. Cl.
CPC .......... *C12N 15/70* (2013.01); *C12N 2310/14* (2013.01); *C12N 2320/50* (2013.01)

(56) References Cited

U.S. PATENT DOCUMENTS

| | | | |
|---|---|---|---|
| 2010/0297736 | A1 | 11/2010 | Duhring et al. |
| 2011/0125118 | A1 | 5/2011 | Lynch |
| 2011/0244575 | A1 | 10/2011 | Lipscomb |
| 2012/0052547 | A1 | 3/2012 | Swartz |
| 2012/0107892 | A1 | 5/2012 | Agbogbo et al. |
| 2012/0214170 | A1 | 8/2012 | Moore |
| 2015/0072399 | A1 | 3/2015 | Lynch et al. |

FOREIGN PATENT DOCUMENTS

| | | | |
|---|---|---|---|
| WO | 2001068883 | A1 | 9/2001 |
| WO | 2003054140 | A9 | 2/2004 |
| WO | 2008141174 | A2 | 11/2008 |
| WO | 2010141468 | A1 | 12/2010 |
| WO | 2012129450 | A1 | 9/2012 |
| WO | 2013176772 | A1 | 11/2013 |
| WO | 2014160025 | A2 | 10/2014 |
| WO | 2015191638 | A1 | 12/2015 |
| WO | 2018156646 | A1 | 8/2018 |

OTHER PUBLICATIONS

Fang, Shi-Ming et al., "A Practical Strategy to Discover New Antitumor Compounds by Activating Silent Metabolite Production in Fungi by Diethyl Sulphate Mutagenesis," Marine Drugs, vol. 12, pp. 1788-1814, 2014.

Torella, et al. Tailored fatty acid synthesis via dynamic control of fatty acid elongation. Proc Natl Acad Sci U S A. Jul. 9, 2013;110(28):11290-5. doi: 10.1073/pnas.1307129110. Epub Jun. 24, 2003.

International Preliminary Report on Patentability dated Dec. 15, 2016 from related International App. No. PCT/US2015035306.

UK Combined Examination and Search Report dated Dec. 8, 2016, from related UK Application No. GB1511937.3.

UK Examination Report dated Apr. 1, 2019 from related UK Application No. GB1511937.3.

English Translation of Mar. 12, 2019 Office Action related to Japanese application JP2016-572578.

Lynch et al., "Standarized two-stage bioprocess development using synthetic metabolic valves and dynamic metabolic control", Abstracts of Papers ; ACS National Meeting & Exposition; 249th National Meeting and Exposition of the American-Chemical-Society (ACS), vol. 249, p. BIOT418, Mar. 13, 2015.

Brockman et al., "Dynamic knockdown of *E. coli* central metabolism for redirecting fluxes of primary metabolites", Metabolic Engineering, vol. 28., pp. 104-113, Dec. 24, 2014.

Kim et al., "A genetic strategy to identify targets for the development of drugs that prevent bacterial persistence", Proc. Natl. Acad. Sci. USA (2013); vol. 110, pp. 19095-19100.

Qi et al, "Repurposing CRISPR as an RNA-guided platform for sequence-specific control of gene expression," Cell (2013); vol. 152, pp. 1173-1183.

Office Action issued in European patent application No. 15845669.9, dated Dec. 3, 2018, 6 pages.

Extended European search report issued in patent application No. 15845669.9, dated Jan. 1, 2018, 10 pages.

Yuki Soma et al: "Metabolic flux redirection from a central metabolic pathway toward a synthetic pathway using a metabolic toggle switch", Metabolic Engineering, vol. 23, May 1, 2014, pp. 175-184.

Kathleen E. McGinness et al: "Engineering Controllable Protein Degradation", Molecular Cell., vol. 22, No. 5, Jun. 1, 2006, pp. 701-707.

Levchenko Igor et al: "A specificity-enhancing factor for the CIpXP degradation machine", Science, vol. 289, No. 5488, Sep. 29, 2000, pp. 2354-2356.

Examination Report issued in European patent application No. 15845669.9 dated Sep. 26, 2019.

COMPOSITIONS AND METHODS FOR RAPID AND DYNAMIC FLUX CONTROL USING SYNTHETIC METABOLIC VALVES

CROSS-REFERENCE TO RELATED APPLICATIONS

This application is a § 371 U.S. National Stage of International Application PCT/US2015/035306, filed Jun. 11, 2015, which claims the benefit of U.S. Provisional Application No. 62/010,574, filed Jun. 11, 2014, the entire content of which are incorporated by reference herein in their entirety.

FEDERALLY SPONSORED RESEARCH OR DEVELOPMENT

This invention was made with government support under Federal Grant No. MCB-1445726 awarded by the National Science Foundation and Federal Contract No. HR0011-14-C-0075 awarded by the Defense Advanced Research Projects Agency of the United States Department of Defense. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "OLG Ref 210-44 ST25.txt". The sequence listing is 184,352 bytes in size, and was created on Jun. 11, 2015. It is hereby incorporated by reference in its entirety.

FIELD OF THE INVENTION

This invention relates to metabolically engineered microorganisms, such as bacterial and or fungal strains, and bioprocesses utilizing such strains. These strains enable the dynamic control of metabolic pathways.

BACKGROUND OF THE INVENTION

Petroleum is the primary feedstock, not only for the fuels we use, but the majority of the chemicals we consume as well. The chemical industry is heavily reliant on this non-renewable resource. Replacement of petroleum with renewable feedstocks ensures longer-term viability and environmental sustainability. Novel fermentation based processes to make chemicals have been a contributing technology, enabling the change to renewable feedstocks (Werpy & Peterson, Top Value Added Chemicals from Biomass. Volume I—Results of Screening for Potential Candidates from Sugars and Synthesis Gas., Yixiang et al. "Green" Chemicals from Renewable Agricultural Biomass—A Mini Review. The Open Agriculture Journal, 2008). These fermentation processes have made rapid advancements in recent years due to technology developments in the fields of fermentation science, synthetic biology, as well as metabolic and enzyme engineering (Jarboe, L. R., et al., Metabolic engineering for production of biorenewable fuels and chemicals: contributions of synthetic biology. J Biomed Biotechnol, 2010, Lee, J. W., et al., Systems metabolic engineering of microorganisms for natural and non-natural chemicals. Nat Chem Biol, 2012). Despite these substantial advances, most successful examples of rationale directed engineering approaches have also greatly relied on numerous cycles of trial and error. The field of metabolic engineering has historically been limited in predicting the behavior of complex biological systems in-vivo, from simplified models and basic in-vitro biochemical principles. Such rational approaches have required significant a priori knowledge of microbial physiology that in many cases is incomplete. This is particularly true for complex phenotypes that require an intricate balance between the activities of many seemingly unrelated gene products. In many cases it has proven much more difficult than expected to integrate a possibly well characterized production pathway into a living host and balance the complex requirements of both biomass growth and production.

One solution is the development of platform microbial strains that utilize synthetic metabolic valves (SMVs) that can decouple growth from product formation. These strains enable the dynamic control of metabolic pathways, including those that when altered have negative effects on microorganism growth. Dynamic control over metabolism is accomplished via a combination of methodologies including but not limited to transcriptional silencing and controlled enzyme proteolysis. These microbial strains are utilized in a multi-stage bioprocess encompassing as least two stages, the first stage in which microorganisms are grown and metabolism can be optimized for microbial growth and at least one other stage in which growth can be slowed or stopped, and dynamic changes can be made to metabolism to improve production of desired product, such as a chemical or fuel. The transition of growing cultures between stages and the manipulation of metabolic fluxes can be controlled by artificial chemical inducers or preferably by controlling the level of key limiting nutrients. In addition, genetic modifications may be made to provide metabolic pathways for the biosynthesis of one or more chemical or fuel products. Also, genetic modifications may be made to enable the utilization of a variety of carbon feedstocks including but not limited sugars such as glucose, sucrose, xylose, arabinose, mannose, and lactose, oils, carbon dioxide, carbon monoxide, methane, methanol and formaldehyde.

This approach allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following enables these synthetic valves: 1) transcriptional gene silencing or repression technologies in combination with 2) inducible enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

A simplified two-stage bioprocess using synthetic metabolic valves is depicted in FIG. 1, strains are grown in a minimal media with a single limiting nutrient such as inorganic phosphate. During this growth phase cells are not producing any product other than biomass and as a result are not subject to any possible toxic or unwanted side effects of product formation. Biomass growth and yield can be optimized. As the limiting nutrient is depleted, cell growth is stopped. Simultaneously, these strains will be engineered to contain synthetic metabolic valves, which silence genes and enzymes essential for growth and redirect carbon, electrons and energy to any molecule of interest. This process utilizes a novel combination of a two-stage production and concurrent metabolic engineering strategy.

There is significant precedent in the biotechnology industry for using and scaling two stage processes similar to that described in FIG. 1. Many similar processes are routinely used for the heterologous expression of proteins. In these standard processes cells are grown to a productive or "primed" state for protein synthesis (such as mid-exponential phase in *E. coli*) and then induced to express a heterologous protein. In many cases, the diversion of cellular amino acids and energy to the heterologous protein has a significant effect on, if not halting, cellular growth. It is not surprising that these types of processes have not been developed for the biological production of small molecules as historically most successful efforts to metabolically engineer the production of small molecules have leveraged the power of anaerobic metabolism to couple product formation with growth.

Anaerobic growth-coupled product formation enables the use of powerful growth based selections to identify better producers. The faster the cells grow the more product they make. This has allowed for the classical selection of industrial strains for many natural products such as ethanol and isobutanol. However, the requirement for anaerobic production greatly limits the number and variety of different molecules or products that can be made using synthetic biology. Numerous products would require aerobic metabolism to supply the needed energy and cofactors to allow for a thermodynamically feasible metabolic pathway. In these cases a generic and robust aerobic production platform would greatly simplify the optimization and scale up of a diverse number of products. A controlled multi-stage process, enabled by synthetic metabolic valves, supplies such a platform.

Synthetic metabolic valves enable synthetic biologists and metabolic engineers the ability to decouple the complex metabolic and thermodynamic needs of growth from those of product formation. This decoupling also enables the removal of growth based regulatory mechanisms that may inhibit product formation and allows for the silencing of essential metabolic pathways that may detract from or interfere with production. These essential interfering metabolic pathways could include amino acid biosynthesis or the citric acid cycle as well as the biosynthesis of many secondary metabolites, and those pathways involved in maintaining intracellular redox and energy balances. These pathways have traditionally been off limits to many metabolic engineering strategies, as attempts at manipulation have led to growth defects.

SUMMARY OF THE INVENTION

According to one embodiment, the invention is directed to methods to construct controllable synthetic metabolic valves. In certain of these embodiments synthetic metabolic valves are used to controllably reduce or eliminate flux through one more metabolic pathways. In further embodiments, flux is reduced or eliminated through one or more metabolic pathways whose enzymes are essential for microbial growth in a given environment. In other embodiments, the invention is related to genetically modified microorganisms that utilize one or more synthetic metabolic valves thereby enabling dynamic control over metabolic pathways. Other embodiments of the invention are directed to multistage bioprocesses that utilize genetically modified microorganism that in turn utilize one or more synthetic metabolic valves that enable dynamic flux control. Still in other embodiments of the invention, the transitions between stages in multistage bioprocesses using genetically modified microorganisms are controlled by the addition of chemical inducers or by the control of key nutrient levels. Additional genetic modifications may be added to a microorganism to enable the conversion of carbon feedstocks to chemical or fuel products. In certain embodiments, carbon feedstocks can include, but are not limited to the sugars: glucose, sucrose xylose, arabinose, mannose, lactose, or alternatively carbon dioxide, carbon monoxide, methane, methanol, formaldehyde, or oils. In addition, genetic modifications to produce chemical or fuel products from various carbon feedstocks can include metabolic pathways utilizing, but not limited to, the central metabolites acetyl-CoA, malonyl-CoA, pyruvate, oxaloacetate, erthyrose-4-phosphate, xylulose-5-phosphate, alpha-ketoglutarate and citrate. Products that can be derived from these central metabolites include but are not limited to acetate, alcohols (ethanol, butanol, hexanol, and longer n-alcohols), organic acids (3-hydroxyprpionic acid, lactic acid, itaconic acid), amino acids (alanine, serine, valine), fatty acids and their derivatives (fatty acid methyl esters (FAMEs), fatty aldehydes, alkenes, alkanes) and isoprenoids.

In various embodiments, the increased production of acetate from acetyl-phosphate may occur via the increased expression of an acetate kinase. A non-limiting example is the acetate kinase from *E. coli* encoded by the ackA gene. Increased expression of an acetate kinase may optionally be combined with genetic modifications that result decreased activity phosphoacetyltransferase such as that encoded by the pta gene of *E. coli*.

In various embodiments, the increased production of ethanol from acetyl-CoA may occur via the increased expression of an oxygen tolerant ethanol dehydrogenase, such as the enzyme from *E. coli* encoded by the adhE gene with a mutation Glu568Lys as taught by Dellomonaco et al, AEM. August 2010, Vol. 76, No. 15, p 5067. and Holland-Staley et al. JBACs. November 2000, Vol. 182, No. 21, p 6049.

In various embodiments, the increased production of butyrate from acetyl-CoA may occur via the increased expression of butyrate pathway enzymes including an acetoacetyl-CoA thiolase, crotonase, crotonyl-CoA reductase, butyrate phospho-transferase and butyrate kinase as taught by Fischer et al, Appl Microbiol Biotechnol. 2010, September, Vol. 88, No. 1, p. 265-275. Alternatively, increased butyrate may be accomplished via the increased expression of butyrate pathway enzymes including an acetoacetyl-CoA synthase, crotonase, crotonyl-CoA reductase and butyryl-CoA thioesterase as taught by PCT/US2012/030209.

In various embodiments, the increased production of n-butanol from acetyl-CoA may occur via the increased expression of n-butanol pathway enzymes including an acetoacetyl-CoA thiolase, crotonase, crotonyl-CoA reductase, butyryl-CoA reductase and butyraldehyde reductase as taught by Atsumi et al, Metabolic Engineering. 2008. November, Vol. 10, No. 6, p. 305).

In various embodiments, the increased production of fatty acids of chain length greater than 4, from acetyl-CoA may occur via the increased expression of a fatty acid synthesis pathway enzymes including an ketoacetyl-CoA synthase, 3-hydroxyacyl-CoA dehydratase, an enoyl-CoA reductase, and a acyl-CoA thioesterase as taught by PCT/US2012/030209.

In various embodiments, the increased production of fatty acid methyl esters from acetyl-CoA may occur via the increased expression of fatty acid methyl ester synthesis pathway enzymes including an ketoacetyl-CoA synthase, 3-hydroxyacyl-CoA dehydratase, an enoyl-CoA reductase, and a acyl-CoA wax ester synthase as taught by: PCT/US2012/030209 and US 20110146142 A1.

In various embodiments, the increased production of n-hexanol from acetyl-CoA may occur via the increased expression of a fatty acid synthesis pathway enzymes including an ketoacetyl-CoA thiolases, 3-hydroxyacyl-CoA dehydratase, an enoyl-CoA reductase, and a acyl-CoA thioesterase as taught by Dekishima et al. J Am Chem Soc. 2011. August. Vol. 133, No. 30, p. 1139.

In various embodiments, the increased production of n-alcohols of chain length greater than 4, from acetyl-CoA may occur via the increased expression of a fatty acid synthesis pathway enzymes including an ketoacetyl-CoA synthase, 3-hydroxyacyl-CoA dehydratase, an enoyl-CoA reductase, as taught by PCT/US2012/030209 and a fatty acyl-CoA reductase and fatty aldehyde reductase as taught by Yan-Ning Zheng et al. Microbial Cell Factories. 2012. Vol. 11:65.

In various embodiments, the increased production of n-alkenes can be accomplished by first producing n-alcohols as described elsewhere followed by the chemical dehydration of the n-alcohol to an n-alkene by catalytic methods well known in the art.

In various embodiments, the increased production of n-alkanes can be accomplished by first producing fatty acids as described elsewhere followed by the chemical decarboxylation of the n-alcohol to an alkane by catalytic methods well known in the art.

In various embodiments, the increased production of isoprene from acetyl-CoA may occur via the increased expression of pathway enzymes including an acetoacetyl-CoA thiolase, hydroxymethylglutaryl-CoA synthase, hydroxymethylglutaryl-CoA reductase, mevalonate kinase, phosphomevalonate kinase, mevalonte diphosphate decarboxylase, isopentenyl-diphosphate isomerase and isoprene synthase as taught by US 20120276603 A1.

In various embodiments, the increased production of a product from acetyl-CoA may occur via both the increased expression of an acetyl-CoA carboxylase enzyme which can convert acetyl-CoA into malonyl-CoA and the increased expression of a production pathway comprising multiple pathway enzymes which can convert malonyl-CoA further to a product.

In various embodiments, the increased production of a product from malonyl-CoA may occur via both the increased activity of an acetyl-CoA carboxylase enzyme which can caused by mutation of one or more fatty acid synthesis enzymes such as is taught by PCT/US2012/030209, PCT/US2011/0222790 and 3. UK Patent GB2473755 and the increased expression of a production pathway comprising multiple pathway enzymes which can convert malonyl-CoA further to a product.

Within the scope of the invention are genetically modified microorganism, wherein the microorganism is capable of producing an acetyl-CoA derived product at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

Within the scope of the invention are genetically modified microorganism, wherein the microorganism is capable of producing a product derived from any key metabolic intermediate including but not limited to malonyl-CoA, pyruvate, oxaloacetate, erthyrose-4-phosphate, xylulose-5-phosphate, alpha-ketoglutarate and citrate at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

In various embodiments, the invention includes a culture system comprising a carbon source in an aqueous medium and a genetically modified microorganism according to any one of claims herein, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
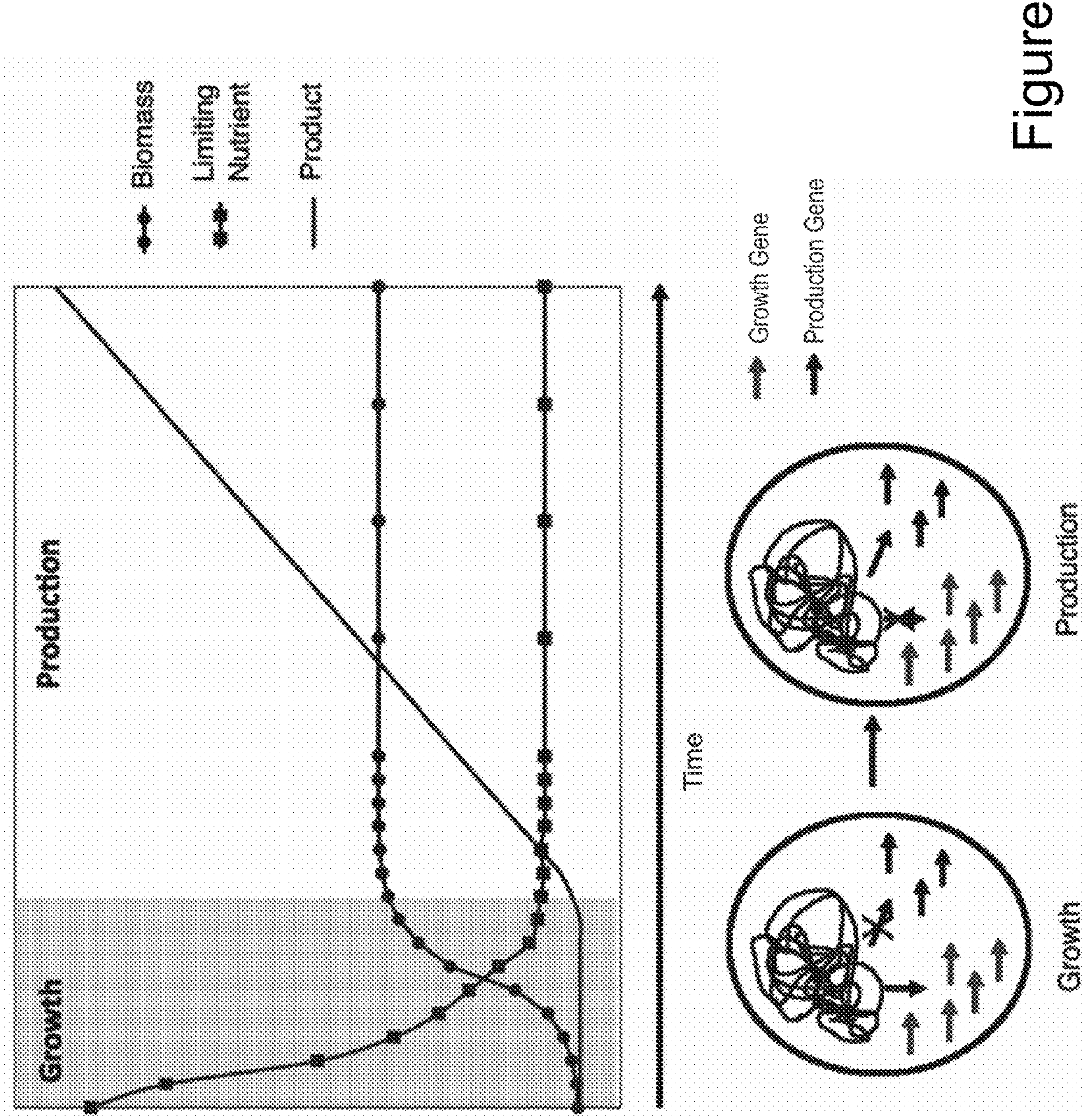
FIG. 1 depicts an overview of a two-phase fermentation processes utilizing a microbe with synthetic metabolic valves. Top Panel: Overview of the fermentation process. Biomass is grown in minimal media with a single limiting macronutrient, such as inorganic phosphate. As the biomass level (black line) or number of cells increases the limiting nutrient (red line) is depleted. When the limiting nutrient is completely consumed, biomass growth is halted. Simultaneously the limitation induces metabolic changes to initiate product biosynthesis through engineered synthetic valves. Lower Panel: Metabolic Changes in the Two Phase Process. In correlation with the system level changes, metabolic changes are induced upon depletion of the limiting nutrient. Specifically, genes encoding metabolic pathways essential for cellular growth "growth genes" are active in the growth phase while genes encoding product biosynthesis "product genes" are silenced. Upon entry into the production phase triggered by nutrient depletion, "growth genes" are silenced and "product genes" are activated.

The present invention is related to various production methods and/or genetically modified microorganisms that have utility for fermentative production of various chemical products, to methods of making such chemical products that utilize populations of these microorganisms in vessels, and to systems for chemical production that employ these microorganisms and methods. Among the benefits of the present invention is the increased ability to reduce or eliminate metabolic pathways required for microbial growth that may interfere with production.

Definitions

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, Enzyme Nomenclature, Academic Press, Inc., New York 2007.

The term "heterologous DNA," "heterologous nucleic acid sequence," and the like as used herein refers to a nucleic acid sequence wherein at least one of the following is true: (a) the sequence of nucleic acids foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as an nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a Universal Protein Resource (Uniprot) identification number, which would be well known to one skilled in the art (Uniprot is maintained by and available through the UniProt Consortium).

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

Prophetic examples provided herein are meant to be broadly exemplary and not limiting in any way.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-µ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

I. Carbon Sources

Bio-production media, which is used in the present invention with recombinant microorganisms must contain suitable carbon sources or substrates for both growth and production stages. Suitable substrates may include, but are not limited to glucose, sucrose, xylose, mannose, arabinose, oils, carbon dioxide, carbon monoxide, methane, methanol, formaldehyde and glycerol. It is contemplated that all of the above mentioned carbon substrates and mixtures thereof are suitable in the present invention as a carbon source(s).

II. Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

The examples describe specific modifications and evaluations to certain bacterial and fungal microorganisms. The scope of the invention is not meant to be limited to such species, but to be generally applicable to a wide range of suitable microorganisms.

More particularly, based on the various criteria described herein, suitable microbial hosts for the bio-production of a chemical product generally may include, but are not limited to the organisms described in the Common Methods Section III. Media and Culture Conditions In addition to an appropriate carbon source, such as selected from one of the herein-disclosed types, bio-production media must contain suitable minerals, salts, cofactors, buffers and other components, known to those skilled in the art, suitable for the growth of the cultures and promotion of the enzymatic pathway necessary for chemical product bio-production under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art.

Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges.

Bio-productions may be performed under aerobic, microaerobic or anaerobic conditions with or without agitation.

IV. Bio-Production Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering.

The following published resources are incorporated by reference herein for their respective teachings to indicate the level of skill in these relevant arts, and as needed to support a disclosure that teaches how to make and use methods of industrial bio-production of chemical product(s) produced under the invention, from sugar sources, and also industrial systems that may be used to achieve such conversion with any of the recombinant microorganisms of the present invention (Biochemical Engineering Fundamentals, 2nd Ed. J. E. Bailey and D. F. Ollis, McGraw Hill, New York, 1986, entire book for purposes indicated and Chapter 9, pages 533-657 in particular for biological reactor design; Unit Operations of Chemical Engineering, 5th Ed., W. L. McCabe et al., McGraw Hill, New York 1993, entire book for purposes indicated, and particularly for process and separation technologies analyses; Equilibrium Staged Separations, P. C. Wankat, Prentice Hall, Englewood Cliffs, N.J. USA, 1988, entire book for separation technologies teachings).

The amount of a product produced in a bio-production media generally can be determined using a number of methods known in the art, for example, high performance liquid chromatography (HPLC), gas chromatography (GC), or GC/Mass Spectroscopy (MS).

V. Genetic Modifications, Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli*, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvate-formate lyase (pflB), methylglyoxal synthase (mgsA), acetate kinase (ackA), alcohol dehydrogenase (adhE), the clpXP protease specificity enhancing factor (sspB), the ATP-dependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. For example, one enzyme encoded by one gene or a combination of numerous enzymes encoded by numerous genes in *E. coli* may be designed as synthetic metabolic valves to alter metabolism and improve product formation. Representative genes in *E. coli* may include but are not limited to the following: fabI, zwf, gltA, ppc, udhA, lpd, sucD, aceA, pfkA, ion, rpoS, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

In addition to the above-described genetic modifications, in various embodiments genetic modifications, including synthetic metabolic valves also are provided to increase the pool and availability of the cofactor NADPH and/or NADH which may be consumed in the production of a product.

More generally, and depending on the particular metabolic pathways of a microorganism selected for genetic modification, any subgroup of genetic modifications may be made to decrease cellular production of fermentation product(s) other than the desired fermentation product, selected from the group consisting of acetate, acetoin, acetone, acrylic, malate, fatty acid ethyl esters, isoprenoids, glycerol, ethylene glycol, ethylene, propylene, butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fused alcohols, and 1,2-propanediol, 1,3-propanediol, formate, fumaric acid, propionic acid, succinic acid, valeric acid, maleic acid and poly-hydroxybutyrate. Gene deletions may be made as disclosed generally herein, and other approaches may also be used to achieve a desired decreased cellular production of selected fermentation products other than the desired products.

VI. Synthetic Metabolic Valves

Figure 2:
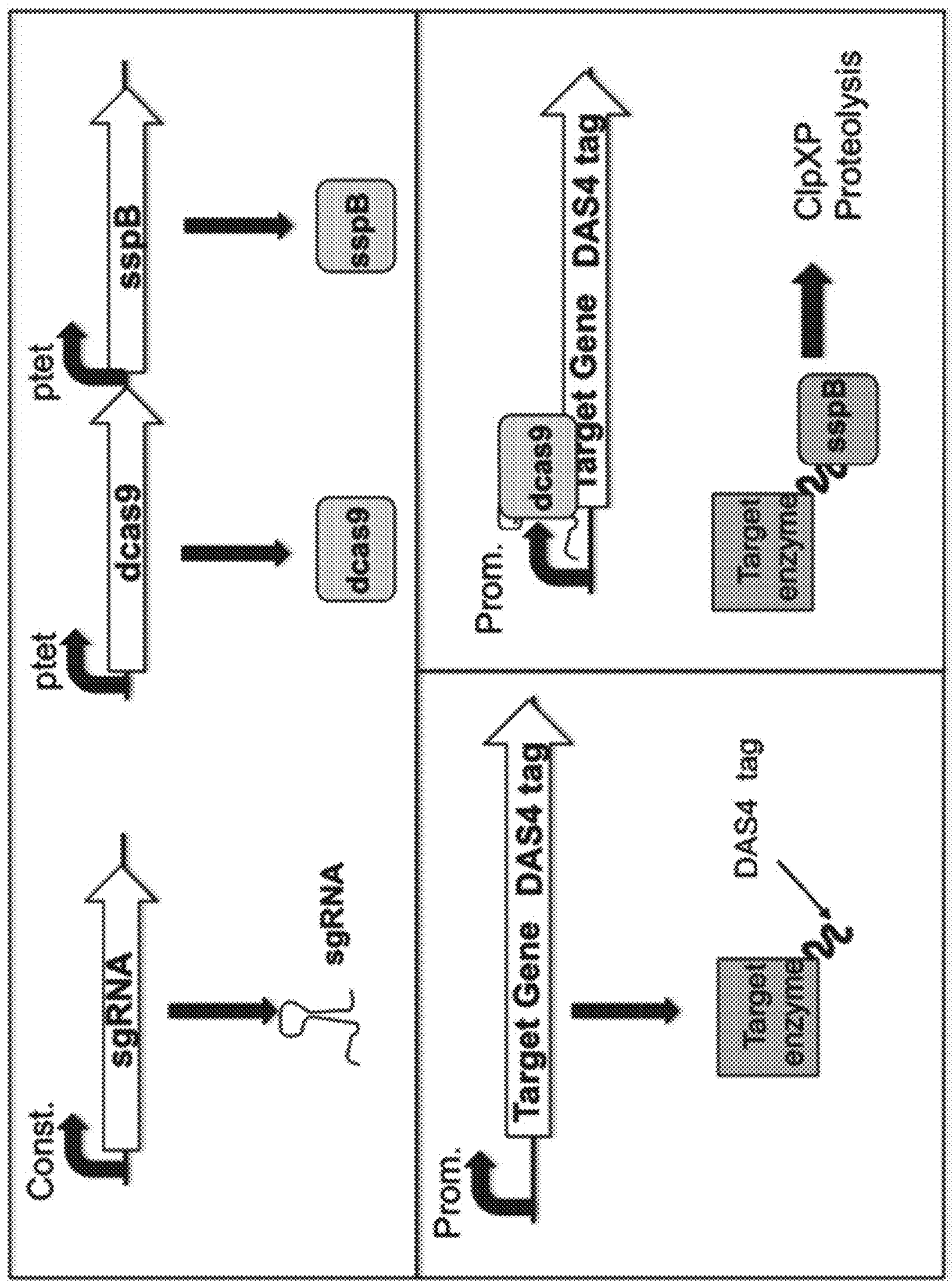
FIG. 2 depicts an overview of a synthetic metabolic valve in *E. coli* using a combination of CRISPR interference gene silencing and controlled protein degradation. Upper Panel: (LEFT) Constructs are made to express small guide RNAs to target a gene of interest in addition to (RIGHT) the controlled induction of a cascade protein complex such as catalytically inactive Cas9 or dCas9 as well as the controlled induction of the chaperone (clpXP enhancing factor) sspB. Expression can be controlled such as by the controlled ptet promoter induced by aTc. The constructs produce dCas9 and sspB proteins in addition to a targeting sgRNA. Bottom Panel: (LEFT) The target gene/protein contains a C-terminal DAS4 tag for binding to sspB. (RIGHT) When expression is induced, dCas9 is targeted to the gene of interest by the targeting sgRNA thereby silencing transcription. Concurrently, the expression of sspB results in the binding of sspB to the DAS4 C-terminal tag of protein that has already been translated. The sspB/DAS4 complex is then targeted for degradation by the clpXP protease.
Figure 3:
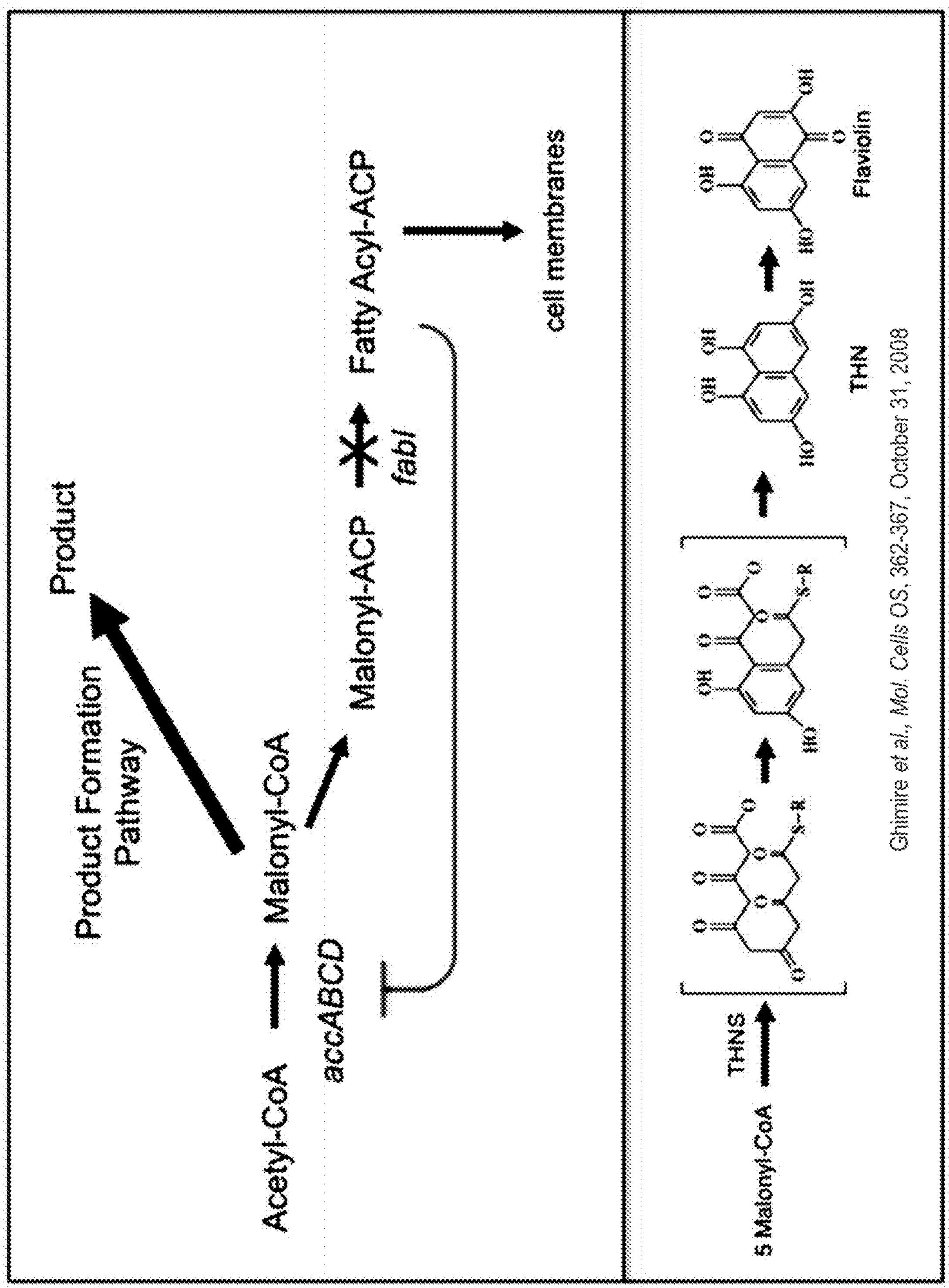
FIG. 3 depicts the production of tetrahydroxynapthalene (THN) by redirecting flux from malonyl-CoA. Upper Panel: An overview of redirecting flux from growth to product by controlling fabI (enoyl-coA reductase levels) in *E. coli*. In *E. coli*, the primary fate of the intermediate malonyl-CoA is to provide precursors for fatty acid synthesis. The key enzyme controlling the rate of lipid synthesis, acetyl-CoA carboxylase, encoded by the accABCD genes, is strongly inhibited by the fatty acid production intermediates, fatty acyl-ACPs. Removal of fabI leads to a decrease in acyl-ACP pools and a reduction in inhibition of acetyl-CoA carboxylase allowing malonyl-CoA levels to accumulate and be used for product synthesis. The removal of fabI limits lipid production and halts growth. Lowe Panel: One potential product from malonyl-CoA is tetrahydroxynapthalene (THN). THN is produced from 5 molecules of malonyl-CoA via the polyketide synthase, THN synthase encoded by the rppA gene of *S. coelicolor.*

In particular the invention describes the construction of synthetic metabolic valves comprising one or more or a combination of the following: controlled gene silencing and controlled proteolysis. It is appreciated that one well skilled in the art is aware of several methodologies for gene silencing and controlled proteolysis. An example of the combination of CRISPR interference based gene silencing and controlled proteolysis is illustrated in FIG. 2.

VI.A Gene Silencing

In particular the invention describes the use of controlled gene silencing to help enable the control over metabolic fluxes in controlled multi-stage fermentation processes. There are several methodologies known in the art for controlled gene silencing, including but not limited to mRNA silencing or RNA interference, silencing via transcriptional repressors and CRISPR interference. Methodologies and mechanisms for RNA interference are taught by Agrawal et al. "RNA Interference: Biology, Mechanism, and Applications" Microbiology and Molecular Biology Reviews, December 2003; 67(4) p 657-685. DOI: 10.1128/MMBR.67.657-685.2003. Methodologies and mechanisms for CRISRPR interference are taught by Qi et al. "Repurposing CRISPR as an RNA-guided platform for sequence-specific control of gene expression" Cell February 2013; 152(5) p 1173-1183. DOI: 10.1016/j.cell.2013.02.022. In addition, methodologies and mechanisms for CRISRPR interference using the native *E. coli* CASCADE system are taught by Luo et al. "Repurposing endogenous type I CRISPR-Cas systems for programmable gene repression" NAR. October 2014; DOI: 10.1093. In additional numerous transcriptional repressor systems are well known in the art and can be used to turn off gene expression.

VI.B Controlled Proteolysis

In particular the invention describes the use of controlled protein degradation or proteolysis to help enable the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation are taught by McGinness et al, "Engineering controllable protein degradation", Mol Cell. June 2006; 22(5) p 701-707. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments the cleavage can be expected lead to protein inactivation or degradation. For example Schmidt et al, "ClpS is the recognition component for *Escherichia coli* substrates of the N-end rule degradation pathway" Molecular Microbiology March 2009. 72(2), 506-517. doi:10.1111, teaches that an N-terminal sequence can be added to a protein of interest in enable clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus. The preference of using an N-terminal vs. C-terminal tag will largely depend on whether either tag affects protein function prior to the controlled onset of degradation.

The invention describes the use of controlled protein degradation or proteolysis to help enable the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host. For example Grilly et al, "A synthetic gene network for tuning protein degradation in *Saccharomyces cerevisiae*" Molecular Systems Biology 3, Article 127. doi:10.1038, teaches the expression and use of the *E. coli* clpXP protease in the yeast *Saccharomyces cerevisiae*. Such approaches can be used to transfer the methodology for synthetic metabolic valves to any genetically tractable host.

VI.C Synthetic Metabolic Valve Control

In particular the invention describes the use of synthetic metabolic valves to control metabolic fluxes in multi-stage fermentation processes. There are numerous methodologies known in the art to induce expression that can be used at the transition between stages in multi-stage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

VII. Disclosed Embodiments are Non-Limiting

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a figure), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. (See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986.) These published resources are incorporated by reference herein for their respective teachings of standard laboratory methods found therein. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls. Subject matter in the Examples is incorporated into this section to the extent not already present.

EXAMPLES

The examples herein provide some examples, not meant to be limiting. All reagents, unless otherwise indicated, are obtained commercially. Species and other phylogenic identifications are according to the classification known to a person skilled in the art of microbiology, molecular biology and biochemistry.

The names and city addresses of major suppliers are provided herein.

Example 1: Dynamic Flux Control Using Temperature Sensitive Enzymes to Improve Malonyl-CoA Flux in *E. coli*

Figure 4:
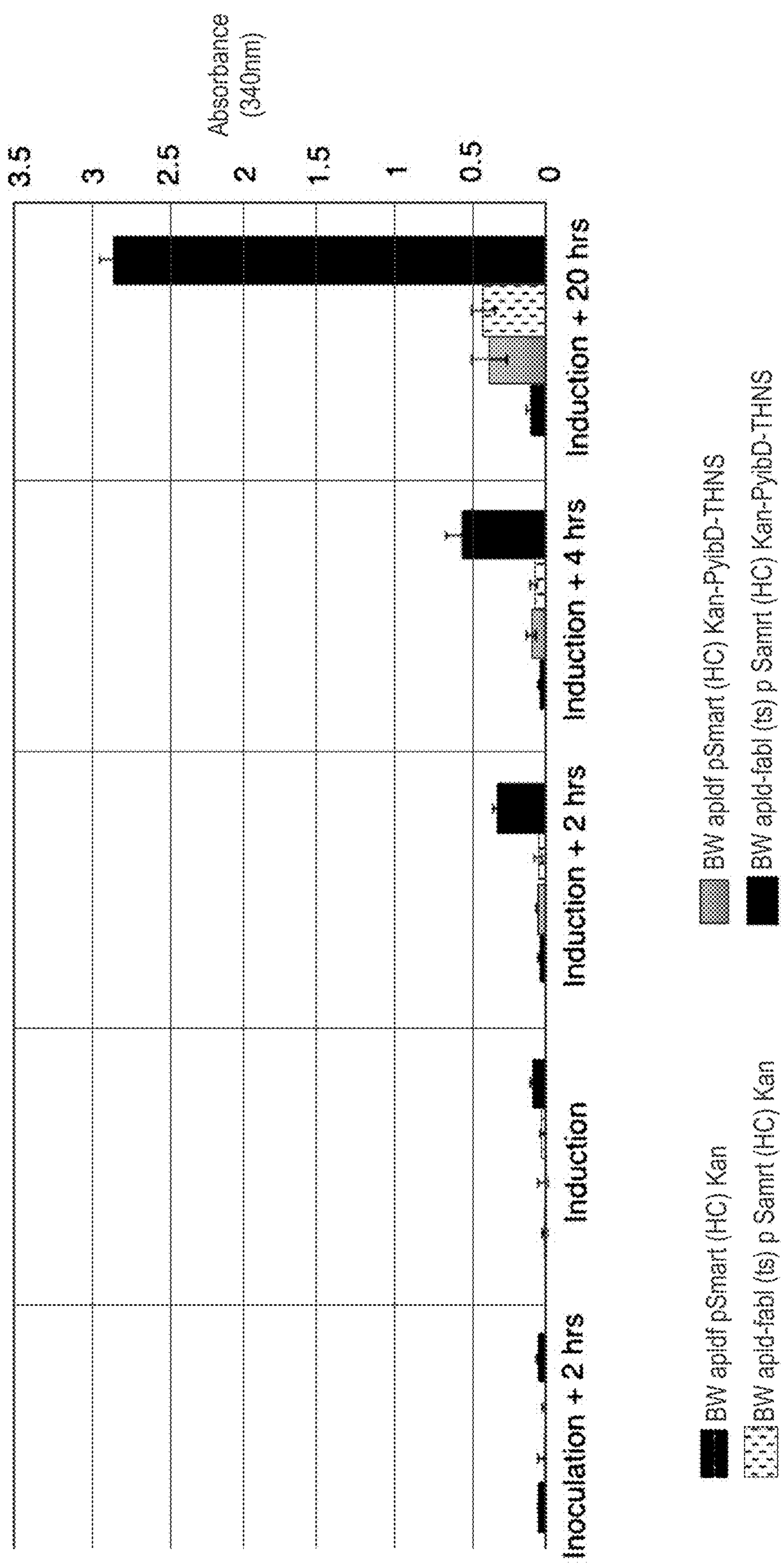
FIG. 4 depicts increased production of tetrahydroxynapthalene from malonyl-CoA in a two stage process as a result of the controlled inactivation of a temperature sensitive fabI allele. Improved production of THN by redirecting malonyl-CoA flux, using a temperature controlled process to inactivate a temperature sensitive allele of fabI. Strains as listed BWalpdf (BW25113: ΔldhA, ApflB, ΔpoxB, ΔackA-pta, ΔadhE), BWalpdf-fabI(ts) (BW25113: ΔldhA, ΔpflB, ΔpoxB, ΔackA-pta, ΔadhE, fabI(F241S), gentR). Plasmids are i) pSMART-HC-Kan-yibD-THNS and ii) pSMART-HC-Kan (control).

This example describes the increased production of tetrahydroxynaphtalene (THN) in *E. coli* from the intermediate malonyl-CoA using the controlled inactivation of fabI via a temperature sensitive allele. Briefly, strain BWapldf (BW25113:ΔldhA, ΔpflB, ΔpoxB, ΔackA-pta, ΔadhE) was further genetically modified so that the fabI gene was mutated to contain both a temperature sensitive (ts) mutation (F241S) as well as to incorporate gentamicin resistance cassette a the C-terminus of the fabI gene. This was accomplished using standard recombineering protocols. The strain was further modified to express the tetrahydroxynapthalene (THN) synthase gene (rppA from *Steptomyces coelicolor*) under phosphate limiting conditions by transformation with the plasmid pSMART-HC-Kan-yibD-THNS (SEQ ID NO:1). Control strains were made with a control empty vector pSMART-HC-Kan (Genbank Accession # AF532107.1), obtained from Lucigen. This high copy plasmid conferring kanamycin resistance was constructed using routine molecular biology methods utilizing the pSMART-HC-Kan kit obtained from Lucigen. The rppA gene under the control of the promoter of low phosphate induced yibD(waaH) gene of *E. coli*. This strain, as well as controls, were evaluated for THN production using the two-stage protocol as outline in the Common Methods section "Shake Flask Protocol-1". Relative THN production was quantified by measuring the absorbance of the supernatant at 340 nm. FIG. 4 summarizes the results.

Example 2: A Synthetic Metabolic Valve to Improve Malonyl-CoA Flux in *E. coli*

Figure 5:
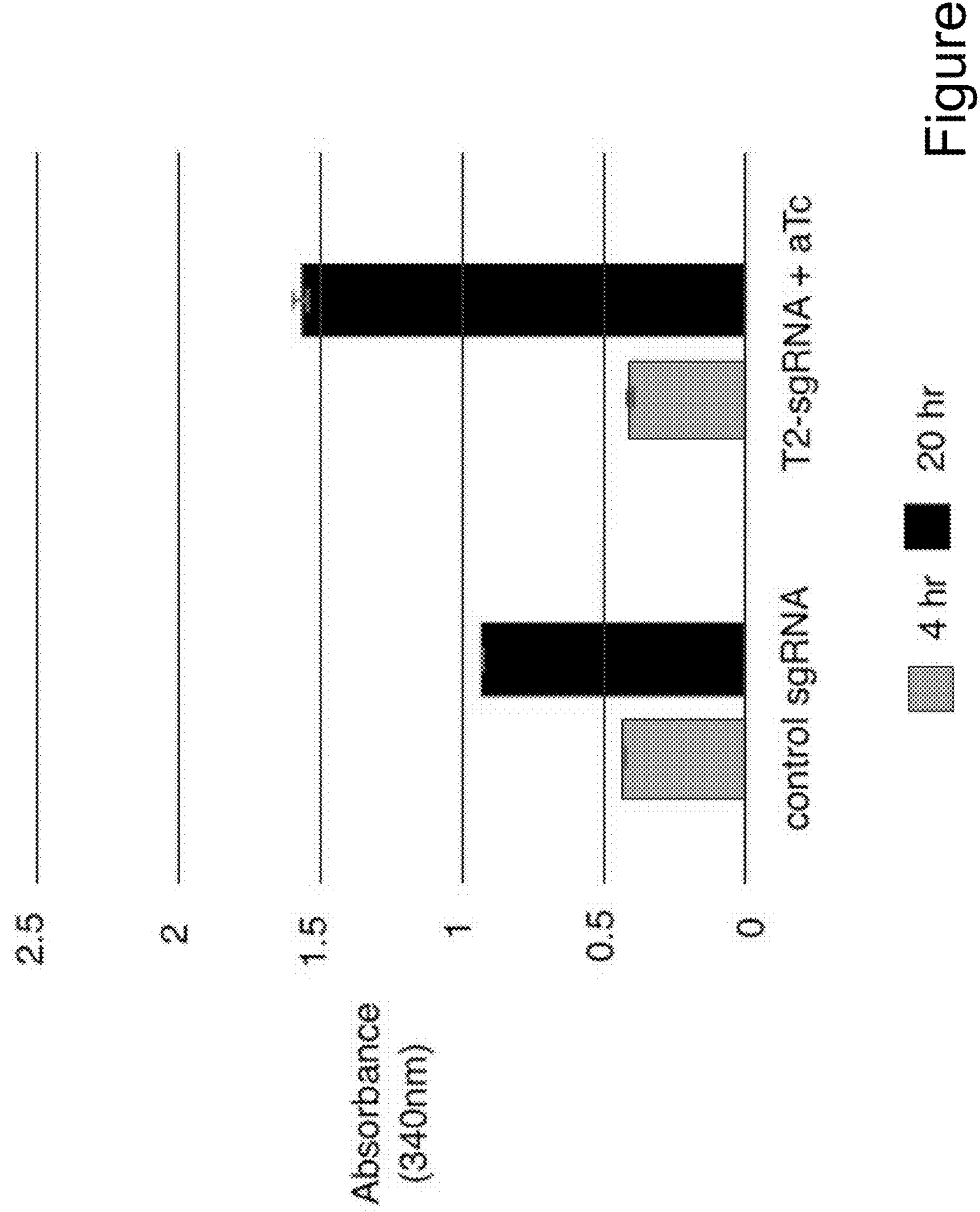
FIG. 5 depicts increased production of tetrahydroxynapthalene from malonyl-CoA in a two stage process as a result of a combination of controlled protein degradation and gene silencing. Improved production of THN by redirecting malonyl-CoA flux, using a synthetic metabolic vlae comprising a combination of CRISPR interference gene silencing and controlled proteolysis as outlined in FIG. 2. THN production at 4 hrs and 20 hrs is compared for two strains. LEFT: Strain BW25113: ΔldhA, ΔpflB, ΔpoxB, ΔackA-pta, ΔadhE, ΔsspB, fabI::DAS4, gentR containing plasmids i) pSMART-HC-Kan-yibD-THNS ii) pdCas9-ptet-sspB and iii) pCDF-control lacking a targeting sgRNA. RIGHT: Strain BW25113: ΔldhA, ΔpflB, ΔpoxB, ΔackA-pta, ΔadhE, ΔsspB, fabI::DAS4, gentR containing plasmids i) pSMART-HC-Kan-yibD-THNS ii) pdCas9-ptet-sspB and iii) pCDF-T2-fabIsgRNA expressing a sgRNA targeting fabI.

This example describes the increased production of tetrahydroxynaphtalene (THN) in *E. coli* from the intermediate malonyl-CoA using the controlled repression of fabI using synthetic metabolic valve technology. In this example a combination of CRISPR interference gene silencing technology and controlled protein degradation was used in a two-stage process. Briefly, strain BWapldf (BW25113: ΔldhA, 4pflB, ΔpoxB, ΔackA-pta, ΔadhE) was further genetically modified so that the fabI gene was tagged to contain a C-terminal DAS4 tag as well as to incorporate gentamicin resistance cassette a the C-terminus of the fabI gene. The C-terminal nucleotide sequence encoding the DAS4 tag was integrated as the following sequence: 5'-GCGGCCAACGATGAAAACTATTCTGAAAACTATGCGGATGCGTCT-34 (SEQ ID NO: 48). This was accomplished using standard recombineering protocols. In addition, the strain was further modified so as to delete the sspB gene. This was also performed with standard recombineering methods. In addition, these strains were still further modified to contain three plasmids, the first plasmid expresses the tetrahydroxynapthalene (THN) synthase gene, pSMART-HC-Kan-yibD-THNS (SEQ ID NO:1), as described above. The second plasmid was constructed to express a small guide RNA targeting the fabI gene from a high copy spectinomycin resistance plasmid derived from pCDF-lb, which was obtained from EMD Millipore Biosciences. The plasmid, pCDF-T2-fabIsgRNA (SEQ ID NO:2), expresses a small guide RNA to use with *S. pyogenes* dCas9. The specific fabI T2 targeting sequence is given by 5'-CAGCCTGCTCCGGTCGGACCG-3' (SEQ ID NO:47). A control plasmid was also made missing any targeting sequence as described by Qi et al. Cell February 2013; 152(5) p 1173-1183. DOI: 10.1016/j.cell.2013.02.022. The last plasmid, pdCas9-ptet-sspB (SEQ ID NO:3), was derived from the plasmid pdCas9-bacteria, from Qi et al, which was obtained from Addgene (Cambridge, Mass. 02139; Plasmid ID 44249). Briefly, pdCas9-bacteria was linearized and the sspB gene was introduced under the control of an additional ptet promoter at the 3' of the catalytically inactive dcas9 gene. The addition of anhydrotetracycline (aTc) will induce expression of both dCas9 as well as sspB from this Chloramphenicol resistance conferring plasmid. All plasmids were constructed using standard molecular biology methods and sequences confirmed by DNA sequencing. These strains, as well as controls, were evaluated for THN production using the two-stage protocol as outline in the Common Methods section "Shake Flask Protocol-2". Relative THN production was quantified by measuring the absorbance of the supernatant at 340 nm. FIG. 5 summarizes the results.

Example 3: General Example

Numerous microbial strains, such as any of the strains listed in the Common Methods Section, may be genetically modified to express enzymes for the biosynthesis of a product. In addition these modified microbial strains can be further modified to contain a controllable synthetic metabolic valve for the dynamic reduction in enzyme activity of one or more metabolic pathways including those required for growth. These valves may utilize one or a combination of methods including gene silencing and controlled proteolysis. Further these modified strains may be used in a multistage fermentation process wherein transition between stages is concurrent with controlled activation of these valves. Specifically, any of these microbial strains may also be further engineered to express a heterologous production pathway enabling the product formation.

Example 4: *E coli* Host Strain Construction

Briefly, strain BWapldf (BW25113:ΔldhA, ΔpflB, ΔpoxB, ΔackA-pta, ΔadhE) was further genetically modified for the deletion of the following genes: arcA, iclR and sspB, to construct strain DLF_0002. This was also performed with standard scarless recombineering methods. To construct a strain capable of both crispr based gene silencing using the native CASCADE system in *E. coli* as well as controlled proteolysis, the cas3 gene of *E. coli* was first deleted. This gene was replaced with a sequence to enable both constitutive expression of the casABCDE-cas1,2 operon enabling CASCADE based gene silencing, as well as a construct allowing for the low phosphate induction of the sspB chaperone. The DNA sequence integrated was ordered as a single synthetic construct: SEQ ID NO:4, and integrated using standard recombineering methodologies. In the place of the cas3 gene, this construct integrates a transcriptional terminator, followed by the low phosphate inducible *E. coli* ugpB gene promoter and the sspB gene. The sspB gene is followed by another transcriptional terminator and a subsequent constitutive proB promoter adapted from (Davis, J H., Rubin, A J., and Sauer, R T. NAR. February 2011; 39(3) p 1131-1141. DOI: 10.1093) to drive constant expression of the CASCADE operon. The resulting strain is termed DLF_0025.

A derivative of *E. coli* strain DLF_0025 was constructed to utilize a non-PTS dependent glucose uptake system. PTS (phosphotransferase system) based sugar uptake is well known in the art and links the phosphorylation of glucose to the production of pyruvate. Alternative uptake has been previously described in *E. coli*, (Hernandez-Montalvo, V., et al., Biotechnol Bioeng.. September 2003; 83(6) p 687-694.), and relies on the overexpression of the *E. coli* galP permease and glucokinase (glk gene) along with the deletion of the *E. coli* ptsG gene. The ptsG gene was deleted and replaced with a constitutively expressed glucokinase construct, this construct was ordered as a single synthetic linear DNA construct (SEQ ID NO:5) and integrated according to standard methodologies. In addition, the galP promoter was also replaced via chromosomal replacement using another single synthetic linear DNA construct (SEQ ID NO:6), the resulting strain was called DLF_0286. In both cases the proC promoter was used to drive constitutive expression (Davis, J H., Rubin, A J., and Sauer, R T. NAR. February 2011; 39(3) p 1131-1141. DOI: 10.1093).

*E. coli* strains DLF_0025 and DLF_0286 were further modified for the controlled proteolysis of key enzymes in central metabolism including: 1) enoyl-ACP reductase encoded by the fabI gene, involved in fatty acid biosynthesis, 2) citrate synthase encoded by the gltA gene, involved in citric acid cycle, 3) soluble transhydrogenase encoded by the udhA gene, involved in NADPH metabolism, 4) glucose-6-phosphate-1-dehydrogenase encoded by the zwf gene, involved in the pentose phosphate pathway and 5) the lipoamide dehydrogenase or E3 component of the pyruvate dehydrogenase complex encoded by lpd gene. C-terminal DAS+4 tags enabling sspB controlled proteolysis were integrated at the 3' end of each of the above genes as the following sequence: 5'-GCGGCCAACGATGAAAACTATTCTGAAAACTATGCGGATGCGTCT-3' (SEQ ID NO:48). This was accomplished by the insertion of single DNA cassettes containing the DAS4 tags, targeting sequences as well as a downstream antibiotic resistance cassette. The fabI-DAS4 tag and lpd-DAS4 tag were followed by a gentamicin resistance cassette, the gltA-DAS4 tag was followed by a zeocin resistance cassette, and the udhA-DAS4 and zwf-DAS4 tags were both followed by a blasticidin resistance cassette. The integrated sequences used for the C-terminal taggingfabI, lpd, gltA, udhA and zwf are SEQ ID NO:7, SEQ ID NO:8, SEQ ID NO:9 SEQ ID NO:10 and SEQ ID NO:11 respectively. Strains with single and combinations of DAS4 tagged enzymes were constructed. Host strain genotypes are listed in Table 1.

TABLE 1

*E. coli* Host Strains

| Strain ID | Genotype |
|---|---|
| BW25113 | F-, λ⁻, Δ(araD-araB)567, ΔlacZ4787(::rrnB-3), rph-1, Δ(rhaD-rhaB)568, hsdR514 |
| BWapldf | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt |
| DLF_0002 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB |
| DLF_0025 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB |
| DLF_0286 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP |
| DLF_0043 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS+4:zeoR |
| DLF_0028 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR |
| DLF_0031 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR |
| DLF_0038 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR, udhA-DAS+4:bsdR |
| DLF_0040 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR, zwf-DAS+4:bsdR |
| DLF_0039 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR, gltA-DAS+4:zeoR |
| DLF_0047 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR, gltA-DAS+4:zeoR, udhA-DAS+4:bsdR |

TABLE 1-continued

| *E. coli* Host Strains | |
|---|---|
| Strain ID | Genotype |
| DLF_0167 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR, gltA-DAS+4:zeoR, zwf-DAS+4:bsdR |
| DLF_0041 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, gltA-DAS+4:zeoR, |
| DLF_0165 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, zwf-DAS+4:bsdR |
| DLF_0042 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, udhA-DAS+4:bsdR |
| DLF_0049 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, gltA-DAS+4:zeoR, udhA-DAS+4:bsdR |
| DLF_0048 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, gltA-DAS+4:zeoR, zwf-DAS+4:bsdR |
| DLF_0045 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS+4:zeoR, udhA-DAS+4:bsdR |
| DLF_0044 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS+4:zeoR, zwf-DAS+4:bsdR |
| DLF_0287 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR |
| DLF_0288 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, zwf-DAS+4:bsdR |
| DLF_0289 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, udhA-DAS+4:bsdR |
| DLF_0290 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, zwf-DAS+4:bsdR, fabI-DAS+4:gentR |
| DLF_0291 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, udhA-DAS+4:bsdR, fabI-DAS+4:gentR |

Example 5: Low Phosphate Gene Expression in *E. coli*

Figure 6:
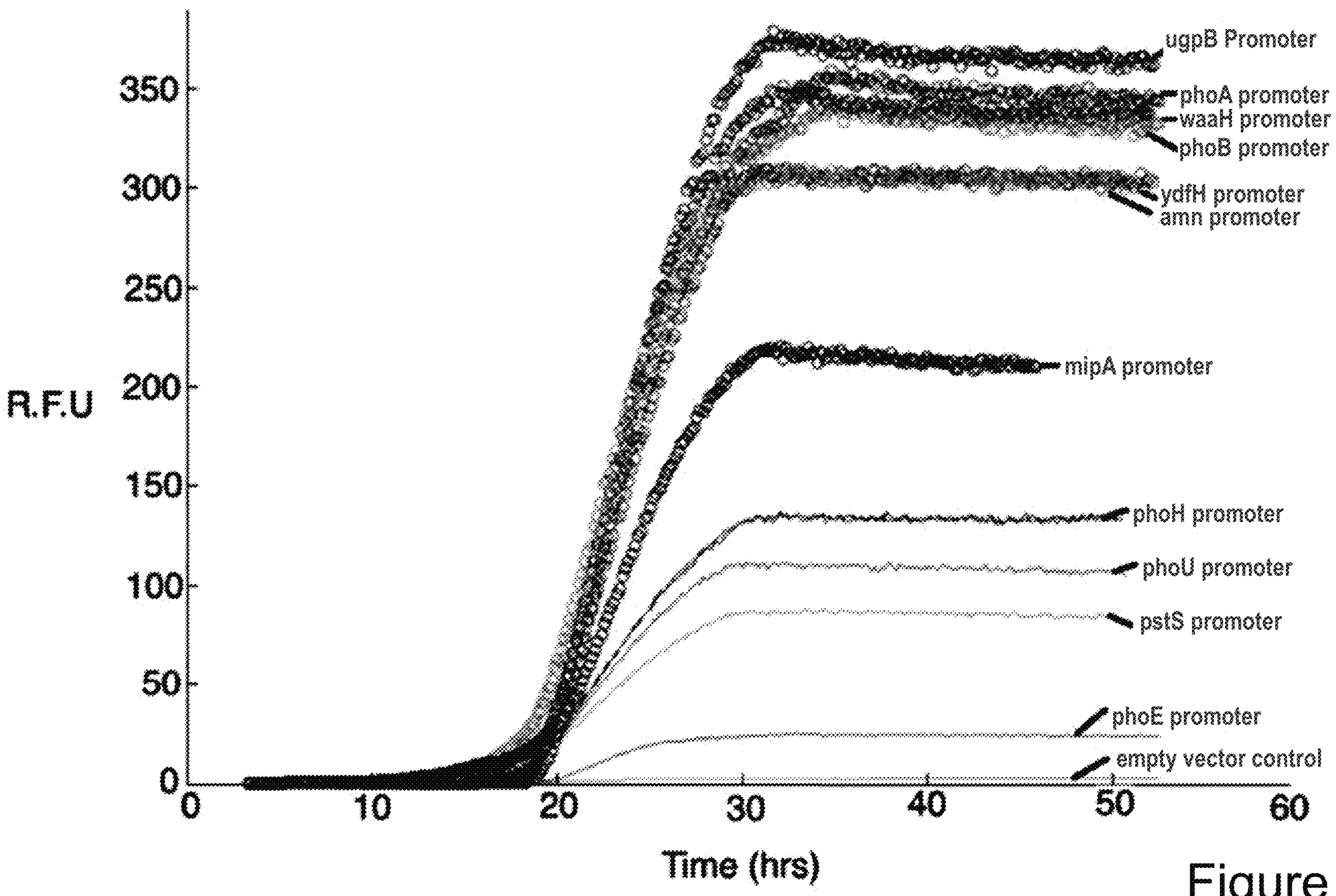
FIG. 6 depicts the low phosphate induction of a GFP reporter with various low phosphate inducible promoters. A comparison of the low phosphate inducible expression for the following gene promoters: amn, phoA, phoB, phoE, phoH, phoU, mipA, pstS, ugpB, waaH and ydfH, is shown. An ultraviolet excitable, green fluorescent protein (GFPuv) reporter gene was used and relative fluorescent units (RFU) are plotted as a function of time. Growth stops and phosphate depletion begins at about 15-20 hrs.

In order to evaluate different low phosphate induction schemes to control synthetic metabolic valves, several known low phosphate inducible promoters form *E. coli* were evaluated with a ultraviolet excitable, green fluorescent protein (GFPuv) reporter gene. These gene promoters included those for the following genes: amn, phoA, phoB, phoE, phoH, phoU, mipA, pstS, ugpB, waaH and ydfH, were evaluated for low phosphate induction. Reporter plasmids linking each promoter to a GFPuv gene reporter were constructed and sequences are as follows: pSMART-amnp-GFPuv (SEQ ID NO:36), pSMART-phoAp-GFPuv (SEQ ID NO:37), pSMART-phoBp-GFPuv (SEQ ID NO:38), pSMART-phoEp-GFPuv (SEQ ID NO:38), pSMART-phoHp-GFPuv (SEQ ID NO:40), pSMART-phoUp-GFPuv (SEQ ID NO:41), pSMART-mipAp-GFPuv (SEQ ID NO:42), pSMART-pstSp-GFPuv (SEQ ID NO:43), pSMART-ugpBp-GFPuv (SEQ ID NO:12), pSMART-waaHp-GFPuv (SEQ ID NO:44), and pSMART-ydfHp-GFPuv (SEQ ID NO:45). Briefly, plasmids were transformed into *E. coli* strain BWapldf (Refer to Example 4). Colonies were used to inoculate 4 mL of SM3 media with kanamycin (Refer to Common Methods Section) and incubated overnight at 37 degrees Celsius and a shaking speed of 225 rpm. After overnight growth, cells were normalized to an optical density at 600 nm of 5, and 40 μL of normalized culture was used to inoculate 760 μL of fresh FGM3 (Refer to Common Methods Section) medium with kanamycin in wells of a 48 well FlowerPlate™ B which was transferred into a BioLector Microbioreactor both obtained from M2P Labs (Baesweiler, Germany). The BioLector Microbioreactor can continuously measure fluorescence. Cells were incubated in the Microreactor at 37 degrees Celsius and a shaking speed of 1200 rpm for 60 hrs. Growth stopped and phosphate depletion begins at about 15-20 hrs (data not shown for clarity). Fluorescence results for each reporter construct as well as an empty vector control are reported as relative fluorescence units (R.F.U) in FIG. 6. All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, N.C., USA) was used for plasmid DNA sequence confirmations. Standard codon optimization was performed to optimize constructs for expression in *E. coli.*

Example 6: pCASCADE Plasmid Cloning pCASCADE-control (SEQ ID NO:13) was prepared by swapping the tetracycline inducible promoter in perRNA plasmid (Luo et al. "Repurposing endogenous type I CRISPR-Cas systems for programmable gene repression" NAR. October 2014; DOI: 10.1093.) with an insulated ugpB promoter. The plasmid was constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, N.C., USA) was used for plasmid DNA sequence confirmations.

Additional pCASCADE plasmids with single RNA guides were prepared via Q5 site-directed mutagenesis (New England Biolabs, Ipswich, Mass., USA),) following manufacturer's protocol, except that 5% v/v DMSO was added to the Q5 PCR reaction. For example pCASCADE-gltA2 (SEQ ID NO:14) was prepared using pCASCADE-control as template and the following primers: gltA2-FOR 5'-GGGACAGTTATTAGTTCGAGTTCCCCGCGCCA GCGGGGATAAACCGAAAAAAAAACCCC-3' (SEQ ID NO:49) and gltA2-REV 5'-GAATGAATTGGTCAATACG-GTTTATCCCCGCTGGCGCGGGGAACTCGAGGTGGT ACCAGATCT-3' (SEQ ID NO:50). Additional pCASCADE plasmids including pCASCADE-fabI (SEQ ID NO:15), pCASCADE-udhA, (SEQ ID NO:16), pCASCADE-zwf (SEQ ID NO:17) and pCASCADE-gltA1 (SEQ ID NO:18) were prepared in a similar manner by exchanging the guide RNA targeting sequence using Q5 mutagenesis.

Additional pCASCADE plasmids with multiple RNA guides were prepared as follows. For example pCASCADE-gltA2-udhA (SEQ ID NO:19) plasmid was prepared by amplifying gltA2 guide half and udhA guide half from pCASCADE-gltA2 and pCASCADE-udhA respectively using Q5 High-Fidelity 2× Master Mix (NEB, MA). The primers used: G2U-FOR1: 5'-CCGGATGAGCAT-TCATCAGGCGGGCAAG-3' (SEQ ID NO:51), REV1: 5'-CGGTTTATCCCCGCTGGCGCGGGGAACTC-GAACTTCATAACTTTTAC-3' (SEQ ID NO:52) and FOR2: 5'-GCGCCAGCGGGGATAAACCGTTACCAT-TCTGTTG-3' (SEQ ID NO:53) and REV2: 5'-CTTGC-CCGCCTGATGAATGCTCATCCGG-3' (SEQ ID NO:54). PCR products were purified by gel-extraction and were then used for Gibson Assembly (NEB, MA). pCASCADE-fabI-udhA (SEQ ID NO:20), pCASCADE-fabI-gltA1 (SEQ ID NO:21), pCASCADE-fabI-gltA2 (SEQ ID NO:22), pCASCADE-fabI-zwf (SEQ ID NO:23), pCASCADE-gltA1-udhA (SEQ ID NO:24), pCASCADE-gltA2-udhA (SEQ ID NO:25), pCASCADE-gltA1-zwf (SEQ ID NO:26), pCASCADE-gltA2-zwf (SEQ ID NO:27), were all prepared in a similar way by amplification of each guide and part of the vector backbone followed by Gibson Assembly. All plasmid sequences were confirmed by DNA sequencing (Eton Bioscience, Research Triangle Park, N.C., USA).

Figure 7:
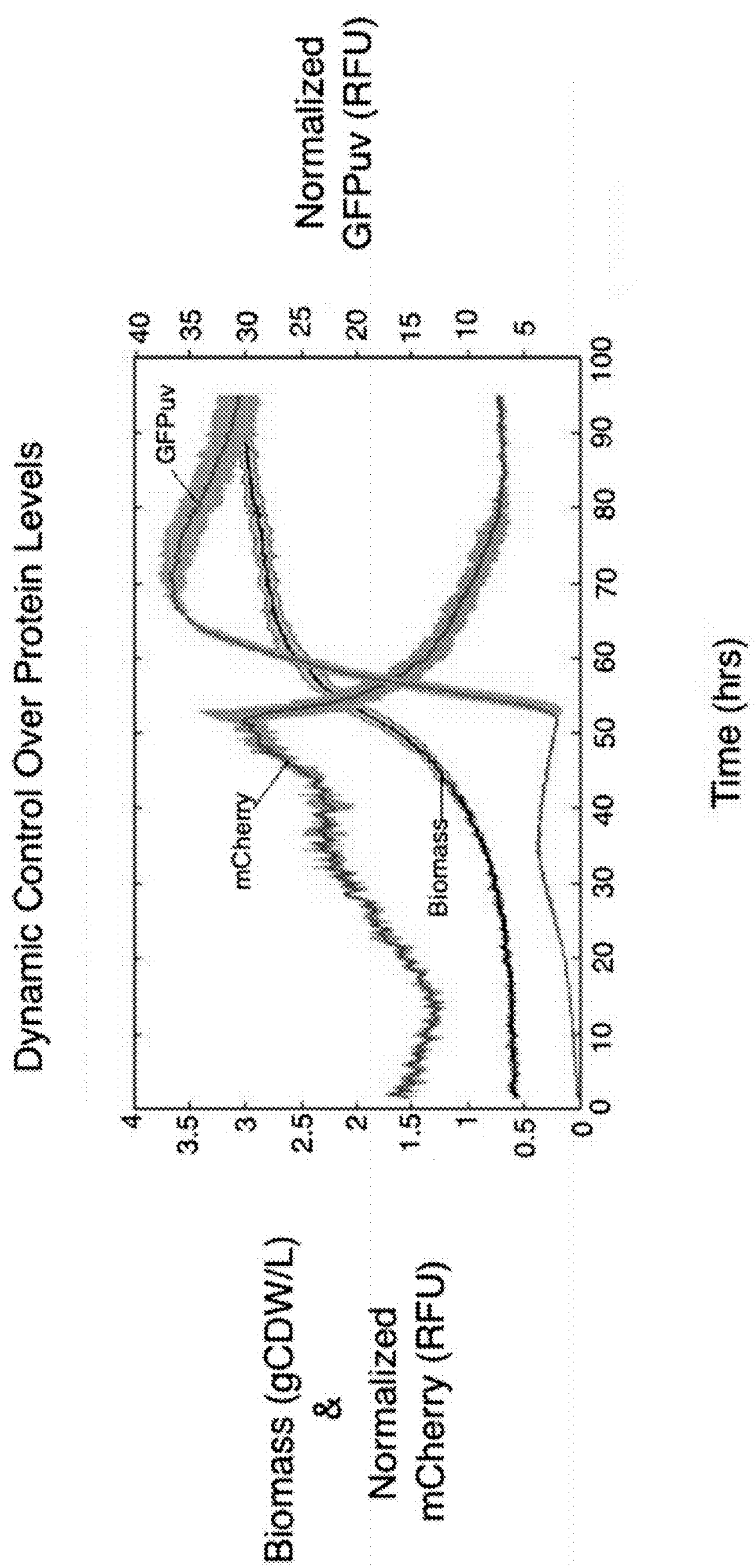
FIG. 7 depicts the dynamic control over protein levels in *E. coli* using the CASCADE System and controlled proteolysis. Strain DLF_0025 (enabling low phosphate DAS+4 degradation) has been modified to constitutively express a mCherry protein with a C-terminal DAS+4 degradation tag. In addition the strain has been modified for the low phosphate induction of GFPuv as well as a guide RNA repressing mCherry expression. As cells grow phosphate is depleted, and cells "turn off" mCherry and "turn on" GFPuv. Biomass is plotted as grams cell dry weight per liter, GFPuv and mCherry are plotted as relative fluorescence units (RFU) which are normalized to biomass levels.

Example 7: Dynamic Control Over Protein Levels in *E. coli* Using the CASCADE System and Controlled Proteolysis All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, N.C., USA) was used for plasmid DNA sequence confirmations. Standard codon optimization was performed to optimize constructs for expression in *E. coli*. First a plasmid expressing a low phosphate inducible (utilizing the low phosphate inducible waaH gene promoter from *E. coli*), ultraviolet excitable, green fluorescent protein (GFPuv) was constructed using standard cloning techniques and called pSMART-waaHp-GFPuv (SEQ ID NO:12). Secondly, a compatible vector with the constitutive expression of a red fluorescent protein (mCherry), tagged with a DAS+4 tag enabling controlled proteolysis was constructed pBT1-mCherry-DAS+4 (SEQ ID NO:28). Constitutive expression was achieved using a proD promoter (Davis, J H., Rubin, A J., and Sauer, RT. NAR. February 2011; 39(3) p 1131-1141. DOI: 10.1093). Lastly, another compatible vector enabling the low phosphate expression (utilizing the low phosphate inducible ugpB gene promoter from *E. coli*) expression of a gene silencing guide RNA targeting the proD promoter was constructed (Refer to Example 6 for methods) and called pCASCADE-proD (SEQ ID NO:29). These plasmids were transformed into several host strains as described in Example 4, including strain DLF_0025 to create several strains. Colonies were used to inoculate 4 mL of SM3 media with kanamycin (Refer to Common Methods Section) and incubated overnight at 37 degrees Celsius and a shaking speed of 225 rpm. After overnight growth, cells were normalized to an optical density at 600 nm of 5, and 40 μL of normalized culture was used to inoculate 760 μL of fresh FGM3 (Refer to Common Methods Section) medium with kanamycin in wells of a 48 well FlowerPlate™ B which was transferred into a BioLector Microbioreactor both obtained from M2P Labs (Baesweiler, Germany). The BioLector Microbioreactor can continuously measure fluorescence and biomass levels. Cells were incubated in the Microreactor at 37 degrees Celsius and a shaking speed of 1200 rpm for 60 hrs. Fluorescence results for each reporter construct as well as an empty vector control are reported as relative fluorescence units (R.F.U) normalized to biomass levels are depicted in FIG. 7. All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, N.C., USA) was used for plasmid DNA sequence confirmations. Standard codon optimization was performed to optimize constructs for expression in *E. coli.*

Example 8: *E. coli* Pathway Plasmid Cloning

All production plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, N.C., USA) was used for plasmid DNA sequence confirmations. Standard codon optimization was performed to optimize constructs for expression in *E. coli.*

A plasmid expressing an NADPH dependent 3-hydroxypropionic acid (3-HP) production pathway was constructed as an operon of two genes. The mcr gene from *Chloroflexus auranticus* (CaMCR), encoding a malonyl-CoA reductase (Uniprot # A9WIU3), and the ydfG gene from *E. coli*, encoding an NADPH dependent 3-HP dehydrogenase (Uniprot # P39831) were used. Only the C-terminal end (residues 550-1219) of the mcr enzyme encoding the malonyl-CoA reductase domain was utilized (Liu, C., Wang, Q., Ding., Y and Zhao, Gu., PLOS One. September 2013. DOI: 10.1371). The operon was assembled into the pSMART-HC-Kan vector, resulting in plasmid pSMART-3HP1, (SEQ ID NO:30).

A plasmid expressing a malonic acid production pathway was constructed from a single gene encoding a triple mutant (E95N/Q384A/F304R) *Pseudomonas fulva* (strain 12-X) isobutyryl-CoA thioesterase (Uniprot # F6AA82), with altered specificity (Steen, E., Patent Application PCT/US2014/047645). This gene was cloned behind the phosphate dependent waaH gene promoter from *E. coli*. The gene was then assembled into the pSMART-HC-Kan vector (Lucigen, Middleton Wis.), resulting in plasmid pSMART-F6AA82M, (SEQ ID NO:31).

A plasmid expressing an NADPH dependent L-alanine production pathway was constructed from a single gene encoding a double mutant (Leu197Arg Asp196A1a) *Bacillus subtilis* alanine dehydrogenase (AlaDH) (Uniprot # Q08352), with NADPH cofactor specificity (Haas, T., et al. Patent Application PCT/EP2013/057855). This gene was cloned behind the phosphate dependent waaH gene promoter from *E. coli*. The gene was then assembled into the pSMART-HC-Kan vector (Lucigen, Middleton Wis.), resulting in plasmid pSMART-Ala1, (SEQ ID NO:32). A additional plasmid expressing the same NADPH dependent L-alanine production pathway was constructed using the phosphate dependent ugpB gene promoter from *E. coli*. The gene was then assembled into the pSMART-HC-Kan vector (Lucigen, Middleton Wis.), resulting in plasmid pSMART-Ala2, (SEQ ID NO:46).

A plasmid expressing a mevalonate production pathway was constructed from two genes assembled into two transcriptional units. First, the mvaE gene from *Enterococcus faecalis* encoding a bifunctional acetoacetyl-CoA thiolase, and NADPH dependent HMG-CoA reductase (Uniprot # Q9FD70) was cloned behind an insulated version of the phosphate dependent waaH gene promoter from *E. coli*. Additionally, the mvaS gene, also from *E. faecalis*, encoding a hydroxymethylglutaryl-CoA synthase (Uniprot # Q9FD71) was cloned behind an insulated version of the phosphate dependent mipA gene promoter from *E. coli*. The mvaS expression construct was cloned behind the mvaE construct and both assembled into the pSMART-HC-Kan vector, resulting in plasmid pSMART-Mev1, (SEQ ID NO:33).

A plasmid expressing an NADH dependent 2,3-butanediol production pathway was constructed as an operon of three genes. The budA, budB and budC genes from *Enterobacter cloacae* subsp. *dissolvens* SDM, encoding an α-acetolactate decarboxylase, an acetolactate synthase and acetoin reductase, respectively, were cloned behind the phosphate dependent waaH gene promoter from *E. coli*. The operon was assembled into the pSMART-HC-Kan vector, resulting in plasmid pSMART-2,3-BDO1, (SEQ ID NO:34).

A plasmid expressing an NADPH dependent 2,3-butanediol production pathway was constructed as an operon of three genes. The budA, budB genes from *Enterobacter cloacae* subsp. *dissolvens* SDM, encoding an α-acetolactate decarboxylase, an acetolactate synthase, and a Glu221Ser/Ile222Arg/Ala223Ser triple mutant bdhl gene from *S. cerevisiae*, encoding an NADPH dependent acetoin reductase (Ehsani, M., Fernandez, M R., Biosca J A and Dequin, S. Biotechnol Bioeng. 2009 Oct. 1; 104(2):381-9. doi: 10.1002) respectively, were cloned behind the phosphate dependent waaH gene promoter from *E. coli*. The operon was assembled into the pSMART-HC-Kan vector, resulting in plasmid pSMART-2,3-BDO2 (SEQ ID NO:35).

Example 9: Production of 3-Hydroxypropionic Acid (3-HP) in *E. coli*, from Malonyl-CoA and NADPH in 96 Well Plates Several *E. coli* strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol-1" as described in the Common Methods Section. Products levels were then measured using the analytical methods as described in the Common Methods Section. These strains and the associated production data are given in Table 2.

TABLE 2

3-HP Production from malonyl-CoA and NADPH in 96 well plates

| Strain | Host Strain | pCASCADE plasmid | Production Plasmid | Final 3-HP Titer (g/L) | Final 3-HP Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 10 | DLF_0286 | | | 0 | 0 |
| 11 | DLF_0286 | | Empty vector | 0 | 0 |
| 12 | DLF_0039 | | pSMART-3HP1 | 0 | 0 |
| 13 | DLF_0028 | pCASCADE-fabI | pSMART-3HP1 | 0 | 0 |
| 14 | DLF_0028 | pCASCADE-fabI-zwf | pSMART-3HP1 | 0 | 0 |
| 15 | DLF_0043 | pCASCADE-fabI | pSMART-3HP1 | 0 | 0 |
| 16 | DLF_0025 | pCASCADE-fabI | pSMART-3HP1 | 0.02 | 0.03 |
| 17 | DLF_0045 | pCASCADE-udhA-gltA2 | pSMART-3HP1 | 0.11 | 0.06 |
| 18 | DLF_0025 | | pSMART-3HP1 | 0.16 | 0.14 |
| 19 | DLF_0043 | pCASCADE-gltA2 | pSMART-3HP1 | 0.19 | 0.06 |
| 20 | DLF_0025 | pCASCADE-fabI-udhA | pSMART-3HP1 | 0.36 | 0.18 |
| 21 | DLF_0046 | | pSMART-3HP1 | 0.41 | 0.14 |

TABLE 2-continued

3-HP Production from malonyl-CoA and NADPH in 96 well plates

| Strain | Host Strain | pCASCADE plasmid | Production Plasmid | Final 3-HP Titer (g/L) | Final 3-HP Std Deviation |
|---|---|---|---|---|---|
| 22 | DLF_0039 | pCASCADE-fabI-gltA2 | pSMART-3HP1 | 0.45 | 0.29 |
| 23 | DLF_0028 | | pSMART-3HP1 | 0.55 | 0.24 |
| 24 | DLF_0025 | pCASCADE-udhA | pSMART-3HP1 | 0.57 | 0.14 |
| 25 | DLF_0046 | pCASCADE-fabI-udhA | pSMART-3HP1 | 0.58 | 0.09 |
| 26 | DLF_0025 | pCASCADE-fabI-zwf | pSMART-3HP1 | 0.66 | 0.26 |
| 27 | DLF_0046 | pCASCADE-fabI-zwf | pSMART-3HP1 | 0.89 | 0.11 |
| 28 | DLF_0047 | pCASCADE-fabI-gltA1 | pSMART-3HP1 | 1.00 | 1.74 |
| 29 | DLF_0038 | pCASCADE-fabI-udhA | pSMART-3HP1 | 1.58 | 0.32 |
| 30 | DLF_0039 | pCASCADE-gltA1 | pSMART-3HP1 | 1.66 | 0.34 |
| 31 | DLF_0047 | pCASCADE-fabI | pSMART-3HP1 | 1.82 | 0.41 |
| 32 | DLF_0047 | pCASCADE-fabI-zwf | pSMART-3HP1 | 2.05 | 0.16 |
| 33 | DLF_0038 | | pSMART-3HP1 | 2.09 | 0.34 |
| 34 | DLF_0047 | pCASCADE-fabI-udhA | pSMART-3HP1 | 2.28 | 0.39 |
| 35 | DLF_0047 | pCASCADE-udhA | pSMART-3HP1 | 2.33 | 1.30 |
| 36 | DLF_0291 | pCASCADE-gltA2 | pSMART-3HP1 | 3.17 | 0.93 |
| 37 | DLF_0291 | pCASCADE-udhA-gltA2 | pSMART-3HP1 | 4.95 | 2.18 |

Figure 8:
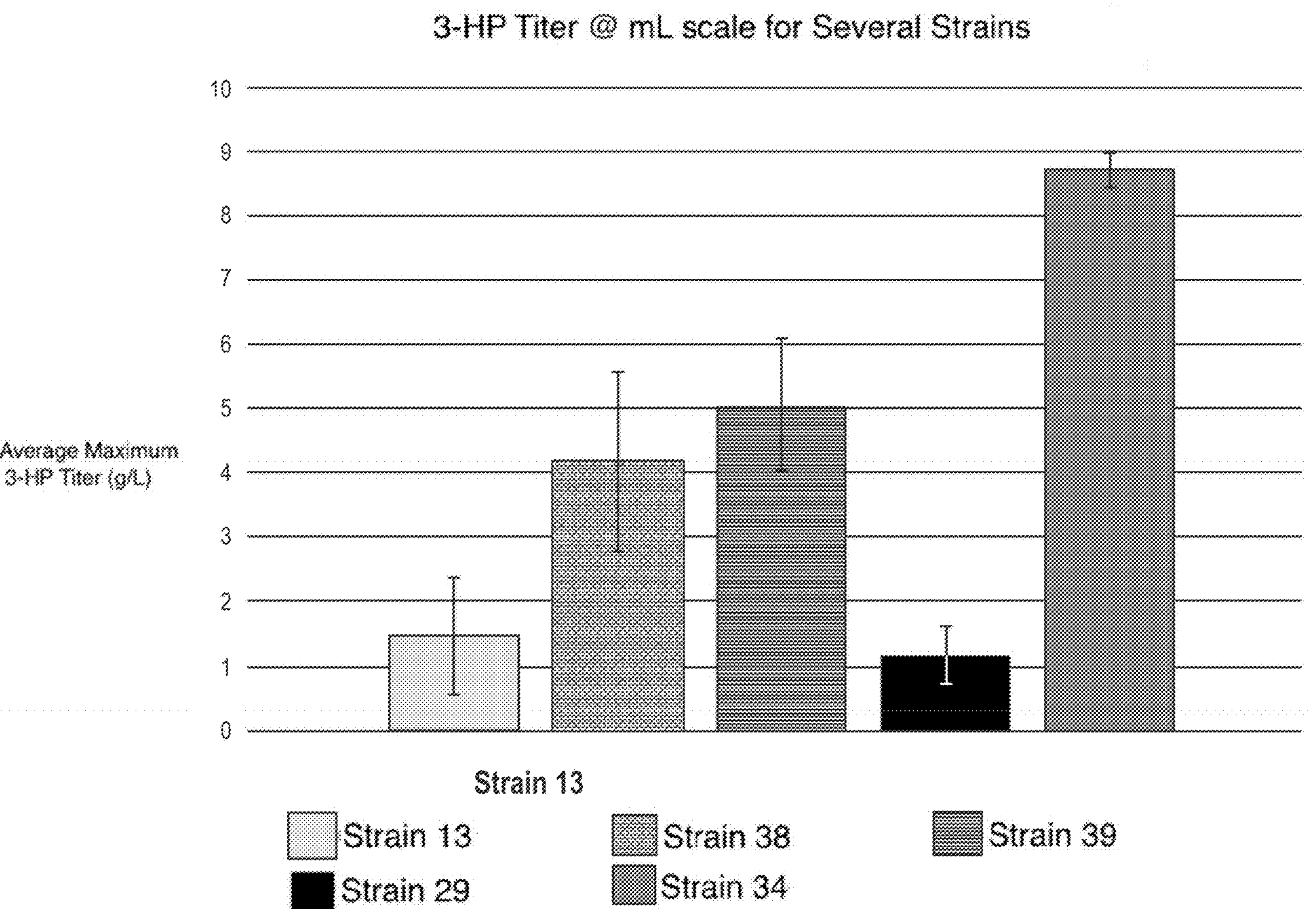
FIG. 8 depicts the production of 3-HP from malonyl-CoA and NADPH at mL scale. Average Maximal 3-HP titers are plotted for several production strains.

Example 10: Production of 3-Hydroxypropionic Acid (3-HP) in *E. coli*, from Malonyl-CoA and NADPH at mL Scale Several *E. coli* strains were constructed utilizing a combination of host strains as described in Example 5, production pathway plasmids as described in Example 6 and CASCADE based gene silencing constructs such as those described in Example 7. Strains were then evaluated for product formation using the standard mL scale evaluation protocol "Micro24 Protocol-1" as described in the Common Methods Section. Products levels were then measured using the analytical methods as described in the Common Methods Section. Summary metrics are listed in Table 3 and shown in FIG. 8.

TABLE 3

3-HP Summary Production metrics for 3-HP produced from malonyl-CoA and NADPH at mL scale.

| Strain | Host Strain | pCASCADE plasmid | Production Plasmid | Final 3-HP Titer (g/L) |
|---|---|---|---|---|
| 18 | DLF_0025 | | pSMART-3HP1 | Below Detection |
| 13 | DLF_0028 | pCASCADE-fabI | pSMART-3HP1 | 1.48 ± 0.91 |
| 38 | DLF_0038 | pCASCADE-fabI | pSMART-3HP1 | 4.19 ± 1.39 |
| 39 | DLF_0038 | pCASCADE-udhA | pSMART-3HP1 | 5.07 ± 1.03 |
| 29 | DLF_0038 | pCASCADE-fabI-udhA | pSMART-3HP1 | 1.17 ± 0.44 |
| 34 | DLF_0047 | pCASCADE-fabI-udhA | pSMART-3HP1 | 8.71 ± 0.28 |

Example 11: Production of 3-Hydroxypropionic Acid (3-HP) in *E. coli*, from Malonyl-CoA and NADPH L Scale

Figure 9:
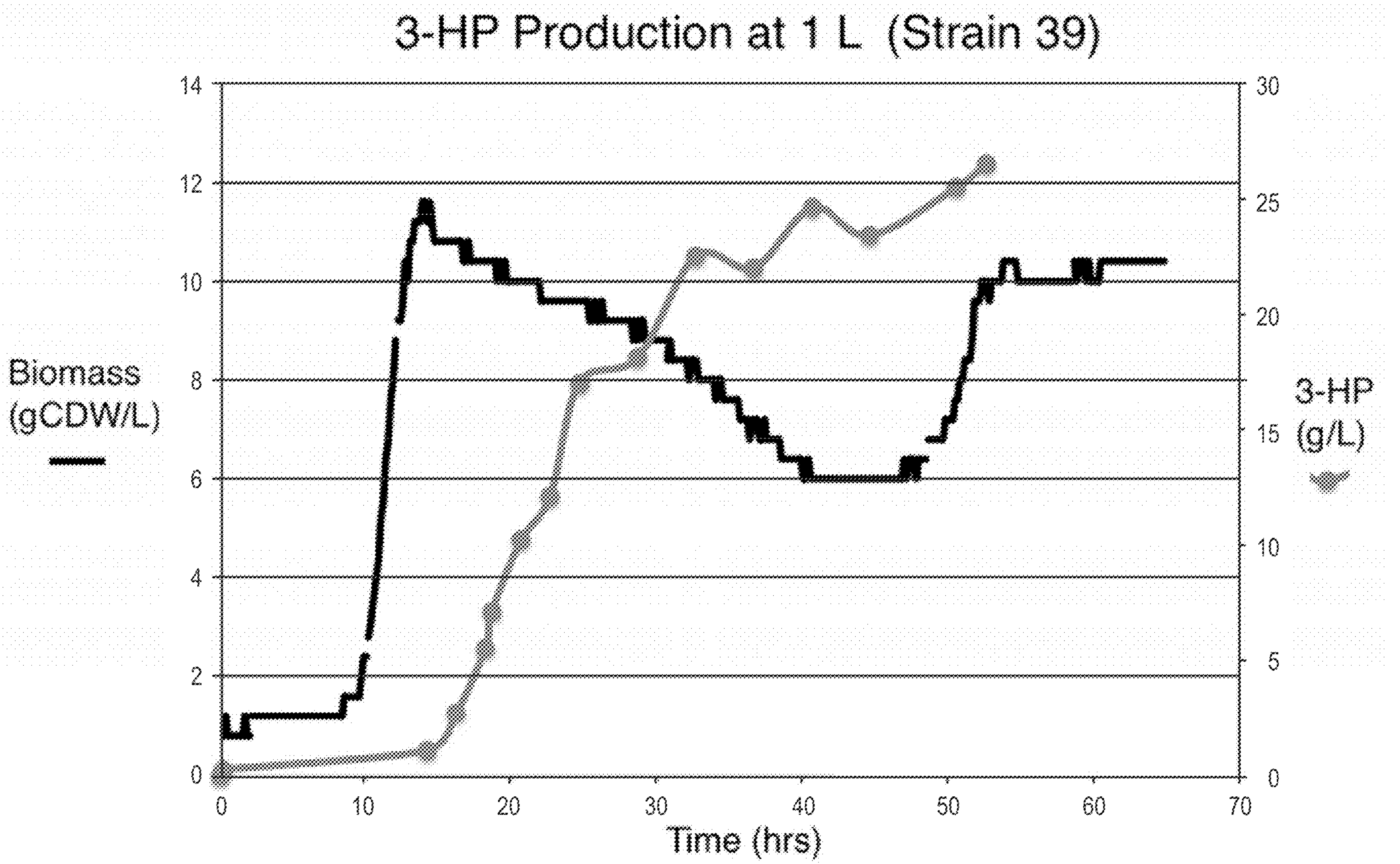
FIG. 9 depicts the production of 3-HP from malonyl-CoA and NADPH at L scale. Biomass and 3-HP titers are plotted as a function of time.

*E. coli* strain 39 from Example 10, was evaluated at 1 L scale using the standard evaluation protocol "1 L Fermentation Protocol-1" as described in the Common Methods Section. Products levels were then measured using the analytical methods as described in the Common Methods Section. Biomass growth and 3-HP production are shown in FIG. 9.

Example 12: Production of Malonic Acid in *E. coli*, from Malonyl-CoA in 96 Well Plates Several *E. coli* strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol-1" as described in the Common Methods Section. Products levels were then measured using the analytical methods as described in the Common Methods Section. These strains and the associated production data are given in Table 4.

TABLE 4

Malonic Acid Production from malonyl-CoA in 96 well plates

| Strain | Host Strain | pCASCADE plasmid | Production Plasmid | Final Malonic Acid Titer (g/L) | Final Malonic Acid Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 10 | DLF_0286 | | | 0 | 0 |
| 11 | DLF_0286 | | Empty vector | 0 | 0 |
| 40 | DLF_0025 | pCASCADE-control | Empty vector | 0 | 0 |
| 41 | DLF_0025 | pCASCADE-control | pSMART-F6AA82M | 0 | 0 |
| 42 | DLF_0028 | pCASCADE-control | pSMART-F6AA82M | 0.19 | 0.095 |
| 43 | DLF_0039 | pCASCADE-control | pSMART-F6AA82M | 0 | 0 |
| 44 | DLF_0039 | pCASCADE-gltA1 | pSMART-F6AA82M | 0 | 0 |
| 45 | DLF_0039 | pCASCADE-gltA2 | pSMART-F6AA82M | 0 | 0 |

TABLE 4-continued

Malonic Acid Production from malonyl-CoA in 96 well plates

| Strain | Host Strain | pCASCADE plasmid | Production Plasmid | Final Malonic Acid Titer (g/L) | Final Malonic Acid Std Deviation |
|---|---|---|---|---|---|
| 46 | DLF_0039 | pCASCADE-zwf | pSMART-F6AA82M | 0 | 0 |
| 47 | DLF_0290 | pCASCADE-control | pSMART-F6AA82M | 0.017 | 0.029 |
| 48 | DLF_0167 | pCASCADE-control | pSMART-F6AA82M | 0.45 | 0.04 |

Example 13: Production of Alanine in *E. coli*, from Pyruvate in 96 Well Plates Several *E. coli* strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol-1" as described in the Common Methods Section. Products levels were then measured using the analytical methods as described in the Common Methods Section. These strains and the associated production data are given in Table 5.

TABLE 5

Alanine Production from pyruvate and NADPH in 96 well plates

| Strain | Host Strain | pCASCADE plasmid | Production Plasmid | Final Alanine Titer (g/L) | Final Alanine Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 49 | DLF_0042 | | pSMART-Ala1 | 2.62 | 0.069 |
| 50 | DLF_0043 | pCASCADE-udhA-gltA1 | pSMART-Ala2 | 0 | 0 |
| 51 | DLF_0041 | pCASCADE-udhA-gltA1 | pSMART-Ala2 | 0.23 | 0.075 |
| 52 | DLF_0041 | | pSMART-Ala1 | 0.71 | 0.256 |
| 53 | DLF_0049 | pCASCADE-udhA-gltA2 | pSMART-Ala2 | 1.26 | 0.737 |
| 54 | DLF_0025 | | pSMART-Ala1 | 1.39 | 0.338 |
| 55 | DLF_0049 | | pSMART-Ala1 | 1.48 | 0.136 |
| 56 | DLF_0031 | | pSMART-Ala1 | 1.62 | 0.245 |
| 57 | DLF_0042 | pCASCADE-udhA | pSMART-Ala2 | 1.63 | 0.190 |
| 58 | DLF_0043 | | pSMART-Ala1 | 1.64 | 0.104 |
| 59 | DLF_0043 | pCASCADE-gltA2 | pSMART-Ala2 | 1.72 | 0.355 |
| 60 | DLF_0049 | pCASCADE-udhA | pSMART-Ala2 | 2.42 | 0.105 |
| 61 | DLF_0045 | pCASCADE-udhA-gltA2 | pSMART-Ala2 | 2.44 | 0.125 |

TABLE 5-continued

Alanine Production from pyruvate and NADPH in 96 well plates

| Strain | Host Strain | pCASCADE plasmid | Production Plasmid | Final Alanine Titer (g/L) | Final Alanine Std Deviation |
|---|---|---|---|---|---|
| 62 | DLF_0049 | pCASCADE-gltA2 | pSMART-Ala2 | 2.74 | 0.551 |
| 63 | DLF_0041 | pCASCADE-gltA2 | pSMART-Ala2 | 3.32 | 1.501 |
| 64 | DLF_0045 | | pSMART-Ala1 | 3.65 | 0.441 |
| 65 | DLF_0043 | pCASCADE-udhA-gltA2 | pSMART-Ala2 | 4.03 | 0.202 |

Example 14: Production of Alanine in *E. coli*, from Pyruvate at mL Scale

Figure 10:
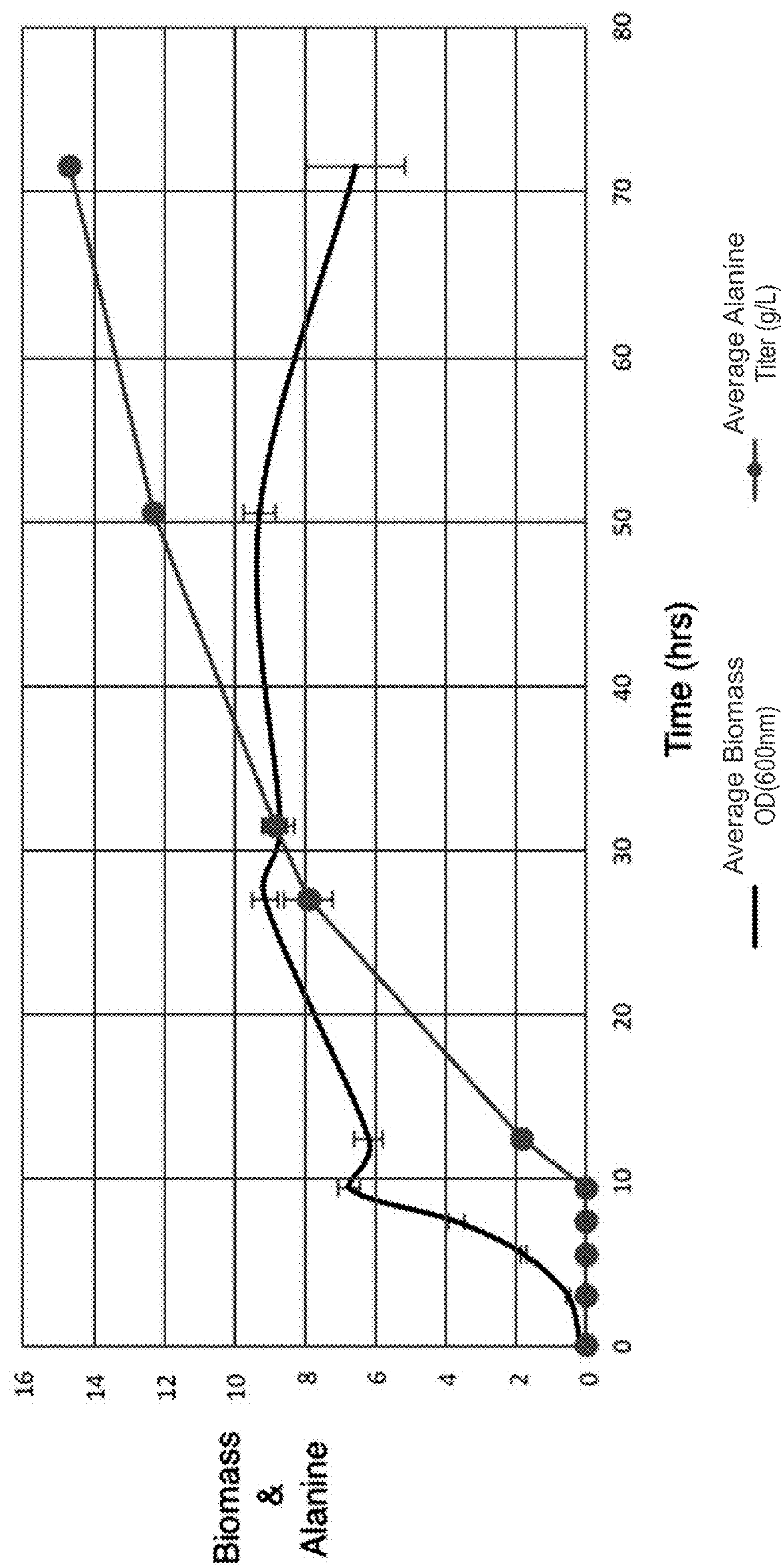
FIG. 10 depicts the production of alanine from pyruvate and NADPH at mL scale. Biomass and alanine titers are plotted as a function of time.

*E. coli* strain 49 from Example 13, was evaluated at mL scale using the standard evaluation protocol "Micro24 Protocol-1" as described in the Common Methods Section. Products levels were then measured using the analytical methods as described in the Common Methods Section. Biomass growth and alanine production are shown in FIG. 10.

Example 15: Production of Alanine in *E. coli*, from Pyruvate at L Scale

Figure 11:
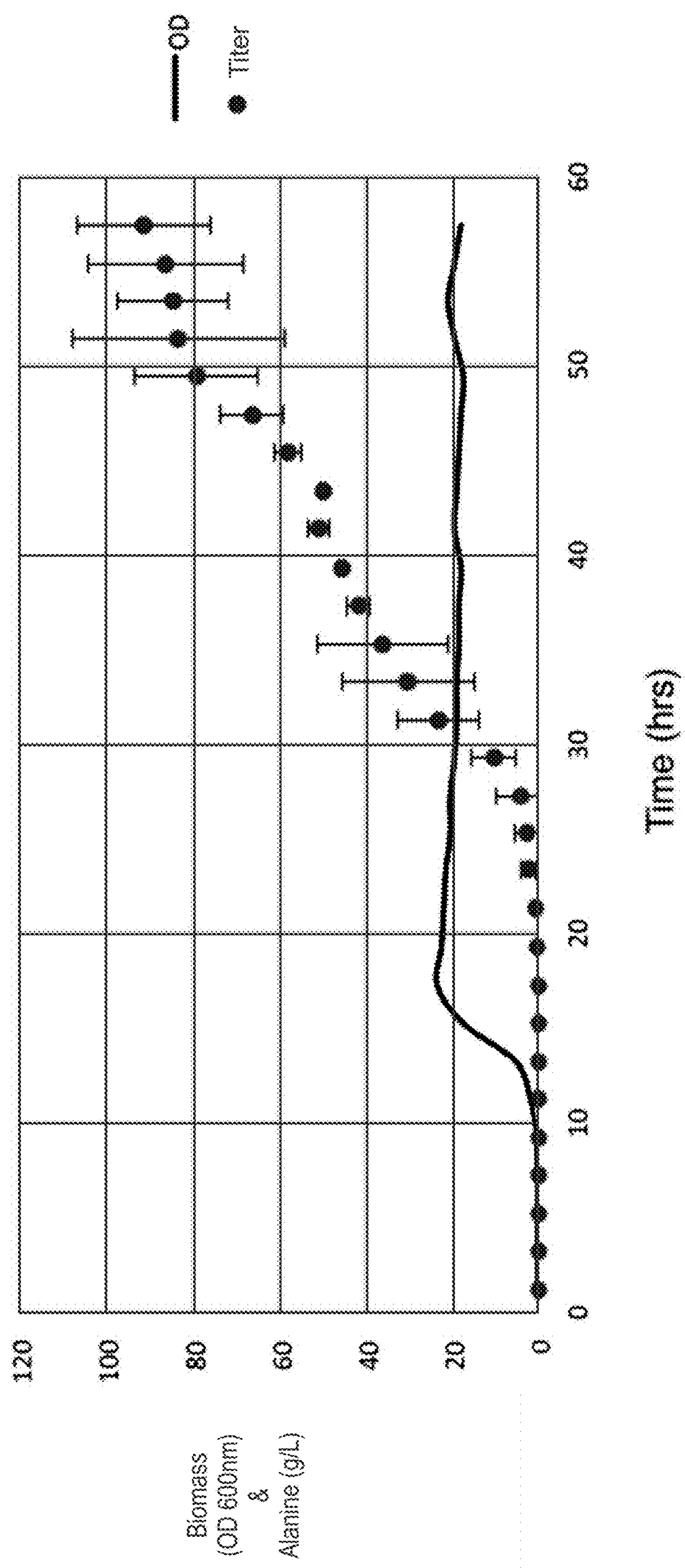
FIG. 11 depicts the production of alanine from pyruvate and NADPH at the L scale. Biomass and alanine titers are plotted as a function of time.

*E. coli* strain 60 from Example 13, was evaluated at 1 L scale using the standard evaluation protocol "1 L Fermentation Protocol-1" as described in the Common Methods Section. Products levels were then measured using the analytical methods as described in the Common Methods Section. Biomass growth and alanine production are shown in FIG. 11.

Figure 12:
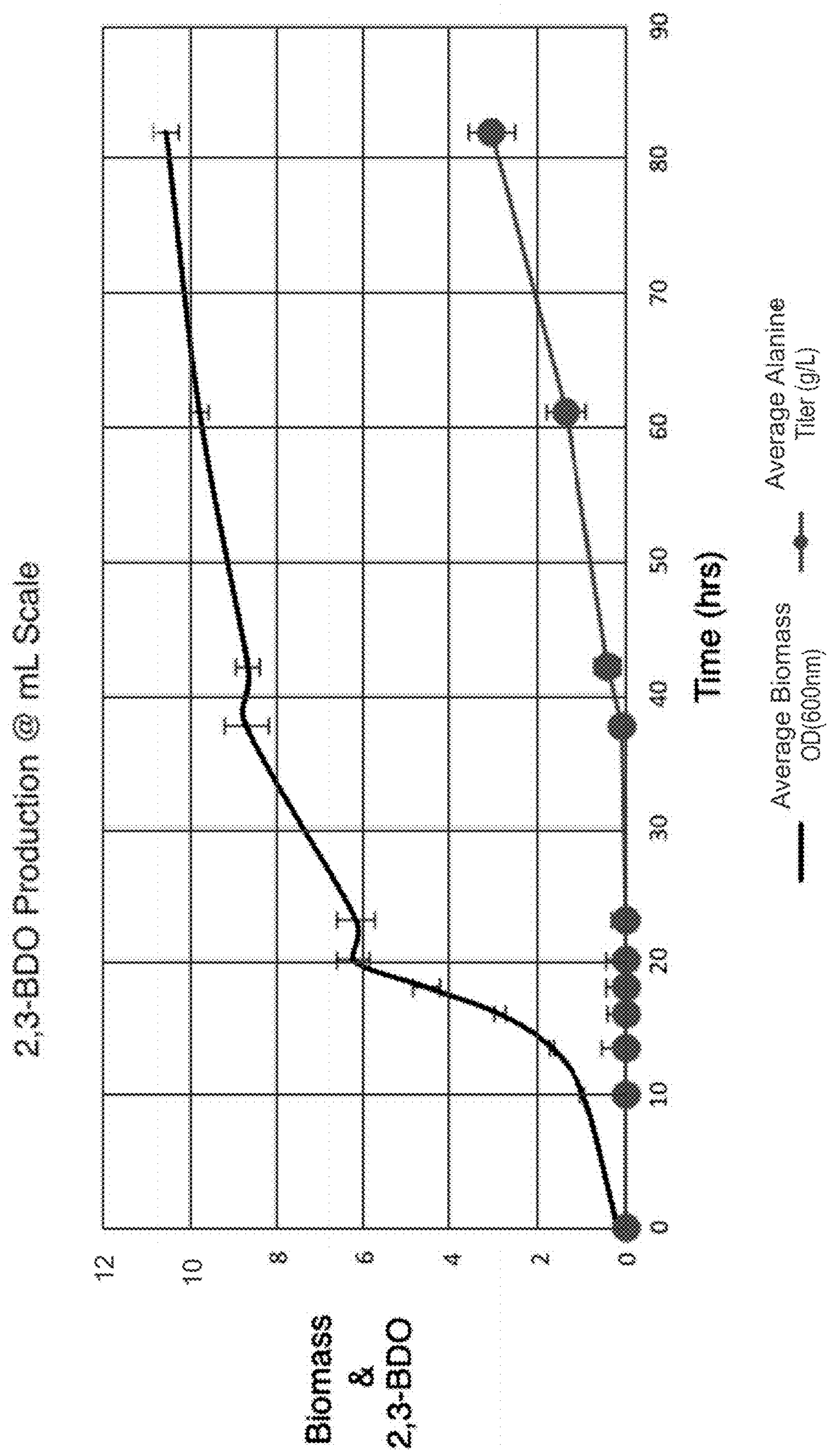
FIG. 12 depicts the production of 2,3-butanediol from pyruvate and NADH at mL scale. Biomass and 2,3-butanediol titers are plotted as a function of time.

Example 16: Production of 2,3-Butanediol in *E. coli*, from Pyruvate and NADH at mL Scale An *E. coli* strain was made by transforming host strain DLF_00165 with both plasmid pSMART-2,3-BDO1 and pCASCADE-zwf (Refer to Examples 4, 6 and 8). This strain was evaluated at mL scale using the standard evaluation protocol "Micro24 Protocol-1" as described in the Common Methods Section. Products levels were then measured using the analytical methods as described in the Common Methods Section. Biomass growth and alanine production are shown in FIG. 12.

Figure 13:
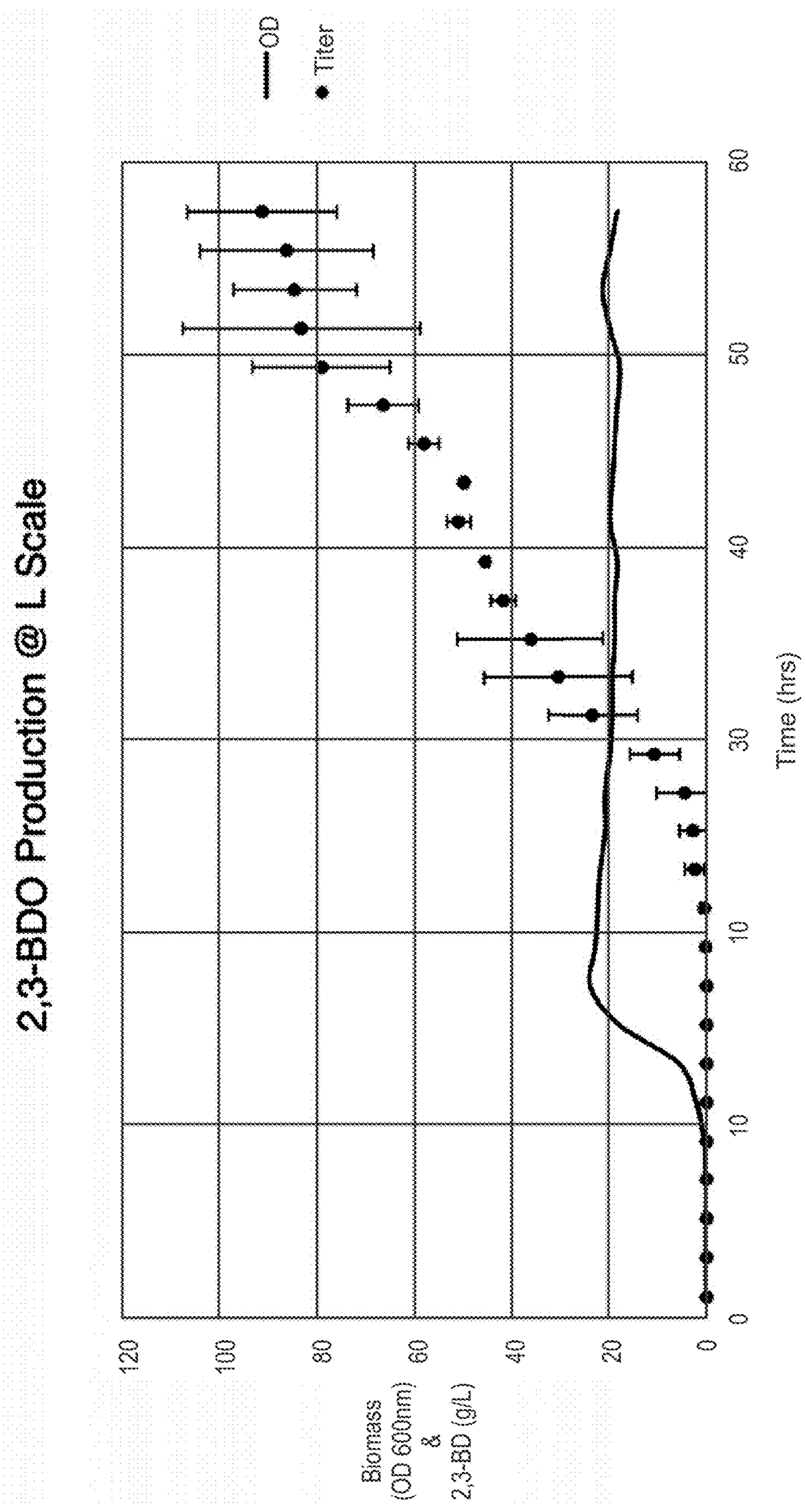
FIG. 13 depicts the production of 2,3-butanediol from pyruvate and NADH at L scale. Biomass and 2,3-butanediol titers are plotted as a function of time.

Example 17: Production of 2,3-Butanediol in *E. coli*, from Pyruvate and NADH at L Scale An *E. coli* strain was made by transforming host strain DLF_00165 with both plasmid pSMART-2,3-BDO1 and pCASCADE-zwf (Refer to Examples 4, 6 and 8). This strain was evaluated at 1 L scale using the standard evaluation protocol "1 L Fermentation Protocol-1" as described in the Common Methods Section. Products levels were then measured using the analytical methods as described in the Common Methods Section. Biomass growth and alanine production are shown in FIG. 13.

Figure 14:
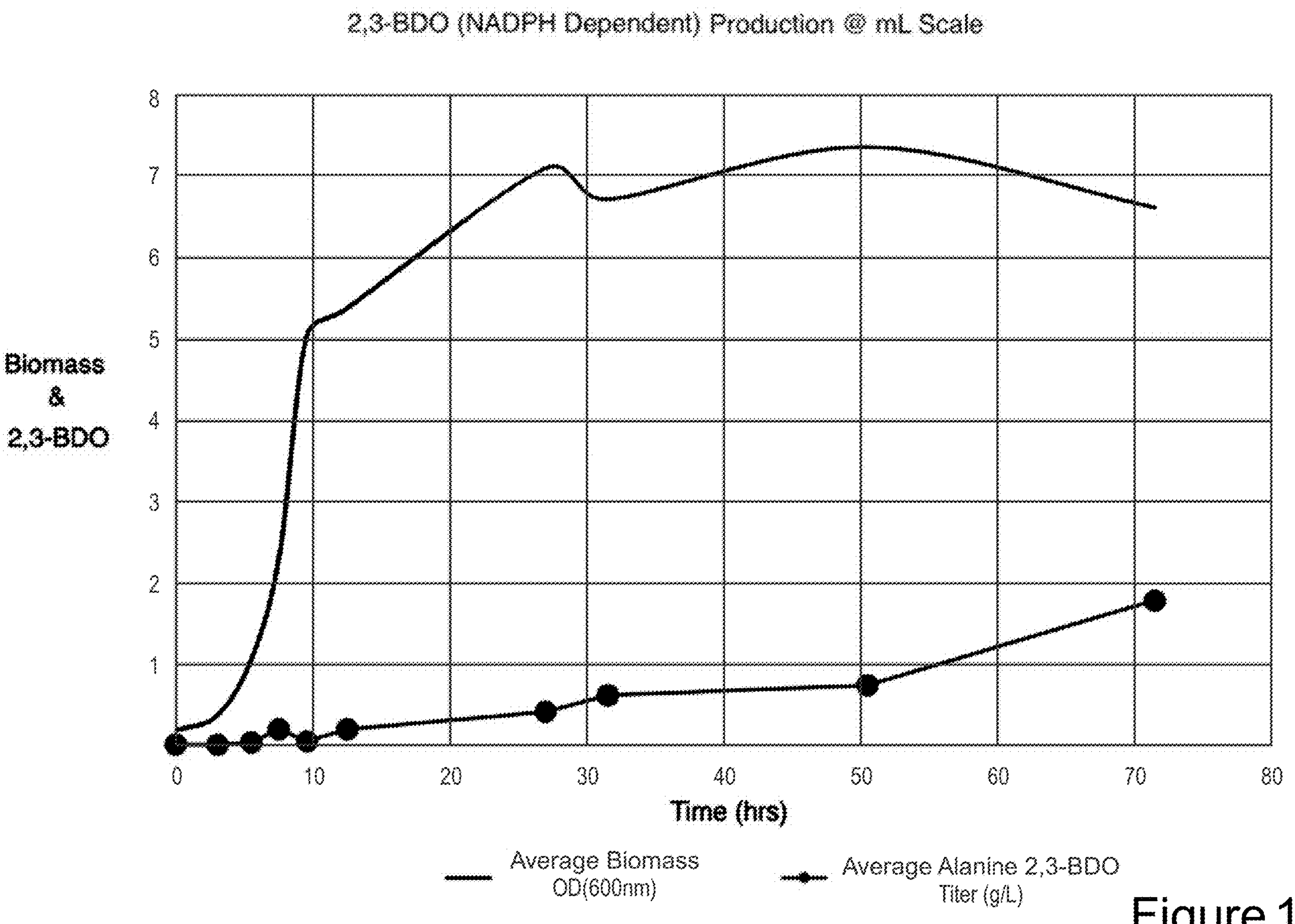
FIG. 14 depicts the production of 2,3-butanediol from pyruvate and NADPH at mL scale. Biomass and 2,3-butanediol titers are plotted as a function of time.

Example 18: Production of 2,3-Butanediol in *E. coli*, from Pyruvate and NADPH at mL Scale An *E. coli* strain was made by transforming host strain DLF_00049 with both plasmid pSMART-2,3-BDO2 and pCASCADE-udhA (Refer to Examples 4, 6 and 8). This strain was evaluated at mL scale using the standard evaluation protocol "Micro24 Protocol-1" as described in the Common Methods Section. Products levels were then measured using the analytical methods as described in the Common Methods Section. Biomass growth and alanine production are shown in FIG. 14.

Figure 15:
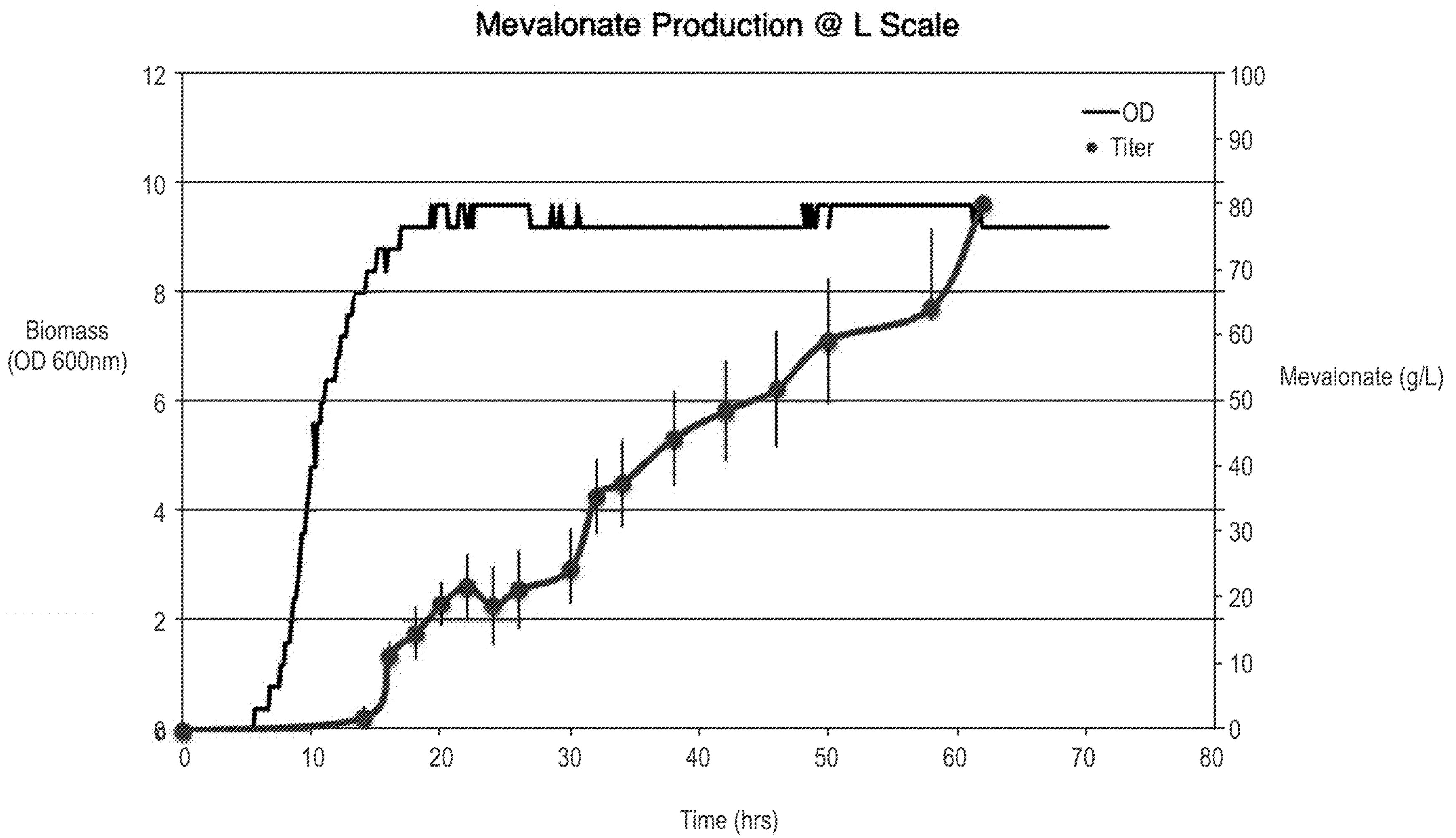
FIG. 15 depicts the production of mevalonic acid from acetyl-CoA and NADPH at L scale. Biomass and mevalonic acid titers are plotted as a function of time.

Example 19: Production of Mevalonic Acid in *E. coli*, from Acetyl-CoA and NADPH at L Scale An *E. coli* strain was made by transforming host strain DLF_0004 with plasmid pSMART-Mev1 (Refer to Examples 4 and 8). This strain was evaluated at 1 L scale using the standard evaluation protocol "1 L Fermentation Protocol-1" as described in the Common Methods Section. Products levels were then measured using the analytical methods as described in the Common Methods Section. Biomass growth and alanine production are shown in FIG. 15.

Common Methods Section

All methods in this Section are provided for incorporation into the Examples where so referenced.

Subsection I. Microorganism Species and Strains, Cultures, and Growth Media

Microbial species, that may be utilized as needed, are as follows:

*Acinetobacter calcoaceticus* (DSMZ #1139) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of there suspended *A. calcoaceticus* culture are made into BHI and are allowed to grow for aerobically for 48 hours at 37° C. at 250 rpm until saturated.

*Bacillus subtilis* is a gift from the Gill lab (University of Colorado at Boulder) and is obtained as an actively growing culture. Serial dilutions of the actively growing *B. subtilis* culture are made into Luria Broth (RPI Corp, Mt. Prospect, Ill., USA) and are allowed to grow for aerobically for 24 hours at 37° C. at 250 rpm until saturated.

*Chlorobium limicola* (DSMZ #245) is obtained from the German Collection of Microorganisms and Cell Cultures (Braunschweig, Germany) as a vacuum dried culture. Cultures are then resuspended using Pfennig's Medium I and II (#28 and 29) as described per DSMZ instructions. *C. limicola* is grown at 25° C. under constant vortexing.

*Citrobacter braakii* (DSMZ #30040) is obtained from the German Collection of Microorganisms and Cell Cultures (Braunschweig, Germany) as a vacuum dried culture. Cultures are then resuspended in Brain Heart Infusion(BHI) Broth (RPI Corp, Mt. Prospect, Ill., USA). Serial dilutions of the resuspended *C. braakii* culture are made into BHI and are allowed to grow for aerobically for 48 hours at 30° C. at 250 rpm until saturated.

*Clostridium acetobutylicum* (DSMZ #792) is obtained from the German Collection of Microorganisms and Cell Cultures (Braunschweig, Germany) as a vacuum dried culture. Cultures are then resuspended in *Clostridium acetobutylicum* medium (#411) as described per DSMZ instructions. *C. acetobutylicum* is grown anaerobically at 37° C. at 250 rpm until saturated.

*Clostridium aminobutyricum* (DSMZ #2634) is obtained from the German Collection of Microorganisms and Cell Cultures (Braunschweig, Germany) as a vacuum dried culture. Cultures are then resuspended in *Clostridium aminobutyricum* medium (#286) as described per DSMZ instructions. *C. aminobutyricum* is grown anaerobically at 37° C. at 250 rpm until saturated.

*Clostridium kluyveri* (DSMZ #555) is obtained from the German Collection of Microorganisms and Cell Cultures (Braunschweig, Germany) as an actively growing culture. Serial dilutions of *C. kluyveri* culture are made into *Clostridium kluyveri* medium (#286) as described per DSMZ instructions. *C. kluyveri* is grown anaerobically at 37° C. at 250 rpm until saturated.

*Cornyebacterium glutamicum* (DSMZ #1412) is obtained from the German Collection of Microorganisms and Cell Cultures (Braunschweig, Germany) as an actively growing culture. Serial dilutions of *C. glutamicum* culture are made into *C. glutamicum* medium (#1) as described per DSMZ instructions. *C. glutamicum* is grown aerobically or anaerobically at 37° C. at 250 rpm until saturated.

*Cupriavidus metallidurans* (DMSZ #2839) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. metallidurans* culture are made into BHI and are allowed to grow for aerobically for 48 hours at 30° C. at 250 rpm until saturated.

*Cupriavidus necator* (DSMZ #428) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. necator* culture are made into BHI and are allowed to grow for aerobically for 48 hours at 30° C. at 250 rpm until saturated. As noted elsewhere, previous names for this species are *Alcaligenes eutrophus* and *Ralstonia eutrophus*.

*Desulfovibrio fructosovorans* (DSMZ #3604) is obtained from the German Collection of Microorganisms and Cell Cultures (Braunschweig, Germany) as a vacuum dried culture. Cultures are then resuspended in *Desulfovibrio fructosovorans* medium (#63) as described per DSMZ instructions. *D. fructosovorans* is grown anaerobically at 37° C. at 250 rpm until saturated.

*Escherichia coli* strain BW25113 is obtained from the Yale Genetic Stock Center (New Haven, Conn. 06520) and is obtained as an actively growing culture. Serial dilutions of the actively growing *E. coli* K12 culture are made into Luria Broth (RPI Corp, Mt. Prospect, Ill., USA) and are allowed to grow for aerobically for 24 hours at 37° C. at 250 rpm until saturated.

*Escherichia coli* strain BWapldf is a generous gift from George Chen from Tsinghua University in China. Serial dilutions of the actively growing *E. coli* BWapldf is culture are made into Luria Broth (RPI Corp, Mt. Prospect, Ill., USA) and are allowed to grow for aerobically for 24 hours at 37° C. at 250 rpm until saturated.

*Halobacterium salinarum* (DSMZ #1576) is obtained from the German Collection of Microorganisms and Cell Cultures (Braunschweig, Germany) as a vacuum dried culture. Cultures are then resuspended in *Halobacterium* medium (#97) as described per DSMZ instructions. *H. salinarum* is grown aerobically at 37° C. at 250 rpm until saturated.

*Lactobacillus delbrueckii* (#4335) is obtained from WYEAST USA (Odell, Oreg., USA) as an actively growing culture. Serial dilutions of the actively growing *L. delbrueckii* culture are made into Brain Heart Infusion (BHI)

broth (RPI Corp, Mt. Prospect, Ill., USA) and are allowed to grow for aerobically for 24 hours at 30° C. at 250 rpm until saturated.

*Metallosphaera sedula* (DSMZ #5348) is obtained from the German Collection of Microorganisms and Cell Cultures (Braunschweig, Germany) as an actively growing culture. Serial dilutions of *M. sedula* culture are made into *Metallosphaera* medium (#485) as described per DSMZ instructions. *M. sedula* is grown aerobically at 65° C. at 250 rpm until saturated.

*Methylococcus capsulatus* Bath (ATCC #33009) is obtained from the American Type Culture Collection (ATCC) (Manassas, Va. 20108 USA) as a vacuum dried culture. Cultures are then resuspended in ATCC® Medium 1306: Nitrate mineral salts medium (NMS) under a 50% air 50% methane atmosphere (ATCC, Manassas, Va. 20108 USA) and are allowed to grow at 45° C.

*Methylococcus thermophilus* IMV 2 Yu T is obtained. Cultures are then resuspended in ATCC® Medium 1306: Nitrate mineral salts medium (NMS) under a 50% air 50% methane atmosphere (ATCC, Manassas, Va. 20108 USA) and are allowed to grow at 50° C.

*Methylosinus tsporium* (ATCC #35069) is obtained from the American Type Culture Collection (ATCC) (Manassas, Va. 20108 USA) as a vacuum dried culture. Cultures are then resuspended in ATCC® Medium 1306: Nitrate mineral salts medium (NMS) under a 50% air 50% methane atmosphere (ATCC, Manassas, Va. 20108 USA) and are allowed to grow at 30° C.

*Pichia pastoris* (*Komagataella pastoris*) (DSMZ #70382) is obtained from the German Collection of Microorganisms and Cell Cultures (Braunschweig, Germany) as a vacuum dried culture. Cultures are then resuspended in YPD-medium (#393) as described per DSMZ instructions. *Pichia pastoris* is grown aerobically at 30° C. at 250 rpm until saturated.

*Propionibacterium freudenreichii* subsp. *shermanii* (DSMZ #4902) is obtained from the German Collection of Microorganisms and Cell Cultures (Braunschweig, Germany) as a vacuum dried culture. Cultures are then resuspended in PYG-medium (#104) as described per DSMZ instructions. *P. freudenreichii* subsp. *shermanii* is grown anaerobically at 30° C. at 250 rpm until saturated.

*Pseudomonas putida* is a gift from the Gill lab (University of Colorado at Boulder) and is obtained as an actively growing culture. Serial dilutions of the actively growing *P. putida* culture are made into Luria Broth (RPI Corp, Mt. Prospect, Ill., USA) and are allowed to grow for aerobically for 24 hours at 37° C. at 250 rpm until saturated.

*Saccharomyces cerevisiae* strains can be obtained from the American Type Culture Collection (ATCC) (Manassas, Va. 20108 USA) as a vacuum dried culture. Cultures are then resuspended in YPD Media and allowed to grow at 30° C.

*Streptococcus mutans* (DSMZ #6178) is obtained from the German Collection of Microorganisms and Cell Cultures (Braunschweig, Germany) as a vacuum dried culture. Cultures are then resuspended in Luria Broth (RPI Corp, Mt. Prospect, Ill., USA). *S. mutans* is grown aerobically at 37° C. at 250 rpm until saturated.

*Yarrowia lipolytica* (DSMZ #1345) is obtained from the German Collection of Microorganisms and Cell Cultures (Braunschweig, Germany) as a vacuum dried culture. Cultures are then resuspended in YPD-medium (#393) as described per DSMZ instructions *Yarrowia lipolytica* is grown aerobically at 37° C. at 250 rpm until saturated.

Subsection II. Molecular Biology Techniques—DNA Cloning

In addition to the above or below specific examples, this example is meant to describe a non-limiting approach to genetic modification of a selected microorganism to introduce, remove or alter a nucleic acid sequence of interest. Alternatives and variations are provided within this general example. The methods of this example are conducted to achieve a combination of desired genetic modifications in a selected microorganism species, such as a combination of genetic modifications as described in sections herein, and their functional equivalents, such as in other bacterial and other microorganism species.

A gene or other nucleic acid sequence segment of interest is identified in a particular species (such as *E. coli* as described herein) and a nucleic acid sequence comprising that gene or segment is obtained.

Based on the nucleic acid sequences at the ends of or adjacent the ends of the segment of interest, 5' and 3' nucleic acid primers are prepared. Each primer is designed to have a sufficient overlap section that hybridizes with such ends or adjacent regions. Such primers may include enzyme recognition sites for restriction digest of transposase insertion that could be used for subsequent vector incorporation or genomic insertion. These sites are typically designed to be outward of the hybridizing overlap sections. Numerous contract services are known that prepare primer sequences to order (e.g., Integrated DNA Technologies, Coralville, Iowa USA).

Once primers are designed and prepared, polymerase chain reaction (PCR) is conducted to specifically amplify the desired segment of interest. This method results in multiple copies of the region of interest separated from the microorganism's genome. The microorganism's DNA, the primers, and a thermophilic polymerase are combined in a buffer solution with potassium and divalent cations (e.g., Mg or Mn) and with sufficient quantities of deoxynucleoside triphosphate molecules. This mixture is exposed to a standard regimen of temperature increases and decreases. However, temperatures, components, concentrations, and cycle times may vary according to the reaction according to length of the sequence to be copied, annealing temperature approximations and other factors known or readily learned through routine experimentation by one skilled in the art.

In an alternative embodiment the segment of interest may be synthesized, such as by a commercial vendor, and prepared via PCR, rather than obtaining from a microorganism or other natural source of DNA.

The nucleic acid sequences then are purified and separated, such as on an agarose gel via electrophoresis. Optionally, once the region is purified it can be validated by standard DNA sequencing methodology and may be introduced into a vector. Any of a number of vectors may be used, which generally comprise markers known to those skilled in the art, and standard methodologies are routinely employed for such introduction. Commonly used vector systems are well known in the art. Similarly, the vector then is introduced into any of a number of host cells. Commonly used host cells are *E. coli* strains. Some of these vectors possess promoters, such as inducible promoters, adjacent the region into which the sequence of interest is inserted (such as into a multiple cloning site). The culturing of such plasmid-laden cells permits plasmid replication and thus replication of the segment of interest, which often corresponds to expression of the segment of interest.

Various vector systems comprise a selectable marker, such as an expressible gene encoding a protein needed for growth or survival under defined conditions. Common selectable markers contained on backbone vector sequences include genes that encode for one or more proteins required for antibiotic resistance as well as genes required to complement auxotrophic deficiencies or supply critical nutrients not present or available in a particular culture media. Vectors also comprise a replication system suitable for a host cell of interest.

The plasmids containing the segment of interest can then be isolated by routine methods and are available for introduction into other microorganism host cells of interest. Various methods of introduction are known in the art and can include vector introduction or genomic integration. In various alternative embodiments the DNA segment of interest may be separated from other plasmid DNA if the former will be introduced into a host cell of interest by means other than such plasmid.

While steps of the general prophetic example involve use of plasmids, other vectors known in the art may be used instead. These include cosmids, viruses (e.g., bacteriophage, animal viruses, plant viruses), and artificial chromosomes (e.g., yeast artificial chromosomes (YAC) and bacteria artificial chromosomes (BAC)).

Host cells into which the segment of interest is introduced may be evaluated for performance as to a particular enzymatic step, and/or tolerance or bio-production of a chemical compound of interest. Selections of better performing genetically modified host cells may be made, selecting for overall performance, tolerance, or production or accumulation of the chemical of interest.

It is noted that this procedure may incorporate a nucleic acid sequence for a single gene (or other nucleic acid sequence segment of interest), or multiple genes (under control of separate promoters or a single promoter), and the procedure may be repeated to create the desired heterologous nucleic acid sequences in expression vectors, which are then supplied to a selected microorganism so as to have, for example, a desired complement of enzymatic conversion step functionality for any of the herein-disclosed metabolic pathways. However, it is noted that although many approaches rely on expression via transcription of all or part of the sequence of interest, and then translation of the transcribed mRNA to yield a polypeptide such as an enzyme, certain sequences of interest may exert an effect by means other than such expression.

The specific laboratory methods used for these approaches are well-known in the art and may be found in various references known to those skilled in the art, such as Sambrook and Russell, Molecular Cloning: A Laboratory Manual, Third Edition 2001 (volumes 1-3), Cold Spring Harbor Laboratory Press, Cold Spring Harbor, N.Y. (hereinafter, Sambrook and Russell, 2001).

As an alternative to the above, other genetic modifications may also be practiced, such as a deletion of a nucleic acid sequence of the host cell's genome. One non-limiting method to achieve this is by use of Red/ET recombination, known to those of ordinary skill in the art and described in U.S. Pat. Nos. 6,355,412 and 6,509,156, issued to Stewart et al. and incorporated by reference herein for its teachings of this method. Material and kits for such method are available from Gene Bridges (Gene Bridges GmbH, Dresden, Germany), and the method may proceed by following the manufacturer's instructions. Targeted deletion of genomic DNA may be practiced to alter a host cell's metabolism so as to reduce or eliminate production of undesired metabolic products. This may be used in combination with other genetic modifications such as described herein in this general example.

In addition to the above, longer purified double stranded DNA fragments can now be specified and ordered from a variety of vendors. These DNA pieces can easily be assembled together into plasmid vectors as well as longer synthetic DNA constructs using Gibson Assembly methodologies as taught by Gibson, D. G., et al. "Enzymatic assembly of DNA molecules up to several hundred kilobases" Nature Methods. May 2009. Vol(6) p. 343-345. doi:10.1038.

In addition to the above, once synthetic genetic parts such as open reading frames, promoters and terminators have been synthesized, it is well known in the art, that these parts can easily be shuffled into numerous different combinations using numerous variant assembly technologies, such as Golden Gate Assembly taught by Engler, C., Kandzia, R., and Marillonnet, S., "A one pot, one step, precision cloning method with high throughput capability". PLoS ONE 2008; 3(11):e3647. doi: 10.1371.

Subsection III. Molecular Biology Techniques—Chromosomal Modifications in *E. coli*

Chromosomal modifications can be made to *E. coli* using one of many methods including phage transduction and recombineering. It is appreciated that one skilled in the art is well versed in these methods. Of particular use are scarless recombineering methods, which allow for the precise deletion or addition of sequences to the chromosome without any unneeded sequences remaining such as that taught by Li, X., et al. "Positive and negative selection using the tetA-sacB cassette: recombineering and P1 transduction in *Escherichia* coli". Nucleic Acids Res. December 2013. 41(22) doi: 10.1093.

Subsection IV. Molecular Biology Techniques—Chromosomal Modifications in *Saccharomyces cerevisiae*.

Chromosomal modifications can be made to many yeast strains including *Saccharomyces cerevisiae*. using methods well known in the art for homologous recombination. It is appreciated that one skilled in the art is well versed in these methods.

Subsection V: Media for *E. coli*

GM25 media: GM25 minimal growth media for *E. coli* contained per liter: 736 mL sterile distilled, deionized water, 2.0 mL of 100× Trace Metals Stock, 100 mL of 10×GM phosphate salts, 2.0 mL of 2M $MgSO_4$, 50 mL of 500 g/L glucose, 100 mL of 1 M MOPS buffer, pH 7.4, and 10.0 mL of 100 g/L Yeast Extract. The 100× Trace Metal Stock was prepared in 1.0 L of distilled, deionized water with 10.0 mL of concentrated HCl with 5.0 g $CaCl_2$*$2H_2O$, 1.00 g $FeCl_3$*$6H_2O$, 0.05 g $CoCl_2$*$6H_2O$, 0.3 g $CuCl_2$*$2H_2O$, 0.02 g $ZnCl_2$, 0.02 g $Na_2MoO_4$*$2H_2O$, 0.01 g $H_3BO_3$, and 0.04 g $MnCl_2$*$4H_2O$ and 0.2 μm sterile-filtered. The 10×GM Phosphate Salts were prepared in 1.0 L of distilled, deionized water with 3 g $K_2HPO_4$, 2 g $KH_2PO_4$, 30 g $(NH_4)_2SO_4$, and 1.5 g Citric Acid (anhydrous) and autoclaved. The 2M $MgSO_4$ was prepared in 1.0 L of distilled, deionized water with 240.0 g of anhydrous $MgSO_4$ and 0.2 μm sterile-filtered. The 500 g/L Glucose solution was prepared in 1.0 L of heated distilled, deionized water and 500 g of anhydrous dextrose and 0.2 μm sterile-filtered. The 1 M 4-Morpholinopropanesulfonic acid (MOPS) buffer was prepared in 700.0 mL of distilled, deionized water with 210.0 g MOPS and 30.0 mL 50% KOH solution. The pH was measured with stirring and final adjustments made to pH 7.4 by slowly adding 50% KOH and Q.S. to a final volume of 1.0 L. The final pH 7.4 solution was 0.2 μm sterile-filtered. PM25 media: PM25 minimal production media for *E. coli* contained per liter: 636 mL sterile distilled, deionized water, 2.0 mL of 100× Trace Metals Stock, 100 mL of 10×PM phosphate-free salts, 2.0 mL of 2M $MgSO_4$, 50 mL of 500 g/L glucose, 200 mL of 1 M MOPS buffer, pH 7.4, and 10 mL of 1 mg/mL Thiamine. The 100× Trace Metal Stock was prepared in 1.0 L of distilled, deionized water with 10.0 mL of concentrated HCl with 5.0 g $CaCl_2$*$2H_2O$, 1.00 g $FeCl_3$*$6H_2O$, 0.05 g $CoCl_2$*$6H_2O$, 0.3 g $CuCl_2$*$2H_2O$, 0.02 g $ZnCl_2$, 0.02 g $Na_2MoO_4$*$2H_2O$, 0.01 g $H_3BO_3$, and 0.04 g $MnCl_2$*$4H_2O$ and 0.2 μm sterile-filtered. The 10×PM Phosphate-Free Salts were prepared in 1.0 L of distilled, deionized water with 30 g $(NH_4)_2SO_4$ and 1.5 g Citric Acid (anhydrous) and autoclaved. The 2M $MgSO_4$ was prepared in 1.0 L of distilled, deionized water with 240.0 g of anhydrous $MgSO_4$ and 0.2 μm sterile-filtered. The 500 g/L Glucose solution was prepared in 1.0 L of heated distilled, deionized water and 500 g of anhydrous dextrose and 0.2 μm sterile-filtered. The 1 M 4-Morpholinopropanesulfonic acid (MOPS) buffer was prepared in 700.0 mL of distilled, deionized water with 210.0 g MOPS and 30.0 mL 50% KOH solution. The pH was measured with stirring and final adjustments made to pH 7.4 by slowly adding 50% KOH and Q.S. to a final volume of 1.0 L. The final pH 7.4 solution was 0.2 μm sterile-filtered.

SM3 Media: SM3 minimal media for *E. coli* contained per liter: 596.2 mL sterile distilled, deionized water, 2.0 mL of 100× Trace Metals Stock, 100 mL of 10× Ammonium Citrate 30 Salts, 3.6 mL of Phosphate Buffer, pH=6.8, 2 mL of 40 mM Fe(II) sulfate, 1.0 mL of 2M $MgSO_4$, 5.0 mL of 10 mM $CaSO_4$, 90 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. Prepare a 1 M Potassium 3-(N-morpholino)propanesulfonic Acid (MOPS) and adjust to pH 7.4 with KOH (~40 mL). Filter sterilize (0.2 um) and store at room temperature in the dark. Prepare a 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4$*$7H_2O$, 5.0 g $CuSO_4$*$5H_2O$, 0.6 g $ZnSO_4$*$7H_2O$, 0.2 g $Na_2MoO_4$*$2H_2O$, 0.1 g $H_3BO_3$, and 0.3 g $MnSO_4$*$H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

SM10 Media: SM10 minimal media for *E. coli* contained per liter: 574.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM $CaSO_4$, 90 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Prepare a 1 M Potassium 3-(N-morpholino) propanesulfonic Acid (MOPS) and adjust to pH 7.4 with KOH (~40 mL). Filter sterilize (0.2 um) and store at room temperature in the dark. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4$*$7H_2O$, 5.0 g $CuSO_4$*$5H_2O$, 0.6 g $ZnSO_4$*$7H_2O$, 0.2 g $Na_2MoO_4$*$2H_2O$, 0.1 g $H_3BO_3$, and 0.3 g $MnSO_4$*$H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

SM10++ Media: SM10 minimal media for *E. coli* contained per liter: 549.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM $CaSO_4$, 90 mL of 500 g/L glucose, 200 mL of 1 M MOPS buffer, pH 7.4, and 0.2 mL of 1 mg/mL Thiamine and 25.0 mL of 100 g/L Yeast Extract and 25.0 mL of 100 g/L Casamino acids. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare a 1 M Potassium 3-(N-morpholino) propanesulfonic Acid (MOPS) and adjust to pH 7.4 with KOH (~40 mL). Filter sterilize (0.2 um) and store at room temperature in the dark. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4$*$7H_2O$, 5.0 g $CuSO_4$*$5H_2O$, 0.6 g $ZnSO_4$*$7H_2O$, 0.2 g $Na_2MoO_4$*$2H_2O$, 0.1 g $H_3BO_3$, and 0.3 g $MnSO_4$*$H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

FGM3 Media: FGM3 media for *E. coli* contained per liter: 636.2 mL sterile distilled, deionized water, 2.0 mL of 100× Trace Metals Stock, 100 mL of 10× Ammonium Citrate 20 Salts, 3.6 mL of Phosphate Buffer, pH=6.8, 2 mL of 40 mM Fe(II) sulfate, 1.0 mL of 2M $MgSO_4$, 5.0 mL of 10 mM 2M $CaSO_4$, 50 mL of 500 g/L glucose, 200 mL of 1 M MOPS buffer, pH 7.4, and 0.2 mL of 1 mg/mL Thiamine. Prepare 1 liter of 10× concentrated Ammonium-Citrate 20 salts by mixing 20 g of $(NH_4)_2SO_4$ and 1.5 g Citric Acid in water with stirring. Autoclave and store at room temperature. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4$*$7H_2O$, 5.0 g $CuSO_4$*$5H_2O$, 0.6 g $ZnSO_4$*$7H_2O$, 0.2 g $Na_2MoO_4$*$2H_2O$, 0.1 g $H_3BO_3$, and 0.3 g $MnSO_4$*$H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

FGM10 Media: FGM10 media for *E. coli* contained per liter: 824.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM 2M $CaSO_4$, 50 mL of 500 g/L glucose, and 0.2 mL of 1 mg/mL Thiamine. Prepare 1 liter of 10× concentrated Ammonium-Citrate 90 salts by mixing 90 g of $(NH_4)_2SO_4$ and 2.5 g Citric Acid Autoclave and store at room temperature. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4$*$7H_2O$, 5.0 g $CuSO_4$*$5H_2O$, 0.6 g $ZnSO_4$*$7H_2O$, 0.2 g $Na_2MoO_4$*$2H_2O$, 0.1 g $H_3BO_3$, and 0.3 g $MnSO_4$*$H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

96WPM Media: 96WPM media for *E. coli* contained per liter: 638.8 mL sterile distilled, deionized water, 2.0 mL of 100× Trace Metals Stock, 100 mL of 10× Ammonium Citrate 30 Salts, 2 mL of 40 mM Fe(II) sulfate, 2.0 mL of 2M $MgSO_4$, 5.0 mL of 10 mM 2M $CaSO_4$, 50 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. Prepare a 1 M Potassium 3-(N-morpholino)propanesulfonic Acid (MOPS) and adjust to pH 7.4 with KOH (~40 mL). Filter sterilize (0.2 um) and store at room temperature in the dark. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4$*$7H_2O$, 5.0 g $CuSO_4$*$5H_2O$, 0.6 g $ZnSO_4$*$7H_2O$, 0.2 g $Na_2MoO_4$*$2H_2O$, 0.1 g $H_3BO_3$, and 0.3 g $MnSO_4$*$H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

Antibiotic concentrations: Unless other wise stated standard final concentrations of antibiotic in media are kanamycin (35 ug/mL), ampicillin (100 ug/ml), spectinomycin (100 ug/ml), chloramphenicol (20 ug/ml), anhydrotetracycline (50 ng/ml), gentamicin (10 ug/ml), zeocin (50 ug/ml), blasticidin (50 ug/ml). Low salt medium such as low salt LB medium is used when using blasticidin or zeocin as selective antibiotics.

Subsection VI: Protocols for Production in *E. coli*

Shake Flask Protocol-1

Bioproduction is demonstrated at a 50-mL scale using GM25 minimal defined media without phosphate. Cultures are started from single colonies by standard practice into 50 mL of GM25 media containing 3.2 mM phosphate plus appropriate antibiotics and grown to stationary phase overnight at 30° C. with rotation at 200 rpm. The optical density ($OD_{600}$, 1 cm pathlength) of each stationary phase culture is measured and the entire culture is transferred to 50 mL conical tubes and centrifuged at 4,000 rpm for 15 minutes. A 20 optical density resuspension is generated for each culture by calculating the volume of GM25 media to add to the pellet. Two and a half mL of this resuspension is added to 50 mL of PM25 media plus appropriate antibiotic in triplicate 250-ml non-baffled flasks and incubated at 30° C., 200 rpm. To monitor cell growth and production by these cultures, samples (2 ml) are withdrawn at designated time points for optical density measurements at 600 nm ($OD_{600}$, 1 cm pathlength). Samples are centrifuged at 14,000 rpm for 5 minutes and the supernatant retained at −20° C. for analyte measurements. Cultures are shifted to production by changing the temperature of the shaking incubator to 37° C. at 4 hours post-inoculation. A sample is collected at this time point as well as 6-, 8-, and 24-hours post-inoculation for optical density and product measurement.

Shake Flask Protocol-2

Bioproduction is demonstrated at a 50-mL scale in GM25 minimal defined media without phosphate. Cultures are started from single colonies by standard practice into 50 mL of GM25 media containing 3.2 mM phosphate plus appropriate antibiotic(s) and grown to stationary phase overnight at 37° C. with rotation at 200 rpm. The optical density ($OD_{600}$, 1 cm pathlength) of each stationary phase culture is measured and the entire culture was transferred to 50 mL conical tubes and centrifuged at 4,000 rpm for 15 minutes. A 20 optical density resuspension is generated for each culture by calculating the volume of GM25 media to add to the pellet. Two and a half mL of this resuspension is added to 50 mL of PM25 media plus antibiotics in triplicate 250-ml non-baffled flasks and incubated at 37° C., 200 rpm. To monitor cell growth and production by these cultures, samples (2 ml) are withdrawn at designated time points for optical density measurements at 600 nm ($OD_{600}$, 1 cm pathlength). Samples are centrifuged at 14,000 rpm for 5 minutes and the supernatant retained at −20° C. for analyte measurements. Cultures are shifted to production by inducing the cultures using 50 ng/mL of anhydrotetracycline (aTc) at inoculation. A sample was collected at this time point as well as 4 and 20-hours post-inoculation for optical density and product measurement.

96 Well Plate Protocol-1

Bioproduction is demonstrated at μL in minimal medium. Colonies were used to inoculate individual wells in standard 96 well plates, filled with 150 μL of SM10++ medium with the appropriate antibiotics as needed. Plates were covered with sandwich covers (Model # CR1596 obtained from EnzyScreen, Haarlam, The Netherlands). These covers ensure minimal evaporative loss during incubation. To ensure adequate aeration, the inoculated 96 well plates and sandwich covers were clamped into place into a Mini Shaking Incubator (VWR Catalog #12620-942, VWR International LLC., Radnor, Pa., USA.) at a temperature set to 37 degrees Celsius and a shaking speed of 1100 rpm. The plate clamps used were obtained from Enzyscreen (Model # CR1600, EnzyScreen, Haarlam, The Netherlands). Importantly, the shaker used had an orbit of 0.125 inches or 3 mm. This combination of orbit and minimal shaking speed is required to obtain needed mass transfer coefficient and enable adequate culture oxygenation. Cultures were grown for 16 hours.

After 16 hours of growth, 10 μL samples were taken to measure the optical density at 600 nm (OD(600 nm)). This was done using a plate spectrophotometer. Overnight cell densities at this point often range from 5-15 OD(600 nm). Cells from 100 μL of overnight growth in each well were pelleted by centrifugation, excess media was removed and cells were resuspended in 150 μL of 96WPM, which contains no phosphate. Subsequently cells were once again pelleted and again excess media was removed. Using the overnight measured optical densities, enough fresh 96WPM was added to each well, so upon re-suspension a final OD(600 nm) of 20 was obtained. 7.5 μL of the normalized and washed cultures of OD(600 nm)=20, was used to inoculate 150 μL of fresh 96WPM, plus appropriate antibiotics, in wells of a new standard 96 well plate. Plates were covered with sandwich covers (Model # CR1596 obtained from Enzy Screen, Haarlam, The Netherlands) and clamped into place into a Mini Shaking Incubator (VWR Catalog #12620-942, VWR International LLC., Radnor, Pa., USA.) at a temperature set to 37 degrees Celsius and a shaking speed of 1100 rpm. The plate clamps used were obtained from Enzyscreen (Model # CR1600, EnzyScreen, Haarlam, The Netherlands). Cultures were incubated for 24 hours. After 16-24 hours of production, 100 μL samples from each well were pelleted by centrifugation and the supernatant collected for subsequent analytical analyes.

Micro24 Protocol-1

Bioproduction is demonstrated at mL scale in minimal medium. Seeds were prepared as follows. Colonies were used to inoculate 4 mL of SM10 medium, with appropriate antibiotics as needed, into a sterile 14 mL culture tube. Culture tubes were incubated overnight at 37 degrees Celsius in a standard floor model shaking incubator at 225 rpm. After overnight growth, 2.5 mL of these cultures were used to inoculate 50 mL of fresh SM10 medium, plus appropriate antibiotics as needed, in a 250 mL volume disposable and sterile rectangular cell culture flask, such as a Cellstar™ Cell Culture Flask (VWR Catalog #82050-856, VWR International LLC., Radnor, Pa., USA.). These seed cultures were incubated at 37 degrees Celsius in a standard floor model shaking incubator at 225 rpm. Samples were taken every few hours to measure the growth by optical density (OD(600 nm)), until they reached at an OD(600 nm) in the range of 4-10. At this point, cells were harvested by centrifugation, excess media removed and resuspended in fresh SM10 media to obtain a final OD(600 nm) of 10. 500 μL of washed and normalized cells was added to 500 μL of 30% sterile glycerol in water, mixed and frozen in cryovial (seed vials) at minus 80 degrees Celsius in a ultralow temperature freezer.

The Micro-24™ Microreactor system (Pall Corporation, Exton, Pa., USA) was used to evaluate strains at the mL scale. Pall 24-well PERC cassettes (Catalogue # MRT-PRC) were used for cell growth and production along with stainless steel check valve caps (Catalogue # MRT-CAP-E24). The experimental protocol was set up with an initial volume of 3 mL of FGM3 medium, with appropriate antibiotics as needed, and an agitation of 1000 rpm. pH control was initially turned off. The temperature was controlled at 37 degrees Celsius, with an environmental temperature of 35 degrees Celsius. Oxygen control was initially turned off with monitoring enabled. Frozen seed vials were thawed on ice and 150 μL was used to inoculate each 3 mL culture in each Micro24 cassette well. Samples were collected at inoculation and at regular intervals. Optical density of samples was measured at 600 nm, glucose using a YSI biochemistry analyzer was measured as described below. In addition, supernatants were collected for subsequent analytical analyses. pH control was turned on for each well at the point at which the culture's optical densities as measured at 600 nm was greater than 1.0. pH control was achieved with pressured ammonium hydroxide gas. In addition, oxygen control was turned on for each well when the dissolved oxygen reached below 60%. Glucose boluses of 10 g/L were added both 24 and 48 hours post inoculation using a sterile 500 g/L stock solution.

1 L Fermentation Protocol-1

Bioproduction is demonstrated at L scale in minimal medium. Seeds were prepared as follows. Colonies were used to inoculate 4 mL of SM10 medium, with appropriate antibiotics as needed, into a sterile 14 mL culture tube. Culture tubes were incubated overnight at 37 degrees Celsius in a standard floor model shaking incubator at 225 rpm. After overnight growth, 2.5 mL of these cultures were used to inoculate 50 mL of fresh SM10 medium, plus appropriate antibiotics as needed, in a 250 mL volume disposable and sterile rectangular cell culture flask, such as a Cellstar™ Cell Culture Flask (VWR Catalog #82050-856, VWR International LLC., Radnor, Pa., USA.). These seed cultures were incubated at 37 degrees Celsius in a standard floor model shaking incubator at 225 rpm. Samples were taken every few hours to measure the growth by optical density (OD(600 nm)), until they reached at an OD(600 nm) in the range of 4-10. At this point, cells were harvested by centrifugation, excess media removed and resuspended in fresh SM10 media to obtain a final OD(600 nm) of 10. 3.5 mL of washed and normalized cells was added to 3.5 mL of 30% sterile glycerol in water, mixed and frozen in cryovial (seed vials) at minus 80 degrees Celsius in a ultralow temperature freezer.

An Infors-HT Multifors (Laurel, Md., USA) parallel bioreactor system was used to perform 1 L fermentations, including three gas connection mass flow controllers configured for air, oxygen and nitrogen gases. Vessels used had a total volume of 1400 mL and a working volume of up to 1 L. Online pH and $pO_2$ monitoring and control were accomplished with Hamilton probes. Offgas analysis was accomplished with a multiplexed Blue-in-One BlueSens gas analyzer (BlueSens. Northbrook, Ill., USA). Culture densities were continually monitored using Optek 225 mm OD probes, (Optek, Germantown, Wis., USA). The system used was running IrisV6.0 command and control software and integrated with a Seg-flow automated sampling system (Flownamics, Rodeo, Calif. USA), including FISP cell free sampling probes, a Segmod 4800 and FlowFraction 96 well plate fraction collector.

Tanks were filled with 800 mL of FGM10 Medium, with enough phosphate to target a final *E. coli* biomass concentration close to 10 g dry cell weight per liter. Antibiotics were added as appropriate. Frozen seed vials were thawed on ice and 7 mL of seed culture was used to inoculate the tanks. After inoculation, tanks were controlled at 37 degrees Celsius and pH 6.8 using a 10M solution of sodium hydroxide solution as a titrant. The following oxygen control scheme was used to maintain a dissolved oxygen set point of 25%. First gas flow rate was increased from a minimum of 0.3 L/min of air to 0.8 L/min of air, subsequently, if more aeration was needed, agitation was increased from a minimum of 300 rpm to a maximum of 1000 rpm. Finally if more oxygen was required to achieve a 25% set point, oxygen supplementation was included using the integrated mass flow controllers. A constant concentrated sterile filtered glucose feed (500 g/L) was added to the tanks at a rate of 2 mL/hr, once agitation reached 800 rpm. Fermentation runs were extended for up to 70 hrs and samples automatically withdrawn every 2-4 hrs. Samples were saved for subsequent analytical analysis.

Subsection VII: Analytical Methods

Analytical Methods have been developed for all anticipated metabolites and products.

Quantification of Organic and Amino Acids

A reverse phase UPLC-MS/MS method was developed for the simultaneous quantification of organic and amino acids. Chromatographic separation was performed using an Acquity CSH $C_{18}$ column (100 mm×2.1 i.d., 1.7 μm; Waters Corp., Milford, Mass., USA) at 45 degrees C. The following eluents were used: solvent A: $H_2O$, 0.2% formic acid and 0.05% ammonium (v/v); solvent B: MeOH, 0.1% formic acid and 0.05% ammonium (v/v). The gradient elution was as follows: 0-0.2 min isocratic 5% B, 0.2-1.0 min linear from 5% to 90% B, 1.0-1.5 min isocratic 90% B, and 1.5-1.8 min linear from 90% to 5% B, with 1.8-3.0 min for initial conditions of 5% B for column equilibration. The flow rate remained constant at 0.4 ml/min. A 5 μl sample injection volume was used. UPLC method development was carried out using standard aqueous stock solutions of analytes. Separations were performed using an Acquity H-Class UPLC integrated with a Xevo™ TQD Mass spectrometer (Waters Corp., Milford, Mass. USA). MS/MS parameters including MRM transitions were tuned for each analyte and are listed in Table 6 below. Adipic acid at a concentration of 36 mg/L was used as an internal standard for normalization in all samples. Peak integration and further analysis was performed using Mass Lynx v4.1 software. The linear range for all metabolites was 2-50 mg/L. Samples were diluted as needed to be within the accurate linear range.

TABLE 6

MS/MS parameters

| Analyte | Retention Time (min) | ESI Mode | MRM Transition(s) | Cone Voltage | Collision Energy |
|---|---|---|---|---|---|
| 3-hydroxypropionic Acid | 1.04 | – | 88.94 → 59.09 | 22 | 8 |
| Alanine | 0.63 | + | 89.95 → 44.08 | 15 | 9 |
| α-ketoglutaric Acid | 1.97 | – | 144.80 → 56.90 | 13 | 11 |
| Citric Acid | 1.76 | – | 190.87 → 110.92 | 25 | 11 |
| Fumaric Acid | 1.91 | – | 114.72 → 70.94 | 21 | 7 |
| Glutamic Acid | 0.67 | – | 145.89 → 102.02 | 29 | 11 |
| Glyoxylic Acid | 0.83 | – | 72.84 → 44.98 | 33 | 7 |

TABLE 6-continued

MS/MS parameters

| Analyte | Retention Time (min) | ESI Mode | MRM Transition(s) | Cone Voltage | Collision Energy |
|---|---|---|---|---|---|
| Lactic Acid | 1.18 | – | 88.94 → 43.08 | 26 | 8 |
| Malic Acid | 1.06 | – | 132.80 → 70.98 | 27 | 13 |
| Malonic Acid | 1.45 | – | 102.85 → 59.09 | 15 | 9 |
| Mevalonic Acid | 1.85 | – | 146.91 → 59.03 | 23 | 11 |
| Pyruvic Acid | 1.81 | – | 87.00 → 43.05 | 20 | 7 |
| Succinic Acid | 1.72 | – | 116.74 → 72.96 | 25 | 11 |
| Itaconic Acid | 1.86 | + | 130.87 → 84.98 | 20 | 12 |
| Adipic Acid | 2.0 | + | 144.77 → 82.96 | 32 | 12 |

Quantification of 2,3 Butanediol Using Mass Spectrometry

A rapid UPLC-MS/MS method was developed for the quantification of 2,3 butanediol (2,3-BDO). Chromatographic separation was performed using an Acquity UPLC BEH $C_{18}$ column (50 mm×2.1 i.d., 1.7 μm; Waters Corp., Milford, Mass., USA) at 45 degrees C. Isopropanol with 0.1% formic acid and 0.05% ammonium (v/v) was used in an isocratic separation. A 5 μl sample injection volume was used. UPLC method development was carried out using standard aqueous stock solutions of analytes. Separations were performed using an Acquity H-Class UPLC integrated with a Xevo™ TQD Mass spectrometer (Waters Corp., Milford, Mass. USA). An MRM transition for 2,3-BDO of 90.972→55.074 was used along with a cone voltage of 16V and Collision Energy of 10V, operating in ESI+ mode. Adipic acid at a concentration of 36 mg/L was used as an internal standard for normalization in all samples. The Adipic acid was measured in ESI—mode with an MRM transition of 144.77-82.96, a cone voltage of 32V and collision energy of 12 V. Both 2,3-BDO and adipic acid eluted at 0.38 minutes. Peak integration and further analysis was performed using Mass Lynx v4.1 software.

Quantification of Diols using Refractive Index

A confirmatory HPLC method was developed for the quantification of 2,3 butanediol stereoisomers. Chromatographic separation was performed using a Biorad Aminex HPX-87H column (300×7.8 mm, 1.7 μm; Biorad, Hercules, Calif. USA). The isocratic separation was run at room temperature with 5 mM sulfuric acid as the mobile phase. The flow rate remained constant at 0.4 ml/min for 40 minutes after an injection. A 10 μl sample injection volume was used. Method development was carried out using standard aqueous stock solutions of analytes. Separations were performed using an Acquity H-Class UPLC integrated with an ESAT/IN refractive index (RI) detector. (Waters Corp., Milford, Mass. USA). Meso-2,3-butanediol eluted at 24.9 minutes, while (R,R)-2,3-butanediol eluted at 26.3 minutes. Peaks were integrated using Masslynx Software v4.1.

Quantification of Glucose

A YSI biochemistry analyzer, model 2950M (YSI Incorporated, Yellow Springs Ohio, USA) was used to routinely measure glucose concentrations as well as ethanol. The instrument was used according to manufacturer's instructions, using all reagents as supplied from YSI.

What is claimed:

1. A bioprocess for production of an isopreniod product from a genetically modified microorganism, the bioprocess comprising:

providing a genetically modified microorganism that may express a heterologous enzyme of an isoprenoid product production pathway and also comprises a synthetic metabolic valve, wherein the synthetic metabolic valve characterized by both: (i) controlled transcriptional gene silencing of a gene encoding a first enzyme, and (ii) controlled proteolysis of a second enzyme;

in a first stage, growing the genetically modified microorganism in a media; and in a second stage, reducing the genetically modified microorganism growth of the first stage and expressing the heterologous enzyme of the isoprenoid product production pathway, thereby producing the isoprenoid product, wherein, a transition from the first stage to the second stage is at least partially controlled by depletion of a level of a limiting nutrient from the media and, as the limiting nutrient is depleted from the media, growth of the genetically modified microorganism is stopped, and the transition comprising silencing the gene of the first enzyme and proteolysis the second enzyme, wherein at least one of the first enzymes is selected from the group consisting of: enoyl-ACP reductase (fabI), citrate synthase (OA), soluble transhydrogenase (udhA), glucose-6-phosphate-1-dehydrogenase (DO, or lipoamide dehydrogenase (lpd), and combinations thereof; and wherein at least one of the second enzymes is selected from the group consisting of: enoyl-ACP reductase (fabI), citrate synthase (OA), soluble transhydrogenase (udhA), glucose-6-phosphate-1-dehydrogenase (DO, or lipoamide dehydrogenase (lpd), and combinations thereof.

2. The bioprocess of claim 1, wherein the transcriptional gene silencing includes expressing (i) a gene encoding a small guide RNA specific for targeting the first enzyme essential for growth of the genetically modified microorganism, and (ii) a gene encoding a dCas9 protein.

3. The bioprocess of claim 1, wherein the controlled proteolysis of a second enzyme includes expressing a proteolytic enzyme enhancing factor sspB.

4. The bioprocess of claim 3, wherein the controlled proteolysis comprises adding a C-terminal peptide tag to the second enzyme essential for growth of the genetically modified microorganism, such that the tagged enzyme is targeted for proteolyis by clpXP protease only upon the expression of sspB.

5. The bioprocess of claim 1, wherein the genetically modified microorganism is characterized by deletion of a naturally occurring sspB gene.

6. The bioprocess of claim 1, wherein the genetically modified microorganism is characterized by deletion of a naturally occurring cas3 gene.

7. The bioprocess of claim 1, wherein the isoprenoid product is formed from acetyl CoA and NADH, and the heterologous enzyme is selected from the group consisting of: acetoacetyl-CoA thiolase, hydroxymethylglutaryl-CoA synthase, hydroxymethylglutaryl-CoA reductase, mevalonate kinase, phosphomevalonate kinase, mevalonate diphosphate decarboxylase, isopentenyl-disphophate isomerase, and isoprene synthase, and combinations thereof.

8. The bioprocess of claim 1, the heterologous enzyme comprising a combination of a mvaE gene encoding a bifunctional acetoacetyl-CoA thiolase and NADPH dependent HMG-CoA reductase, and a mvaS gene encoding hydroxymethylglutaryl-CoA synthase co-expressed in the genetically modified microorganism.

9. The bioprocess of claim 1, the isoprenoid product comprising mevalonate, mevalonate-5-phosphate, isopentenyl diphosphate (IPP), dimethylallyl diphosphate (DMAPP), or isoprene.

10. The bioprocess of claim 1, wherein the limiting nutrient is selected from the group consisting of phosphate, nitrogen, sulfur, and magnesium, and combinations thereof.

11. The bioprocess of claim 1, wherein the limiting nutrient comprises inorganic phosphate.

12. The bioprocess of claim 1, wherein the transition from the first stage to the second stage is at least partially controlled by chemical inducer that is selected from a group consisting of tetracycline, anhydrotetracycline, lactose, IPTG (isopropyl-beta-D-1-thiogalactopyranoside), arabinose, raffinose, and tryptophan, and combinations thereof.

13. The bioprocess of claim 1, wherein the transition from the first stage to the second stage is at least partially controlled by a temperature sensitive allele of an enzyme essential for growth of the genetically modified microorganism.

14. The bioprocess of claim 1, wherein the first enzyme essential for growth of the genetically modified microorganism and the second enzyme essential for growth of the genetically modified microorganism are the same.

15. The bioprocess of claim 1, wherein the genetically modified microorganism is characterized by disruption or deletion of a gene naturally occurring in the genetically modified microorganism, the naturally occurring gene selected from the group consisting of a gene encoding lactate dehydrogenase (ldhA), phosphate acetyltransferase (pta), pyruvate oxidase (poxB), pyruvate-formate lyase (pflB), the methylglyoxal synthase (mgsA), acetate kinase (ackA), alcohol dehydrogenase (adhE), ATP-dependent Lon protease (ion), outer membrane protease (ompT), arcA transcriptional dual regulator (arcA), iclR transcriptional regulator (iclR), and combinations thereof.

16. The bioprocess of claim 1, further comprising a second synthetic metabolic valve controlling at least one enzyme essential for growth of the genetically modified microorganism that is selected from the group consisting of: sucD, ace A, pfkA, Ion, rpoS, tktA or tktB.

17. The bioprocess of claim 1, further comprising a second synthetic metabolic valve that increases the pool and availability of the cofactor NADPH or NADH.

18. The bioprocess of claim 1, wherein acyl-CoA accumulates in the first stage, the acyl-CoA used in the second stage for the isoprenoid production pathway.

* * * * *

SEQUENCE LISTING

<160> NUMBER OF SEQ ID NOS: 54

<210> SEQ ID NO 1
<211> LENGTH: 3111
<212> TYPE: DNA
<213> ORGANISM: Artificial Sequence
<220> FEATURE:
<223> OTHER INFORMATION: Plasmid pSMART-HC-Kan-yibD-THNS

<400> SEQUENCE: 1

```
gtgcgtaatt gtgctgatct cttatatagc tgctctcatt atctctctac cctgaagtga     60
ctctctcacc tgtaaaaata atatctcaca ggcttaatag tttcttaata caaagcctgt    120
aaaacgtcag gataacttct gtgtaggagg ataatctatg gcaactctct gccgtccgtc    180
cgtgagtgtg ccggagcatg ttatcacgat ggaagaaacc cttgaactgg cccgtcgtcg    240
tcatacggat catccacagc tgcccctggc gctgcgctta attgaaaaca ccggtgttcg    300
cacgcgtcat attgttcaac cgatcgagga taccctggag catccagggt ttgaagatcg    360
caataaagta tacgagcgcg aggccaaatc gcgtgtgccg gcggtaatcc aacgcgccct    420
ggacgacgcg gagcttctgg cgacggacat tgacgttatt atctatgtct catgcacggg    480
ttttatgatg cctagtctta ctgcttggtt aatcaacgaa atgggcttcg acagcacgac    540
ccgccaaatt cctatcgcac agcttggctg tgcggccggt ggtgccgcga ttaaccgcgc    600
tcacgatttt tgcacggcat atcctgaagc aaatgcgctg atcgttgcct gcgaattctg    660
cagcctgtgt tatcagccca cagatctcgg tgtaggttct ctcctgtgca acggtctgtt    720
cggtgatgga attgctgcgg ctgtggtgcg cggacgtggt ggtacggggg ttcgcttgga    780
gcgtaacggc agctacttaa ttccaaaaac cgaagattgg atcatgtatg atgtgaaagc    840
aaccggtttc cacttcttac tggataagcg cgtcccggcc accatggaac ccttggcgcc    900
ggctctgaaa gaactcgcgg gcgagcatgg ttgggacgcc agtgatctgg atttttatat    960
tgttcacgcc ggtggtccgc gtattttaga cgacttgagt actttccttg aggtggatcc   1020
gcatgcgttt cgtttttccc gtgctaccct gaccgagtat ggtaacattg cgtcagcagt   1080
cgtgctggat gcgttacgcc gcttgttcga tgaaggcggt gtggaggaag gtgcgcgcgg   1140
tctgctggcg gggttcgggc caggtattac agccgaaatg tcactgggct gctggcaaac   1200
cgcgtagtaa ccggcttatc ggtcagtttc acctgattta cgtaaaaacc cgcttcggcg   1260
ggtttttgct tttggagggg cagaaagatg aatgactgtc cacgacgcta tacccaaaag   1320
aaagacgaat tctctagata tcgctcaata ctgaccattt aaatcatacc tgacctccat   1380
agcagaaagt caaaagcctc cgaccggagg cttttgactt gatcggcacg taagaggttc   1440
caactttcac cataatgaaa taagatcact accgggcgta tttttttgagt tatcgagatt   1500
ttcaggagct aaggaagcta aaatgagcca tattcaacgg gaaacgtctt gctcgaggcc   1560
gcgattaaat tccaacatgg atgctgattt atatgggtat aaatgggctc gcgataatgt   1620
cgggcaatca ggtgcgacaa tctatcgatt gtatgggaag cccgatgcgc cagagttgtt   1680
tctgaaacat ggcaaaggta gcgttgccaa tgatgttaca gatgagatgg tcaggctaaa   1740
ctggctgacg gaatttatgc ctcttccgac catcaagcat tttatccgta ctcctgatga   1800
tgcatggtta ctcaccactg cgatccccagg gaaaacagca ttccaggtat tagaagaata   1860
tcctgattca ggtgaaaata ttgttgatgc gctggcagtg ttcctgcgcc ggttgcattc   1920
gattcctgtt tgtaattgtc cttttaacgg cgatcgcgta tttcgtctcg ctcaggcgca   1980
atcacgaatg aataacggtt tggttggtgc gagtgatttt gatgacgagc gtaatggctg   2040
```

gcctgttgaa caagtctgga aagaaatgca taagcttttg ccattctcac cggattcagt 2100
cgtcactcat ggtgatttct cacttgataa ccttattttt gacgagggga aattaatagg 2160
ttgtattgat gttggacgag tcggaatcgc agaccgatac caggatcttg ccatcctatg 2220
gaactgcctc ggtgagtttt ctccttcatt acagaaacgg ctttttcaaa aatatggtat 2280
tgataatcct gatatgaata aattgcagtt tcacttgatg ctcgatgagt ttttctaatg 2340
agggcccaaa tgtaatcacc tggctcacct tcgggtgggc ctttctgcgt tgctggcgtt 2400
tttccatagg ctccgccccc ctgacgagca tcacaaaaat cgatgctcaa gtcagaggtg 2460
gcgaaacccg acaggactat aaagatacca ggcgtttccc cctggaagct ccctcgtgcg 2520
ctctcctgtt ccgaccctgc cgcttaccgg atacctgtcc gcctttctcc cttcgggaag 2580
cgtggcgctt tctcatagct cacgctgtag gtatctcagt tcggtgtagg tcgttcgctc 2640
caagctgggc tgtgtgcacg aaccccccgt tcagcccgac cgctgcgcct tatccggtaa 2700
ctatcgtctt gagtccaacc cggtaagaca cgacttatcg ccactggcag cagccactgg 2760
taacaggatt agcagagcga ggtatgtagg cggtgctaca gagttcttga agtggtggcc 2820
taactacggc tacactagaa gaacagtatt tggtatctgc gctctgctga agccagttac 2880
ctcggaaaaa gagttggtag ctcttgatcc ggcaaacaaa ccaccgctgg tagcggtggt 2940
ttttttgttt gcaagcagca gattacgcgc agaaaaaaag gatctcaaga agatcctttg 3000 atttctacc gaagaaaggc ccacccgtga aggtgagcca gtgagttgat tgcagtccag 3060
ttacgctgga gtctgaggct cgtcctgaat gatatcaagc ttgaattcgt t 3111

<210> SEQ ID NO 2
<211> LENGTH: 2386
<212> TYPE: DNA
<213> ORGANISM: Artificial Sequence
<220> FEATURE:
<223> OTHER INFORMATION: Plasmid pCDF-T2-fabIsgRNA

<400> SEQUENCE: 2
gcactgaaat ctagagcggt tcagtagaaa agatcaaagg atcttcttga gatccttttt 60
ttctgcgcgt aatcttttgc cctgtaaacg aaaaaaccac ctggggaggt ggtttgatcg 120
aaggttaagt cagttgggga actgcttaac cgtggtaact ggctttcgca gagcacagca 180
accaaatctg tccttccagt gtagccggac tttggcgcac acttcaagag caaccgcgtg 240
tttagctaaa caaatcctct gcgaactccc agttaccaat ggctgctgcc agtggcgttt 300
taccgtgctt ttccgggttg gactcaagtg aacagttacc ggataaggcg cagcagtcgg 360
gctgaacggg gagttcttgc ttacagccca gcttggagcg aacgacctac accgagccga 420
gataccagtg tgtgagctat gagaaagcgc cacacttccc gtaagggaga aaggcggaac 480
aggtatccgg taaacggcag ggtcggaaca ggagagcgca agagggagcg acccgccgga 540
aacggtgggg atctttaagt cctgtcgggt ttcgcccgta ctgtcagatt catggttgag 600
cctcacggct cccacagatg caccggaaaa gcgtctgttt atgtgaactc tggcaggagg 660
gcggagccta tggaaaaacg ccaccggcgc ggccctgctg ttttgcctca catgttagtc 720
ccctgcttat ccacggaatc tgtgggtaac tttgtatgtg tccgcagcgc ccgccgcagt 780
ctcacgcccg gagcgtagcg accgagtgag ctagctattt gtttattttt ctaaatacat 840
tcaaatatgt atccgctcat gagacaataa ccctgataaa tgcttcaata atattgaaaa 900
aggaagagta tgagggaagc ggtgatcgcc gaagtatcga ctcaactatc agaggtagtt 960

-continued

```
ggcgtcatcg agcgccatct cgaaccgacg ttgctggccg tacatttgta cggctccgca   1020

gtggatggcg gcctgaagcc acacagtgat attgatttgc tggttacggt gaccgtaagg   1080

cttgatgaaa caacgcggcg agctttgatc aacgaccttt tggaaacttc ggcttcccct   1140

ggagagagcg agattctccg cgctgtagaa gtcaccattg ttgtgcacga cgacatcatt   1200

ccgtggcgtt atccagctaa gcgcgaactg caatttggag aatggcagcg caatgacatt   1260

cttgcaggta tcttcgagcc agccacgatc gacattgatc tggctatctt gctgacaaaa   1320

gcaagagaac atagcgttgc cttggtaggt ccagcggcgg aggaactctt tgatccggtt   1380

cctgaacagg atctatttga ggcgctaaat gaaaccttaa cgctatggaa ctcgccgccc   1440

gactgggctg gcgatgagcg aaatgtagtg cttacgttgt cccgcatttg gtacagcgca   1500

gtaaccggca aaatcgcgcc gaaggatgtc gctgccgact gggcaatgga gcgcctgccg   1560

gcccagtatc agcccgtcat acttgaagct agacaggctt atcttggaca agaagaagat   1620

cgcttggcct cgcgcgcaga tcagttggaa gaatttgtcc actacgtgaa aggcgagatc   1680

accaaggtag tcggcaaata atgtctaaca attcgttcaa cactataggg cgaattgaag   1740

gaaggccgtc aaggccgcat tgaggctcgt cctgaatgat atcaagcttg aattcgttga   1800

attctaaaga tctttgacag ctagctcagt cctaggtata atactagtca gcctgctccg   1860

gtcggaccgt tttagagcta gaaatagcaa gttaaaataa ggctagtccg ttatcaactt   1920

gaaaaagtgg caccgagtcg gtgctttttt tgaagcttgg gcccgaacaa aaactcatct   1980

cagaagagga tctgaatagc gccgtcgacc atcatcatca tcatcattga gtttaaacgg   2040

tctccagctt ggctgttttg gcggatgaga gaagattttc agcctgatac agattaaatc   2100

agaacgcaga agcggtctga taaaacagaa tttgcctggc ggcagtagcg cggtggtccc   2160

acctgacccc atgccgaact cagaagtgaa acgccgtagc gccgatggta gtgtggggtc   2220

tccccatgcg agagtaggga actgccaggc atcaaataaa acgaaaggct cagtcgaaag   2280

actgggcctt tcgttttatc tgttgtttgt cggtgaactg gatccttact cgagtctaga   2340

ctgcagctgg gcctcatggg ccttcctttc actgcccgct ttccag                  2386
```

<210> SEQ ID NO 3
<211> LENGTH: 7413
<212> TYPE: DNA
<213> ORGANISM: Artificial Sequence
<220> FEATURE:
<223> OTHER INFORMATION: Plasmid pdCas9-ptet-sspB

<400> SEQUENCE: 3

```
gacgtcttaa gacccacttt cacatttaag ttgtttttct aatccgcata tgatcaattc     60

aaggccgaat aagaaggctg gctctgcacc ttggtgatca aataattcga tagcttgtcg    120

taataatggc ggcatactat cagtagtagg tgtttccctt tcttctttag cgacttgatg    180

ctcttgatct tccaatacgc aacctaaagt aaaatgcccc acagcgctga gtgcatataa    240

tgcattctct agtgaaaaac cttgttggca taaaaaggct aattgatttt cgagagtttc    300

atactgtttt tctgtaggcc gtgtacctaa atgtactttt gctccatcgc gatgacttag    360

taaagcacat ctaaaacttt tagcgttatt acgtaaaaaa tcttgccagc tttccccttc    420

taaagggcaa aagtgagtat ggtgcctatc taacatctca atggctaagg cgtcgagcaa    480

agcccgctta ttttttacat gccaatacaa tgtaggctgc tctacaccta gcttctgggc    540

gagtttacgg gttgttaaac cttcgattcc gacctcatta agcagctcta atgcgctgtt    600

aatcacttta cttttatcta atctagacat cattaattcc taatttttgt tgacactcta    660
```

-continued

```
tcgttgatag agttatttta ccactcccta tcagtgatag agaaaagaat tcaaaagatc    720
taaagaggag aaaggatcta tggataagaa atactcaata ggcttagcta tcggcacaaa    780
tagcgtcgga tgggcggtga tcactgatga atataaggtt ccgtctaaaa agttcaaggt    840
tctgggaaat acagaccgcc acagtatcaa aaaaaatctt ataggggctc ttttatttga    900
cagtggagag acagcggaag cgactcgtct caaacggaca gctcgtagaa ggtatacacg    960
tcggaagaat cgtatttgtt atctacagga gatttttca aatgagatgg cgaaagtaga   1020
tgatagtttc tttcatcgac ttgaagagtc tttttggtg gaagaagaca agaagcatga   1080
acgtcatcct atttttggaa atatagtaga tgaagttgct tatcatgaga aatatccaac   1140
tatctatcat ctgcgaaaaa aattggtaga ttctactgat aaagcggatt tgcgcttaat   1200
ctatttggcc ttagcgcata tgattaagtt tcgtggtcat tttttgattg agggagattt   1260
aaatcctgat aatagtgatg tggacaaact atttatccag ttggtacaaa cctacaatca   1320
attatttgaa gaaaaccta ttaacgcaag tggagtagat gctaaagcga ttctttctgc   1380
acgattgagt aaatcaagac gattagaaaa tctcattgct cagctccccg gtgagaagaa   1440
aaatggctta tttgggaatc tcattgcttt gtcattgggt ttgaccccta attttaaatc   1500
aaattttgat ttggcagaag atgctaaatt acagctttca aaagatactt acgatgatga   1560
tttagataat ttattggcgc aaattggaga tcaatatgct gatttgtttt tggcagctaa   1620
gaatttatca gatgctattt tactttcaga tatcctaaga gtaaatactg aaataactaa   1680
ggctccccta tcagcttcaa tgattaaacg ctacgatgaa catcatcaag acttgactct   1740
tttaaaagct ttagttcgac aacaacttcc agaaaagtat aaagaaatct tttttgatca   1800
atcaaaaaac ggatatgcag gttatattga tgggggagct agccaagaag aattttataa   1860
atttatcaaa ccaattttag aaaaaatgga tggtactgag gaattattgg tgaaactaaa   1920
tcgtgaagat ttgctgcgca agcaacggac ctttgacaac ggctctattc cccatcaaat   1980
tcacttgggt gagctgcatg ctattttgag aagacaagaa gacttttatc catttttaaa   2040
agacaatcgt gagaagattg aaaaaatctt gacttttcga attccttatt atgttggtcc   2100
attggcgcgt ggcaatagtc gttttgcatg gatgactcgg aagtctgaag aaacaattac   2160
cccatggaat tttgaagaag ttgtcgataa aggtgcttca gctcaatcat ttattgaacg   2220
catgacaaac tttgataaaa atcttccaaa tgaaaaagta ctaccaaaac atagtttgct   2280
ttatgagtat tttacggttt ataacgaatt gacaaaggtc aaatatgtta ctgaaggaat   2340
gcgaaaacca gcatttcttt caggtgaaca gaagaaagcc attgttgatt tactcttcaa   2400
aacaaatcga aaagtaaccg ttaagcaatt aaaagaagat tatttcaaaa aaatagaatg   2460
ttttgatagt gttgaaattt caggagttga agatagattt aatgcttcat taggtaccta   2520
ccatgatttg ctaaaaatta ttaaagataa agatttttg gataatgaag aaaatgaaga   2580
tatcttagag gatattgttt taacattgac cttatttgaa gatagggaga tgattgagga   2640
aagacttaaa acatatgctc acctctttga tgataaggtg atgaaacagc ttaaacgtcg   2700
ccgttatact ggttggggac gtttgtctcg aaaattgatt aatggtatta gggataagca   2760
atctggcaaa acaatattag atttttgaa atcagatggt tttgccaatc gcaattttat   2820
gcagctgatc catgatgata gtttgacatt taaagaagac attcaaaaag cacaagtgtc   2880
tggacaaggc gatagtttac atgaacatat tgcaaattta gctggtagcc ctgctattaa   2940
aaaaggtatt ttacagactg taaaagttgt tgatgaattg gtcaaagtaa tggggcggca   3000
```

```
taagccagaa aatatcgtta ttgaaatggc acgtgaaaat cagacaactc aaaagggcca   3060
gaaaaattcg cgagagcgta tgaaacgaat cgaagaaggt atcaaagaat taggaagtca   3120
gattcttaaa gagcatcctg ttgaaaatac tcaattgcaa aatgaaaagc tctatctcta   3180
ttatctccaa aatggaagag acatgtatgt ggaccaagaa ttagatatta atcgtttaag   3240
tgattatgat gtcgatgcca ttgttccaca aagtttcctt aaagacgatt caatagacaa   3300
taaggtctta acgcgttctg ataaaaatcg tggtaaatcg gataacgttc caagtgaaga   3360
agtagtcaaa aagatgaaaa actattggag acaacttcta aacgccaagt taatcactca   3420
acgtaagttt gataatttaa cgaaagctga acgtggaggt ttgagtgaac ttgataaagc   3480
tggttttatc aaacgccaat tggttgaaac tcgccaaatc actaagcatg tggcacaaat   3540
tttggatagt cgcatgaata ctaaatacga tgaaaatgat aaacttattc gagaggttaa   3600
agtgattacc ttaaaatcta aattagtttc tgacttccga aaagatttcc aattctataa   3660
agtacgtgag attaacaatt accatcatgc ccatgatgcg tatctaaatg ccgtcgttgg   3720
aactgctttg attaagaaat atccaaaact tgaatcggag tttgtctatg gtgattataa   3780
agtttatgat gttcgtaaaa tgattgctaa gtctgagcaa gaaataggca aagcaaccgc   3840
aaaatatttc ttttactcta atatcatgaa cttcttcaaa acagaaatta cacttgcaaa   3900
tggagagatt cgcaaacgcc ctctaatcga aactaatggg gaaactggag aaattgtctg   3960
ggataaaggg cgagattttg ccacagtgcg caaagtattg tccatgcccc aagtcaatat   4020
tgtcaagaaa acagaagtac agacaggcgg attctccaag gagtcaattt taccaaaaag   4080
aaattcggac aagcttattg ctcgtaaaaa agactgggat ccaaaaaaat atggtggttt   4140
tgatagtcca acggtagctt attcagtcct agtggttgct aaggtggaaa aagggaaatc   4200
gaagaagtta aaatccgtta aagagttact agggatcaca attatggaaa gaagttcctt   4260
tgaaaaaaat ccgattgact tttagaagc taaaggatat aaggaagtta aaaaagactt   4320
aatcattaaa ctacctaaat atagtctttt tgagttagaa aacggtcgta aacggatgct   4380
ggctagtgcc ggagaattac aaaaaggaaa tgagctggct ctgccaagca aatatgtgaa   4440
tttttatat ttagctagtc attatgaaaa gttgaagggt agtccagaag ataacgaaca   4500
aaaacaattg tttgtggagc agcataagca ttatttagat gagattattg agcaaatcag   4560
tgaattttct aagcgtgtta ttttagcaga tgccaattta gataaagttc ttagtgcata   4620
taacaaacat agagacaaac caatacgtga acaagcagaa aatattattc atttatttac   4680
gttgacgaat cttggagctc ccgctgcttt taaatatttt gatacaacaa ttgatcgtaa   4740
acgatatacg tctacaaaag aagttttaga tgccactctt atccatcaat ccatcactgg   4800
tctttatgaa acacgcattg atttgagtca gctaggaggt gactaactcg agccggctta   4860
tcggtcagtt tcacctgatt tacgtaaaaa cccgcttcgg cgggtttttg cttttggagg   4920
ggcagaaaga tgaatgactg tccacgacgc tatacccaaa agaaatccct atcagtgata   4980
gagattgaca tccctatcag tgatagagat actgagcaca tcagcaggac gcactgacca   5040
agaggagaaa ggatctatgg atttgtcaca gctaacacca cgtcgtccct atctgctgcg   5100
tgcattctat gagtggttgc tggataacca gctcacgccg cacctggtgg tggatgtgac   5160
gctccctggc gtgcaggttc ctatggaata tgcgcgtgac gggcaaatcg tactcaacat   5220
tgcgccgcgt gctgtcggca atctggaact ggcgaatgat gaggtgcgct ttaacgcgcg   5280
ctttggtggc attccgcgtc aggtttctgt gccgctggct gccgtgctgg ctatctacgc   5340
ccgtgaaaat ggcgcaggca cgatgtttga gcctgaagct gcctacgatg aagataccag   5400
```

```
catcatgaat gatgaagagg catcggcaga caacgaaacc gttatgtcgg ttattgatgg   5460

cgacaagcca gatcacgatg atgacactca tcctgacgat gaacctccgc agccaccacg   5520

cggtggtcga ccggcattac gcgttgtgaa gtaactcgag taaggatctc caggcatcaa   5580

ataaaacgaa aggctcagtc gaaagactgg gcctttcgtt ttatctgttg tttgtcggtg   5640

aacgctctct actagagtca cactggctca ccttcgggtg ggcctttctg cgtttatacc   5700

tagggatata ttccgcttcc tcgctcactg actcgctacg ctcggtcgtt cgactgcggc   5760

gagcggaaat ggcttacgaa cggggcggag atttcctgga agatgccagg aagatactta   5820

acagggaagt gagagggccg cggcaaagcc gtttttccat aggctccgcc cccctgacaa   5880

gcatcacgaa atctgacgct caaatcagtg gtggcgaaac ccgacaggac tataaagata   5940

ccaggcgttt ccccctggcg gctccctcgt gcgctctcct gttcctgcct ttcggtttac   6000

cggtgtcatt ccgctgttat ggccgcgttt gtctcattcc acgcctgaca ctcagttccg   6060

ggtaggcagt tcgctccaag ctggactgta tgcacgaacc ccccgttcag tccgaccgct   6120

gcgccttatc cggtaactat cgtcttgagt ccaacccgga aagacatgca aaagcaccac   6180

tggcagcagc cactggtaat tgatttagag gagttagtct tgaagtcatg cgccggttaa   6240

ggctaaactg aaaggacaag ttttggtgac tgcgctcctc caagccagtt acctcggttc   6300

aaagagttgg tagctcagag aaccttcgaa aaaccgccct gcaaggcggt tttttcgttt   6360

tcagagcaag agattacgcg cagaccaaaa cgatctcaag aagatcatct tattaatcag   6420

ataaaatatt tctagatttc agtgcaattt atctcttcaa atgtagcacc tgaagtcagc   6480

cccatacgat ataagttgtt actagtgctt ggattctcac caataaaaaa cgcccggcgg   6540

caaccgagcg ttctgaacaa atccagatgg agttctgagg tcattactgg atctatcaac   6600

aggagtccaa gcgagctcga tatcaaatta cgccccgccc tgccactcat cgcagtactg   6660

ttgtaattca ttaagcattc tgccgacatg gaagccatca caaacggcat gatgaacctg   6720

aatcgccagc ggcatcagca ccttgtcgcc ttgcgtataa tatttgccca tggtgaaaac   6780

gggggcgaag aagttgtcca tattggccac gtttaaatca aaactggtga aactcaccca   6840

gggattggct gagacgaaaa acatattctc aataaaccct ttagggaaat aggccaggtt   6900

ttcaccgtaa cacgccacat cttgcgaata tatgtgtaga aactgccgga aatcgtcgtg   6960

gtattcactc cagagcgatg aaaacgtttc agtttgctca tggaaaacgg tgtaacaagg   7020

gtgaacacta tcccatatca ccagctcacc gtctttcatt gccatacgaa attccggatg   7080

agcattcatc aggcgggcaa gaatgtgaat aaaggccgga taaaacttgt gcttattttt   7140

ctttacggtc tttaaaaagg ccgtaatatc cagctgaacg gtctggttat aggtacattg   7200

agcaactgac tgaaatgcct caaaatgttc tttacgatgc cattgggata tatcaacggt   7260

ggtatatcca gtgatttttt tctccatttt agcttcctta gctcctgaaa atctcgataa   7320

ctcaaaaaat acgcccggta gtgatcttat ttcattatgg tgaaagttgg aacctcttac   7380

gtgccgatca acgtctcatt ttcgccagat atc                                7413
```

```
<210> SEQ ID NO 4
<211> LENGTH: 974
<212> TYPE: DNA
<213> ORGANISM: Artificial Sequence
<220> FEATURE:
<223> OTHER INFORMATION: Synthetic Construct Delta-cas3::ugpBp-sspB-proB

<400> SEQUENCE: 4
```

```
caagacatgt gtatatcact gtaattcgat atttatgagc agcatcgaaa aatagcccgc     60
tgatatcatc gataatacta aaaaaacagg gaggctatta ccaggcatca aataaaacga    120
aaggctcagt cgaaagactg ggcctttcgt tttatctgtt gtttgtcggt gaacgctctc    180
tactagagtc acactggctc accttcgggt gggcctttct gcgtttatat ctttctgaca    240
ccttactatc ttacaaatgt aacaaaaaag ttatttttct gtaattcgag catgtcatgt    300
taccccgcga gcataaaacg cgtgtgtagg aggataatct atggatttgt cacagctaac    360
accacgtcgt ccctatctgc tgcgtgcatt ctatgagtgg ttgctggata accagctcac    420
gccgcacctg gtggtggatg tgacgctccc tggcgtgcag gttcctatgg aatatgcgcg    480
tgacgggcaa atcgtactca acattgcgcc gcgtgctgtc ggcaatctgg aactggcgaa    540
tgatgaggtg cgctttaacg cgcgctttgg tggcattccg cgtcaggttt ctgtgccgct    600
ggctgccgtg ctggctatct acgcccgtga aaatggcgca ggcacgatgt ttgagcctga    660
agctgcctac gatgaagata ccagcatcat gaatgatgaa gaggcatcgg cagacaacga    720
aaccgttatg tcggttattg atggcgacaa gccagatcac gatgatgaca ctcatcctga    780
cgatgaacct ccgcagccac cacgcggtgg tcgaccggca ttacgcgttg tgaagtaatt    840
gacggctagc tcagtcctag gtacagtgct agccatatga aggagaacaa atgaatttgc    900
ttattgataa ctggatccct gtacgcccgc gaaacggggg gaaagtccaa atcataaatc    960
tgcaatcgct atac                                                      974
```

```
<210> SEQ ID NO 5
<211> LENGTH: 1500
<212> TYPE: DNA
<213> ORGANISM: Artificial Sequence
<220> FEATURE:
<223> OTHER INFORMATION: Linear DNA Construct Delta-ptsG::proC-glk

<400> SEQUENCE: 5
```

```
ggctgtgttg aaaggtgttg ccgttgaaga actggcgcag gtaaccaccg ataacttcgc     60
ccgtctgttt cacatcgacg cttcccgcct tcaatccatc cgttgaatga gtttttttaa    120
agctcgtaat taatacttcg ctcttcatgc cgccgcaaac ccgccccctg acagggcggg    180
gtttcgccgc acgtctccat cgcttgccca agttgtgaag cacagctaac accacgtcgt    240
ccctatctgc tgccctaggt ctatgagtgg ttgctggata actttacggg catgcataag    300
gctcgtatga tatattcagg gagaccacaa cggtttccct ctacaaataa ttttgtttaa    360
ctttcgtaga agagcacttc cacacttctg gaaaaaggag atataccatg accaagtatg    420
ccctggtcgg tgacgtaggt ggtaccaatg cacgtctcgc tctctgtgat atcgcaagcg    480
gggaaatttc tcaggccaaa acatattccg ggttggatta ccccagctta gaagccgtga    540
ttcgtgtcta tttagaagaa cataaagtag aagtcaaaga cggttgtatt gctattgcgt    600
gccccatcac tggggattgg gtagcaatga ccaaccatac ctgggcgttt tctattgccg    660
agatgaaaaa aaatctgggt ttctcacacc tggagatcat caacgatttt accgcggtga    720
gcatggcgat cccaatgtta aaaaaggaac acttaattca gttcggcggg gcagaacctg    780
tggagggcaa gccgatcgcg gtttatggtg caggcacagg cttaggtgtc gcgcacttgg    840
tacatgttga caagcgctgg gtgagtttgc cgggcgaagg cggccacgtg gattttgccc    900
ccaattctga agaggaggcg attattctgg aaatcttgcg tgcagaaatc ggtcatgtgt    960
ctgccgaacg tgtgctgagt ggtccaggtc tggtgaatct gtaccgcgct attgtcaaag   1020
cggataaccg cctgccagaa aaccttaaac cgaaagatat caccgaacgt gccttggccg   1080
```

```
actcctgtac cgattgccgc cgcgcactta gtctgttttg cgttatcatg ggtcgttttg   1140

gcggcaacct cgcgctgaac ctggggacct ttggcggtgt ttttattgcg ggaggtattg   1200

ttccacgctt tttagaattt ttcaaagcca gtggctttcg cgcggccttc gaagacaagg   1260

gacgttttaa agaatacgta catgatatcc cagtctattt aattgttcac gataacccag   1320

gactgttagg ctctggtgcc catctgcgtc agacattggg ccatattctg taatccgtaa   1380

gacgttgggg agactaaggc agccagatgg ctgccttttt tacaggtgtt attcagaatt   1440

gatacgtgcc ggtaatgctg aaattacgcg gtgtgccgta gacgatagaa ccttccacgt   1500
```

<210> SEQ ID NO 6
<211> LENGTH: 1332
<212> TYPE: DNA
<213> ORGANISM: Artificial Sequence
<220> FEATURE:
<223> OTHER INFORMATION: Linear DNA Construct proC-galP

<400> SEQUENCE: 6

```
tatgtcgcga aaaacatcgt tgctgctggc ctggccgatc gttgtgaaat tcaggtttcc     60

tacgcaatcg gcgtggctga accgacctcc atcatggtag aaactttcgg tactgagaaa    120

gtgccttctg aacaactgac cctgctggta cgtgagttct tcgacctgcg cccatacggt    180

ctgattcaga tgctggatct gctgcacccg atctacaaag aaaccgcagc atacggtcac    240

tttggtcgtg aacatttccc gtgggaaaaa accgacaaag cgcagctgct gcgcgatgct    300

gccggtctga agtaatcttt cttcacctgc gttcaaagga cttcgctctt catgccgccg    360

caaaccccgc ccctgacagg gcggggtttc gccgcacgtc tccatcgctt gcccaagttg    420

tgaagcacag ctaacaccac gtcgtcccta tctgctgccc taggtctatg agtggttgct    480

ggataacttt acgggcatgc ataaggctcg tatgatatat tcagggagac cacaacggtt    540

tccctctaca aataattttg tttaactttc gtagaagagc acttccacac ttctggaaaa    600

aggagatata ccatgccaga tgccaaaaag caaggccgtt ctaacaaggc aatgacattc    660

ttcgtgtgct tccttgcggc gcttgccggc ctcttgttcg gcttggacat cggcgtcatt    720

gccggtgctt taccatttat cgctgacgaa ttccagatca cctcgcacac gcaagaatgg    780

gtcgtaagct ccatgatgtt cggtgcggca gtcggtgcgg tgggcagcgg ctggctctcc    840

tttaaactcg ggcgcaaaaa gagcctgatg atcggcgcaa ttttgtttgt tgccggttcg    900

ctgttctctg cggctgcgcc aaacgttgaa gtactgattc tttcccgcgt tctactgggg    960

ctggcggtgg gtgtggcctc ttataccgca ccgctgtacc tctctgaaat tgcgccggaa   1020

aaaattcgtg gcagtatgat ctcgatgtat cagttgatga tcactatcgg gatcctcggt   1080

gcttatcttt ctgataccgc cttcagctac accggtgcat ggcgctggat gctgggtgtg   1140

attatcatcc cggcaatttt gctgctgatt ggtgtcttct tcctgccaga cagcccacgt   1200

tggtttgccg ccaaacgccg ttttgttgat gccgaacgcg tgctgctacg cctgcgtgac   1260

accagcgcgg aagcgaaacg cgaactggat gaaatccgtg aaagtttgca ggttaaacag   1320

agtggctggg cg                                                       1332
```

<210> SEQ ID NO 7
<211> LENGTH: 970
<212> TYPE: DNA
<213> ORGANISM: Artificial Sequence
<220> FEATURE:
<223> OTHER INFORMATION: fabI-DAS+4:gentR

<400> SEQUENCE: 7

```
ctattgaaga tgtgggtaac tctgcggcat tcctgtgctc cgatctctct gccggtatct     60
ccggtgaagt ggtccacgtt gacggcggtt tcagcattgc tgcaatgaac gaactcgaac    120
tgaaagcggc caacgatgaa aactattctg aaaactatgc ggatgcgtct taataggaag    180
ttcctattct ctagaaagta taggaacttc cgaatccatg tgggagttta ttcttgacac    240
agatatttat gatataataa ctgagtaagc ttaacataag gaggaaaaac atatgttacg    300
cagcagcaac gatgttacgc agcagggcag tcgccctaaa acaaagttag gtggctcaag    360
tatgggcatc attcgcacat gtaggctcgg ccctgaccaa gtcaaatcca tgcgggctgc    420
tcttgatctt ttcggtcgtg agttcggaga cgtagccacc tactcccaac atcagccgga    480
ctccgattac ctcgggaact tgctccgtag taagacattc atcgcgcttg ctgccttcga    540
ccaagaagcg gttgttggcg ctctcgcggc ttacgttctg cccaagtttg agcagccgcg    600
tagtgagatc tatatctatg atctcgcagt ctccggcgag caccggaggc agggcattgc    660
caccgcgctc atcaatctcc tcaagcatga ggccaacgcg cttggtgctt atgtgatcta    720
cgtgcaagca gattacggtg acgatcccgc agtggctctc tatacaaagt tgggcatacg    780
ggaagaagtg atgcactttg atatcgaccc aagtaccgcc acctaagaag ttcctattct    840
ctagaaagta taggaacttc cgttctgttg gtaaagatgg gcggcgttct gccgcccgtt    900
atctctgtta tacctttctg atatttgtta tcgccgatcc gtctttctcc ccttcccgcc    960
ttgcgtcagg                                                           970
```

<210> SEQ ID NO 8
<211> LENGTH: 1026
<212> TYPE: DNA
<213> ORGANISM: Artificial Sequence
<220> FEATURE:
<223> OTHER INFORMATION: lpd-DAS+4:gentR

<400> SEQUENCE: 8

```
ggtactaacg gcggcgagct gctgggtgaa atcggcctgg caatcgaaat gggttgtgat     60
gctgaagaca tcgcactgac catccacgcg cacccgactc tgcacgagtc tgtgggcctg    120
gcggcagaag tgttcgaagg tagcattacc gacctgccga acccgaaagc gaagaagaag    180
gcggccaacg atgaaaacta ttctgaaaac tatgcggatg cgtcttaata gcgaatccat    240
gtgggagttt attcttgaca cagatattta tgatataata actgagtaag cttaacataa    300
ggaggaaaaa catatgttac gcagcagcaa cgatgttacg cagcagggca gtcgccctaa    360
aacaaagtta ggtggctcaa gtatgggcat cattcgcaca tgtaggctcg gccctgacca    420
agtcaaatcc atgcgggctg ctcttgatct tttcggtcgt gagttcggag acgtagccac    480
ctactcccaa catcagccgg actccgatta cctcgggaac ttgctccgta gtaagacatt    540
catcgcgctt gctgccttcg accaagaagc ggttgttggc gctctcgcgg cttacgttct    600
gcccaagttt gagcagccgc gtagtgagat ctatatctat gatctcgcag tctccggcga    660
gcaccggagg cagggcattg ccaccgcgct catcaatctc ctcaagcatg aggccaacgc    720
gcttggtgct tatgtgatct acgtgcaagc agattacggt gacgatcccg cagtggctct    780
ctatacaaag ttgggcatac gggaagaagt gatgcacttt gatatcgacc caagtaccgc    840
cacctaattt ttcgtttgcc ggaacatccg gcaattaaaa aagcggctaa ccacgccgct    900
ttttttacgt ctgcaattta cctttccagt cttcttgctc cacgttcaga gagacgttcg    960
catactgctg accgttgctc gttattcagc ctgacagtat ggttactgtc gtttagacgt   1020
```

```
tgtggg                                                              1026

<210> SEQ ID NO 9
<211> LENGTH: 869
<212> TYPE: DNA
<213> ORGANISM: Artificial Sequence
<220> FEATURE:
<223> OTHER INFORMATION: gltA-DAS+4:zeoR

<400> SEQUENCE: 9

gtattccgtc ttccatgttc accgtcattt tcgcaatggc acgtaccgtt ggctggatcg     60

cccactggag cgaaatgcac agtgacggta tgaagattgc ccgtccgcgt cagctgtata    120

caggatatga aaaacgcgac tttaaaagcg atatcaagcg tgcggccaac gatgaaaact    180

attctgaaaa ctatgcggat gcgtcttaat agttgacaat taatcatcgg catagtatat    240

cggcatagta taatacgact cactatagga gggccatcat ggccaagttg accagtgccg    300

ttccggtgct caccgcgcgc gacgtcgccg gagcggtcga gttctggacc gaccggctcg    360

ggttctcccg ggacttcgtg gaggacgact tcgccggtgt ggtccgggac gacgtgaccc    420

tgttcatcag cgcggtccag gaccaggtgg tgccggacaa caccctggcc tgggtgtggg    480

tgcgcggcct ggacgagctg tacgccgagt ggtcggaggt cgtgtccacg aacttccggg    540

acgcctccgg gccggccatg accgagatcg gcgagcagcc gtgggggcgg gagttcgccc    600

tgcgcgaccc ggccggcaac tgcgtgcact ttgtggcaga ggagcaggac tgaggataag    660

taatggttga ttgctaagtt gtaaatattt taacccgccg ttcatatggc gggttgattt    720

ttatatgcct aaacacaaaa aattgtaaaa ataaaatcca ttaacagacc tatatagata    780

tttaaaaaga atagaacagc tcaaattatc agcaacccaa tactttcaat taaaaacttc    840

atggtagtcg catttataac cctatgaaa                                      869

<210> SEQ ID NO 10
<211> LENGTH: 852
<212> TYPE: DNA
<213> ORGANISM: Artificial Sequence
<220> FEATURE:
<223> OTHER INFORMATION: udhA-DAS+4:bsdR

<400> SEQUENCE: 10

tctgggtatt cactgctttg gcgagcgcgc tgccgaaatt attcatatcg gtcaggcgat     60

tatggaacag aaaggtggcg gcaacactat tgagtacttc gtcaacacca cctttaacta    120

cccgacgatg gcggaagcct atcgggtagc tgcgttaaac ggtttaaacc gcctgtttgc    180

ggccaacgat gaaaactatt ctgaaaacta tgcggatgcg tcttaatagt tgacaattaa    240

tcatcggcat agtatatcgg catagtataa tacgactcac tataggaggg ccatcatgaa    300

gaccttcaac atctctcagc aggatctgga gctggtggag gtcgccactg agaagatcac    360

catgctctat gaggacaaca agcaccatgt cggggcggcc atcaggacca agactgggga    420

gatcatctct gctgtccaca ttgaggccta cattggcagg gtcactgtct gtgctgaagc    480

cattgccatt gggtctgctg tgagcaacgg gcagaaggac tttgacacca ttgtggctgt    540

caggcacccc tactctgatg aggtggacag atccatcagg gtggtcagcc cctgtggcat    600

gtgcagagag ctcatctctg actatgctcc tgactgcttt gtgctcattg agatgaatgg    660

caagctggtc aaaaccacca ttgaggaact catccccctc aagtacacca ggaactaaag    720

taaaacttta tcgaaatggc catccattct tgcgcggatg gcctctgcca gctgctcata    780
```

gcggctgcgc agcggtgagc caggacgata aaccaggcca atagtgcggc gtggttccgg 840
cttaatgcac gg 852

<210> SEQ ID NO 11
<211> LENGTH: 898
<212> TYPE: DNA
<213> ORGANISM: Artificial Sequence
<220> FEATURE:
<223> OTHER INFORMATION: zwf-DAS+4:bsdR

<400> SEQUENCE: 11
gaagtggaag aagcctggaa atgggtagac tccattactg aggcgtgggc gatggacaat 60
gatgcgccga aaccgtatca ggccggaacc tggggacccg ttgcctcggt ggcgatgatt 120
acccgtgatg gtcgttcctg gaatgagttt gaggcggcca acgatgaaaa ctattctgaa 180
aactatgcgg atgcgtctta atagttgaca attaatcatc ggcatagtat atcggcatag 240
tataatacga ctcactatag gagggccatc atgaagacct tcaacatctc tcagcaggat 300
ctggagctgg tggaggtcgc cactgagaag atcaccatgc tctatgagga caacaagcac 360
catgtcgggg cggccatcag gaccaagact ggggagatca tctctgctgt ccacattgag 420
gcctacattg gcagggtcac tgtctgtgct gaagccattg ccattgggtc tgctgtgagc 480
aacgggcaga aggactttga caccattgtg gctgtcaggc acccctactc tgatgaggtg 540
gacagatcca tcagggtggt cagcccctgt ggcatgtgca gagagctcat ctctgactat 600
gctcctgact gctttgtgct cattgagatg aatggcaagc tggtcaaaac caccattgag 660
gaactcatcc ccctcaagta caccaggaac taaagtaata tctgcgctta tcctttatgg 720
ttattttacc ggtaacatga tcttgcgcag attgtagaac aatttttaca ctttcaggcc 780
tcgtgcggat tcacccacga ggcttttttt attacactga ctgaaacgtt tttgccctat 840
gagctccggt tacaggcgtt tcagtcataa atcctctgaa tgaaacgcgt tgtgaatc 898

<210> SEQ ID NO 12
<211> LENGTH: 3037
<212> TYPE: DNA
<213> ORGANISM: Artificial Sequence
<220> FEATURE:
<223> OTHER INFORMATION: Plasmid pSMART-waaHp-GFPuv

<400> SEQUENCE: 12
tgcccaggca tcaaataaaa cgaaaggctc agtcgaaaga ctgggccttt cgttttatct 60
gttgtttgtc ggtgaacgct ctctactaga gtcacactgg ctcaccttcg ggtgggcctt 120
tctgcgttta tacacagcta acaccacgtc gtccctatct gctgccctag gtctatgagt 180
ggttgctgga taacgtgcgt aattgtgctg atctcttata tagctgctct cattatctct 240
ctaccctgaa gtgactctct cacctgtaaa aataatatct cacaggctta atagtttctt 300
aatacaaagc ctgtaaaacg tcaggataac ttctatattc agggagacca caacggtttc 360
cctctacaaa taattttgtt taactttcgt gtgtaggagg ataatctatg gctagcaaag 420
gagaagaact tttcactgga gttgtcccaa ttcttgttga attagatggt gatgttaatg 480
ggcacaaatt ttctgtcagt ggagagggtg aaggtgatgc tacatacgga aagcttaccc 540
ttaaatttat ttgcactact ggaaaactac ctgttccatg gccaacactt gtcactactt 600
tctcttatgg tgttcaatgc ttttcccgtt atccggatca tatgaaacgg catgactttt 660
tcaagagtgc catgcccgaa ggttatgtac aggaacgcac tatatctttc aaagatgacg 720
ggaactacaa gacgcgtgct gaagtcaagt ttgaaggtga tacccttgtt aatcgtatcg 780

```
agttaaaagg tattgatttt aaagaagatg gaaacattct cggacacaaa ctcgagtaca    840
actataactc acacaatgta tacatcacgg cagacaaaca aaagaatgga atcaaagcta    900
acttcaaaat tcgccacaac attgaagatg gatccgttca actagcagac cattatcaac    960
aaaatactcc aattggcgat ggccctgtcc ttttaccaga caaccattac ctgtcgacac   1020
aatctgccct ttcgaaagat cccaacgaaa agcgtgacca catggtcctt cttgagtttg   1080
taactgctgc tgggattaca catggcatgg atgagctcta caaataatga ggatccccgg   1140
cttatcggtc agtttcacct gatttacgta aaaacccgct tcggcgggtt tttgcttttg   1200
gaggggcaga aagatgaatg actgtccacg acgctatacc caaaagaaag acgaattctc   1260
tagatatcgc tcaatactga ccatttaaat catacctgac ctccatagca gaaagtcaaa   1320
agcctccgac cggaggcttt tgacttgatc ggcacgtaag aggttccaac tttcaccata   1380
atgaaataag atcactaccg ggcgtatttt ttgagttatc gagattttca ggagctaagg   1440
aagctaaaat gagccatatt caacgggaaa cgtcttgctc gaggccgcga ttaaattcca   1500
acatggatgc tgatttatat gggtataaat gggctcgcga taatgtcggg caatcaggtg   1560
cgacaatcta tcgattgtat gggaagcccg atgcgccaga gttgtttctg aaacatggca   1620
aaggtagcgt tgccaatgat gttacagatg agatggtcag gctaaactgg ctgacggaat   1680
ttatgcctct tccgaccatc aagcatttta tccgtactcc tgatgatgca tggttactca   1740
ccactgcgat cccagggaaa acagcattcc aggtattaga agaatatcct gattcaggtg   1800
aaaatattgt tgatgcgctg gcagtgttcc tgcgccggtt gcattcgatt cctgtttgta   1860
attgtccttt taacggcgat cgcgtatttc gtctcgctca ggcgcaatca cgaatgaata   1920
acggtttggt tggtgcgagt gattttgatg acgagcgtaa tggctggcct gttgaacaag   1980
tctggaaaga aatgcataag cttttgccat tctcaccgga ttcagtcgtc actcatggtg   2040
atttctcact tgataacctt atttttgacg aggggaaatt aataggttgt attgatgttg   2100
gacgagtcgg aatcgcagac cgataccagg atcttgccat cctatggaac tgcctcggtg   2160
agttttctcc ttcattacag aaacggcttt ttcaaaaata tggtattgat aatcctgata   2220
tgaataaatt gcagtttcac ttgatgctcg atgagttttt ctaatgaggg cccaaatgta   2280
atcacctggc tcaccttcgg gtgggccttt ctgcgttgct ggcgtttttc cataggctcc   2340
gcccccctga cgagcatcac aaaaatcgat gctcaagtca gaggtggcga aacccgacag   2400
gactataaag ataccaggcg tttccccctg gaagctccct cgtgcgctct cctgttccga   2460
ccctgccgct taccggatac ctgtccgcct ttctcccttc gggaagcgtg gcgctttctc   2520
atagctcacg ctgtaggtat ctcagttcgg tgtaggtcgt tcgctccaag ctgggctgtg   2580
tgcacgaacc ccccgttcag cccgaccgct gcgccttatc cggtaactat cgtcttgagt   2640
ccaacccggt aagacacgac ttatcgccac tggcagcagc cactggtaac aggattagca   2700
gagcgaggta tgtaggcggt gctacagagt tcttgaagtg gtggcctaac tacggctaca   2760
ctagaagaac agtatttggt atctgcgctc tgctgaagcc agttacctcg gaaaaagagt   2820
tggtagctct tgatccggca aacaaaccac cgctggtagc ggtggttttt ttgtttgcaa   2880
gcagcagatt acgcgcagaa aaaaaggatc tcaagaagat cctttgattt tctaccgaag   2940
aaaggcccac ccgtgaaggt gagccagtga gttgattgca gtccagttac gctggagtct   3000
gaggctcgtc ctgaatgata tcaagcttga attcgtt                            3037
```

<210> SEQ ID NO 13

```
<211> LENGTH: 2780
<212> TYPE: DNA
<213> ORGANISM: Artificial Sequence
<220> FEATURE:
<223> OTHER INFORMATION: pCASCADE-Control Plasmid

<400> SEQUENCE: 13

gacgtcttaa gacccacttt cacatttaag ttgtttttct aatccgcata tgatcaattc     60
aaggccgaat aagaaggctg gctctgcacc ttggtgatca aataattcga tagcttgtcg    120
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgaaaa aaaaaccccg cccctgacag ggcggggttt tttttcctag ggatatattc   1080
cgcttcctcg ctcactgact cgctacgctc ggtcgttcga ctgcggcgag cggaaatggc   1140
ttacgaacgg ggcggagatt tcctggaaga tgccaggaag atacttaaca gggaagtgag   1200
agggccgcgg caaagccgtt tttccatagg ctccgccccc ctgacaagca tcacgaaatc   1260
tgacgctcaa atcagtggtg gcgaaacccg acaggactat aaagatacca ggcgtttccc   1320
cctggcggct ccctcgtgcg ctctcctgtt cctgcctttc ggtttaccgg tgtcattccg   1380
ctgttatggc cgcgtttgtc tcattccacg cctgacactc agttccgggt aggcagttcg   1440
ctccaagctg gactgtatgc acgaaccccc cgttcagtcc gaccgctgcg ccttatccgg   1500
taactatcgt cttgagtcca acccggaaag acatgcaaaa gcaccactgg cagcagccac   1560
tggtaattga tttagaggag ttagtcttga agtcatgcgc cggttaaggc taaactgaaa   1620
ggacaagttt tggtgactgc gctcctccaa gccagttacc tcggttcaaa gagttggtag   1680
ctcagagaac cttcgaaaaa ccgccctgca aggcggtttt ttcgttttca gagcaagaga   1740
ttacgcgcag accaaaacga tctcaagaag atcatcttat taatcagata aaatatttct   1800
agatttcagt gcaatttatc tcttcaaatg tagcacctga agtcagcccc atacgatata   1860
agttgttact agtgcttgga ttctcaccaa taaaaaacgc ccggcggcaa ccgagcgttc   1920
tgaacaaatc cagatggagt tctgaggtca ttactggatc tatcaacagg agtccaagcg   1980
agctcgatat caaattacgc cccgccctgc cactcatcgc agtactgttg taattcatta   2040
agcattctgc cgacatggaa gccatcacaa acggcatgat gaacctgaat cgccagcggc   2100
atcagcacct tgtcgccttg cgtataatat ttgcccatgg tgaaaacggg ggcgaagaag   2160
```

```
ttgtccatat tggccacgtt taaatcaaaa ctggtgaaac tcacccaggg attggctgag   2220

acgaaaaaca tattctcaat aaaccctta gggaaatagg ccaggttttc accgtaacac   2280

gccacatctt gcgaatatat gtgtagaaac tgccggaaat cgtcgtggta ttcactccag   2340

agcgatgaaa acgtttcagt ttgctcatgg aaaacggtgt aacaagggtg aacactatcc   2400

catatcacca gctcaccgtc tttcattgcc atacgaaatt ccggatgagc attcatcagg   2460

cgggcaagaa tgtgaataaa ggccggataa aacttgtgct tatttttctt tacggtcttt   2520

aaaaaggccg taatatccag ctgaacggtc tggttatagg tacattgagc aactgactga   2580

aatgcctcaa aatgttcttt acgatgccat tgggatatat caacggtggt atatccagtg   2640

atttttttct ccattttagc ttccttagct cctgaaaatc tcgataactc aaaaaatacg   2700

cccggtagtg atcttatttc attatggtga aagttggaac ctcttacgtg ccgatcaacg   2760

tctcatttc gccagatatc                                               2780
```

<210> SEQ ID NO 14
<211> LENGTH: 2843
<212> TYPE: DNA
<213> ORGANISM: Artificial Sequence
<220> FEATURE:
<223> OTHER INFORMATION: pCASCADE-gltA2 Plasmid

<400> SEQUENCE: 14

```
gacgtcttaa gacccacttt cacatttaag ttgtttttct aatccgcata tgatcaattc     60

aaggccgaat aagaaggctg gctctgcacc ttggtgatca aataattcga tagcttgtcg    120

taataatggc ggcatactat cagtagtagg tgtttccctt tcttctttag cgacttgatg    180

ctcttgatct tccaatacgc aacctaaagt aaaatgcccc acagcgctga gtgcatataa    240

tgcattctct agtgaaaaac cttgttggca taaaaaggct aattgatttt cgagagtttc    300

atactgtttt tctgtaggcc gtgtacctaa atgtactttt gctccatcgc gatgacttag    360

taaagcacat ctaaaacttt tagcgttatt acgtaaaaaa tcttgccagc tttccccttc    420

taaagggcaa aagtgagtat ggtgcctatc taacatctca atggctaagg cgtcgagcaa    480

agcccgctta ttttttacat gccaatacaa tgtaggctgc tctacaccta gcttctgggc    540

gagtttacgg gttgttaaac cttcgattcc gacctcatta agcagctcta atgcgctgtt    600

aatcacttta cttttatcta atctagacat catccaggca tcaaataaaa cgaaaggctc    660

agtcgaaaga ctgggccttt cgttttatct gttgtttgtc ggtgaacgct ctctactaga    720

gtcacactgg ctcaccttcg ggtgggcctt tctgcgttta tacacagcta acaccacgtc    780

gtccctatct gctgccctag gtctatgagt ggttgctgga taactctttc tgacacctta    840

ctatcttaca aatgtaacaa aaaagttatt tttctgtaat tcgagcatgt catgttaccc    900

cgcgagcata aaacgcgtat attcagggag accacaacgg tttccctcta caaataattt    960

tgtttaactt tgaattcaaa agatctggta ccacctcgag ttccccgcgc cagcggggat   1020

aaaccgtatt gaccaattca ttcgggacag ttattagttc gagttccccg cgccagcggg   1080

gataaaccga aaaaaaaacc ccgcccctga cagggcgggg tttttttcc tagggatata   1140

ttccgcttcc tcgctcactg actcgctacg ctcggtcgtt cgactgcggc gagcggaaat   1200

ggcttacgaa cggggcggag atttcctgga agatgccagg aagatactta acagggaagt   1260

gagagggccg cggcaaagcc gtttttccat aggctccgcc cccctgacaa gcatcacgaa   1320

atctgacgct caaatcagtg gtggcgaaac ccgacaggac tataaagata ccaggcgttt   1380
```

```
cccccctggcg gctccctcgt gcgctctcct gttcctgcct ttcggtttac cggtgtcatt   1440

ccgctgttat ggccgcgttt gtctcattcc acgcctgaca ctcagttccg ggtaggcagt   1500

tcgctccaag ctggactgta tgcacgaacc ccccgttcag tccgaccgct gcgccttatc   1560

cggtaactat cgtcttgagt ccaacccgga aagacatgca aaagcaccac tggcagcagc   1620

cactggtaat tgatttagag gagttagtct tgaagtcatg cgccggttaa ggctaaactg   1680

aaaggacaag ttttggtgac tgcgctcctc caagccagtt acctcggttc aaagagttgg   1740

tagctcagag aaccttcgaa aaaccgccct gcaaggcggt tttttcgttt tcagagcaag   1800

agattacgcg cagaccaaaa cgatctcaag aagatcatct tattaatcag ataaaatatt   1860

tctagatttc agtgcaattt atctcttcaa atgtagcacc tgaagtcagc cccatacgat   1920

ataagttgtt actagtgctt ggattctcac caataaaaaa cgcccggcgg caaccgagcg   1980

ttctgaacaa atccagatgg agttctgagg tcattactgg atctatcaac aggagtccaa   2040

gcgagctcga tatcaaatta cgccccgccc tgccactcat cgcagtactg ttgtaattca   2100

ttaagcattc tgccgacatg gaagccatca caaacggcat gatgaacctg aatcgccagc   2160

ggcatcagca ccttgtcgcc ttgcgtataa tatttgccca tggtgaaaac gggggcgaag   2220

aagttgtcca tattggccac gtttaaatca aaactggtga aactcaccca gggattggct   2280

gagacgaaaa acatattctc aataaaccct ttagggaaat aggccaggtt ttcaccgtaa   2340

cacgccacat cttgcgaata tatgtgtaga aactgccgga aatcgtcgtg gtattcactc   2400

cagagcgatg aaaacgtttc agtttgctca tggaaaacgg tgtaacaagg gtgaacacta   2460

tcccatatca ccagctcacc gtctttcatt gccatacgaa attccggatg agcattcatc   2520

aggcgggcaa gaatgtgaat aaaggccgga taaaacttgt gcttattttt ctttacggtc   2580

tttaaaaagg ccgtaatatc cagctgaacg gtctggttat aggtacattg agcaactgac   2640

tgaaatgcct caaaatgttc tttacgatgc cattgggata tatcaacggt ggtatatcca   2700

gtgatttttt tctccatttt agcttcctta gctcctgaaa atctcgataa ctcaaaaaat   2760

acgcccggta gtgatcttat ttcattatgg tgaaagttgg aacctcttac gtgccgatca   2820

acgtctcatt ttcgccagat atc                                            2843
```

```
<210> SEQ ID NO 15
<211> LENGTH: 2841
<212> TYPE: DNA
<213> ORGANISM: Artificial Sequence
<220> FEATURE:
<223> OTHER INFORMATION: pCASCADE-fabI Plasmid

<400> SEQUENCE: 15

gacgtcttaa gacccacttt cacatttaag ttgtttttct aatccgcata tgatcaattc     60

aaggccgaat aagaaggctg gctctgcacc ttggtgatca aataattcga tagcttgtcg    120

taataatggc ggcatactat cagtagtagg tgtttccctt tcttctttag cgacttgatg    180

ctcttgatct tccaatacgc aacctaaagt aaaatgcccc acagcgctga gtgcatataa    240

tgcattctct agtgaaaaac cttgttggca taaaaaggct aattgatttt cgagagtttc    300

atactgtttt tctgtaggcc gtgtacctaa atgtactttt gctccatcgc gatgacttag    360

taaagcacat ctaaaacttt tagcgttatt acgtaaaaaa tcttgccagc tttccccttc    420

taaagggcaa aagtgagtat ggtgcctatc taacatctca atggctaagg cgtcgagcaa    480

agcccgctta ttttttacat gccaatacaa tgtaggctgc tctacaccta gcttctgggc    540

gagtttacgg gttgttaaac cttcgattcc gacctcatta agcagctcta atgcgctgtt    600
```

```
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgttga ttataataac cgtttatctg ttcgtatcga gttccccgcg ccagcgggga   1080
taaaccgaaa aaaaaacccc gcccctgaca gggcggggtt ttttttccta gggatatatt   1140
ccgcttcctc gctcactgac tcgctacgct cggtcgttcg actgcggcga gcggaaatgg   1200
cttacgaacg gggcggagat ttcctggaag atgccaggaa gatacttaac agggaagtga   1260
gagggccgcg gcaaagccgt ttttccatag gctccgcccc cctgacaagc atcacgaaat   1320
ctgacgctca aatcagtggt ggcgaaaccc gacaggacta taaagatacc aggcgtttcc   1380
ccctggcggc tccctcgtgc gctctcctgt tcctgccttt cggtttaccg gtgtcattcc   1440
gctgttatgg ccgcgtttgt ctcattccac gcctgacact cagttccggg taggcagttc   1500
gctccaagct ggactgtatg cacgaacccc ccgttcagtc cgaccgctgc gccttatccg   1560
gtaactatcg tcttgagtcc aacccggaaa gacatgcaaa agcaccactg gcagcagcca   1620
ctggtaattg atttagagga gttagtcttg aagtcatgcg ccggttaagg ctaaactgaa   1680
aggacaagtt ttggtgactg cgctcctcca agccagttac ctcggttcaa agagttggta   1740
gctcagagaa ccttcgaaaa accgccctgc aaggcggttt tttcgttttc agagcaagag   1800
attacgcgca gaccaaaacg atctcaagaa gatcatctta ttaatcagat aaaatatttc   1860
tagatttcag tgcaatttat ctcttcaaat gtagcacctg aagtcagccc catacgatat   1920
aagttgttac tagtgcttgg attctcacca ataaaaaacg cccggcggca accgagcgtt   1980
ctgaacaaat ccagatggag ttctgaggtc attactggat ctatcaacag gagtccaagc   2040
gagctcgata tcaaattacg ccccgccctg ccactcatcg cagtactgtt gtaattcatt   2100
aagcattctg ccgacatgga agccatcaca aacggcatga tgaacctgaa tcgccagcgg   2160
catcagcacc ttgtcgcctt gcgtataata tttgcccatg gtgaaaacgg gggcgaagaa   2220
gttgtccata ttggccacgt ttaaatcaaa actggtgaaa ctcacccagg gattggctga   2280
gacgaaaaac atattctcaa taaacccttt agggaaatag gccaggtttt caccgtaaca   2340
cgccacatct tgcgaatata tgtgtagaaa ctgccggaaa tcgtcgtggt attcactcca   2400
gagcgatgaa aacgtttcag tttgctcatg gaaaacggtg taacaagggt gaacactatc   2460
ccatatcacc agctcaccgt ctttcattgc catacgaaat tccggatgag cattcatcag   2520
gcgggcaaga atgtgaataa aggccggata aaacttgtgc ttatttttct ttacggtctt   2580
taaaaaggcc gtaatatcca gctgaacggt ctggttatag gtacattgag caactgactg   2640
aaatgcctca aaatgttctt tacgatgcca ttgggatata tcaacggtgg tatatccagt   2700
gatttttttc tccattttag cttccttagc tcctgaaaat ctcgataact caaaaaatac   2760
gcccggtagt gatcttattt cattatggtg aaagttggaa cctcttacgt gccgatcaac   2820
gtctcatttt cgccagatat c                                             2841
```

<210> SEQ ID NO 16

<211> LENGTH: 2841
<212> TYPE: DNA
<213> ORGANISM: Artificial Sequence
<220> FEATURE:
<223> OTHER INFORMATION: pCASCADE-udhA Plasmid

<400> SEQUENCE: 16
gacgtcttaa gacccacttt cacatttaag ttgtttttct aatccgcata tgatcaattc 60
aaggccgaat aagaaggctg gctctgcacc ttggtgatca aataattcga tagcttgtcg 120
taataatggc ggcatactat cagtagtagg tgtttccctt tcttctttag cgacttgatg 180
ctcttgatct tccaatacgc aacctaaagt aaaatgcccc acagcgctga gtgcatataa 240
tgcattctct agtgaaaaac cttgttggca taaaaaggct aattgatttt cgagagtttc 300
atactgtttt tctgtaggcc gtgtacctaa atgtactttt gctccatcgc gatgacttag 360
taaagcacat ctaaaacttt tagcgttatt acgtaaaaaa tcttgccagc tttccccttc 420
taaagggcaa aagtgagtat ggtgcctatc taacatctca atggctaagg cgtcgagcaa 480
agcccgctta tttttacat gccaatacaa tgtaggctgc tctacaccta gcttctgggc 540
gagtttacgg gttgttaaac cttcgattcc gacctcatta agcagctcta atgcgctgtt 600
aatcacttta cttttatcta atctagacat catccaggca tcaaataaaa cgaaaggctc 660
agtcgaaaga ctgggccttt cgttttatct gttgtttgtc ggtgaacgct ctctactaga 720
gtcacactgg ctcaccttcg ggtgggcctt tctgcgttta tacacagcta acaccacgtc 780
gtccctatct gctgccctag gtctatgagt ggttgctgga taactctttc tgacacctta 840
ctatcttaca aatgtaacaa aaaagttatt tttctgtaat tcgagcatgt catgttaccc 900
cgcgagcata aaacgcgtat attcagggag accacaacgg tttccctcta caaataattt 960
tgtttaactt tgaattcaaa agatctggta ccacctcgag ttccccgcgc cagcggggat 1020
aaaccgttac cattctgttg cttttatgta taagaatcga gttccccgcg ccagcgggga 1080
taaaccgaaa aaaaaacccc gcccctgaca gggcggggtt tttttcccta gggatatatt 1140
ccgcttcctc gctcactgac tcgctacgct cggtcgttcg actgcggcga gcggaaatgg 1200
cttacgaacg gggcggagat ttcctggaag atgccaggaa gatacttaac agggaagtga 1260
gagggccgcg gcaaagccgt ttttccatag gctccgcccc cctgacaagc atcacgaaat 1320
ctgacgctca aatcagtggt ggcgaaaccc gacaggacta taaagatacc aggcgtttcc 1380
ccctggcggc tccctcgtgc gctctcctgt tcctgccttt cggtttaccg gtgtcattcc 1440
gctgttatgg ccgcgtttgt ctcattccac gcctgacact cagttccggg taggcagttc 1500
gctccaagct ggactgtatg cacgaacccc ccgttcagtc cgaccgctgc gccttatccg 1560
gtaactatcg tcttgagtcc aacccggaaa gacatgcaaa agcaccactg gcagcagcca 1620
ctggtaattg atttagagga gttagtcttg aagtcatgcg ccggttaagg ctaaactgaa 1680
aggacaagtt ttggtgactg cgctcctcca agccagttac ctcggttcaa agagttggta 1740
gctcagagaa ccttcgaaaa accgccctgc aaggcggttt tttcgttttc agagcaagag 1800
attacgcgca gaccaaaacg atctcaagaa gatcatctta ttaatcagat aaaatatttc 1860
tagatttcag tgcaatttat ctcttcaaat gtagcacctg aagtcagccc catacgatat 1920
aagttgttac tagtgcttgg attctcacca ataaaaaacg cccggcggca accgagcgtt 1980
ctgaacaaat ccagatggag ttctgaggtc attactggat ctatcaacag gagtccaagc 2040
gagctcgata tcaaattacg ccccgccctg ccactcatcg cagtactgtt gtaattcatt 2100
aagcattctg ccgacatgga agccatcaca aacggcatga tgaacctgaa tcgccagcgg 2160

```
catcagcacc ttgtcgcctt gcgtataata tttgcccatg gtgaaaacgg gggcgaagaa   2220

gttgtccata ttggccacgt ttaaatcaaa actggtgaaa ctcacccagg gattggctga   2280

gacgaaaaac atattctcaa taaacccttt agggaaatag gccaggtttt caccgtaaca   2340

cgccacatct tgcgaatata tgtgtagaaa ctgccggaaa tcgtcgtggt attcactcca   2400

gagcgatgaa aacgtttcag tttgctcatg gaaaacggtg taacaagggt gaacactatc   2460

ccatatcacc agctcaccgt ctttcattgc catacgaaat tccggatgag cattcatcag   2520

gcgggcaaga atgtgaataa aggccggata aaacttgtgc ttatttttct ttacggtctt   2580

taaaaaggcc gtaatatcca gctgaacggt ctggttatag gtacattgag caactgactg   2640

aaatgcctca aaatgttctt tacgatgcca ttgggatata tcaacggtgg tatatccagt   2700

gatttttttc tccattttag cttccttagc tcctgaaaat ctcgataact caaaaaatac   2760

gcccggtagt gatcttattt cattatggtg aaagttggaa cctcttacgt gccgatcaac   2820

gtctcatttt cgccagatat c                                              2841
```

```
<210> SEQ ID NO 17
<211> LENGTH: 2841
<212> TYPE: DNA
<213> ORGANISM: Artificial Sequence
<220> FEATURE:
<223> OTHER INFORMATION: pCASCADE-zwf Plasmid

<400> SEQUENCE: 17

gacgtcttaa gacccacttt cacatttaag ttgtttttct aatccgcata tgatcaattc     60

aaggccgaat aagaaggctg gctctgcacc ttggtgatca aataattcga tagcttgtcg    120

taataatggc ggcatactat cagtagtagg tgtttccctt tcttctttag cgacttgatg    180

ctcttgatct tccaatacgc aacctaaagt aaaatgcccc acagcgctga gtgcatataa    240

tgcattctct agtgaaaaac cttgttggca taaaaaggct aattgatttt cgagagtttc    300

atactgtttt tctgtaggcc gtgtacctaa atgtactttt gctccatcgc gatgacttag    360

taaagcacat ctaaaacttt tagcgttatt acgtaaaaaa tcttgccagc tttccccttc    420

taaagggcaa aagtgagtat ggtgcctatc taacatctca atggctaagg cgtcgagcaa    480

agcccgctta tttttttacat gccaatacaa tgtaggctgc tctacaccta gcttctgggc    540

gagtttacgg gttgttaaac cttcgattcc gacctcatta agcagctcta atgcgctgtt    600

aatcacttta cttttatcta atctagacat catccaggca tcaaataaaa cgaaaggctc    660

agtcgaaaga ctgggccttt cgttttatct gttgtttgtc ggtgaacgct ctctactaga    720

gtcacactgg ctcaccttcg ggtgggcctt tctgcgttta tacacagcta acaccacgtc    780

gtccctatct gctgccctag gtctatgagt ggttgctgga taactctttc tgacacctta    840

ctatcttaca aatgtaacaa aaaagttatt tttctgtaat tcgagcatgt catgttaccc    900

cgcgagcata aaacgcgtat attcagggag accacaacgg tttccctcta caaataattt    960

tgtttaactt tgaattcaaa agatctggta ccacctcgag ttccccgcgc cagcggggat   1020

aaaccgctcg taaaagcagt acagtgcacc gtaagatcga gttccccgcg ccagcgggga   1080

taaaccgaaa aaaaaacccc gcccctgaca gggcggggtt ttttttccta gggatatatt   1140

ccgcttcctc gctcactgac tcgctacgct cggtcgttcg actgcggcga gcggaaatgg   1200

cttacgaacg gggcggagat ttcctggaag atgccaggaa gatacttaac agggaagtga   1260

gagggccgcg gcaaagccgt ttttccatag gctccgcccc cctgacaagc atcacgaaat   1320
```

```
ctgacgctca aatcagtggt ggcgaaaccc gacaggacta taaagatacc aggcgtttcc   1380
ccctggcggc tccctcgtgc gctctcctgt tcctgccttt cggtttaccg gtgtcattcc   1440
gctgttatgg ccgcgtttgt ctcattccac gcctgacact cagttccggg taggcagttc   1500
gctccaagct ggactgtatg cacgaacccc ccgttcagtc cgaccgctgc gccttatccg   1560
gtaactatcg tcttgagtcc aacccggaaa gacatgcaaa agcaccactg gcagcagcca   1620
ctggtaattg atttagagga gttagtcttg aagtcatgcg ccggttaagg ctaaactgaa   1680
aggacaagtt ttggtgactg cgctcctcca agccagttac ctcggttcaa agagttggta   1740
gctcagagaa ccttcgaaaa accgccctgc aaggcggttt tttcgttttc agagcaagag   1800
attacgcgca gaccaaaacg atctcaagaa gatcatctta ttaatcagat aaaatatttc   1860
tagatttcag tgcaatttat ctcttcaaat gtagcacctg aagtcagccc catacgatat   1920
aagttgttac tagtgcttgg attctcacca ataaaaaacg cccggcggca accgagcgtt   1980
ctgaacaaat ccagatggag ttctgaggtc attactggat ctatcaacag gagtccaagc   2040
gagctcgata tcaaattacg ccccgccctg ccactcatcg cagtactgtt gtaattcatt   2100
aagcattctg ccgacatgga agccatcaca aacggcatga tgaacctgaa tcgccagcgg   2160
catcagcacc ttgtcgcctt gcgtataata tttgcccatg gtgaaaacgg gggcgaagaa   2220
gttgtccata ttggccacgt ttaaatcaaa actggtgaaa ctcacccagg gattggctga   2280
gacgaaaaac atattctcaa taaacccttt agggaaatag gccaggtttt caccgtaaca   2340
cgccacatct tgcgaatata tgtgtagaaa ctgccggaaa tcgtcgtggt attcactcca   2400
gagcgatgaa aacgtttcag tttgctcatg gaaaacggtg taacaagggt gaacactatc   2460
ccatatcacc agctcaccgt ctttcattgc catacgaaat tccggatgag cattcatcag   2520
gcgggcaaga atgtgaataa aggccggata aaacttgtgc ttatttttct ttacggtctt   2580
taaaaaggcc gtaatatcca gctgaacggt ctggttatag gtacattgag caactgactg   2640
aaatgcctca aaatgttctt tacgatgcca ttgggatata tcaacggtgg tatatccagt   2700
gatttttttc tccattttag cttccttagc tcctgaaaat ctcgataact caaaaaatac   2760
gcccggtagt gatcttattt cattatggtg aaagttggaa cctcttacgt gccgatcaac   2820
gtctcatttt cgccagatat c                                             2841
```

<210> SEQ ID NO 18
<211> LENGTH: 2842
<212> TYPE: DNA
<213> ORGANISM: Artificial Sequence
<220> FEATURE:
<223> OTHER INFORMATION: pCASCADE-gltA1 Plasmid

<400> SEQUENCE: 18

```
gacgtcttaa gacccacttt cacatttaag ttgtttttct aatccgcata tgatcaattc     60
aaggccgaat aagaaggctg gctctgcacc ttggtgatca aataattcga tagcttgtcg    120
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
```

```
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgaaaa gcatataatg cgtaaaagtt atgaagttcg agttccccgc gccagcgggg   1080
ataaaccgaa aaaaaaaccc cgcccctgac agggcggggt ttttttccct agggatatat   1140
tccgcttcct cgctcactga ctcgctacgc tcggtcgttc gactgcggcg agcggaaatg   1200
gcttacgaac ggggcggaga tttcctggaa gatgccagga agatacttaa cagggaagtg   1260
agagggccgc ggcaaagccg tttttccata ggctccgccc ccctgacaag catcacgaaa   1320
tctgacgctc aaatcagtgg tggcgaaacc cgacaggact ataaagatac caggcgtttc   1380
cccctggcgg ctccctcgtg cgctctcctg ttcctgcctt tcggtttacc ggtgtcattc   1440
cgctgttatg gccgcgtttg tctcattcca cgcctgacac tcagttccgg gtaggcagtt   1500
cgctccaagc tggactgtat gcacgaaccc cccgttcagt ccgaccgctg cgccttatcc   1560
ggtaactatc gtcttgagtc caacccggaa agacatgcaa aagcaccact ggcagcagcc   1620
actggtaatt gatttagagg agttagtctt gaagtcatgc gccggttaag gctaaactga   1680
aaggacaagt tttggtgact gcgctcctcc aagccagtta cctcggttca aagagttggt   1740
agctcagaga accttcgaaa aaccgccctg caaggcggtt ttttcgtttt cagagcaaga   1800
gattacgcgc agaccaaaac gatctcaaga agatcatctt attaatcaga taaaatattt   1860
ctagatttca gtgcaattta tctcttcaaa tgtagcacct gaagtcagcc ccatacgata   1920
taagttgtta ctagtgcttg gattctcacc aataaaaaac gcccggcggc aaccgagcgt   1980
tctgaacaaa tccagatgga gttctgaggt cattactgga tctatcaaca ggagtccaag   2040
cgagctcgat atcaaattac gccccgccct gccactcatc gcagtactgt tgtaattcat   2100
taagcattct gccgacatgg aagccatcac aaacggcatg atgaacctga atcgccagcg   2160
gcatcagcac cttgtcgcct tgcgtataat atttgcccat ggtgaaaacg ggggcgaaga   2220
agttgtccat attggccacg tttaaatcaa aactggtgaa actcacccag ggattggctg   2280
agacgaaaaa catattctca ataaaccctt tagggaaata ggccaggttt tcaccgtaac   2340
acgccacatc ttgcgaatat atgtgtagaa actgccggaa atcgtcgtgg tattcactcc   2400
agagcgatga aaacgtttca gtttgctcat ggaaaacggt gtaacaaggg tgaacactat   2460
cccatatcac cagctcaccg tctttcattg ccatacgaaa ttccggatga gcattcatca   2520
ggcgggcaag aatgtgaata aaggccggat aaaacttgtg cttatttttc tttacggtct   2580
ttaaaaaggc cgtaatatcc agctgaacgg tctggttata ggtacattga gcaactgact   2640
gaaatgcctc aaaatgttct ttacgatgcc attgggatat atcaacggtg gtatatccag   2700
tgattttttt ctccatttta gcttccttag ctcctgaaaa tctcgataac tcaaaaaata   2760
cgcccggtag tgatcttatt tcattatggt gaaagttgga acctcttacg tgccgatcaa   2820
cgtctcattt tcgccagata tc                                            2842
```

<210> SEQ ID NO 19
<211> LENGTH: 2903
<212> TYPE: DNA
<213> ORGANISM: Artificial Sequence
<220> FEATURE:
<223> OTHER INFORMATION: pCASCADE-gltA2-udhA Plasmid

<400> SEQUENCE: 19

```
gacgtcttaa gacccacttt cacatttaag ttgtttttct aatccgcata tgatcaattc      60
aaggccgaat aagaaggctg gctctgcacc ttggtgatca aataattcga tagcttgtcg     120
taataatggc ggcatactat cagtagtagg tgtttccctt tcttctttag cgacttgatg     180
ctcttgatct tccaatacgc aacctaaagt aaaatgcccc acagcgctga gtgcatataa     240
tgcattctct agtgaaaaac cttgttggca taaaaaggct aattgatttt cgagagtttc     300
atactgtttt tctgtaggcc gtgtacctaa atgtactttt gctccatcgc gatgacttag     360
taaagcacat ctaaaacttt tagcgttatt acgtaaaaaa tcttgccagc tttccccttc     420
taaagggcaa aagtgagtat ggtgcctatc taacatctca atggctaagg cgtcgagcaa     480
agcccgctta tttttacat gccaataaat gtaggctgct ctacacctag cttctgggcg     540
agtttacggg ttgttaaacc ttcgattccg acctcattaa gcagctctaa tgcgctgtta     600
atcactttac ttttatctaa tctagacatc atccaggcat caaataaaac gaaaggctca     660
gtcgaaagac tgggcctttc gttttatctg ttgtttgtcg gtgaacgctc tctactagag     720
tcacactggc tcaccttcgg gtgggccttt ctgcgtttat acacagctaa caccacgtcg     780
tccctatctg ctgccctagg tctatgagtg gttgctggat aactctttct gacaccttac     840
tatcttacaa atgtaacaaa aaagttattt ttctgtaatt cgagcatgtc atgttacccc     900
gcgagcataa aacgcgtata ttcagggaga ccacaacggt ttccctctac aaataatttt     960
gtttaacttt gaattcaaaa gatctggtac cacctcgagt tccccgcgcc agcggggata    1020
aaccgtattg accaattcat tcgggacagt tattagttcg agttccccgc gccagcgggg    1080
ataaaccgtt accattctgt tgcttttatg tataagaatc gagttccccg cgccagcggg    1140
gataaaccga aaaaaaaacc ccgcccctga cagggcgggg tttttttttcc tagggatata    1200
ttccgcttcc tcgctcactg actcgctacg ctcggtcgtt cgactgcggc gagcggaaat    1260
ggcttacgaa cggggcggag atttcctgga agatgccagg aagatactta acagggaagt    1320
gagagggccg cggcaaagcc gtttttccat aggctccgcc cccctgacaa gcatcacgaa    1380
atctgacgct caaatcagtg gtggcgaaac ccgacaggac tataaagata ccaggcgttt    1440
cccctggcg gctccctcgt gcgctctcct gttcctgcct ttcggtttac cggtgtcatt    1500
ccgctgttat ggccgcgttt gtctcattcc acgcctgaca ctcagttccg ggtaggcagt    1560
tcgctccaag ctggactgta tgcacgaacc ccccgttcag tccgaccgct gcgccttatc    1620
cggtaactat cgtcttgagt ccaacccgga aagacatgca aaagcaccac tggcagcagc    1680
cactggtaat tgatttagag gagttagtct tgaagtcatg cgccggttaa ggctaaactg    1740
aaaggacaag ttttggtgac tgcgctcctc caagccagtt acctcggttc aaagagttgg    1800
tagctcagag aaccttcgaa aaaccgccct gcaaggcggt tttttcgttt tcagagcaag    1860
agattacgcg cagaccaaaa cgatctcaag aagatcatct tattaatcag ataaaatatt    1920
tctagatttc agtgcaattt atctcttcaa atgtagcacc tgaagtcagc cccatacgat    1980
ataagttgtt actagtgctt ggattctcac caataaaaaa cgcccggcgg caaccgagcg    2040
ttctgaacaa atccagatgg agttctgagg tcattactgg atctatcaac aggagtccaa    2100
```

```
gcgagctcga tatcaaatta cgccccgccc tgccactcat cgcagtactg ttgtaattca   2160
ttaagcattc tgccgacatg gaagccatca caaacggcat gatgaacctg aatcgccagc   2220
ggcatcagca ccttgtcgcc ttgcgtataa tatttgccca tggtgaaaac gggggcgaag   2280
aagttgtcca tattggccac gtttaaatca aaactggtga aactcaccca gggattggct   2340
gagacgaaaa acatattctc aataaaccct ttagggaaat aggccaggtt ttcaccgtaa   2400
cacgccacat cttgcgaata tatgtgtaga aactgccgga aatcgtcgtg gtattcactc   2460
cagagcgatg aaaacgtttc agtttgctca tggaaaacgg tgtaacaagg gtgaacacta   2520
tcccatatca ccagctcacc gtctttcatt gccatacgaa attccggatg agcattcatc   2580
aggcgggcaa gaatgtgaat aaaggccgga taaaacttgt gcttattttt ctttacggtc   2640
tttaaaaagg ccgtaatatc cagctgaacg gtctggttat aggtacattg agcaactgac   2700
tgaaatgcct caaaatgttc tttacgatgc cattgggata tatcaacggt ggtatatcca   2760
gtgatttttt tctccatttt agcttcctta gctcctgaaa atctcgataa ctcaaaaaat   2820
acgcccggta gtgatcttat ttcattatgg tgaaagttgg aacctcttac gtgccgatca   2880
acgtctcatt ttcgccagat atc                                           2903
```

<210> SEQ ID NO 20
<211> LENGTH: 2902
<212> TYPE: DNA
<213> ORGANISM: Artificial Sequence
<220> FEATURE:
<223> OTHER INFORMATION: pCASCADE-fabI-udhA Plasmid

<400> SEQUENCE: 20

```
gacgtcttaa gacccacttt cacatttaag ttgtttttct aatccgcata tgatcaattc     60
aaggccgaat aagaaggctg gctctgcacc ttggtgatca aataattcga tagcttgtcg    120
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta tttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgttga ttataataac cgtttatctg ttcgtatcga gttccccgcg ccagcgggga   1080
taaaccgtta ccattctgtt gcttttatgt ataagaatcg agttccccgc gccagcgggg   1140
ataaaccgaa aaaaaaaccc cgcccctgac agggcggggt tttttttcct agggatatat   1200
```

```
tccgcttcct cgctcactga ctcgctacgc tcggtcgttc gactgcggcg agcggaaatg   1260

gcttacgaac ggggcggaga tttcctggaa gatgccagga agatacttaa cagggaagtg   1320

agagggccgc ggcaaagccg tttttccata ggctccgccc ccctgacaag catcacgaaa   1380

tctgacgctc aaatcagtgg tggcgaaacc cgacaggact ataaagatac caggcgtttc   1440

cccctggcgg ctccctcgtg cgctctcctg ttcctgcctt tcggtttacc ggtgtcattc   1500

cgctgttatg gccgcgtttg tctcattcca cgcctgacac tcagttccgg gtaggcagtt   1560

cgctccaagc tggactgtat gcacgaaccc cccgttcagt ccgaccgctg cgccttatcc   1620

ggtaactatc gtcttgagtc caacccggaa agacatgcaa aagcaccact ggcagcagcc   1680

actggtaatt gatttagagg agttagtctt gaagtcatgc gccggttaag gctaaactga   1740

aaggacaagt tttggtgact gcgctcctcc aagccagtta cctcggttca aagagttggt   1800

agctcagaga accttcgaaa aaccgccctg caaggcggtt ttttcgtttt cagagcaaga   1860

gattacgcgc agaccaaaac gatctcaaga agatcatctt attaatcaga taaaatattt   1920

ctagatttca gtgcaattta tctcttcaaa tgtagcacct gaagtcagcc ccatacgata   1980

taagttgtta ctagtgcttg gattctcacc aataaaaaac gcccggcggc aaccgagcgt   2040

tctgaacaaa tccagatgga gttctgaggt cattactgga tctatcaaca ggagtccaag   2100

cgagctcgat atcaaattac gccccgccct gccactcatc gcagtactgt tgtaattcat   2160

taagcattct gccgacatgg aagccatcac aaacggcatg atgaacctga atcgccagcg   2220

gcatcagcac cttgtcgcct tgcgtataat atttgcccat ggtgaaaacg ggggcgaaga   2280

agttgtccat attggccacg tttaaatcaa aactggtgaa actcacccag ggattggctg   2340

agacgaaaaa catattctca ataaaccctt tagggaaata ggccaggttt tcaccgtaac   2400

acgccacatc ttgcgaatat atgtgtagaa actgccggaa atcgtcgtgg tattcactcc   2460

agagcgatga aaacgtttca gtttgctcat ggaaaacggt gtaacaaggg tgaacactat   2520

cccatatcac cagctcaccg tctttcattg ccatacgaaa ttccggatga gcattcatca   2580

ggcgggcaag aatgtgaata aaggccggat aaaacttgtg cttatttttc tttacggtct   2640

ttaaaaaggc cgtaatatcc agctgaacgg tctggttata ggtacattga gcaactgact   2700

gaaatgcctc aaaatgttct ttacgatgcc attgggatat atcaacggtg gtatatccag   2760

tgattttttt ctccatttta gcttccttag ctcctgaaaa tctcgataac tcaaaaaata   2820

cgcccggtag tgatcttatt tcattatggt gaaagttgga acctcttacg tgccgatcaa   2880

cgtctcattt tcgccagata tc                                             2902
```

<210> SEQ ID NO 21
<211> LENGTH: 2903
<212> TYPE: DNA
<213> ORGANISM: Artificial Sequence
<220> FEATURE:
<223> OTHER INFORMATION: pCASCADE-fabI-gltA1 Plasmid

<400> SEQUENCE: 21

```
gacgtcttaa gacccacttt cacatttaag ttgtttttct aatccgcata tgatcaattc     60

aaggccgaat aagaaggctg gctctgcacc ttggtgatca aataattcga tagcttgtcg    120

taataatggc ggcatactat cagtagtagg tgtttccctt tcttctttag cgacttgatg    180

ctcttgatct tccaatacgc aacctaaagt aaaatgcccc acagcgctga gtgcatataa    240

tgcattctct agtgaaaaac cttgttggca taaaaaggct aattgatttt cgagagtttc    300

atactgtttt tctgtaggcc gtgtacctaa atgtactttt gctccatcgc gatgacttag    360
```

```
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgttga ttataataac cgtttatctg ttcgtatcga gttccccgcg ccagcgggga   1080
taaaccgaaa agcatataat gcgtaaaagt tatgaagttc gagttccccg cgccagcggg   1140
gataaaccga aaaaaaaacc ccgcccctga cagggcgggg ttttttttcc tagggatata   1200
ttccgcttcc tcgctcactg actcgctacg ctcggtcgtt cgactgcggc gagcggaaat   1260
ggcttacgaa cggggcggag atttcctgga agatgccagg aagatactta acagggaagt   1320
gagagggccg cggcaaagcc gtttttccat aggctccgcc cccctgacaa gcatcacgaa   1380
atctgacgct caaatcagtg gtggcgaaac ccgacaggac tataaagata ccaggcgttt   1440
ccccctggcg gctccctcgt gcgctctcct gttcctgcct ttcggtttac cggtgtcatt   1500
ccgctgttat ggccgcgttt gtctcattcc acgcctgaca ctcagttccg ggtaggcagt   1560
tcgctccaag ctggactgta tgcacgaacc ccccgttcag tccgaccgct gcgccttatc   1620
cggtaactat cgtcttgagt ccaacccgga aagacatgca aaagcaccac tggcagcagc   1680
cactggtaat tgatttagag gagttagtct tgaagtcatg cgccggttaa ggctaaactg   1740
aaaggacaag ttttggtgac tgcgctcctc caagccagtt acctcggttc aaagagttgg   1800
tagctcagag aaccttcgaa aaaccgccct gcaaggcggt tttttcgttt tcagagcaag   1860
agattacgcg cagaccaaaa cgatctcaag aagatcatct tattaatcag ataaaatatt   1920
tctagatttc agtgcaattt atctcttcaa atgtagcacc tgaagtcagc cccatacgat   1980
ataagttgtt actagtgctt ggattctcac caataaaaaa cgcccggcgg caaccgagcg   2040
ttctgaacaa atccagatgg agttctgagg tcattactgg atctatcaac aggagtccaa   2100
gcgagctcga tatcaaatta cgccccgccc tgccactcat cgcagtactg ttgtaattca   2160
ttaagcattc tgccgacatg gaagccatca caaacggcat gatgaacctg aatcgccagc   2220
ggcatcagca ccttgtcgcc ttgcgtataa tatttgccca tggtgaaaac gggggcgaag   2280
aagttgtcca tattggccac gtttaaatca aaactggtga aactcaccca gggattggct   2340
gagacgaaaa acatattctc aataaaccct ttagggaaat aggccaggtt ttcaccgtaa   2400
cacgccacat cttgcgaata tatgtgtaga aactgccgga aatcgtcgtg gtattcactc   2460
cagagcgatg aaaacgtttc agtttgctca tggaaaacgg tgtaacaagg gtgaacacta   2520
tcccatatca ccagctcacc gtctttcatt gccatacgaa attccggatg agcattcatc   2580
aggcgggcaa gaatgtgaat aaaggccgga taaaacttgt gcttattttt ctttacggtc   2640
tttaaaaagg ccgtaatatc cagctgaacg gtctggttat aggtacattg agcaactgac   2700
```

tgaaatgcct caaaatgttc tttacgatgc cattgggata tatcaacggt ggtatatcca 2760
gtgatttttt tctccatttt agcttcctta gctcctgaaa atctcgataa ctcaaaaaat 2820
acgcccggta gtgatcttat ttcattatgg tgaaagttgg aacctcttac gtgccgatca 2880
acgtctcatt ttcgccagat atc 2903

<210> SEQ ID NO 22
<211> LENGTH: 2904
<212> TYPE: DNA
<213> ORGANISM: Artificial Sequence
<220> FEATURE:
<223> OTHER INFORMATION: pCASCADE-fabI-gltA2 Plasmid

<400> SEQUENCE: 22
gacgtcttaa gacccacttt cacatttaag ttgtttttct aatccgcata tgatcaattc 60
aaggccgaat aagaaggctg gctctgcacc ttggtgatca aataattcga tagcttgtcg 120
taataatggc ggcatactat cagtagtagg tgtttccctt tcttctttag cgacttgatg 180
ctcttgatct tccaatacgc aacctaaagt aaaatgcccc acagcgctga gtgcatataa 240
tgcattctct agtgaaaaac cttgttggca taaaaaggct aattgatttt cgagagtttc 300
atactgtttt tctgtaggcc gtgtacctaa atgtactttt gctccatcgc gatgacttag 360
taaagcacat ctaaaacttt tagcgttatt acgtaaaaaa tcttgccagc tttccccttc 420
taaagggcaa aagtgagtat ggtgcctatc taacatctca atggctaagg cgtcgagcaa 480
agcccgctta tttttacat gccaatacaa tgtaggctgc tctacaccta gcttctgggc 540
gagtttacgg gttgttaaac cttcgattcc gacctcatta agcagctcta atgcgctgtt 600
aatcacttta cttttatcta atctagacat catccaggca tcaaataaaa cgaaaggctc 660
agtcgaaaga ctgggccttt cgttttatct gttgtttgtc ggtgaacgct ctctactaga 720
gtcacactgg ctcaccttcg ggtgggcctt tctgcgttta tacacagcta acaccacgtc 780
gtccctatct gctgccctag gtctatgagt ggttgctgga taactctttc tgacacctta 840
ctatcttaca aatgtaacaa aaaagttatt tttctgtaat tcgagcatgt catgttaccc 900
cgcgagcata aaacgcgtat attcagggag accacaacgg tttccctcta caaataattt 960
tgtttaactt tgaattcaaa agatctggta ccacctcgag ttccccgcgc cagcggggat 1020
aaaccgttga ttataataac cgtttatctg ttcgtatcga gttccccgcg ccagcgggga 1080
taaaccgtat tgaccaattc attcgggaca gttattagtt cgagttcccc gcgccagcgg 1140
ggataaaccg aaaaaaaaac ccgccccctg acagggcggg gtttttttc ctagggatat 1200 attccgcttc ctcgctcact gactcgctac gctcggtcgt tcgactgcgg cgagcggaaa 1260
tggcttacga acggggcgga gatttcctgg aagatgccag gaagatactt aacagggaag 1320
tgagagggcc gcggcaaagc cgtttttcca taggctccgc ccccctgaca agcatcacga 1380
aatctgacgc tcaaatcagt ggtggcgaaa cccgacagga ctataaagat accaggcgtt 1440
tccccctggc ggctccctcg tgcgctctcc tgttcctgcc tttcggttta ccggtgtcat 1500
tccgctgtta tggccgcgtt tgtctcattc cacgcctgac actcagttcc gggtaggcag 1560
ttcgctccaa gctggactgt atgcacgaac cccccgttca gtccgaccgc tgcgccttat 1620
ccggtaacta tcgtcttgag tccaacccgg aaagacatgc aaaagcacca ctggcagcag 1680
ccactggtaa ttgatttaga ggagttagtc ttgaagtcat gcgccggtta aggctaaact 1740
gaaaggacaa gttttggtga ctgcgctcct ccaagccagt tacctcggtt caaagagttg 1800
gtagctcaga gaaccttcga aaaaccgccc tgcaaggcgg tttttcgtt ttcagagcaa 1860 gagattacgc gcagaccaaa acgatctcaa gaagatcatc ttattaatca gataaaatat 1920
ttctagattt cagtgcaatt tatctcttca aatgtagcac ctgaagtcag ccccatacga 1980
tataagttgt tactagtgct tggattctca ccaataaaaa acgcccggcg gcaaccgagc 2040
gttctgaaca aatccagatg gagttctgag gtcattactg gatctatcaa caggagtcca 2100
agcgagctcg atatcaaatt acgccccgcc ctgccactca tcgcagtact gttgtaattc 2160
attaagcatt ctgccgacat ggaagccatc acaaacggca tgatgaacct gaatcgccag 2220
cggcatcagc accttgtcgc cttgcgtata atatttgccc atggtgaaaa cgggggcgaa 2280
gaagttgtcc atattggcca cgtttaaatc aaaactggtg aaactcaccc agggattggc 2340
tgagacgaaa aacatattct caataaaccc tttagggaaa taggccaggt tttcaccgta 2400
acacgccaca tcttgcgaat atatgtgtag aaactgccgg aaatcgtcgt ggtattcact 2460
ccagagcgat gaaaacgttt cagtttgctc atggaaaacg gtgtaacaag ggtgaacact 2520
atcccatatc accagctcac cgtctttcat tgccatacga aattccggat gagcattcat 2580
caggcgggca agaatgtgaa taaaggccgg ataaaacttg tgcttatttt tctttacggt 2640
ctttaaaaag gccgtaatat ccagctgaac ggtctggtta taggtacatt gagcaactga 2700
ctgaaatgcc tcaaaatgtt ctttacgatg ccattgggat atatcaacgg tggtatatcc 2760
agtgattttt ttctccattt tagcttcctt agctcctgaa aatctcgata actcaaaaaa 2820
tacgcccggt agtgatctta tttcattatg gtgaaagttg gaacctctta cgtgccgatc 2880
aacgtctcat tttcgccaga tatc 2904

<210> SEQ ID NO 23
<211> LENGTH: 2902
<212> TYPE: DNA
<213> ORGANISM: Artificial Sequence
<220> FEATURE:
<223> OTHER INFORMATION: pCASCADE-fabI-zwf Plasmid

<400> SEQUENCE: 23
gacgtcttaa gacccacttt cacatttaag ttgtttttct aatccgcata tgatcaattc 60
aaggccgaat aagaaggctg gctctgcacc ttggtgatca aataattcga tagcttgtcg 120
taataatggc ggcatactat cagtagtagg tgtttccctt tcttctttag cgacttgatg 180
ctcttgatct tccaatacgc aacctaaagt aaaatgcccc acagcgctga gtgcatataa 240
tgcattctct agtgaaaaac cttgttggca taaaaaggct aattgatttt cgagagtttc 300
atactgtttt tctgtaggcc gtgtacctaa atgtactttt gctccatcgc gatgacttag 360
taaagcacat ctaaaacttt tagcgttatt acgtaaaaaa tcttgccagc tttccccttc 420
taaagggcaa aagtgagtat ggtgcctatc taacatctca atggctaagg cgtcgagcaa 480
agcccgctta tttttacat gccaatacaa tgtaggctgc tctacaccta gcttctgggc 540
gagtttacgg gttgttaaac cttcgattcc gacctcatta agcagctcta atgcgctgtt 600
aatcacttta cttttatcta atctagacat catccaggca tcaaataaaa cgaaaggctc 660
agtcgaaaga ctgggccttt cgttttatct gttgtttgtc ggtgaacgct ctctactaga 720
gtcacactgg ctcaccttcg ggtgggcctt tctgcgttta tacacagcta acaccacgtc 780
gtccctatct gctgccctag gtctatgagt ggttgctgga taactctttc tgacacctta 840
ctatcttaca aatgtaacaa aaaagttatt tttctgtaat tcgagcatgt catgttaccc 900
cgcgagcata aaacgcgtat attcagggag accacaacgg tttccctcta caaataattt 960

```
tgtttaactt tgaattcaaa agatctggta ccacctcgag ttccccgcgc cagcggggat   1020

aaaccgttga ttataataac cgtttatctg ttcgtatcga gttccccgcg ccagcgggga   1080

taaaccgctc gtaaaagcag tacagtgcac cgtaagatcg agttccccgc gccagcgggg   1140

ataaaccgaa aaaaaaaccc cgcccctgac agggcggggt ttttttttcct agggatatat   1200

tccgcttcct cgctcactga ctcgctacgc tcggtcgttc gactgcggcg agcggaaatg   1260

gcttacgaac ggggcggaga tttcctggaa gatgccagga agatacttaa cagggaagtg   1320

agagggccgc ggcaaagccg tttttccata ggctccgccc ccctgacaag catcacgaaa   1380

tctgacgctc aaatcagtgg tggcgaaacc cgacaggact ataaagatac caggcgtttc   1440

cccctggcgg ctccctcgtg cgctctcctg ttcctgcctt tcggtttacc ggtgtcattc   1500

cgctgttatg gccgcgtttg tctcattcca cgcctgacac tcagttccgg gtaggcagtt   1560

cgctccaagc tggactgtat gcacgaaccc cccgttcagt ccgaccgctg cgccttatcc   1620

ggtaactatc gtcttgagtc caacccggaa agacatgcaa aagcaccact ggcagcagcc   1680

actggtaatt gatttagagg agttagtctt gaagtcatgc gccggttaag gctaaactga   1740

aaggacaagt tttggtgact gcgctcctcc aagccagtta cctcggttca aagagttggt   1800

agctcagaga accttcgaaa aaccgccctg caaggcggtt ttttcgtttt cagagcaaga   1860

gattacgcgc agaccaaaac gatctcaaga agatcatctt attaatcaga taaaatattt   1920

ctagatttca gtgcaattta tctcttcaaa tgtagcacct gaagtcagcc ccatacgata   1980

taagttgtta ctagtgcttg gattctcacc aataaaaaac gcccggcggc aaccgagcgt   2040

tctgaacaaa tccagatgga gttctgaggt cattactgga tctatcaaca ggagtccaag   2100

cgagctcgat atcaaattac gccccgccct gccactcatc gcagtactgt tgtaattcat   2160

taagcattct gccgacatgg aagccatcac aaacggcatg atgaacctga atcgccagcg   2220

gcatcagcac cttgtcgcct tgcgtataat atttgcccat ggtgaaaacg ggggcgaaga   2280

agttgtccat attggccacg tttaaatcaa aactggtgaa actcacccag ggattggctg   2340

agacgaaaaa catattctca ataaaccctt tagggaaata ggccaggttt tcaccgtaac   2400

acgccacatc ttgcgaatat atgtgtagaa actgccggaa atcgtcgtgg tattcactcc   2460

agagcgatga aaacgtttca gtttgctcat ggaaaacggt gtaacaaggg tgaacactat   2520

cccatatcac cagctcaccg tctttcattg ccatacgaaa ttccggatga gcattcatca   2580

ggcgggcaag aatgtgaata aaggccggat aaaacttgtg cttatttttc tttacggtct   2640

ttaaaaaggc cgtaatatcc agctgaacgg tctggttata ggtacattga gcaactgact   2700

gaaatgcctc aaaatgttct ttacgatgcc attgggatat atcaacggtg gtatatccag   2760

tgattttttt ctccatttta gcttccttag ctcctgaaaa tctcgataac tcaaaaaata   2820

cgcccggtag tgatcttatt tcattatggt gaaagttgga acctcttacg tgccgatcaa   2880

cgtctcattt tcgccagata tc                                             2902
```

```
<210> SEQ ID NO 24
<211> LENGTH: 2903
<212> TYPE: DNA
<213> ORGANISM: Artificial Sequence
<220> FEATURE:
<223> OTHER INFORMATION: pCASCADE-gltA1-udhA Plasmid

<400> SEQUENCE: 24

gacgtcttaa gacccacttt cacatttaag ttgtttttct aatccgcata tgatcaattc     60

aaggccgaat aagaaggctg gctctgcacc ttggtgatca aataattcga tagcttgtcg    120
```

```
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta tttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgaaaa gcatataatg cgtaaaagtt atgaagttcg agttccccgc gccagcgggg   1080
ataaaccgtt accattctgt tgcttttatg tataagaatc gagttccccg cgccagcggg   1140
gataaaccga aaaaaaaacc ccgcccctga cagggcgggg tttttttcc tagggatata   1200
ttccgcttcc tcgctcactg actcgctacg ctcggtcgtt cgactgcggc gagcggaaat   1260
ggcttacgaa cggggcggag atttcctgga agatgccagg aagatactta acagggaagt   1320
gagagggccg cggcaaagcc gtttttccat aggctccgcc cccctgacaa gcatcacgaa   1380
atctgacgct caaatcagtg gtggcgaaac ccgacaggac tataaagata ccaggcgttt   1440
cccctggcg gctccctcgt gcgctctcct gttcctgcct ttcggtttac cggtgtcatt   1500
ccgctgttat ggccgcgttt gtctcattcc acgcctgaca ctcagttccg ggtaggcagt   1560
tcgctccaag ctggactgta tgcacgaacc ccccgttcag tccgaccgct gcgccttatc   1620
cggtaactat cgtcttgagt ccaacccgga aagacatgca aaagcaccac tggcagcagc   1680
cactggtaat tgatttagag gagttagtct tgaagtcatg cgccggttaa ggctaaactg   1740
aaaggacaag ttttggtgac tgcgctcctc caagccagtt acctcggttc aaagagttgg   1800
tagctcagag aaccttcgaa aaaccgccct gcaaggcggt tttttcgttt tcagagcaag   1860
agattacgcg cagaccaaaa cgatctcaag aagatcatct tattaatcag ataaaatatt   1920
tctagatttc agtgcaattt atctcttcaa atgtagcacc tgaagtcagc cccatacgat   1980
ataagttgtt actagtgctt ggattctcac caataaaaaa cgcccggcgg caaccgagcg   2040
ttctgaacaa atccagatgg agttctgagg tcattactgg atctatcaac aggagtccaa   2100
gcgagctcga tatcaaatta cgccccgccc tgccactcat cgcagtactg ttgtaattca   2160
ttaagcattc tgccgacatg gaagccatca caaacggcat gatgaacctg aatcgccagc   2220
ggcatcagca ccttgtcgcc ttgcgtataa tatttgccca tggtgaaaac gggggcgaag   2280
aagttgtcca tattggccac gtttaaatca aaactggtga aactcaccca gggattggct   2340
gagacgaaaa acatattctc aataaaccct ttagggaaat aggccaggtt ttcaccgtaa   2400
cacgccacat cttgcgaata tatgtgtaga aactgccgga aatcgtcgtg gtattcactc   2460
```

```
cagagcgatg aaaacgtttc agtttgctca tggaaaacgg tgtaacaagg gtgaacacta   2520

tcccatatca ccagctcacc gtctttcatt gccatacgaa attccggatg agcattcatc   2580

aggcgggcaa gaatgtgaat aaaggccgga taaaacttgt gcttattttt ctttacggtc   2640

tttaaaaagg ccgtaatatc cagctgaacg gtctggttat aggtacattg agcaactgac   2700

tgaaatgcct caaaatgttc tttacgatgc cattgggata tatcaacggt ggtatatcca   2760

gtgatttttt tctccatttt agcttcctta gctcctgaaa atctcgataa ctcaaaaaat   2820

acgcccggta gtgatcttat ttcattatgg tgaaagttgg aacctcttac gtgccgatca   2880

acgtctcatt ttcgccagat atc                                           2903
```

<210> SEQ ID NO 25
<211> LENGTH: 2904
<212> TYPE: DNA
<213> ORGANISM: Artificial Sequence
<220> FEATURE:
<223> OTHER INFORMATION: pCASCADE-gltA2-udhA Plasmid

<400> SEQUENCE: 25

```
gacgtcttaa gacccacttt cacatttaag ttgtttttct aatccgcata tgatcaattc     60

aaggccgaat aagaaggctg gctctgcacc ttggtgatca aataattcga tagcttgtcg    120

taataatggc ggcatactat cagtagtagg tgtttccctt tcttctttag cgacttgatg    180

ctcttgatct tccaatacgc aacctaaagt aaaatgcccc acagcgctga gtgcatataa    240

tgcattctct agtgaaaaac cttgttggca taaaaaggct aattgatttt cgagagtttc    300

atactgtttt tctgtaggcc gtgtacctaa atgtactttt gctccatcgc gatgacttag    360

taaagcacat ctaaaacttt tagcgttatt acgtaaaaaa tcttgccagc tttccccttc    420

taaagggcaa aagtgagtat ggtgcctatc taacatctca atggctaagg cgtcgagcaa    480

agcccgctta tttttacat gccaatacaa tgtaggctgc tctacaccta gcttctgggc    540

gagtttacgg gttgttaaac cttcgattcc gacctcatta agcagctcta atgcgctgtt    600

aatcacttta cttttatcta atctagacat catccaggca tcaaataaaa cgaaaggctc    660

agtcgaaaga ctgggccttt cgttttatct gttgtttgtc ggtgaacgct ctctactaga    720

gtcacactgg ctcaccttcg ggtgggcctt tctgcgttta tacacagcta acaccacgtc    780

gtccctatct gctgccctag gtctatgagt ggttgctgga taactctttc tgacacctta    840

ctatcttaca aatgtaacaa aaaagttatt tttctgtaat tcgagcatgt catgttaccc    900

cgcgagcata aaacgcgtat attcagggag accacaacgg tttccctcta caaataattt    960

tgtttaactt tgaattcaaa agatctggta ccacctcgag ttccccgcgc cagcggggat   1020

aaaccgtatt gaccaattca ttcgggacag ttattagttc gagttccccg cgccagcggg   1080

gataaaccgt taccattctg ttgcttttat gtataagaat cgagttcccc gcgccagcgg   1140

ggataaaccg aaaaaaaaac cccgcccctg acagggcggg gttttttttc ctagggatat   1200

attccgcttc ctcgctcact gactcgctac gctcggtcgt tcgactgcgg cgagcggaaa   1260

tggcttacga acggggcgga gatttcctgg aagatgccag gaagatactt aacagggaag   1320

tgagagggcc gcggcaaagc cgtttttcca taggctccgc ccccctgaca agcatcacga   1380

aatctgacgc tcaaatcagt ggtggcgaaa cccgacagga ctataaagat accaggcgtt   1440

tcccccctggc ggctccctcg tgcgctctcc tgttcctgcc tttcggttta ccggtgtcat   1500

tccgctgtta tggccgcgtt tgtctcattc cacgcctgac actcagttcc gggtaggcag   1560

ttcgctccaa gctggactgt atgcacgaac cccccgttca gtccgaccgc tgcgccttat   1620
```

ccggtaacta tcgtcttgag tccaacccgg aaagacatgc aaaagcacca ctggcagcag 1680
ccactggtaa ttgatttaga ggagttagtc ttgaagtcat gcgccggtta aggctaaact 1740
gaaaggacaa gttttggtga ctgcgctcct ccaagccagt tacctcggtt caaagagttg 1800
gtagctcaga gaaccttcga aaaaccgccc tgcaaggcgg ttttttcgtt ttcagagcaa 1860
gagattacgc gcagaccaaa acgatctcaa gaagatcatc ttattaatca gataaaatat 1920
ttctagattt cagtgcaatt tatctcttca aatgtagcac ctgaagtcag ccccatacga 1980
tataagttgt tactagtgct tggattctca ccaataaaaa acgcccggcg gcaaccgagc 2040
gttctgaaca aatccagatg gagttctgag gtcattactg gatctatcaa caggagtcca 2100
agcgagctcg atatcaaatt acgccccgcc ctgccactca tcgcagtact gttgtaattc 2160
attaagcatt ctgccgacat ggaagccatc acaaacggca tgatgaacct gaatcgccag 2220
cggcatcagc accttgtcgc cttgcgtata atatttgccc atggtgaaaa cgggggcgaa 2280
gaagttgtcc atattggcca cgtttaaatc aaaactggtg aaactcaccc agggattggc 2340
tgagacgaaa aacatattct caataaaccc tttagggaaa taggccaggt tttcaccgta 2400
acacgccaca tcttgcgaat atatgtgtag aaactgccgg aaatcgtcgt ggtattcact 2460
ccagagcgat gaaaacgttt cagtttgctc atggaaaacg gtgtaacaag ggtgaacact 2520
atcccatatc accagctcac cgtctttcat tgccatacga aattccggat gagcattcat 2580
caggcgggca agaatgtgaa taaaggccgg ataaaacttg tgcttatttt tctttacggt 2640
ctttaaaaag gccgtaatat ccagctgaac ggtctggtta taggtacatt gagcaactga 2700
ctgaaatgcc tcaaaatgtt ctttacgatg ccattgggat atatcaacgg tggtatatcc 2760
agtgattttt ttctccattt tagcttcctt agctcctgaa aatctcgata actcaaaaaa 2820
tacgcccggt agtgatctta tttcattatg gtgaaagttg gaacctctta cgtgccgatc 2880
aacgtctcat tttcgccaga tatc 2904

<210> SEQ ID NO 26
<211> LENGTH: 2903
<212> TYPE: DNA
<213> ORGANISM: Artificial Sequence
<220> FEATURE:
<223> OTHER INFORMATION: pCASCADE-gltA1-zwf Plasmid

<400> SEQUENCE: 26
gacgtcttaa gacccacttt cacatttaag ttgtttttct aatccgcata tgatcaattc 60
aaggccgaat aagaaggctg gctctgcacc ttggtgatca aataattcga tagcttgtcg 120
taataatggc ggcatactat cagtagtagg tgtttccctt tcttctttag cgacttgatg 180
ctcttgatct tccaatacgc aacctaaagt aaaatgcccc acagcgctga gtgcatataa 240
tgcattctct agtgaaaaac cttgttggca taaaaaggct aattgatttt cgagagtttc 300
atactgtttt tctgtaggcc gtgtacctaa atgtactttt gctccatcgc gatgacttag 360
taaagcacat ctaaaacttt tagcgttatt acgtaaaaaa tcttgccagc tttccccttc 420
taaagggcaa aagtgagtat ggtgcctatc taacatctca atggctaagg cgtcgagcaa 480
agcccgctta ttttttacat gccaatacaa tgtaggctgc tctacaccta gcttctgggc 540
gagtttacgg gttgttaaac cttcgattcc gacctcatta agcagctcta atgcgctgtt 600
aatcacttta cttttatcta atctagacat catccaggca tcaaataaaa cgaaaggctc 660
agtcgaaaga ctgggccttt cgttttatct gttgtttgtc ggtgaacgct ctctactaga 720

```
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgaaaa gcatataatg cgtaaaagtt atgaagttcg agttccccgc gccagcgggg   1080
ataaaccgct cgtaaaagca gtacagtgca ccgtaagatc gagttccccg cgccagcggg   1140
gataaaccga aaaaaaaacc ccgcccctga cagggcgggg ttttttttcc tagggatata   1200
ttccgcttcc tcgctcactg actcgctacg ctcggtcgtt cgactgcggc gagcggaaat   1260
ggcttacgaa cggggcggag atttcctgga agatgccagg aagatactta acagggaagt   1320
gagagggccg cggcaaagcc gtttttccat aggctccgcc cccctgacaa gcatcacgaa   1380
atctgacgct caaatcagtg gtggcgaaac ccgacaggac tataaagata ccaggcgttt   1440
cccctggcg gctccctcgt gcgctctcct gttcctgcct ttcggtttac cggtgtcatt   1500
ccgctgttat ggccgcgttt gtctcattcc acgcctgaca ctcagttccg ggtaggcagt   1560
tcgctccaag ctggactgta tgcacgaacc ccccgttcag tccgaccgct gcgccttatc   1620
cggtaactat cgtcttgagt ccaacccgga aagacatgca aaagcaccac tggcagcagc   1680
cactggtaat tgatttagag gagttagtct tgaagtcatg cgccggttaa ggctaaactg   1740
aaaggacaag ttttggtgac tgcgctcctc caagccagtt acctcggttc aaagagttgg   1800
tagctcagag aaccttcgaa aaaccgccct gcaaggcggt tttttcgttt tcagagcaag   1860
agattacgcg cagaccaaaa cgatctcaag aagatcatct tattaatcag ataaaatatt   1920
tctagatttc agtgcaattt atctcttcaa atgtagcacc tgaagtcagc cccatacgat   1980
ataagttgtt actagtgctt ggattctcac caataaaaaa cgcccggcgg caaccgagcg   2040
ttctgaacaa atccagatgg agttctgagg tcattactgg atctatcaac aggagtccaa   2100
gcgagctcga tatcaaatta cgccccgccc tgccactcat cgcagtactg ttgtaattca   2160
ttaagcattc tgccgacatg gaagccatca caaacggcat gatgaacctg aatcgccagc   2220
ggcatcagca ccttgtcgcc ttgcgtataa tatttgccca tggtgaaaac gggggcgaag   2280
aagttgtcca tattggccac gtttaaatca aaactggtga aactcaccca gggattggct   2340
gagacgaaaa acatattctc aataaaccct ttagggaaat aggccaggtt ttcaccgtaa   2400
cacgccacat cttgcgaata tatgtgtaga aactgccgga aatcgtcgtg gtattcactc   2460
cagagcgatg aaaacgtttc agtttgctca tggaaaacgg tgtaacaagg gtgaacacta   2520
tcccatatca ccagctcacc gtctttcatt gccatacgaa attccggatg agcattcatc   2580
aggcgggcaa gaatgtgaat aaaggccgga taaaacttgt gcttattttt ctttacggtc   2640
tttaaaaagg ccgtaatatc cagctgaacg gtctggttat aggtacattg agcaactgac   2700
tgaaatgcct caaaatgttc tttacgatgc cattgggata tatcaacggt ggtatatcca   2760
gtgatttttt tctccatttt agcttcctta gctcctgaaa atctcgataa ctcaaaaaat   2820
acgcccggta gtgatcttat ttcattatgg tgaaagttgg aacctcttac gtgccgatca   2880
acgtctcatt ttcgccagat atc                                           2903
```

<210> SEQ ID NO 27
<211> LENGTH: 2904
<212> TYPE: DNA
<213> ORGANISM: Artificial Sequence
<220> FEATURE:
<223> OTHER INFORMATION: pCASCADE-gltA2-zwf Plasmid

<400> SEQUENCE: 27

```
gacgtcttaa gacccacttt cacatttaag ttgtttttct aatccgcata tgatcaattc     60
aaggccgaat aagaaggctg gctctgcacc ttggtgatca aataattcga tagcttgtcg    120
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta tttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgtatt gaccaattca ttcgggacag ttattagttc gagttccccg cgccagcggg   1080
gataaaccgc tcgtaaaagc agtacagtgc accgtaagat cgagttcccc gcgccagcgg   1140
ggataaaccg aaaaaaaaac cccgcccctg acagggcggg gtttttttc ctagggatat   1200
attccgcttc ctcgctcact gactcgctac gctcggtcgt tcgactgcgg cgagcggaaa   1260
tggcttacga acggggcgga gatttcctgg aagatgccag gaagatactt aacagggaag   1320
tgagagggcc gcggcaaagc cgtttttcca taggctccgc ccccctgaca agcatcacga   1380
aatctgacgc tcaaatcagt ggtggcgaaa cccgacagga ctataaagat accaggcgtt   1440
tccccctggc ggctccctcg tgcgctctcc tgttcctgcc tttcggttta ccggtgtcat   1500
tccgctgtta tggccgcgtt tgtctcattc cacgcctgac actcagttcc gggtaggcag   1560
ttcgctccaa gctggactgt atgcacgaac cccccgttca gtccgaccgc tgcgccttat   1620
ccggtaacta tcgtcttgag tccaacccgg aaagacatgc aaaagcacca ctggcagcag   1680
ccactggtaa ttgatttaga ggagttagtc ttgaagtcat gcgccggtta aggctaaact   1740
gaaaggacaa gttttggtga ctgcgctcct ccaagccagt tacctcggtt caaagagttg   1800
gtagctcaga gaaccttcga aaaaccgccc tgcaaggcgg ttttttcgtt ttcagagcaa   1860
gagattacgc gcagaccaaa acgatctcaa gaagatcatc ttattaatca gataaaatat   1920
ttctagattt cagtgcaatt tatctcttca aatgtagcac ctgaagtcag ccccatacga   1980
tataagttgt tactagtgct tggattctca ccaataaaaa acgcccggcg gcaaccgagc   2040
gttctgaaca aatccagatg gagttctgag gtcattactg gatctatcaa caggagtcca   2100
agcgagctcg atatcaaatt acgccccgcc ctgccactca tcgcagtact gttgtaattc   2160
attaagcatt ctgccgacat ggaagccatc acaaacggca tgatgaacct gaatcgccag   2220
```

```
cggcatcagc accttgtcgc cttgcgtata atatttgccc atggtgaaaa cgggggcgaa   2280

gaagttgtcc atattggcca cgtttaaatc aaaactggtg aaactcaccc agggattggc   2340

tgagacgaaa aacatattct caataaaccc tttagggaaa taggccaggt tttcaccgta   2400

acacgccaca tcttgcgaat atatgtgtag aaactgccgg aaatcgtcgt ggtattcact   2460

ccagagcgat gaaaacgttt cagtttgctc atggaaaacg gtgtaacaag ggtgaacact   2520

atcccatatc accagctcac cgtctttcat tgccatacga aattccggat gagcattcat   2580

caggcgggca agaatgtgaa taaaggccgg ataaaacttg tgcttatttt tctttacggt   2640

ctttaaaaag gccgtaatat ccagctgaac ggtctggtta taggtacatt gagcaactga   2700

ctgaaatgcc tcaaaatgtt ctttacgatg ccattgggat atatcaacgg tggtatatcc   2760

agtgattttt ttctccattt tagcttcctt agctcctgaa aatctcgata actcaaaaaa   2820

tacgcccggt agtgatctta tttcattatg gtgaaagttg gaacctctta cgtgccgatc   2880

aacgtctcat tttcgccaga tatc                                          2904
```

```
<210> SEQ ID NO 28
<211> LENGTH: 3505
<212> TYPE: DNA
<213> ORGANISM: Artificial Sequence
<220> FEATURE:
<223> OTHER INFORMATION: pBT1-mCherry-DAS+4 Vector

<400> SEQUENCE: 28

cgcaaaaaac cccgcttcgg cggggttttt tcgcacgtct ccatcgcttg cccaagttgt     60

gaagcacagc taacaccacg tcgtccctat ctgctgccct aggtctatga gtggttgctg    120

gataacttta cgggcatgca taaggctcgt ataatatatt cagggagacc acaacggttt    180

ccctctacaa ataattttgt ttaactttga tcgcatggtt gctactagag aaagaggaga    240

aatactagat ggtgagcaag ggcgaggagg ataacatggc catcatcaag gagttcatgc    300

gcttcaaggt gcacatggag ggctccgtga acggccacga gttcgagatc gagggcgagg    360

gcgagggccg cccctacgag ggcacccaga ccgccaagct gaaggtgacc aagggtggcc    420

ccctgccctt cgcctgggac atcctgtccc ctcagttcat gtacggctcc aaggcctacg    480

tgaagcaccc cgccgacatc cccgactact tgaagctgtc cttccccgag ggcttcaagt    540

gggagcgcgt gatgaacttc gaggacggcg gcgtggtgac cgtgacccag gactcctccc    600

tgcaggacgg cgagttcatc tacaaggtga agctgcgcgg caccaacttc ccctccgacg    660

gccccgtaat gcagaagaag accatgggct gggaggcctc ctccgagcgg atgtaccccg    720

aggacggcgc cctgaagggc gagatcaagc agaggctgaa gctgaaggac ggcggccact    780

acgacgctga ggtcaagacc acctacaagg ccaagaagcc cgtgcagctg cccggcgcct    840

acaacgtcaa catcaagttg gacatcacct cccacaacga ggactacacc atcgtggaac    900

agtacgaacg cgccgagggc cgccactcca ccggcggcat ggacgaactg tacaaggcgg    960

ccaacgatga aaactattct gaaaactatg cggatgcgtc ttaataagga cgagcctcag   1020

actccagcgt aactggactg aaaacaaact aaagcgccct tgtggcgctt tagttttgtt   1080

ccgcggccac cggctggctc gcttcgctcg gcccgtggac aaccctgctg gacaagctga   1140

tggacaggct gcgcctgccc acgagcttga ccacagggat tgcccaccgg ctacccagcc   1200

ttcgaccaca tacccaccgg ctccaactgc gcggcctgcg gccttgcccc atcaattttt   1260

ttaattttct ctggggaaaa gcctccggcc tgcggcctgc gcgcttcgct tgccggttgg   1320

acaccaagtg gaaggcgggt caaggctcgc gcagcgaccg cgcagcggct tggccttgac   1380
```

```
gcgcctggaa cgacccaagc ctatgcgagt gggggcagtc gaaggcgaag cccgcccgcc   1440
tgccccccga gcctcacggc ggcgagtgcg ggggttccaa gggggcagcg ccaccttggg   1500
caaggccgaa ggccgcgcag tcgatcaaca agccccggag gggccacttt ttgccggagg   1560
gggagccgcg ccgaaggcgt gggggaaccc cgcaggggtg cccttctttg ggcaccaaag   1620
aactagatat agggcgaaat gcgaaagact taaaaatcaa caacttaaaa aaggggggta   1680
cgcaacagct cattgcggca ccccccgcaa tagctcattg cgtaggttaa agaaaatctg   1740
taattgactg ccacttttac gcaacgcata attgttgtcg cgctgccgaa aagttgcagc   1800
tgattgcgca tggtgccgca accgtgcggc accctaccgc atggagataa gcatggccac   1860
gcagtccaga gaaatcggca ttcaagccaa gaacaagccc ggtcactggg tgcaaacgga   1920
acgcaaagcg catgaggcgt gggccgggct tattgcgagg aaacccacgg cggcaatgct   1980
gctgcatcac ctcgtggcgc agatgggcca ccagaacgcc gtggtggtca gccagaagac   2040
actttccaag ctcatcggac gttctttgcg gacggtccaa tacgcagtca aggacttggt   2100
ggccgagcgc tggatctccg tcgtgaagct caacggcccc ggcaccgtgt cggcctacgt   2160
ggtcaatgac cgcgtggcgt ggggccagcc ccgcgaccag ttgcgcctgt cggtgttcag   2220
tgccgccgtg gtggttgatc acgacgacca ggacgaatcg ctgttggggc atggcgacct   2280
gcgccgcatc ccgaccctgt atccgggcga gcagcaacta ccgaccggcc ccggcgagga   2340
gccgcccagc cagcccggca ttccgggcat ggaaccagac ctgccagcct tgaccgaaac   2400
ggaggaatgg gaacggcgcg ggcagcagcg cctgccgatg cccgatgagc cgtgttttct   2460
ggacgatggc gagccgttgg agccgccgac acgggtcacg ctgccgcgcc ggtagtacgt   2520
aagaggttcc aactttcacc ataatgaaat aagatcacta ccgggcgtat tttttgagtt   2580
atcgagattt tcaggagcta aggaagctaa aatgagtatt caacatttcc gtgtcgccct   2640
tattcccttt tttgcggcat tttgccttcc tgtttttgct cacccagaaa cgctggtgaa   2700
agtaaaagat gctgaagatc agttgggtgc acgagtgggt tacatcgaac tggatctcaa   2760
cagcggtaag atccttgaga gttttcgccc cgaagaacgt tttccaatga tgagcacttt   2820
taaagttctg ctatgtggcg cggtattatc ccgtattgac gccgggcaag agcaactcgg   2880
tcgccgcata cactattctc agaatgactt ggttgagtac tcaccagtca cagaaaagca   2940
tctcacggat ggcatgacag taagagaatt atgcagtgct gccataacca tgagtgataa   3000
cactgcggcc aacttacttc tggcaacgat cggaggaccg aaggagctaa ccgctttttt   3060
gcacaacatg ggggatcatg taactcgcct tgatcgttgg gaaccggagc tgaatgaagc   3120
cataccaaac gacgagcgtg acaccacgat gcctgtagca atggcaacaa cgttgcgcaa   3180
actattaact ggcgaactac ttactctagc ttcccggcaa caattaatag actggatgga   3240
ggcggataaa gttgcaggat cacttctgcg ctcggccctc ccggctggct ggtttattgc   3300
tgataaatct ggagccggtg agcgtgggtc tcgcggtatc attgcagcac tggggccaga   3360
tggtaagccc tcccgcatcg tagttatcta cacgacgggg agtcaggcaa ctatggatga   3420
acgaaataga cagatcgctg agataggtgc ctcactgatt aagcattggt aatgaggatc   3480
cccctcaagt caaaagcctc cggtc                                         3505
```

<210> SEQ ID NO 29
<211> LENGTH: 2841
<212> TYPE: DNA
<213> ORGANISM: Artificial Sequence
<220> FEATURE:

<223> OTHER INFORMATION: pCASCADE-proD Plasmid

<400> SEQUENCE: 29

```
gacgtcttaa gacccacttt cacatttaag ttgtttttct aatccgcata tgatcaattc      60
aaggccgaat aagaaggctg gctctgcacc ttggtgatca aataattcga tagcttgtcg     120
taataatggc ggcatactat cagtagtagg tgtttccctt tcttctttag cgacttgatg     180
ctcttgatct tccaatacgc aacctaaagt aaaatgcccc acagcgctga gtgcatataa     240
tgcattctct agtgaaaaac cttgttggca taaaaaggct aattgatttt cgagagtttc     300
atactgtttt tctgtaggcc gtgtacctaa atgtactttt gctccatcgc gatgacttag     360
taaagcacat ctaaaacttt tagcgttatt acgtaaaaaa tcttgccagc tttccccttc     420
taaagggcaa aagtgagtat ggtgcctatc taacatctca atggctaagg cgtcgagcaa     480
agcccgctta tttttacat gccaatacaa tgtaggctgc tctacaccta gcttctgggc      540
gagtttacgg gttgttaaac cttcgattcc gacctcatta agcagctcta atgcgctgtt     600
aatcacttta cttttatcta atctagacat catccaggca tcaaataaaa cgaaaggctc     660
agtcgaaaga ctgggccttt cgttttatct gttgtttgtc ggtgaacgct ctctactaga     720
gtcacactgg ctcaccttcg ggtgggcctt tctgcgttta tacacagcta acaccacgtc     780
gtccctatct gctgccctag gtctatgagt ggttgctgga taactctttc tgacacctta     840
ctatcttaca aatgtaacaa aaaagttatt tttctgtaat tcgagcatgt catgttaccc     900
cgcgagcata aaacgcgtat attcagggag accacaacgg tttccctcta caaataattt     960
tgtttaactt tgaattcaaa agatctggta ccacctcgag ttccccgcgc cagcggggat    1020
aaaccgagtg gttgctggat aactttacgg gcatgctcga gttccccgcg ccagcgggga    1080
taaaccgaaa aaaaaacccc gcccctgaca gggcggggtt ttttttccta gggatatatt    1140
ccgcttcctc gctcactgac tcgctacgct cggtcgttcg actgcggcga gcggaaatgg    1200
cttacgaacg gggcggagat ttcctggaag atgccaggaa gatacttaac agggaagtga    1260
gagggccgcg gcaaagccgt ttttccatag gctccgcccc cctgacaagc atcacgaaat    1320
ctgacgctca aatcagtggt ggcgaaaccc gacaggacta taaagatacc aggcgtttcc    1380
ccctggcggc tccctcgtgc gctctcctgt tcctgccttt cggtttaccg gtgtcattcc    1440
gctgttatgg ccgcgtttgt ctcattccac gcctgacact cagttccggg taggcagttc    1500
gctccaagct ggactgtatg cacgaacccc ccgttcagtc cgaccgctgc gccttatccg    1560
gtaactatcg tcttgagtcc aacccggaaa gacatgcaaa agcaccactg gcagcagcca    1620
ctggtaattg atttagagga gttagtcttg aagtcatgcg ccggttaagg ctaaactgaa    1680
aggacaagtt ttggtgactg cgctcctcca agccagttac ctcggttcaa agagttggta    1740
gctcagagaa ccttcgaaaa accgccctgc aaggcggttt tttcgttttc agagcaagag    1800
attacgcgca gaccaaaacg atctcaagaa gatcatctta ttaatcagat aaaatatttc    1860
tagatttcag tgcaatttat ctcttcaaat gtagcacctg aagtcagccc catacgatat    1920
aagttgttac tagtgcttgg attctcacca ataaaaaacg cccggcggca accgagcgtt    1980
ctgaacaaat ccagatggag ttctgaggtc attactggat ctatcaacag gagtccaagc    2040
gagctcgata tcaaattacg ccccgccctg ccactcatcg cagtactgtt gtaattcatt    2100
aagcattctg ccgacatgga agccatcaca aacggcatga tgaacctgaa tcgccagcgg    2160
catcagcacc ttgtcgcctt gcgtataata tttgcccatg gtgaaaacgg gggcgaagaa    2220
gttgtccata ttggccacgt ttaaatcaaa actggtgaaa ctcacccagg gattggctga    2280
```

```
gacgaaaaac atattctcaa taaacccttt agggaaatag gccaggtttt caccgtaaca   2340

cgccacatct tgcgaatata tgtgtagaaa ctgccggaaa tcgtcgtggt attcactcca   2400

gagcgatgaa aacgtttcag tttgctcatg gaaaacggtg taacaagggt gaacactatc   2460

ccatatcacc agctcaccgt ctttcattgc catacgaaat tccggatgag cattcatcag   2520

gcgggcaaga atgtgaataa aggccggata aaacttgtgc ttatttttct ttacggtctt   2580

taaaaaggcc gtaatatcca gctgaacggt ctggttatag gtacattgag caactgactg   2640

aaatgcctca aaatgttctt tacgatgcca ttgggatata tcaacggtgg tatatccagt   2700

gatttttttc tccattttag cttccttagc tcctgaaaat ctcgataact caaaaaatac   2760

gcccggtagt gatcttattt cattatggtg aaagttggaa cctcttacgt gccgatcaac   2820

gtctcatttt cgccagatat c                                             2841
```

<210> SEQ ID NO 30
<211> LENGTH: 4866
<212> TYPE: DNA
<213> ORGANISM: Artificial Sequence
<220> FEATURE:
<223> OTHER INFORMATION: pSMART-3HP1 Plasmid

<400> SEQUENCE: 30

```
gtgcgtaatt gtgctgatct cttatatagc tgctctcatt atctctctac cctgaagtga     60

ctctctcacc tgtaaaaata atatctcaca ggcttaatag tttcttaata caaagcctgt    120

aaaacgtcag gataacttct tttctggaaa aaggagatat accatggcga cgacgggggc    180

acgtagcgct agtgttggtt gggccgagag cctgatcggt ctgcatttgg gaaaagtggc    240

cttaatcacc ggaggctcag ccggcatcgg cgggcagatc ggccgccttt tagcgctgtc    300

tggcgcgcgt gttatgctgg ccgctcgcga ccgtcacaaa ctcgaacaaa tgcaggccat    360

gattcaatcc gaactggcgg aagttggtta taccgatgtc gaagaccgcg tgcacatcgc    420

gccggggtgt gacgtttcct ctgaagcgca gctggcagat ctggttgaac gcactctgtc    480

agcattcggt accgtggatt atctgatcaa taacgcgggt attgcgggtg tcgaagagat    540

ggttatcgac atgccggtgg aaggctggcg tcatacgtta tttgccaacc ttatctcaaa    600

ttatagcctg atgcgcaaac tggcccctct gatgaagaaa caggggagtg gctatatctt    660

gaacgtctcg tcgtactttg gtggcgaaaa agatgcggct atcccatacc caaatcgtgc    720

cgattatgcg gtttcaaaag ccggtcaacg tgcaatggct gaagtgttcg cccgtttcct    780

cggcccggag atccagatta acgctatcgc cccaggcccg gtggaaggtg accgcctccg    840

cggcacgggc gaacgtcccg gcttgtttgc gcgccgcgcg cgtttgattt tagaaaataa    900

gcgtttaaac gagctgcatg ctgcccttat tgcggctgcg cgtacagatg agcgctccat    960

gcacgaactg gtggaattac tgctgccgaa tgatgtagcg gcactcgagc agaatcccgc   1020

agccccaacg gcgttgcgcg aactcgcgcg ccgttttcgc agcgaaggcg acccggccgc   1080

gtcaagctcc agtgctctgc tcaaccgcag cattgcggcg aagttactgg cccgcctgca   1140

caacggcggc tatgttctgc cggcggatat cttcgccaac ctgccgaacc ctccagaccc   1200

gttcttcacg cgcgcgcaga ttgatcgcga agcccgtaaa gtgcgcgacg ggattatggg   1260

aatgctgtat ctgcagcgca tgcctaccga gtttgacgta gcaatggcta ccgtttacta   1320

tctggcggat cgcaatgtga gtggagagac cttccatccg agtgggggc tgcgttacga   1380

gcgcacacct accggcggtg agttatttgg cctgccgtct cccgagcgcc tggcggagtt   1440
```

```
agttggaagc accgtatatt tgatcggtga acacttaacc gaacatctga acttgctcgc   1500
acgtgcgtat cttgaacgtt acggtgcgcg tcaggttgtt atgatcgtgg aaacggagac   1560
aggcgcggaa accatgcgcc gcttacttca cgaccatgtc gaagcaggtc gccttatgac   1620
cattgtggcg ggtgaccaaa tcgaagccgc catcgaccag gcgattacgc gctacggccg   1680
tcctggtccg gttgtgtgca ccccccttccg ccccccttccg accgtcccgt tagttggccg   1740
caaggactcc gattggagca ccgtactgag tgaagccgaa tttgccgaac tgtgtgaaca   1800
tcaactgaca catcattttc gcgtagcgcg caaaatcgca ctttcggatg gtgcctcact   1860
ggctctggtt acccccgaaa ccacagcgac aagtaccact gaacagttcg ccctggccaa   1920
ctttattaag acaaccctgc acgcttttac ggccactatc ggagttgaaa gtgagcgcac   1980
ggcgcagcgt atcctgatta atcaggtaga cctcacccgt cgtgctcgtg cggaagaacc   2040
acgcgatccg catgaacgtc agcaggaact ggaacgtttc atcgaggcgg tactgctggt   2100
tacggcccca ttaccgccgg aagcagatac ccgctacgct ggccgcatcc accgtgggcg   2160
tgccattact gtctagtaag ctcttcttct ggaaaaagga gatataccat gatcgtttta   2220
gtaactggag caacggcagg ttttggtgaa tgcattactc gtcgttttat tcaacaaggg   2280
cataaagtta tcgccactgg ccgtcgccag gaacggttgc aggagttaaa agacgaactg   2340
ggagataatc tgtatatcgc ccaactggac gttcgcaacc gcgccgctat tgaagagatg   2400
ctggcatcgc ttcctgccga gtggtgcaat attgatatcc tggtaaataa tgccggcctg   2460
gcgttgggca tggagcctgc gcataaagcc agcgttgaag actgggaaac gatgattgat   2520
accaacaaca aaggcctggt atatatgacg cgcgccgtct taccgggtat ggttgaacgt   2580
aatcatggtc atattattaa cattggctca acggcaggta gctggccgta tgccggtggt   2640
aacgtttacg gtgcgacgaa agcgtttgtt cgtcagttta gcctgaatct gcgtacggat   2700
ctgcatggta cggcggtgcg cgtcaccgac atcgaaccgg gtctggtggg tggtaccgag   2760
ttttccaatg tccgctttaa aggcgatgac ggtaaagcag aaaaaaccta tcaaaatacc   2820
gttgcattga cgccagaaga tgtcagcgaa gccgtctggt gggtgtcaac gctgcctgct   2880
cacgtcaata tcaataccct ggaaatgatg ccggttaccc aaagctatgc cggactgaat   2940
gtccaccgtc agtaatagga tcgtcccggc ttatcggtca gtttcacctg atttacgtaa   3000
aaacccgctt cggcgggttt ttgcttttgg aggggcagaa agatgaatga ctgtccacga   3060
cgctataccc aaaagaaaga cgaattctct agatatcgct caatactgac catttaaatc   3120
atacctgacc tccatagcag aaagtcaaaa gcctccgacc ggaggctttt gacttgatcg   3180
gcacgtaaga ggttccaact ttcaccataa tgaaataaga tcactaccgg gcgtattttt   3240
tgagttatcg agattttcag gagctaagga agctaaaatg agccatattc aacgggaaac   3300
gtcttgctcg aggccgcgat taaattccaa catggatgct gatttatatg ggtataaatg   3360
ggctcgcgat aatgtcgggc aatcaggtgc gacaatctat cgattgtatg ggaagcccga   3420
tgcgccagag ttgtttctga aacatggcaa aggtagcgtt gccaatgatg ttacagatga   3480
gatggtcagg ctaaactggc tgacggaatt tatgcctctt ccgaccatca agcattttat   3540
ccgtactcct gatgatgcat ggttactcac cactgcgatc cccagggaaaa cagcattcca   3600
ggtattagaa gaatatcctg attcaggtga aaatattgtt gatgcgctgg cagtgttcct   3660
gcgccggttg cattcgattc ctgtttgtaa ttgtcctttt aacggcgatc gcgtatttcg   3720
tctcgctcag gcgcaatcac gaatgaataa cggtttggtt ggtgcgagtg attttgatga   3780
cgagcgtaat ggctggcctg ttgaacaagt ctggaaagaa atgcataagc ttttgccatt   3840
```

```
ctcaccggat tcagtcgtca ctcatggtga tttctcactt gataacctta tttttgacga   3900
ggggaaatta ataggttgta ttgatgttgg acgagtcgga atcgcagacc gataccagga   3960
tcttgccatc ctatggaact gcctcggtga gttttctcct tcattacaga aacggctttt   4020
tcaaaaatat ggtattgata atcctgatat gaataaattg cagtttcact tgatgctcga   4080
tgagtttttc taatgagggc ccaaatgtaa tcacctggct caccttcggg tgggcctttc   4140
tgcgttgctg gcgtttttcc ataggctccg cccccctgac gagcatcaca aaaatcgatg   4200
ctcaagtcag aggtggcgaa acccgacagg actataaaga taccaggcgt ttccccctgg   4260
aagctccctc gtgcgctctc ctgttccgac cctgccgctt accggatacc tgtccgcctt   4320
tctcccttcg ggaagcgtgg cgctttctca tagctcacgc tgtaggtatc tcagttcggt   4380
gtaggtcgtt cgctccaagc tgggctgtgt gcacgaaccc cccgttcagc ccgaccgctg   4440
cgccttatcc ggtaactatc gtcttgagtc caacccggta agacacgact tatcgccact   4500
ggcagcagcc actggtaaca ggattagcag agcgaggtat gtaggcggtg ctacagagtt   4560
cttgaagtgg tggcctaact acggctacac tagaagaaca gtatttggta tctgcgctct   4620
gctgaagcca gttacctcgg aaaaagagtt ggtagctctt gatccggcaa acaaaccacc   4680
gctggtagcg gtggtttttt tgtttgcaag cagcagatta cgcgcagaaa aaaaggatct   4740
caagaagatc ctttgatttt ctaccgaaga aaggcccacc cgtgaaggtg agccagtgag   4800
ttgattgcag tccagttacg ctggagtctg aggctcgtcc tgaatgatat caagcttgaa   4860
ttcgtt                                                              4866
```

```
<210> SEQ ID NO 31
<211> LENGTH: 3353
<212> TYPE: DNA
<213> ORGANISM: Artificial Sequence
<220> FEATURE:
<223> OTHER INFORMATION: Plasmid pSMART-F6AA82M

<400> SEQUENCE: 31

ccatggttga atgactccta taacgaagtt cacagctaac accacgtcgt ccctatctgc     60
tgccctaggt ctatgagtgg ttgctggata acgtgcgtaa ttgtgctgat ctcttatata    120
gctgctctca ttatctctct accctgaagt gactctctca cctgtaaaaa taatatctca    180
caggcttaat agtttcttaa tacaaagcct gtaaaacgtc aggataactt ctatattcag    240
ggagaccaca acggtttccc tctacaaata attttgttta actttcgaca tggcaaaatc    300
ccccctcgc gacttgctct tcagctttct ggaaaaagga gatataccat gaatgttacg     360
tttgaagaac gtgcgagtct gcacggttac cgtatcggca ttgcaagctt ggatgccccg    420
gcttccttaa acgccttgag cctgcctatg atcgatgcgc tccaagatcg tttgcgcgct    480
tgggcggaag atgccgatat cgcttgcgtt ctgttacgtg gtaatggcag caaggcgttt    540
tgcgctggtg gcgatgtagt tcaattggcc aaaaaatgct tagcaagccc aggtgaagcc    600
ccggaactgg ccgagcgttt tttcgcccgt agctatcgct tggatcatta tttgcacacc    660
taccccaaac cgttgatctg ttgggcccat ggtcacgtgc tgggtggtgg aatgggactt    720
ttacagggcg ccggcatccg tattgtgaca ccatcgtctc gcttagctat gccggaaatt    780
tctatcgggc tgttccctga cgtgggtggc tcccatttcc tgagtcgcct cccgggaaaa    840
ctggggttgt tttcggtct taccgcgtct ccccttaacg cacgcgacgc gctggactta     900
aatctggctg accgtttcct gcttgacacg cagcaggatg cgctgatcga tggtctgatt    960
```

```
cagttaaatt ggcgcgagca acctgatctg cagctgcact ctcttctgaa agctctggaa   1020

cagcaggctc gtagtgagct gccggccgct cagtggttgc ctcgtcgtga acgccttgat   1080

gccctcctgg accaagccac gttaccattg tcctggcagg cgctggcgtc gctcgaaaat   1140

gatgaggatg ctctgttagc taaggcagct aaaacgatgc tgggcggtag cccgctcacc   1200

ggccatctcg tgtggggtca aattcgtcgt gcacgccacc tgtccttggc gcaggtgttt   1260

cagatggaat acggtatgtc attgaactgc tgccgccatc cggagttcgc ggaaggcgtc   1320

cgcgcccgtt tgattgacaa ggatcacgcc ccccattggc actggccgga cgttaaccag   1380

gttccggaac aggtaattgc agcgcatttc gcgccattgg atgatcaccc tttagccgat   1440

ctggcatagt aaccggctta tcggtcagtt tcacctgatt tacgtaaaaa cccgcttcgg   1500

cgggtttttg cttttggagg ggcagaaaga tgaatgactg tccacgacgc tatacccaaa   1560

agaaagacga attctctaga tatcgctcaa tactgaccat ttaaatcata cctgacctcc   1620

atagcagaaa gtcaaaagcc tccgaccgga ggcttttgac ttgatcggca cgtaagaggt   1680

tccaactttc accataatga aataagatca ctaccgggcg tattttttga gttatcgaga   1740

ttttcaggag ctaaggaagc taaaatgagc catattcaac gggaaacgtc ttgctcgagg   1800

ccgcgattaa attccaacat ggatgctgat ttatatgggt ataaatgggc tcgcgataat   1860

gtcgggcaat caggtgcgac aatctatcga ttgtatggga agcccgatgc gccagagttg   1920

tttctgaaac atggcaaagg tagcgttgcc aatgatgtta cagatgagat ggtcaggcta   1980

aactggctga cggaatttat gcctcttccg accatcaagc attttatccg tactcctgat   2040

gatgcatggt tactcaccac tgcgatccca gggaaaacag cattccaggt attagaagaa   2100

tatcctgatt caggtgaaaa tattgttgat gcgctggcag tgttcctgcg ccggttgcat   2160

tcgattcctg tttgtaattg tccttttaac ggcgatcgcg tatttcgtct cgctcaggcg   2220

caatcacgaa tgaataacgg tttggttggt gcgagtgatt ttgatgacga gcgtaatggc   2280

tggcctgttg aacaagtctg gaaagaaatg cataagcttt tgccattctc accggattca   2340

gtcgtcactc atggtgattt ctcacttgat aaccttattt ttgacgaggg gaaattaata   2400

ggttgtattg atgttggacg agtcggaatc gcagaccgat accaggatct tgccatccta   2460

tggaactgcc tcggtgagtt ttctccttca ttacagaaac ggctttttca aaaatatggt   2520

attgataatc ctgatatgaa taaattgcag tttcacttga tgctcgatga gtttttctaa   2580

tgagggccca aatgtaatca cctggctcac cttcgggtgg gcctttctgc gttgctggcg   2640

tttttccata ggctccgccc ccctgacgag catcacaaaa atcgatgctc aagtcagagg   2700

tggcgaaacc cgacaggact ataaagatac caggcgtttc cccctggaag ctccctcgtg   2760

cgctctcctg ttccgaccct gccgcttacc ggatacctgt ccgcctttct cccttcggga   2820

agcgtggcgc tttctcatag ctcacgctgt aggtatctca gttcggtgta ggtcgttcgc   2880

tccaagctgg gctgtgtgca cgaacccccc gttcagcccg accgctgcgc cttatccggt   2940

aactatcgtc ttgagtccaa cccggtaaga cacgacttat cgccactggc agcagccact   3000

ggtaacagga ttagcagagc gaggtatgta ggcggtgcta cagagttctt gaagtggtgg   3060

cctaactacg gctacactag aagaacagta tttggtatct gcgctctgct gaagccagtt   3120

acctcggaaa aagagttggt agctcttgat ccggcaaaca aaccaccgct ggtagcggtg   3180

gtttttttgt ttgcaagcag cagattacgc gcagaaaaaa aggatctcaa gaagatcctt   3240

tgattttcta ccgaagaaag gcccacccgt gaaggtgagc cagtgagttg attgcagtcc   3300

agttacgctg gagtctgagg ctcgtcctga atgatatcaa gcttgaattc gtt          3353
```

<210> SEQ ID NO 32
<211> LENGTH: 3424
<212> TYPE: DNA
<213> ORGANISM: Artificial Sequence
<220> FEATURE:
<223> OTHER INFORMATION: Plasmid pSMART-Ala1

<400> SEQUENCE: 32
ccaggcatca aataaaacga aaggctcagt cgaaagactg ggcctttcgt tttatctgtt 60
gtttgtcggt gaacgctctc tactagagtc acactggctc accttcgggt gggcctttct 120
gcgtttatac acagctaaca ccacgtcgtc cctatctgct gccctaggtc tatgagtggt 180
tgctggataa ctctttctga caccttacta tcttacaaat gtaacaaaaa agttattttt 240
ctgtaattcg agcatgtcat gttaccccgc gagcataaaa cgcgtatatt cagggagacc 300
acaacggttt ccctctacaa ataattttgt ttaactttgg aaaaaggaga tataccatga 360
tcattggggt gccgaaggag atcaaaaata atgagaaccg cgtcgcgttg accccgggag 420
gtgtcagcca gctgatctct aatggccatc gtgtcttagt tgaaacaggc gctggcctgg 480
gttctggctt cgaaaacgag gcctacgaat ctgcaggtgc ggaaattatt gctgatccaa 540
aacaggtctg ggatgcagag atggtcatga aagtgaaaga accgctcccg gaagaatatg 600
tctattttcg taaaggtctg gtgctgttta catatctgca tctggcagct gaaccggagc 660
tcgcacaagc ccttaaagat aaaggtgtca cggccatcgc atacgaaact gtcagcgaag 720
ggcgcacgct gccattactg accccgatgt cagaagtggc aggccgtatg gctgcgcaga 780
tcggcgcaca gtttcttgaa aaaccaaagg gcgggaaggg tattctctta gcaggagtgc 840
cgggcgtcag tcgtgggaaa gtaactatta ttggtggcgg cgtggtagga acaaatgctg 900
ccaaaatggc cgtcggtttg gggggcgacg taacaatcat tgcgcgtaat gccgatcgcc 960
ttcgtcaatt agacgatatc tttggccacc aaatcaaaac cctgatttcg aacccagtca 1020
atatcgcgga tgcggtggcg gaagctgatt tgttgatctg cgccgtgtta attccgggag 1080
cgaaagcacc tacattggtg acggaagaaa tggtgaaaca aatgaaaccg ggttcagtca 1140
ttgttgatgt ggctattgat cagggtggca tcgtggaaac ggtggaccat attaccactc 1200
acgaccagcc gacgtatgaa aaacatggtg tcgtacacta tgcggtggcg aatatgcctg 1260
gtgcggtccc acgtacgagt acaatcgcac tgacaaatgt caccgtgccg tatgcgttgc 1320
aaatcgcgaa caaaggtgcc gtgaaagcgc tggccgacaa tacggcgtta cgtgccggtc 1380
tgaacaccgc taacggtcac gtgacatatg aagcggtcgc gcgtgatttg gggtacgaat 1440
atgtaccggc ggaaaaagcc ttacaagacg aatcgagtgt cgctggtgca tagtaagctc 1500
ttctaatacg actcactata gggccggctt atcggtcagt ttcacctgat ttacgtaaaa 1560
acccgcttcg gcgggttttt gcttttggag gggcagaaag atgaatgact gtccacgacg 1620
ctatacccaa aagaaagacg aattctctag atatcgctca atactgacca tttaaatcat 1680
acctgacctc catagcagaa agtcaaaagc ctccgaccgg aggcttttga cttgatcggc 1740
acgtaagagg ttccaacttt caccataatg aaataagatc actaccgggc gtattttttg 1800
agttatcgag attttcagga gctaaggaag ctaaaatgag ccatattcaa cgggaaacgt 1860
cttgctcgag gccgcgatta aattccaaca tggatgctga tttatatggg tataaatggg 1920
ctcgcgataa tgtcgggcaa tcaggtgcga caatctatcg attgtatggg aagcccgatg 1980
cgccagagtt gtttctgaaa catggcaaag gtagcgttgc caatgatgtt acagatgaga 2040

```
tggtcaggct aaactggctg acggaattta tgcctcttcc gaccatcaag cattttatcc   2100

gtactcctga tgatgcatgg ttactcacca ctgcgatccc agggaaaaca gcattccagg   2160

tattagaaga atatcctgat tcaggtgaaa atattgttga tgcgctggca gtgttcctgc   2220

gccggttgca ttcgattcct gtttgtaatt gtccttttaa cggcgatcgc gtatttcgtc   2280

tcgctcaggc gcaatcacga atgaataacg gtttggttgg tgcgagtgat tttgatgacg   2340

agcgtaatgg ctggcctgtt gaacaagtct ggaaagaaat gcataagctt ttgccattct   2400

caccggattc agtcgtcact catggtgatt tctcacttga taaccttatt tttgacgagg   2460

ggaaattaat aggttgtatt gatgttggac gagtcggaat cgcagaccga taccaggatc   2520

ttgccatcct atggaactgc ctcggtgagt tttctccttc attacagaaa cggctttttc   2580

aaaaatatgg tattgataat cctgatatga ataaattgca gtttcacttg atgctcgatg   2640

agtttttcta atgagggccc aaatgtaatc acctggctca ccttcgggtg ggcctttctg   2700

cgttgctggc gtttttccat aggctccgcc cccctgacga gcatcacaaa aatcgatgct   2760

caagtcagag gtggcgaaac ccgacaggac tataaagata ccaggcgttt ccccctggaa   2820

gctccctcgt gcgctctcct gttccgaccc tgccgcttac cggatacctg tccgcctttc   2880

tcccttcggg aagcgtggcg ctttctcata gctcacgctg taggtatctc agttcggtgt   2940

aggtcgttcg ctccaagctg ggctgtgtgc acgaaccccc cgttcagccc gaccgctgcg   3000

ccttatccgg taactatcgt cttgagtcca acccggtaag acacgactta tcgccactgg   3060

cagcagccac tggtaacagg attagcagag cgaggtatgt aggcggtgct acagagttct   3120

tgaagtggtg gcctaactac ggctacacta gaagaacagt atttggtatc tgcgctctgc   3180

tgaagccagt tacctcggaa aaagagttgg tagctcttga tccggcaaac aaaccaccgc   3240

tggtagcggt ggtttttttg tttgcaagca gcagattacg cgcagaaaaa aaggatctca   3300

agaagatcct ttgatttttct accgaagaaa ggcccacccg tgaaggtgag ccagtgagtt   3360

gattgcagtc cagttacgct ggagtctgag gctcgtcctg aatgatatca agcttgaatt   3420

cgtt                                                                3424
```

<210> SEQ ID NO 33
<211> LENGTH: 6275
<212> TYPE: DNA
<213> ORGANISM: Artificial Sequence
<220> FEATURE:
<223> OTHER INFORMATION: Plasmid pSMART-Mev1

<400> SEQUENCE: 33

```
tgcccaggca tcaaataaaa cgaaaggctc agtcgaaaga ctgggccttt cgttttatct     60

gttgtttgtc ggtgaacgct ctctactaga gtcacactgg ctcaccttcg ggtgggcctt    120

tctgcgttta tacacagcta acaccacgtc gtccctatct gctgccctag gtctatgagt    180

ggttgctgga taacgtgcgt aattgtgctg atctcttata tagctgctct cattatctct    240

ctaccctgaa gtgactctct cacctgtaaa aataatatct cacaggctta atagtttctt    300

aatacaaagc ctgtaaaacg tcaggataac ttctatattc agggagacca caacggtttc    360

cctctacaaa taattttgtt taactttcgt ggaaaaagga gatataccat gaagacggta    420

gttattatcg acgcactgcg taccccccatt ggaaaataca aaggaagtct gagccaggta    480

agcgccgtcg acctgggcac acatgtgacc acgcagttgt tgaagcgtca cagcactatc    540

agcgaggaaa ttgatcaggt catttttggt aatgttctgc aggcgggcaa tgggcagaac    600

cctgcacgtc agattgcaat caactcaggt ttaagccatg aaattccagc gatgacggtc    660
```

```
aatgaggtct gtggcagtgg gatgaaagcg gtaatcctgg ccaaacagtt aatccagctg    720
ggtgaggcgg aggtacttat cgcaggtggt attgaaaaca tgtcacaggc cccgaaactg    780
caacgcttta actacgaaac agaaagctac gatgcgcctt tttcgtccat gatgtatgat    840
ggtcttaccg acgcattcag tggtcaggcg atgggtctga cggccgagaa tgttgctgaa    900
aaataccacg ttacccgtga ggaacaagac caattctctg tccatagcca actcaaagcg    960
gcacaggctc aggcagaagg catttttgcc gatgagattg caccactgga agtttccggc   1020
accctggtgg aaaaggacga gggcattcgt ccgaatagca gtgttgaaaa actcggtact   1080
ttgaaaaccg tattcaaaga ggacggcacg gtgactgccg gtaatgcctc aactatcaac   1140
gacggtgcct cggcactgat tattgcgtct caagaatacg cggaagcgca cggcttgccg   1200
tatctcgcga ttatccgcga ttcagtggag gtcggcatcg atcccgcgta catgggcatt   1260
tcgccgatca aagcaattca gaagcttctg gcacgcaacc agttgacgac cgaagagatt   1320
gatttatacg aaatcaatga agcgttcgcg gcgacctcga ttgtggttca gcgtgaactt   1380
gccctcccgg aagaaaaggt caacatctat ggcggaggca tcagtttggg ccatgccatc   1440
ggagcgaccg gtgcccgtct gctcaccagc ttatcatatc agttgaacca gaaagaaaaa   1500
aagtacggcg ttgcatctct gtgtattggc ggaggtctgg gcctcgccat gttgttagaa   1560
cgtccgcagc aaaaaaaaaa ctcccgcttt tatcagatgt cgccggagga acgtctggcg   1620
agcttgttga acgaagggca gatctctgcc gacactaaaa aggaattcga aaacacggca   1680
ctgagcagtc agattgcgaa ccatatgatt gaaaatcaga tcagcgagac cgaggtgccc   1740
atgggcgtgg gccttcatct cacggtggac gaaacggatt atctggtacc aatggccaca   1800
gaagaaccgt cggtaatcgc cgcgttgtca aatggcgcga aaatcgcgca agggttcaaa   1860
acggtcaacc agcagcgtct catgcgcggc cagatcgtgt tctatgatgt agcagatgca   1920
gagagtctga ttgacgagtt acaggttcgt gagacggaga tttttcagca agccgagctg   1980
tcgtacccga gcattgttaa acgtggcggt ggccttcgtg acttgcagta tcgcgccttc   2040
gacgaatcgt tcgtgagtgt cgactttctg gtagacgtga aggacgccat gggggccaat   2100
atcgttaatg ccatgctgga aggggttgca gagctgtttc gtgagtggtt cgccgaacaa   2160
aaaatcctgt ttagcatctt aagcaattac gcaacggaaa gcgtcgtgac catgaaaacc   2220
gcgatccctg ttagccgcct ttcaaagggc agtaacggtc gtgaaatcgc tgaaaaaatt   2280
gttctcgcgt cccgctatgc atcgttggat ccttatcgcg cggtgacaca caacaaaggc   2340
attatgaatg gtatcgaagc ggtcgttctg gcgaccggca acgatactcg cgccgtgagc   2400
gcgtcctgcc atgcttttgc tgtgaaagag ggccgttatc agggcttgac gtcctggacc   2460
ctggacggtg aacagctgat cggcgaaatc tcggtgcccc tcgccctggc cactgtgggc   2520
ggcgccacaa aagtgttgcc aaaaagccaa gcggcggcgg atctgctggc cgtaactgat   2580
gctaaggaac tgagtcgcgt ggttgccgca gtgggcctgg cccaaaacct ggcagcactg   2640
cgcgcgctgg tttctgaagg catccagaaa ggtcatatgg ccctgcaagc gcgctctctg   2700
gccatgaccg taggggcgac cggcaaggaa gtcgaagcgg tagctcaaca gttaaaacgc   2760
cagaaaacta tgaatcagga tcgtgcgctg gccatcctca atgacctgcg caaacagtaa   2820
tagtcgcgcc gaaaaccccg cttcggcggg gttttgccgc acgtctccat cgcttgccca   2880
agttgtgaag cacagctaac accacgtcgt ccctatctgc tgccctaggt ctatgagtgg   2940
ttgctggata accatccata aattttgcat aattaatgta aagaccaggc tcgccagtaa   3000
```

```
cgctaaattc atttggctgt aagcgcggtg tcatccgcgt caggaaaatt aaacagttac   3060

tttaaaaaat gaaaacgtaa aaaggttggg tttcgatgta ttgacgggta aactttgtcg   3120

cccgctaaac atttgtttat attcagggag accacaacgg tttccctcta caaataattt   3180

tgtttaactt tgctggaaaa aggagatata ccatgaccat tgggattgat aaaatctcgt   3240

ttttcgtgcc tccttattat atcgacatga cggccctggc cgaggctcgc aatgtggatc   3300

ccggcaaatt tcacatcggt atcggccagg accaaatggc ggtgaatccc atctcgcagg   3360

acattgtcac cttcgccgca aacgcagcag aagctatctt gactaaagaa gataaagagg   3420

ccatcgacat ggtgatcgtg ggtacggaaa gctctattga cgaaagtaaa gccgcggcgg   3480

tggtattaca ccgcctgatg ggtatccagc cgtttgcgcg ctcctttgaa atcaaagagg   3540

cctgctacgg cgcaacggct ggactgcaac tcgcgaagaa ccatgttgca ttacatccgg   3600

ataaaaaagt cctggttgtc gcggcggaca tcgcgaaata cggcctgaac tccggcgggg   3660

aaccaacgca gggtgccggc gcagtggcga tgcttgtcgc aagcgagcct cgtatcctgg   3720

ctttaaagga ggacaacgtg atgctgacac aggatattta cgatttttgg cgtcccaccg   3780

gtcatccata tccgatggtt gatggtcctc tgtccaatga aacttatatt cagagcttcg   3840

cgcaagtttg ggatgaacat aagaaacgta ccggtctgga ttttgcggat tacgacgctc   3900

tggcttttca cattccatac acgaaaatgg gcaaaaaagc cctcttagct aaaatctcag   3960

accagaccga ggcagaacag gaacgcattt tagcgcgtta cgaagagtca attatctaca   4020

gccgccgtgt aggtaattta tatacggggt cgctttatct gggattgatt tccttactcg   4080

aaaacgccac aaccctgacg gcgggtaacc aaatcggttt attctcttac ggtagcggtg   4140

ccgttgccga attcttcacg ggtgagctgg ttgccggtta ccagaaccac ttacagaaag   4200

aaacccacct cgccctgctg gacaaccgta ctgaactcag catcgcagaa tatgaggcca   4260

tgttcgccga aacactcgac acggatatcg atcaaacctt agaggatgaa ctcaaatatt   4320

ccatttcagc gattaataac accgtccgct cctatcgcaa ttagtaagat cgtcccggct   4380

tatcggtcag tttcacctga tttacgtaaa aacccgcttc ggcgggtttt tgcttttgga   4440

ggggcagaaa gatgaatgac tgtccacgac gctataccca aaagaaagac gaattctcta   4500

gatatcgctc aatactgacc atttaaatca tacctgacct ccatagcaga aagtcaaaag   4560

cctccgaccg gaggcttttg acttgatcgg cacgtaagag gttccaactt tcaccataat   4620

gaaataagat cactaccggg cgtatttttt gagttatcga gattttcagg agctaaggaa   4680

gctaaaatga gccatattca acgggaaacg tcttgctcga ggccgcgatt aaattccaac   4740

atggatgctg atttatatgg gtataaatgg gctcgcgata atgtcgggca atcaggtgcg   4800

acaatctatc gattgtatgg gaagcccgat gcgccagagt tgtttctgaa acatggcaaa   4860

ggtagcgttg ccaatgatgt tacagatgag atggtcaggc taaactggct gacggaattt   4920

atgcctcttc cgaccatcaa gcattttatc cgtactcctg atgatgcatg gttactcacc   4980

actgcgatcc cagggaaaac agcattccag gtattagaag aatatcctga ttcaggtgaa   5040

aatattgttg atgcgctggc agtgttcctg cgccggttgc attcgattcc tgtttgtaat   5100

tgtcctttta acggcgatcg cgtatttcgt ctcgctcagg cgcaatcacg aatgaataac   5160

ggtttggttg gtgcgagtga ttttgatgac gagcgtaatg gctggcctgt tgaacaagtc   5220

tggaaagaaa tgcataagct tttgccattc tcaccggatt cagtcgtcac tcatggtgat   5280

ttctcacttg ataaccttat ttttgacgag gggaaattaa taggttgtat tgatgttgga   5340

cgagtcggaa tcgcagaccg ataccaggat cttgccatcc tatggaactg cctcggtgag   5400
```

```
ttttctcctt cattacagaa acggcttttt caaaaatatg gtattgataa tcctgatatg   5460

aataaattgc agtttcactt gatgctcgat gagtttttct aatgagggcc caaatgtaat   5520

cacctggctc accttcgggt gggcctttct gcgttgctgg cgtttttcca taggctccgc   5580

ccccctgacg agcatcacaa aaatcgatgc tcaagtcaga ggtggcgaaa cccgacagga   5640

ctataaagat accaggcgtt tccccctgga agctccctcg tgcgctctcc tgttccgacc   5700

ctgccgctta ccggatacct gtccgccttt ctcccttcgg gaagcgtggc gctttctcat   5760

agctcacgct gtaggtatct cagttcggtg taggtcgttc gctccaagct gggctgtgtg   5820

cacgaacccc ccgttcagcc cgaccgctgc gccttatccg gtaactatcg tcttgagtcc   5880

aacccggtaa gacacgactt atcgccactg gcagcagcca ctggtaacag gattagcaga   5940

gcgaggtatg taggcggtgc tacagagttc ttgaagtggt ggcctaacta cggctacact   6000

agaagaacag tatttggtat ctgcgctctg ctgaagccag ttacctcgga aaaagagttg   6060

gtagctcttg atccggcaaa caaaccaccg ctggtagcgg tggttttttt gtttgcaagc   6120

agcagattac gcgcagaaaa aaaggatctc aagaagatcc tttgatttc taccgaagaa    6180

aggcccaccc gtgaaggtga gccagtgagt tgattgcagt ccagttacgc tggagtctga   6240

ggctcgtcct gaatgatatc aagcttgaat tcgtt                             6275
```

<210> SEQ ID NO 34
<211> LENGTH: 5364
<212> TYPE: DNA
<213> ORGANISM: Artificial Sequence
<220> FEATURE:
<223> OTHER INFORMATION: Plasmid pSMART-2,3-BDO1

<400> SEQUENCE: 34

```
gtgcgtaatt gtgctgatct cttatatagc tgctctcatt atctctctac cctgaagtga     60

ctctctcacc tgtaaaaata atatctcaca ggcttaatag tttcttaata caaagcctgt    120

aaaacgtcag gataacttct tggaaaaagg agatatacca tgatgcacag cagcgcatgt    180

gattgtgaag cgagtttgtg cgagacactc cgtggttttt ccgcaaaaca cccggattcc    240

gtaatctacc agacatcact gatgtccgcc cttctgtcag gcgtatatga aggggacacg    300

actattgcgg atcttctggc ccacggcgat tttggcctgg gtacgttcaa tgaactcgac    360

ggcgaaatga tcgcgttttc ttcgcaagtt tatcagctcc gtgcggatgg gagcgcccgc    420

gccgcgaagc cagaacaaaa aacaccgttt gcagtaatga catggttcca accgcagtat    480

cgtaaaactt tcgatgcccc ggtgagtcgt cagcagatcc acgatgtaat cgatcaacag    540

attccttcag acaacctgtt ttgcgcgctg cgtattgacg ggaatttccg tcatgctcac    600

acacgtaccg ttccgcgcca gaccccaccc tatcgcgcga tgaccgatgt gctggatgat    660

caaccggtct ttcgttttaa ccagcgcgaa ggagttctgg tgggttttcg taccccgcaa    720

catatgcagg gtattaacgt ggcgggctac catgagcatt tcattacaga tgatcgccaa    780

ggcggtggtc acctgttgga ttaccagctg gaatctggcg tcctgacttt cggcgagatt    840

cacaaactga tgattgacct gccggcggat tctgcattcc tgcaggcaaa tttgcacccc    900

agcaaccttg atgccgccat ccgctccgtc gagaactaat aggctcttca cttctggaaa    960

aaggagatat accatgaatt ccgaaaaaca atcgcgtcag tgggcacatg gtgctgatat   1020

ggttgtgggc cagctggagg cgcagggggt taaacaggtc tttggtattc cgggtgctaa   1080

gatcgacaaa gtgtttgatt ctttactgga tagctcaatc gagattatcc cggtgcgtca   1140
```

-continued

```
tgaagcaaac gcagcgttca tggccgcggc agttggtcgc cttacgggta aagctggcgt 1200
agccctggtc acaagcggcc ccgggtgctc gaatctcatt accggcattg caaccgcaaa 1260
ttctgaggga gatcctgtag tggcactggg gggcgcggta aaacgtgctg ataaagcgaa 1320
attagttcac cagagtatgg acaccgtcgc gatgttctct ccagtaacca aatatgcggt 1380
tgaagtttct tccccagatg caattgcaga ggtagtatca aacgcttttc gtgccgcgga 1440
acatggccgc ccaggtgggg cgttcgtttc gctgccgcag gatattgtag accaaccggc 1500
gacaggcgcc atcctgcctg catctggccc ggcactgatg ggcccagcgc cagagtcggc 1560
gattaacgat gtggcaaaac ttatcgacaa cgccaaaaac cctgtgattc tgttgggctt 1620
aatggcatca cagccggcta attcggctgc attgcgtaag ctgctggaga agagtcgcat 1680
cccggtgact tccacctacc aagccgccgg agctgtgaac caagaacatt tcacccgctt 1740
cgccggtcgt gttggccttt tcaataacca agcgggagac cgtctgctgc atttggccga 1800
tctcattatc tgtattggat actctccagt cgagtatgaa ccgagcatgt ggaactcggg 1860
tgacgcaacc ctcgttcata ttgacgtgct gccagcttat gaagaacgca actatgtacc 1920
cgatatcgag ttggtaggcg acattgcggc gacactgaac ctgctcgctt cccgcattga 1980
tcataaactg gagctctcgc agcgtgcctc cgagatctta gtcgatcgcc aacaccagcg 2040
cgatctgctg gatcgccgtg gcgcaagctt aaatcaattt gcgctgcatc cattacgtat 2100
cgtccgtgcc atgcaggaca tcgtaaacaa tgacgtaacg ctgaccgtgg acatgggctc 2160
atttcatatt tggatcgcac gctatctcta ttcatttcgc gcacgtcagg tcatgattag 2220
taatgggcaa caaactatgg gcgtggctct gccttgggct atcggtgcgt ggctggtgaa 2280
ccccggccgc aaagtggtga gcgttagcgg tgacggagga tttctgcaga gtagcatgga 2340
gttagaaacc gctgtccgcc tgaacgctaa tgtgttacac atcatttggg tggataatgg 2400
ttataatatg gttgcaatcc aggaggagaa aaagtatcag cgtttaagcg gtgtggcgtt 2460
tggaccggta gatttcaaag cctacgccga tgcattcggc gcccgtggct tcgcggtcga 2520
aagcgcggat gccttagaga gcaccttacg tgcggcaatg gatgtgaatg gtccggccgt 2580
cgtggcgatt ccggtggatt attcggataa tccgctgctg atgggacaac tgcacctttc 2640
gcagatcctg tagtaagctc ttctggaaaa aggagatata ccatgcagaa ggtggcgctc 2700
gttaccggat ctggccaagg cattggcaaa gcgattgcgc ttcgtctggt caaagacgga 2760
ttcgccgttg caattgctga ttacaacgac gaaacggcgc gtgctgtcgc cgatgaaatc 2820
atccgtaatg gtggcaacgc tgtcgcagtg aaagtggacg tctctgatcg cgaccaagta 2880
tttgcagcgg tcgagaaagc acgtaccgct ctgggcggtt tcaacgttat cgtgaacaac 2940
gcgggcattg cgccgtcgac gcctatcgaa agcatcaccc cggagattgt agataaggtg 3000
tacaacatca acgtaaaagg agtaatctgg ggtatgcaag ctgccatcga tgcgttccgc 3060
aaagaggggc acggcggtaa aatcattaac gcgtgttcgc aggctggtca tactggtaac 3120
ccggaactgg cggtttatag cagcagcaaa ttcgccgtgc gtggcctgac ccagaccgct 3180
gcacgcgatc tggcgccgct ggggatcacc gtcaatgcat attgtccggg tatcgtaaaa 3240
accccgatgt gggcggaaat tgatcgccag gtatcagagg ccgctggcaa accgctgggc 3300
tatggcacgg aaacgtttgc caagcgcatc acgttaggcc gtctgtcgga accggaggat 3360
gttgcagcat gcgtctctta cctggcgggc ccggattctg attatatgac gggtcagtcc 3420
ctgctgattg atggtggcat ggtctttaac tagtaagatc gtcccggctt atcggtcagt 3480
ttcacctgat ttacgtaaaa acccgcttcg gcgggttttt gcttttggag gggcagaaag 3540
```

```
atgaatgact gtccacgacg ctatacccaa aagaaagacg aattctctag atatcgctca   3600

atactgacca tttaaatcat acctgacctc catagcagaa agtcaaaagc ctccgaccgg   3660

aggcttttga cttgatcggc acgtaagagg ttccaacttt caccataatg aaataagatc   3720

actaccgggc gtatttttg agttatcgag attttcagga gctaaggaag ctaaaatgag    3780

ccatattcaa cgggaaacgt cttgctcgag gccgcgatta aattccaaca tggatgctga   3840

tttatatggg tataaatggg ctcgcgataa tgtcgggcaa tcaggtgcga caatctatcg   3900

attgtatggg aagcccgatg cgccagagtt gtttctgaaa catggcaaag gtagcgttgc   3960

caatgatgtt acagatgaga tggtcaggct aaactggctg acggaattta tgcctcttcc   4020

gaccatcaag cattttatcc gtactcctga tgatgcatgg ttactcacca ctgcgatccc   4080

agggaaaaca gcattccagg tattagaaga atatcctgat tcaggtgaaa atattgttga   4140

tgcgctggca gtgttcctgc gccggttgca ttcgattcct gtttgtaatt gtccttttaa   4200

cggcgatcgc gtatttcgtc tcgctcaggc gcaatcacga atgaataacg gtttggttgg   4260

tgcgagtgat tttgatgacg agcgtaatgg ctggcctgtt gaacaagtct ggaaagaaat   4320

gcataagctt ttgccattct caccggattc agtcgtcact catggtgatt tctcacttga   4380

taaccttatt tttgacgagg ggaaattaat aggttgtatt gatgttggac gagtcggaat   4440

cgcagaccga taccaggatc ttgccatcct atggaactgc ctcggtgagt tttctccttc   4500

attacagaaa cggctttttc aaaaatatgg tattgataat cctgatatga ataaattgca   4560

gtttcacttg atgctcgatg agtttttcta atgagggccc aaatgtaatc acctggctca   4620

ccttcgggtg ggcctttctg cgttgctggc gtttttccat aggctccgcc cccctgacga   4680

gcatcacaaa aatcgatgct caagtcagag gtggcgaaac ccgacaggac tataaagata   4740

ccaggcgttt ccccctggaa gctccctcgt gcgctctcct gttccgaccc tgccgcttac   4800

cggatacctg tccgcctttc tcccttcggg aagcgtggcg ctttctcata gctcacgctg   4860

taggtatctc agttcggtgt aggtcgttcg ctccaagctg ggctgtgtgc acgaaccccc   4920

cgttcagccc gaccgctgcg ccttatccgg taactatcgt cttgagtcca acccggtaag   4980

acacgactta tcgccactgg cagcagccac tggtaacagg attagcagag cgaggtatgt   5040

aggcggtgct acagagttct tgaagtggtg gcctaactac ggctacacta gaagaacagt   5100

atttggtatc tgcgctctgc tgaagccagt tacctcggaa aaagagttgg tagctcttga   5160

tccggcaaac aaaccaccgc tggtagcggt ggtttttttg tttgcaagca gcagattacg   5220

cgcagaaaaa aaggatctca agaagatcct ttgatttct accgaagaaa ggcccacccg    5280

tgaaggtgag ccagtgagtt gattgcagtc cagttacgct ggagtctgag gctcgtcctg   5340

aatgatatca agcttgaatt cgtt                                          5364
```

<210> SEQ ID NO 35
<211> LENGTH: 5748
<212> TYPE: DNA
<213> ORGANISM: Artificial Sequence
<220> FEATURE:
<223> OTHER INFORMATION: Plasmid pSMART-2,3-BDO2

<400> SEQUENCE: 35

```
gtgcgtaatt gtgctgatct cttatatagc tgctctcatt atctctctac cctgaagtga     60

ctctctcacc tgtaaaaata atatctcaca ggcttaatag tttcttaata caaagcctgt    120

aaaacgtcag gataacttct tggaaaaagg agatatacca tgatgcacag cagcgcatgt    180
```

```
gattgtgaag cgagtttgtg cgagacactc cgtggttttt ccgcaaaaca cccggattcc    240
gtaatctacc agacatcact gatgtccgcc cttctgtcag gcgtatatga aggggacacg    300
actattgcgg atcttctggc ccacggcgat tttggcctgg gtacgttcaa tgaactcgac    360
ggcgaaatga tcgcgttttc ttcgcaagtt tatcagctcc gtgcggatgg gagcgcccgc    420
gccgcgaagc cagaacaaaa aacaccgttt gcagtaatga catggttcca accgcagtat    480
cgtaaaactt tcgatgcccc ggtgagtcgt cagcagatcc acgatgtaat cgatcaacag    540
attccttcag acaacctgtt ttgcgcgctg cgtattgacg ggaatttccg tcatgctcac    600
acacgtaccg ttccgcgcca gaccccaccc tatcgcgcga tgaccgatgt gctggatgat    660
caaccggtct ttcgttttaa ccagcgcgaa ggagttctgg tgggttttcg taccccgcaa    720
catatgcagg gtattaacgt ggcgggctac catgagcatt tcattacaga tgatcgccaa    780
ggcggtggtc acctgttgga ttaccagctg gaatctggcg tcctgacttt cggcgagatt    840
cacaaactga tgattgacct gccggcggat tctgcattcc tgcaggcaaa tttgcacccc    900
agcaaccttg atgccgccat ccgctccgtc gagaactaat aggctcttca cttctggaaa    960
aaggagatat accatgaatt ccgaaaaaca atcgcgtcag tgggcacatg gtgctgatat   1020
ggttgtgggc cagctggagg cgcagggggt taaacaggtc tttggtattc cgggtgctaa   1080
gatcgacaaa gtgtttgatt ctttactgga tagctcaatc gagattatcc cggtgcgtca   1140
tgaagcaaac gcagcgttca tggccgcggc agttggtcgc cttacgggta aagctggcgt   1200
agccctggtc acaagcggcc ccgggtgctc gaatctcatt accggcattg caaccgcaaa   1260
ttctgaggga gatcctgtag tggcactggg gggcgcggta aaacgtgctg ataaagcgaa   1320
attagttcac cagagtatgg acaccgtcgc gatgttctct ccagtaacca aatatgcggt   1380
tgaagtttct tccccagatg caattgcaga ggtagtatca aacgcttttc gtgccgcgga   1440
acatggccgc ccaggtgggg cgttcgtttc gctgccgcag gatattgtag accaaccggc   1500
gacaggcgcc atcctgcctg catctggccc ggcactgatg ggcccagcgc cagagtcggc   1560
gattaacgat gtggcaaaac ttatcgacaa cgccaaaaac cctgtgattc tgttgggctt   1620
aatggcatca cagccggcta attcggctgc attgcgtaag ctgctggaga agagtcgcat   1680
cccggtgact tccacctacc aagccgccgg agctgtgaac caagaacatt tcacccgctt   1740
cgccggtcgt gttggccttt tcaataacca agcgggagac cgtctgctgc atttggccga   1800
tctcattatc tgtattggat actctccagt cgagtatgaa ccgagcatgt ggaactcggg   1860
tgacgcaacc ctcgttcata ttgacgtgct gccagcttat gaagaacgca actatgtacc   1920
cgatatcgag ttggtaggcg acattgcggc gacactgaac ctgctcgctt cccgcattga   1980
tcataaactg gagctctcgc agcgtgcctc cgagatctta gtcgatcgcc aacaccagcg   2040
cgatctgctg gatcgccgtg gcgcaagctt aaatcaattt gcgctgcatc cattacgtat   2100
cgtccgtgcc atgcaggaca tcgtaaacaa tgacgtaacg ctgaccgtgg acatgggctc   2160
atttcatatt tggatcgcac gctatctcta ttcatttcgc gcacgtcagg tcatgattag   2220
taatgggcaa caaactatgg gcgtggctct gccttgggct atcggtgcgt ggctggtgaa   2280
ccccggccgc aaagtggtga gcgttagcgg tgacggagga tttctgcaga gtagcatgga   2340
gttagaaacc gctgtccgcc tgaacgctaa tgtgttacac atcatttggg tggataatgg   2400
ttataatatg gttgcaatcc aggaggagaa aaagtatcag cgtttaagcg gtgtggcgtt   2460
tggaccggta gatttcaaag cctacgccga tgcattcggc gcccgtggct tcgcggtcga   2520
aagcgcggat gccttagaga gcaccttacg tgcggcaatg gatgtgaatg gtccggccgt   2580
```

```
cgtggcgatt ccggtggatt attcggataa tccgctgctg atgggacaac tgcacctttc   2640
gcagatcctg tagtaagctc ttctggaaaa aggagatata ccatgcgtgc gttggcatat   2700
ttcaaaaaag gagacatcca ctttaccaac gatattccgc gtccggagat ccagacggat   2760
gatgaagtga ttattgatgt gagctggtgt gggatttgcg gttcggattt gcatgaatat   2820
ctggatggtc caatttttat gccgaaggat ggcgaatgtc acaaactgag taacgcggcg   2880
ctgcccctgg caatgggaca cgagatgtcg ggaattgtca gtaaagtcgg cccgaaagtg   2940
accaaggtca aagtgggcga tcatgttgtt gttgatgctg catcgtcctg tgccgatctc   3000
cattgctggc cccacagcaa attctataac tctaaacctt gtgacgcgtg tcaacgcgga   3060
tcggagaacc tgtgcacgca tgccggtttt gtcgggcttg ggttatctct tggcggtttt   3120
gcggaacaag tggtggtatc tcaacatcac attattcccg tgccgaagga aatccctctg   3180
gacgtagcag cactggtgga accgctctcg gtaacctggc acgcagtaaa aatttcgggc   3240
tttaagaaag gctcgagtgc actggtgttg gggggccggcc caatcggtct gtgtacgatt  3300
ctggtgctga aaggtatggg tgcgagcaaa atcgtagtta gttcgcgttc cgagcgtcgc   3360
atcgaaatgg caaaaaaact cggcgtcgaa gtgtttaatc catcgaaaca cggccataag   3420
agtattgaaa ttctgcgtgg tctgaccaaa tcacatgacg gtttcgatta tagctatgac   3480
tgcagtggaa ttcaggttac cttcgaaacc agccttaaag cccttacttt taaaggcacc   3540
gccaccaata tcgctgtttg gggtcccaaa cccgtacctt tccagcctat ggatgtgaca   3600
cttcaggaaa aagttatgac gggatccatc ggctacgtgg tggaggactt cgaagaagtg   3660
gtccgtgcca ttcacaacgg agatatcgcg atggaagatt gtaagcagct gattaccggc   3720
aaacagcgca ttgaggatgg gtgggaaaaa ggcttccagg aattaatgga ccacaaagag   3780
tctaatgtaa aaattctgct gaccccgaat aatcatggag aaatgaaata gtaatagtaa   3840
gatcgtcccg gcttatcggt cagtttcacc tgatttacgt aaaaacccgc ttcggcgggt   3900
ttttgctttt ggaggggcag aaagatgaat gactgtccac gacgctatac ccaaaagaaa   3960
gacgaattct ctagatatcg ctcaatactg accatttaaa tcatacctga cctccatagc   4020
agaaagtcaa aagcctccga ccggaggctt ttgacttgat cggcacgtaa gaggttccaa   4080
ctttcaccat aatgaaataa gatcactacc gggcgtattt tttgagttat cgagattttc   4140
aggagctaag gaagctaaaa tgagccatat tcaacgggaa acgtcttgct cgaggccgcg   4200
attaaattcc aacatggatg ctgatttata tgggtataaa tgggctcgcg ataatgtcgg   4260
gcaatcaggt gcgacaatct atcgattgta tgggaagccc gatgcgccag agttgtttct   4320
gaaacatggc aaaggtagcg ttgccaatga tgttacagat gagatggtca ggctaaactg   4380
gctgacggaa tttatgcctc ttccgaccat caagcatttt atccgtactc ctgatgatgc   4440
atggttactc accactgcga tcccagggaa aacagcattc caggtattag aagaatatcc   4500
tgattcaggt gaaaatattg ttgatgcgct ggcagtgttc ctgcgccggt tgcattcgat   4560
tcctgtttgt aattgtcctt ttaacggcga tcgcgtattt cgtctcgctc aggcgcaatc   4620
acgaatgaat aacggtttgg ttggtgcgag tgattttgat gacgagcgta atggctggcc   4680
tgttgaacaa gtctggaaag aaatgcataa gcttttgcca ttctcaccgg attcagtcgt   4740
cactcatggt gatttctcac ttgataacct tatttttgac gaggggaaat taataggttg   4800
tattgatgtt ggacgagtcg gaatcgcaga ccgataccag gatcttgcca tcctatggaa   4860
ctgcctcggt gagttttctc cttcattaca gaaacggctt tttcaaaaat atggtattga   4920
```

```
taatcctgat atgaataaat tgcagtttca cttgatgctc gatgagtttt tctaatgagg   4980

gcccaaatgt aatcacctgg ctcaccttcg ggtgggcctt tctgcgttgc tggcgttttt   5040

ccataggctc cgcccccctg acgagcatca caaaaatcga tgctcaagtc agaggtggcg   5100

aaacccgaca ggactataaa gataccaggc gtttccccct ggaagctccc tcgtgcgctc   5160

tcctgttccg accctgccgc ttaccggata cctgtccgcc tttctccctt cgggaagcgt   5220

ggcgctttct catagctcac gctgtaggta tctcagttcg gtgtaggtcg ttcgctccaa   5280

gctgggctgt gtgcacgaac cccccgttca gcccgaccgc tgcgccttat ccggtaacta   5340

tcgtcttgag tccaacccgg taagacacga cttatcgcca ctggcagcag ccactggtaa   5400

caggattagc agagcgaggt atgtaggcgg tgctacagag ttcttgaagt ggtggcctaa   5460

ctacggctac actagaagaa cagtatttgg tatctgcgct ctgctgaagc cagttacctc   5520

ggaaaaagag ttggtagctc ttgatccggc aaacaaacca ccgctggtag cggtggtttt   5580

tttgtttgca agcagcagat tacgcgcaga aaaaaaggat ctcaagaaga tcctttgatt   5640

ttctaccgaa gaaaggccca cccgtgaagg tgagccagtg agttgattgc agtccagtta   5700

cgctggagtc tgaggctcgt cctgaatgat atcaagcttg aattcgtt               5748
```

<210> SEQ ID NO 36
<211> LENGTH: 2818
<212> TYPE: DNA
<213> ORGANISM: Artificial Sequence
<220> FEATURE:
<223> OTHER INFORMATION: Plasmid pSMART-amnp-GFPuv

<400> SEQUENCE: 36

```
tgaggctcgt cctgaatgat atcaagcttg aattcgttag acagtcaacg cgcttgatag     60

cctggcgaag atcatccgat cttcgcctta cacttttgtt tcacatttct gtgacatact    120

atcggatgtg cggtaattgt atgtgtagga ggataatcta tggctagcaa aggagaagaa    180

cttttcacat ggctagcaaa ggagaagaac ttttcactgg agttgtccca attcttgttg    240

aattagatgg tgatgttaat gggcacaaat tttctgtcag tggagagggt gaaggtgatg    300

ctacatacgg aaagcttacc cttaaattta tttgcactac tggaaaacta cctgttccat    360

ggccaacact tgtcactact ttctcttatg gtgttcaatg cttttcccgt tatccggatc    420

atatgaaacg gcatgacttt ttcaagagtg ccatgcccga aggttatgta caggaacgca    480

ctatatcttt caaagatgac gggaactaca agacgcgtgc tgaagtcaag tttgaaggtg    540

atacccttgt taatcgtatc gagttaaaag gtattgattt taaagaagat ggaaacattc    600

tcggacacaa actcgagtac aactataact cacacaatgt atacatcacg gcagacaaac    660

aaaagaatgg aatcaaagct aacttcaaaa ttcgccacaa cattgaagat ggatccgttc    720

aactagcaga ccattatcaa caaaatactc caattggcga tggccctgtc cttttaccag    780

acaaccatta cctgtcgaca caatctgccc tttcgaaaga tcccaacgaa aagcgtgacc    840

acatggtcct tcttgagttt gtaactgctg ctgggattac acatggcatg gatgagctct    900

acaaataatg aggatccccg gcttatcggt cagtttcacc tgatttacgt aaaaacccgc    960

ttcggcgggt ttttgctttt ggaggggcag aaagatgaat gactgtccac gacgctatac   1020

ccaaaagaaa gacgaattct ctagatatcg ctcaatactg accatttaaa tcatacctga   1080

cctccatagc agaaagtcaa aagcctccga ccggaggctt ttgacttgat cggcacgtaa   1140

gaggttccaa ctttcaccat aatgaaataa gatcactacc gggcgtattt tttgagttat   1200

cgagattttc aggagctaag gaagctaaaa tgagccatat tcaacgggaa acgtcttgct   1260
```

```
cgaggccgcg attaaattcc aacatggatg ctgatttata tgggtataaa tgggctcgcg   1320

ataatgtcgg gcaatcaggt gcgacaatct atcgattgta tgggaagccc gatgcgccag   1380

agttgtttct gaaacatggc aaaggtagcg ttgccaatga tgttacagat gagatggtca   1440

ggctaaactg gctgacggaa tttatgcctc ttccgaccat caagcatttt atccgtactc   1500

ctgatgatgc atggttactc accactgcga tccccaggaa aacagcattc caggtattag   1560

aagaatatcc tgattcaggt gaaaatattg ttgatgcgct ggcagtgttc ctgcgccggt   1620

tgcattcgat tcctgtttgt aattgtcctt ttaacggcga tcgcgtattt cgtctcgctc   1680

aggcgcaatc acgaatgaat aacggtttgg ttggtgcgag tgattttgat gacgagcgta   1740

atggctggcc tgttgaacaa gtctggaaag aaatgcataa gcttttgcca ttctcaccgg   1800

attcagtcgt cactcatggt gatttctcac ttgataacct tatttttgac gaggggaaat   1860

taataggttg tattgatgtt ggacgagtcg gaatcgcaga ccgataccag gatcttgcca   1920

tcctatggaa ctgcctcggt gagttttctc cttcattaca gaaacggctt tttcaaaaat   1980

atggtattga taatcctgat atgaataaat tgcagtttca cttgatgctc gatgagtttt   2040

tctaatgagg gcccaaatgt aatcacctgg ctcaccttcg ggtgggcctt tctgcgttgc   2100

tggcgttttt ccataggctc cgcccccctg acgagcatca caaaaatcga tgctcaagtc   2160

agaggtggcg aaacccgaca ggactataaa gataccaggc gtttccccct ggaagctccc   2220

tcgtgcgctc tcctgttccg accctgccgc ttaccggata cctgtccgcc tttctccctt   2280

cgggaagcgt ggcgctttct catagctcac gctgtaggta tctcagttcg gtgtaggtcg   2340

ttcgctccaa gctgggctgt gtgcacgaac cccccgttca gcccgaccgc tgcgccttat   2400

ccggtaacta tcgtcttgag tccaacccgg taagacacga cttatcgcca ctggcagcag   2460

ccactggtaa caggattagc agagcgaggt atgtaggcgg tgctacagag ttcttgaagt   2520

ggtggcctaa ctacggctac actagaagaa cagtatttgg tatctgcgct ctgctgaagc   2580

cagttacctc ggaaaaagag ttggtagctc ttgatccggc aaacaaacca ccgctggtag   2640

cggtggtttt tttgtttgca agcagcagat tacgcgcaga aaaaaaggat ctcaagaaga   2700

tcctttgatt ttctaccgaa gaaaggccca cccgtgaagg tgagccagtg agttgattgc   2760

agtccagtta cgctggagtc tgaggctcgt cctgaatgat atcaagcttg aattcgtt     2818
```

```
<210> SEQ ID NO 37
<211> LENGTH: 2839
<212> TYPE: DNA
<213> ORGANISM: Artificial Sequence
<220> FEATURE:
<223> OTHER INFORMATION: Plasmid pSMART-phoAp-GFPuv

<400> SEQUENCE: 37

tgaggctcgt cctgaatgat atcaagcttg aattcgttcg attacgtaaa gaagttattg     60

aagcatcctc gtcagtaaaa agttaatctt ttcaacagct gtcataaagt tgtcacggcc    120

gagacttata gtcgctttgt ttttattttt taatgtattt gtagtgtagg aggataatct    180

atggctagca aaggagaaga acttttcaca tggctagcaa aggagaagaa cttttcactg    240

gagttgtccc aattcttgtt gaattagatg gtgatgttaa tgggcacaaa ttttctgtca    300

gtggagaggg tgaaggtgat gctacatacg gaaagcttac ccttaaattt atttgcacta    360

ctggaaaact acctgttcca tggccaacac ttgtcactac tttctcttat ggtgttcaat    420

gcttttcccg ttatccggat catatgaaac ggcatgactt tttcaagagt gccatgcccg    480
```

```
aaggttatgt acaggaacgc actatatctt tcaaagatga cgggaactac aagacgcgtg    540
ctgaagtcaa gtttgaaggt gatacccttg ttaatcgtat cgagttaaaa ggtattgatt    600
ttaaagaaga tggaaacatt ctcggacaca aactcgagta caactataac tcacacaatg    660
tatacatcac ggcagacaaa caaaagaatg gaatcaaagc taacttcaaa attcgccaca    720
acattgaaga tggatccgtt caactagcag accattatca acaaaatact ccaattggcg    780
atggccctgt ccttttacca gacaaccatt acctgtcgac acaatctgcc ctttcgaaag    840
atcccaacga aaagcgtgac cacatggtcc ttcttgagtt tgtaactgct gctgggatta    900
cacatggcat ggatgagctc tacaaataat gaggatcccc ggcttatcgg tcagtttcac    960
ctgatttacg taaaaacccg cttcggcggg tttttgcttt tggaggggca gaaagatgaa   1020
tgactgtcca cgacgctata cccaaaagaa agacgaattc tctagatatc gctcaatact   1080
gaccatttaa atcatacctg acctccatag cagaaagtca aaagcctccg accggaggct   1140
tttgacttga tcggcacgta agaggttcca actttcacca taatgaaata agatcactac   1200
cgggcgtatt ttttgagtta tcgagatttt caggagctaa ggaagctaaa atgagccata   1260
ttcaacggga aacgtcttgc tcgaggccgc gattaaattc caacatggat gctgatttat   1320
atgggtataa atgggctcgc gataatgtcg ggcaatcagg tgcgacaatc tatcgattgt   1380
atgggaagcc cgatgcgcca gagttgtttc tgaaacatgg caaaggtagc gttgccaatg   1440
atgttacaga tgagatggtc aggctaaact ggctgacgga atttatgcct cttccgacca   1500
tcaagcattt tatccgtact cctgatgatg catggttact caccactgcg atccccagga   1560
aaacagcatt ccaggtatta gaagaatatc ctgattcagg tgaaaatatt gttgatgcgc   1620
tggcagtgtt cctgcgccgg ttgcattcga ttcctgtttg taattgtcct tttaacggcg   1680
atcgcgtatt tcgtctcgct caggcgcaat cacgaatgaa taacggtttg gttggtgcga   1740
gtgattttga tgacgagcgt aatggctggc ctgttgaaca agtctggaaa gaaatgcata   1800
agcttttgcc attctcaccg gattcagtcg tcactcatgg tgatttctca cttgataacc   1860
ttatttttga cgaggggaaa ttaataggtt gtattgatgt tggacgagtc ggaatcgcag   1920
accgatacca ggatcttgcc atcctatgga actgcctcgg tgagttttct ccttcattac   1980
agaaacggct ttttcaaaaa tatggtattg ataatcctga tatgaataaa ttgcagtttc   2040
acttgatgct cgatgagttt ttctaatgag ggcccaaatg taatcacctg gctcaccttc   2100
gggtgggcct ttctgcgttg ctggcgtttt tccataggct ccgcccccct gacgagcatc   2160
acaaaaatcg atgctcaagt cagaggtggc gaaacccgac aggactataa agataccagg   2220
cgtttccccc tggaagctcc ctcgtgcgct ctcctgttcc gaccctgccg cttaccggat   2280
acctgtccgc ctttctccct tcgggaagcg tggcgctttc tcatagctca cgctgtaggt   2340
atctcagttc ggtgtaggtc gttcgctcca agctgggctg tgtgcacgaa ccccccgttc   2400
agcccgaccg ctgcgcctta tccggtaact atcgtcttga gtccaacccg gtaagacacg   2460
acttatcgcc actggcagca gccactggta acaggattag cagagcgagg tatgtaggcg   2520
gtgctacaga gttcttgaag tggtggccta actacggcta cactagaaga acagtatttg   2580
gtatctgcgc tctgctgaag ccagttacct cggaaaaaga gttggtagct cttgatccgg   2640
caaacaaacc accgctggta gcggtggttt ttttgtttgc aagcagcaga ttacgcgcag   2700
aaaaaaagga tctcaagaag atcctttgat tttctaccga agaaaggccc acccgtgaag   2760
gtgagccagt gagttgattg cagtccagtt acgctggagt ctgaggctcg tcctgaatga   2820
tatcaagctt gaattcgtt                                                2839
```

<210> SEQ ID NO 38
<211> LENGTH: 2819
<212> TYPE: DNA
<213> ORGANISM: Artificial Sequence
<220> FEATURE:
<223> OTHER INFORMATION: Plasmid pSMART-phoBp-GFPuv

<400> SEQUENCE: 38

```
tgaggctcgt cctgaatgat atcaagcttg aattcgttgc cacggaaatc aataacctga     60
agatatgtgc gacgagcttt tcataaatct gtcataaatc tgacgcataa tgacgtcgca    120
ttaatgatcg caacctattt attgtgtagg aggataatct atggctagca aaggagaaga    180
acttttcaca tggctagcaa aggagaagaa cttttcactg gagttgtccc aattcttgtt    240
gaattagatg gtgatgttaa tgggcacaaa ttttctgtca gtggagaggg tgaaggtgat    300
gctacatacg gaaagcttac ccttaaattt atttgcacta ctggaaaact acctgttcca    360
tggccaacac ttgtcactac tttctcttat ggtgttcaat gcttttcccg ttatccggat    420
catatgaaac ggcatgactt tttcaagagt gccatgcccg aaggttatgt acaggaacgc    480
actatatctt tcaaagatga cgggaactac aagacgcgtg ctgaagtcaa gtttgaaggt    540
gatacccttg ttaatcgtat cgagttaaaa ggtattgatt ttaaagaaga tggaaacatt    600
ctcggacaca aactcgagta caactataac tcacacaatg tatacatcac ggcagacaaa    660
caaaagaatg gaatcaaagc taacttcaaa attcgccaca acattgaaga tggatccgtt    720
caactagcag accattatca acaaaatact ccaattggcg atggccctgt ccttttacca    780
gacaaccatt acctgtcgac acaatctgcc ctttcgaaag atcccaacga aaagcgtgac    840
cacatggtcc ttcttgagtt tgtaactgct gctgggatta cacatggcat ggatgagctc    900
tacaaataat gaggatcccc ggcttatcgg tcagtttcac ctgatttacg taaaaacccg    960
cttcggcggg tttttgcttt tggaggggca gaaagatgaa tgactgtcca cgacgctata   1020
cccaaaagaa agacgaattc tctagatatc gctcaatact gaccatttaa atcatacctg   1080
acctccatag cagaaagtca aaagcctccg accggaggct tttgacttga tcggcacgta   1140
agaggttcca actttcacca taatgaaata agatcactac cgggcgtatt ttttgagtta   1200
tcgagatttt caggagctaa ggaagctaaa atgagccata ttcaacggga aacgtcttgc   1260
tcgaggccgc gattaaattc caacatggat gctgatttat atgggtataa atgggctcgc   1320
gataatgtcg ggcaatcagg tgcgacaatc tatcgattgt atgggaagcc cgatgcgcca   1380
gagttgtttc tgaaacatgg caaaggtagc gttgccaatg atgttacaga tgagatggtc   1440
aggctaaact ggctgacgga atttatgcct cttccgacca tcaagcattt tatccgtact   1500
cctgatgatg catggttact caccactgcg atccccggga aaacagcatt ccaggtatta   1560
gaagaatatc ctgattcagg tgaaaatatt gttgatgcgc tggcagtgtt cctgcgccgg   1620
ttgcattcga ttcctgtttg taattgtcct tttaacggcg atcgcgtatt tcgtctcgct   1680
caggcgcaat cacgaatgaa taacggtttg gttggtgcga gtgattttga tgacgagcgt   1740
aatggctggc ctgttgaaca agtctggaaa gaaatgcata agcttttgcc attctcaccg   1800
gattcagtcg tcactcatgg tgatttctca cttgataacc ttatttttga cgaggggaaa   1860
ttaataggtt gtattgatgt tggacgagtc ggaatcgcag accgatacca ggatcttgcc   1920
atcctatgga actgcctcgg tgagttttct ccttcattac agaaacggct ttttcaaaaa   1980
tatggtattg ataatcctga tatgaataaa ttgcagtttc acttgatgct cgatgagttt   2040
```

-continued

```
ttctaatgag ggcccaaatg taatcacctg gctcaccttc gggtgggcct ttctgcgttg   2100

ctggcgtttt tccataggct ccgcccccct gacgagcatc acaaaaatcg atgctcaagt   2160

cagaggtggc gaaacccgac aggactataa agataccagg cgtttccccc tggaagctcc   2220

ctcgtgcgct ctcctgttcc gaccctgccg cttaccggat acctgtccgc ctttctccct   2280

tcgggaagcg tggcgctttc tcatagctca cgctgtaggt atctcagttc ggtgtaggtc   2340

gttcgctcca agctgggctg tgtgcacgaa ccccccgttc agcccgaccg ctgcgcctta   2400

tccggtaact atcgtcttga gtccaacccg gtaagacacg acttatcgcc actggcagca   2460

gccactggta acaggattag cagagcgagg tatgtaggcg gtgctacaga gttcttgaag   2520

tggtggccta actacggcta cactagaaga acagtatttg gtatctgcgc tctgctgaag   2580

ccagttacct cggaaaaaga gttggtagct cttgatccgg caaacaaacc accgctggta   2640

gcggtggttt ttttgtttgc aagcagcaga ttacgcgcag aaaaaaagga tctcaagaag   2700

atcctttgat tttctaccga agaaaggccc acccgtgaag gtgagccagt gagttgattg   2760

cagtccagtt acgctggagt ctgaggctcg tcctgaatga tatcaagctt gaattcgtt    2819
```

```
<210> SEQ ID NO 39
<211> LENGTH: 2880
<212> TYPE: DNA
<213> ORGANISM: Artificial Sequence
<220> FEATURE:
<223> OTHER INFORMATION: Plasmid pSMART-phoEp-GFPuv

<400> SEQUENCE: 39

tgaggctcgt cctgaatgat atcaagcttg aattcgttag catggcgttt tgttgcgcgg     60

gatcagcaag cctagcggca gttgtttacg cttttattac agatttaata aattaccaca    120

ttttaagaat attattaatc tgtaatatat ctttaacaat ctcaggttaa aaactttcct    180

gttttcaacg ggactctccc gctggtgtag gaggataatc tatggctagc aaaggagaag    240

aacttttcac atggctagca aaggagaaga acttttcact ggagttgtcc caattcttgt    300

tgaattagat ggtgatgtta atgggcacaa attttctgtc agtggagagg gtgaaggtga    360

tgctacatac ggaaagctta cccttaaatt tatttgcact actggaaaac tacctgttcc    420

atggccaaca cttgtcacta ctttctctta tggtgttcaa tgcttttccc gttatccgga    480

tcatatgaaa cggcatgact ttttcaagag tgccatgccc gaaggttatg tacaggaacg    540

cactatatct ttcaaagatg acgggaacta caagacgcgt gctgaagtca agtttgaagg    600

tgataccctt gttaatcgta tcgagttaaa aggtattgat tttaaagaag atggaaacat    660

tctcggacac aaactcgagt acaactataa ctcacacaat gtatacatca cggcagacaa    720

acaaaagaat ggaatcaaag ctaacttcaa aattcgccac aacattgaag atggatccgt    780

tcaactagca gaccattatc aacaaaatac tccaattggc gatggccctg tccttttacc    840

agacaaccat tacctgtcga cacaatctgc cctttcgaaa gatcccaacg aaaagcgtga    900

ccacatggtc cttcttgagt ttgtaactgc tgctgggatt acacatggca tggatgagct    960

ctacaaataa tgaggatccc cggcttatcg gtcagtttca cctgatttac gtaaaaaccc   1020

gcttcggcgg gtttttgctt ttggaggggc agaaagatga atgactgtcc acgacgctat   1080

acccaaaaga aagacgaatt ctctagatat cgctcaatac tgaccattta aatcataccct   1140

gacctccata gcagaaagtc aaaagcctcc gaccggaggc ttttgacttg atcggcacgt   1200

aagaggttcc aactttcacc ataatgaaat aagatcacta ccgggcgtat tttttgagtt   1260

atcgagattt tcaggagcta aggaagctaa aatgagccat attcaacggg aaacgtcttg   1320
```

```
ctcgaggccg cgattaaatt ccaacatgga tgctgattta tatgggtata aatgggctcg   1380
cgataatgtc gggcaatcag gtgcgacaat ctatcgattg tatgggaagc ccgatgcgcc   1440
agagttgttt ctgaaacatg gcaaaggtag cgttgccaat gatgttacag atgagatggt   1500
caggctaaac tggctgacgg aatttatgcc tcttccgacc atcaagcatt ttatccgtac   1560
tcctgatgat gcatggttac tcaccactgc gatccccggg aaaacagcat tccaggtatt   1620
agaagaatat cctgattcag gtgaaaatat tgttgatgcg ctggcagtgt tcctgcgccg   1680
gttgcattcg attcctgttt gtaattgtcc ttttaacggc gatcgcgtat ttcgtctcgc   1740
tcaggcgcaa tcacgaatga ataacggttt ggttggtgcg agtgattttg atgacgagcg   1800
taatggctgg cctgttgaac aagtctggaa agaaatgcat aagcttttgc cattctcacc   1860
ggattcagtc gtcactcatg gtgatttctc acttgataac cttatttttg acgaggggaa   1920
attaataggt tgtattgatg ttggacgagt cggaatcgca gaccgatacc aggatcttgc   1980
catcctatgg aactgcctcg gtgagttttc tccttcatta cagaaacggc tttttcaaaa   2040
atatggtatt gataatcctg atatgaataa attgcagttt cacttgatgc tcgatgagtt   2100
tttctaatga gggcccaaat gtaatcacct ggctcacctt cgggtgggcc tttctgcgtt   2160
gctggcgttt ttccataggc tccgcccccc tgacgagcat cacaaaaatc gatgctcaag   2220
tcagaggtgg cgaaacccga caggactata aagataccag gcgtttcccc ctggaagctc   2280
cctcgtgcgc tctcctgttc cgaccctgcc gcttaccgga tacctgtccg cctttctccc   2340
ttcgggaagc gtggcgcttt ctcatagctc acgctgtagg tatctcagtt cggtgtaggt   2400
cgttcgctcc aagctgggct gtgtgcacga accccccgtt cagcccgacc gctgcgcctt   2460
atccggtaac tatcgtcttg agtccaaccc ggtaagacac gacttatcgc cactggcagc   2520
agccactggt aacaggatta gcagagcgag gtatgtaggc ggtgctacag agttcttgaa   2580
gtggtggcct aactacggct acactagaag aacagtattt ggtatctgcg ctctgctgaa   2640
gccagttacc tcggaaaaag agttggtagc tcttgatccg gcaaacaaac caccgctggt   2700
agcggtggtt tttttgtttg caagcagcag attacgcgca gaaaaaaagg atctcaagaa   2760
gatcctttga ttttctaccg aagaaaggcc cacccgtgaa ggtgagccag tgagttgatt   2820
gcagtccagt tacgctggag tctgaggctc gtcctgaatg atatcaagct tgaattcgtt   2880
```

```
<210> SEQ ID NO 40
<211> LENGTH: 2879
<212> TYPE: DNA
<213> ORGANISM: Artificial Sequence
<220> FEATURE:
<223> OTHER INFORMATION: Plasmid pSMART-phoHp-GFPuv

<400> SEQUENCE: 40
```

```
tgaggctcgt cctgaatgat atcaagcttg aattcgttaa tcctgctgaa agcacacagc     60
tttttcatc actgtcatca ctctgtcatc tttccagtag aaactaatgt cactgaaatg    120
gtgttttata gttaaatata agtaaatata ttgttgcaat aaatgcgaga tctgttgtac    180
ttattaagta gcagcggaag ttcgtgtagg aggataatct atggctagca aaggagaaga    240
acttttcaca tggctagcaa aggagaagaa cttttcactg gagttgtccc aattcttgtt    300
gaattagatg gtgatgttaa tgggcacaaa ttttctgtca gtggagaggg tgaaggtgat    360
gctacatacg gaaagcttac ccttaaattt atttgcacta ctggaaaact acctgttcca    420
tggccaacac ttgtcactac tttctcttat ggtgttcaat gcttttcccg ttatccggat    480
```

```
catatgaaac ggcatgactt tttcaagagt gccatgcccg aaggttatgt acaggaacgc     540
actatatctt tcaaagatga cgggaactac aagacgcgtg ctgaagtcaa gtttgaaggt     600
gataccccttg ttaatcgtat cgagttaaaa ggtattgatt ttaaagaaga tggaaacatt    660
ctcggacaca aactcgagta caactataac tcacacaatg tatacatcac ggcagacaaa     720
caaaagaatg gaatcaaagc taacttcaaa attcgccaca acattgaaga tggatccgtt     780
caactagcag accattatca acaaaatact ccaattggcg atggccctgt ccttttacca     840
gacaaccatt acctgtcgac acaatctgcc ctttcgaaag atcccaacga aaagcgtgac     900
cacatggtcc ttcttgagtt tgtaactgct gctgggatta cacatggcat ggatgagctc     960
tacaaataat gaggatcccc ggcttatcgg tcagtttcac ctgatttacg taaaaacccg    1020
cttcggcggg tttttgcttt tggaggggca gaaagatgaa tgactgtcca cgacgctata    1080
cccaaaagaa agacgaattc tctagatatc gctcaatact gaccatttaa atcatacctg    1140
acctccatag cagaaagtca aaagcctccg accggaggct tttgacttga tcggcacgta    1200
agaggttcca actttcacca taatgaaata agatcactac cgggcgtatt ttttgagtta    1260
tcgagatttt caggagctaa ggaagctaaa atgagccata ttcaacggga aacgtcttgc    1320
tcgaggccgc gattaaattc caacatggat gctgatttat atgggtataa atgggctcgc    1380
gataatgtcg ggcaatcagg tgcgacaatc tatcgattgt atgggaagcc cgatgcgcca    1440
gagttgtttc tgaaacatgg caaaggtagc gttgccaatg atgttacaga tgagatggtc    1500
aggctaaact ggctgacgga atttatgcct cttccgacca tcaagcattt tatccgtact    1560
cctgatgatg catggttact caccactgcg atccccaggga aaacagcatt ccaggtatta   1620
gaagaatatc ctgattcagg tgaaaatatt gttgatgcgc tggcagtgtt cctgcgccgg    1680
ttgcattcga ttcctgtttg taattgtcct tttaacggcg atcgcgtatt tcgtctcgct    1740
caggcgcaat cacgaatgaa taacggtttg gttggtgcga gtgattttga tgacgagcgt    1800
aatggctggc ctgttgaaca agtctggaaa gaaatgcata agcttttgcc attctcaccg    1860
gattcagtcg tcactcatgg tgatttctca cttgataacc ttatttttga cgaggggaaa    1920
ttaataggtt gtattgatgt tggacgagtc ggaatcgcag accgatacca ggatcttgcc    1980
atcctatgga actgcctcgg tgagttttct ccttcattac agaaacggct ttttcaaaaa    2040
tatggtattg ataatcctga tatgaataaa ttgcagtttc acttgatgct cgatgagttt    2100
ttctaatgag ggcccaaatg taatcacctg gctcaccttc gggtgggcct ttctgcgttg    2160
ctggcgtttt tccataggct ccgcccccct gacgagcatc acaaaaatcg atgctcaagt    2220
cagaggtggc gaaacccgac aggactataa agataccagg cgtttccccc tggaagctcc    2280
ctcgtgcgct ctcctgttcc gaccctgccg cttaccggat acctgtccgc ctttctccct    2340
tcgggaagcg tggcgctttc tcatagctca cgctgtaggt atctcagttc ggtgtaggtc    2400
gttcgctcca agctgggctg tgtgcacgaa ccccccgttc agcccgaccg ctgcgcctta    2460
tccggtaact atcgtcttga gtccaacccg gtaagacacg acttatcgcc actggcagca    2520
gccactggta acaggattag cagagcgagg tatgtaggcg gtgctacaga gttcttgaag    2580
tggtggccta actacggcta cactagaaga acagtatttg gtatctgcgc tctgctgaag    2640
ccagttacct cggaaaaaga gttggtagct cttgatccgg caaacaaacc accgctggta    2700
gcggtggttt ttttgtttgc aagcagcaga ttacgcgcag aaaaaaagga tctcaagaag    2760
atcctttgat tttctaccga agaaaggccc acccgtgaag gtgagccagt gagttgattg    2820
cagtccagtt acgctggagt ctgaggctcg tcctgaatga tatcaagctt gaattcgtt     2879
```

<210> SEQ ID NO 41
<211> LENGTH: 2850
<212> TYPE: DNA
<213> ORGANISM: Artificial Sequence
<220> FEATURE:
<223> OTHER INFORMATION: Plasmid pSMART-phoUp-GFPuv

<400> SEQUENCE: 41

```
tgaggctcgt cctgaatgat atcaagcttg aattcgttac cgaactgaag caggattaca     60
ccgtggtgat cgtcacccac aacatgcagc aggctgcgcg ttgttccgac cacacggcgt    120
ttatgtacct gggcgaattg attgagttca gcaacacgga cgatctgttc accagtgtag    180
gaggataatc tatggctagc aaaggagaag aacttttcac atggctagca aaggagaaga    240
acttttcact ggagttgtcc caattcttgt tgaattagat ggtgatgtta atgggcacaa    300
attttctgtc agtggagagg gtgaaggtga tgctacatac ggaaagctta cccttaaatt    360
tatttgcact actggaaaac tacctgttcc atggccaaca cttgtcacta ctttctctta    420
tggtgttcaa tgcttttccc gttatccgga tcatatgaaa cggcatgact ttttcaagag    480
tgccatgccc gaaggttatg tacaggaacg cactatatct ttcaaagatg acgggaacta    540
caagacgcgt gctgaagtca agtttgaagg tgataccctt gttaatcgta tcgagttaaa    600
aggtattgat tttaaagaag atggaaacat tctcggacac aaactcgagt acaactataa    660
ctcacacaat gtatacatca cggcagacaa acaaaagaat ggaatcaaag ctaacttcaa    720
aattcgccac aacattgaag atggatccgt tcaactagca gaccattatc aacaaaatac    780
tccaattggc gatggccctg tccttttacc agacaaccat tacctgtcga cacaatctgc    840
cctttcgaaa gatcccaacg aaaagcgtga ccacatggtc cttcttgagt ttgtaactgc    900
tgctgggatt acacatggca tggatgagct ctacaaataa tgaggatccc cggcttatcg    960
gtcagtttca cctgatttac gtaaaaaccc gcttcggcgg gtttttgctt ttggaggggc   1020
agaaagatga atgactgtcc acgacgctat acccaaaaga aagacgaatt ctctagatat   1080
cgctcaatac tgaccattta aatcatacct gacctccata gcagaaagtc aaaagcctcc   1140
gaccggaggc ttttgacttg atcggcacgt aagaggttcc aactttcacc ataatgaaat   1200
aagatcacta ccgggcgtat tttttgagtt atcgagattt tcaggagcta aggaagctaa   1260
aatgagccat attcaacggg aaacgtcttg ctcgaggccg cgattaaatt ccaacatgga   1320
tgctgattta tatgggtata aatgggctcg cgataatgtc gggcaatcag gtgcgacaat   1380
ctatcgattg tatgggaagc ccgatgcgcc agagttgttt ctgaaacatg gcaaaggtag   1440
cgttgccaat gatgttacag atgagatggt caggctaaac tggctgacgg aatttatgcc   1500
tcttccgacc atcaagcatt ttatccgtac tcctgatgat gcatggttac tcaccactgc   1560
gatccccggg aaaacagcat tccaggtatt agaagaatat cctgattcag gtgaaaatat   1620
tgttgatgcg ctggcagtgt tcctgcgccg gttgcattcg attcctgttt gtaattgtcc   1680
ttttaacggc gatcgcgtat ttcgtctcgc tcaggcgcaa tcacgaatga ataacggttt   1740
ggttggtgcg agtgattttg atgacgagcg taatggctgg cctgttgaac aagtctggaa   1800
agaaatgcat aagcttttgc cattctcacc ggattcagtc gtcactcatg gtgatttctc   1860
acttgataac cttatttttg acgaggggaa attaataggt tgtattgatg ttggacgagt   1920
cggaatcgca gaccgatacc aggatcttgc catcctatgg aactgcctcg gtgagttttc   1980
tccttcatta cagaaacggc tttttcaaaa atatggtatt gataatcctg atatgaataa   2040
```

```
attgcagttt cacttgatgc tcgatgagtt tttctaatga gggcccaaat gtaatcacct   2100

ggctcacctt cgggtgggcc tttctgcgtt gctggcgttt ttccataggc tccgcccccc   2160

tgacgagcat cacaaaaatc gatgctcaag tcagaggtgg cgaaacccga caggactata   2220

aagataccag gcgtttcccc ctggaagctc cctcgtgcgc tctcctgttc cgaccctgcc   2280

gcttaccgga tacctgtccg cctttctccc ttcgggaagc gtggcgcttt ctcatagctc   2340

acgctgtagg tatctcagtt cggtgtaggt cgttcgctcc aagctgggct gtgtgcacga   2400

accccccgtt cagcccgacc gctgcgcctt atccggtaac tatcgtcttg agtccaaccc   2460

ggtaagacac gacttatcgc cactggcagc agccactggt aacaggatta gcagagcgag   2520

gtatgtaggc ggtgctacag agttcttgaa gtggtggcct aactacggct acactagaag   2580

aacagtattt ggtatctgcg ctctgctgaa gccagttacc tcggaaaaag agttggtagc   2640

tcttgatccg gcaaacaaac caccgctggt agcggtggtt tttttgtttg caagcagcag   2700

attacgcgca gaaaaaaagg atctcaagaa gatcctttga ttttctaccg aagaaaggcc   2760

cacccgtgaa ggtgagccag tgagttgatt gcagtccagt tacgctggag tctgaggctc   2820

gtcctgaatg atatcaagct tgaattcgtt                                    2850
```

<210> SEQ ID NO 42
<211> LENGTH: 2900
<212> TYPE: DNA
<213> ORGANISM: Artificial Sequence
<220> FEATURE:
<223> OTHER INFORMATION: Plasmid pSMART-mipAp-GFPuv

<400> SEQUENCE: 42

```
tgaggctcgt cctgaatgat atcaagcttg aattcgttca tccataaatt ttgcataatt     60

aatgtaaaga ccaggctcgc cagtaacgct aaattcattt ggctgtaagc gcggtgtcat    120

ccgcgtcagg aaaattaaac agttacttta aaaaatgaaa acgtaaaaag gttgggtttc    180

gatgtattga cgggtaaact ttgtcgcccg ctaaacattt gtttgtgtag gaggataatc    240

tatggctagc aaaggagaag aacttttcac atggctagca aaggagaaga acttttcact    300

ggagttgtcc caattcttgt tgaattagat ggtgatgtta atgggcacaa attttctgtc    360

agtggagagg gtgaaggtga tgctacatac ggaaagctta cccttaaatt tatttgcact    420

actggaaaac tacctgttcc atggccaaca cttgtcacta ctttctctta tggtgttcaa    480

tgcttttccc gttatccgga tcatatgaaa cggcatgact ttttcaagag tgccatgccc    540

gaaggttatg tacaggaacg cactatatct ttcaaagatg acgggaacta caagacgcgt    600

gctgaagtca agtttgaagg tgataccctt gttaatcgta tcgagttaaa aggtattgat    660

tttaaagaag atggaaacat tctcggacac aaactcgagt acaactataa ctcacacaat    720

gtatacatca cggcagacaa acaaaagaat ggaatcaaag ctaacttcaa aattcgccac    780

aacattgaag atggatccgt tcaactagca gaccattatc aacaaaatac tccaattggc    840

gatggccctg tccttttacc agacaaccat tacctgtcga cacaatctgc cctttcgaaa    900

gatcccaacg aaaagcgtga ccacatggtc cttcttgagt ttgtaactgc tgctgggatt    960

acacatggca tggatgagct ctacaaataa tgaggatccc cggcttatcg gtcagtttca   1020

cctgatttac gtaaaaaccc gcttcggcgg gtttttgctt ttggaggggc agaaagatga   1080

atgactgtcc acgacgctat acccaaaaga aagacgaatt ctctagatat cgctcaatac   1140

tgaccattta aatcatacct gacctccata gcagaaagtc aaaagcctcc gaccggaggc   1200

ttttgacttg atcggcacgt aagaggttcc aactttcacc ataatgaaat aagatcacta   1260
```

```
ccgggcgtat tttttgagtt atcgagattt tcaggagcta aggaagctaa aatgagccat   1320

attcaacggg aaacgtcttg ctcgaggccg cgattaaatt ccaacatgga tgctgattta   1380

tatgggtata aatgggctcg cgataatgtc gggcaatcag gtgcgacaat ctatcgattg   1440

tatgggaagc ccgatgcgcc agagttgttt ctgaaacatg gcaaaggtag cgttgccaat   1500

gatgttacag atgagatggt caggctaaac tggctgacgg aatttatgcc tcttccgacc   1560

atcaagcatt ttatccgtac tcctgatgat gcatggttac tcaccactgc gatccccaggg  1620

aaaacagcat tccaggtatt agaagaatat cctgattcag gtgaaaatat tgttgatgcg   1680

ctggcagtgt tcctgcgccg gttgcattcg attcctgttt gtaattgtcc ttttaacggc   1740

gatcgcgtat ttcgtctcgc tcaggcgcaa tcacgaatga ataacggttt ggttggtgcg   1800

agtgattttg atgacgagcg taatggctgg cctgttgaac aagtctggaa agaaatgcat   1860

aagcttttgc cattctcacc ggattcagtc gtcactcatg gtgatttctc acttgataac   1920

cttatttttg acgaggggaa attaataggt tgtattgatg ttggacgagt cggaatcgca   1980

gaccgatacc aggatcttgc catcctatgg aactgcctcg gtgagttttc tccttcatta   2040

cagaaacggc tttttcaaaa atatggtatt gataatcctg atatgaataa attgcagttt   2100

cacttgatgc tcgatgagtt tttctaatga gggcccaaat gtaatcacct ggctcacctt   2160

cgggtgggcc tttctgcgtt gctggcgttt ttccataggc tccgcccccc tgacgagcat   2220

cacaaaaatc gatgctcaag tcagaggtgg cgaaacccga caggactata aagataccag   2280

gcgtttcccc ctggaagctc cctcgtgcgc tctcctgttc cgaccctgcc gcttaccgga   2340

tacctgtccg cctttctccc ttcgggaagc gtggcgcttt ctcatagctc acgctgtagg   2400

tatctcagtt cggtgtaggt cgttcgctcc aagctgggct gtgtgcacga accccccgtt   2460

cagcccgacc gctgcgcctt atccggtaac tatcgtcttg agtccaaccc ggtaagacac   2520

gacttatcgc cactggcagc agccactggt aacaggatta gcagagcgag gtatgtaggc   2580

ggtgctacag agttcttgaa gtggtggcct aactacggct acactagaag aacagtattt   2640

ggtatctgcg ctctgctgaa gccagttacc tcggaaaaag agttggtagc tcttgatccg   2700

gcaaacaaac caccgctggt agcggtggtt tttttgtttg caagcagcag attacgcgca   2760

gaaaaaaagg atctcaagaa gatcctttga ttttctaccg aagaaaggcc cacccgtgaa   2820

ggtgagccag tgagttgatt gcagtccagt tacgctggag tctgaggctc gtcctgaatg   2880

atatcaagct tgaattcgtt                                               2900
```

<210> SEQ ID NO 43
<211> LENGTH: 2816
<212> TYPE: DNA
<213> ORGANISM: Artificial Sequence
<220> FEATURE:
<223> OTHER INFORMATION: Plasmid pSMART-pstSp-GFPuv

<400> SEQUENCE: 43

```
tgaggctcgt cctgaatgat atcaagcttg aattcgttaa gactttatct ctctgtcata     60

aaactgtcat attccttaca tataactgtc acctgtttgt cctattttgc ttctcgtagc    120

caacaaacaa tgctttatga gtgtaggagg ataatctatg gctagcaaag gagaagaact    180

tttcacatgg ctagcaaagg agaagaactt ttcactggag ttgtcccaat tcttgttgaa    240

ttagatggtg atgttaatgg gcacaaattt tctgtcagtg gagagggtga aggtgatgct    300

acatacggaa agcttaccct taaatttatt tgcactactg gaaaactacc tgttccatgg    360
```

```
ccaacacttg tcactacttt ctcttatggt gttcaatgct tttcccgtta tccggatcat    420
atgaaacggc atgacttttt caagagtgcc atgcccgaag gttatgtaca ggaacgcact    480
atatctttca aagatgacgg gaactacaag acgcgtgctg aagtcaagtt tgaaggtgat    540
acccttgtta atcgtatcga gttaaaaggt attgatttta aagaagatgg aaacattctc    600
ggacacaaac tcgagtacaa ctataactca cacaatgtat acatcacggc agacaaacaa    660
aagaatggaa tcaaagctaa cttcaaaatt cgccacaaca ttgaagatgg atccgttcaa    720
ctagcagacc attatcaaca aaatactcca attggcgatg gccctgtcct tttaccagac    780
aaccattacc tgtcgacaca atctgccctt tcgaaagatc ccaacgaaaa gcgtgaccac    840
atggtccttc ttgagtttgt aactgctgct gggattacac atggcatgga tgagctctac    900
aaataatgag gatccccggc ttatcggtca gtttcacctg atttacgtaa aaacccgctt    960
cggcgggttt ttgcttttgg aggggcagaa agatgaatga ctgtccacga cgctataccc   1020
aaaagaaaga cgaattctct agatatcgct caatactgac catttaaatc atacctgacc   1080
tccatagcag aaagtcaaaa gcctccgacc ggaggctttt gacttgatcg gcacgtaaga   1140
ggttccaact ttcaccataa tgaaataaga tcactaccgg gcgtattttt tgagttatcg   1200
agattttcag gagctaagga agctaaaatg agccatattc aacgggaaac gtcttgctcg   1260
aggccgcgat taaattccaa catggatgct gatttatatg ggtataaatg ggctcgcgat   1320
aatgtcgggc aatcaggtgc gacaatctat cgattgtatg ggaagcccga tgcgccagag   1380
ttgtttctga aacatggcaa aggtagcgtt gccaatgatg ttacagatga gatggtcagg   1440
ctaaactggc tgacggaatt tatgcctctt ccgaccatca agcattttat ccgtactcct   1500
gatgatgcat ggttactcac cactgcgatc cccagggaaaa cagcattcca ggtattagaa  1560
gaatatcctg attcaggtga aaatattgtt gatgcgctgg cagtgttcct gcgccggttg   1620
cattcgattc ctgtttgtaa ttgtcctttt aacggcgatc gcgtatttcg tctcgctcag   1680
gcgcaatcac gaatgaataa cggtttggtt ggtgcgagtg attttgatga cgagcgtaat   1740
ggctggcctg ttgaacaagt ctggaaagaa atgcataagc ttttgccatt ctcaccggat   1800
tcagtcgtca ctcatggtga tttctcactt gataacctta tttttgacga ggggaaatta   1860
ataggttgta ttgatgttgg acgagtcgga atcgcagacc gataccagga tcttgccatc   1920
ctatggaact gcctcggtga gttttctcct tcattacaga aacggctttt tcaaaaatat   1980
ggtattgata atcctgatat gaataaattg cagtttcact tgatgctcga tgagtttttc   2040
taatgagggc ccaaatgtaa tcacctggct caccttcggg tgggcctttc tgcgttgctg   2100
gcgtttttcc ataggctccg cccccctgac gagcatcaca aaaatcgatg ctcaagtcag   2160
aggtggcgaa acccgacagg actataaaga taccaggcgt ttccccctgg aagctccctc   2220
gtgcgctctc ctgttccgac cctgccgctt accggatacc tgtccgcctt tctcccttcg   2280
ggaagcgtgg cgctttctca tagctcacgc tgtaggtatc tcagttcggt gtaggtcgtt   2340
cgctccaagc tgggctgtgt gcacgaaccc cccgttcagc ccgaccgctg cgccttatcc   2400
ggtaactatc gtcttgagtc caacccggta agacacgact tatcgccact ggcagcagcc   2460
actggtaaca ggattagcag agcgaggtat gtaggcggtg ctacagagtt cttgaagtgg   2520
tggcctaact acggctacac tagaagaaca gtatttggta tctgcgctct gctgaagcca   2580
gttacctcgg aaaaagagtt ggtagctctt gatccggcaa acaaaccacc gctggtagcg   2640
gtggtttttt tgtttgcaag cagcagatta cgcgcagaaa aaaaggatct caagaagatc   2700
ctttgatttt ctaccgaaga aaggcccacc cgtgaaggtg agccagtgag ttgattgcag   2760
```

```
tccagttacg ctggagtctg aggctcgtcc tgaatgatat caagcttgaa ttcgtt       2816


<210> SEQ ID NO 44
<211> LENGTH: 2808
<212> TYPE: DNA
<213> ORGANISM: Artificial Sequence
<220> FEATURE:
<223> OTHER INFORMATION: Plasmid pSMART-ugpBp-GFPuv

<400> SEQUENCE: 44

tgaggctcgt cctgaatgat atcaagcttg aattcgtttc tttctgacac cttactatct     60

tacaaatgta acaaaaaagt tatttttctg taattcgagc atgtcatgtt accccgcgag    120

cataaaacgc gtgtgtagga ggataatcta tggctagcaa aggagaagaa cttttcacat    180

ggctagcaaa ggagaagaac ttttcactgg agttgtccca attcttgttg aattagatgg    240

tgatgttaat gggcacaaat tttctgtcag tggagagggt gaaggtgatg ctacatacgg    300

aaagcttacc cttaaattta tttgcactac tggaaaacta cctgttccat ggccaacact    360

tgtcactact ttctcttatg gtgttcaatg cttttcccgt tatccggatc atatgaaacg    420

gcatgacttt ttcaagagtg ccatgcccga aggttatgta caggaacgca ctatatcttt    480

caaagatgac gggaactaca agacgcgtgc tgaagtcaag tttgaaggtg atacccttgt    540

taatcgtatc gagttaaaag gtattgattt taaagaagat ggaaacattc tcggacacaa    600

actcgagtac aactataact cacacaatgt atacatcacg gcagacaaac aaaagaatgg    660

aatcaaagct aacttcaaaa ttcgccacaa cattgaagat ggatccgttc aactagcaga    720

ccattatcaa caaaatactc caattggcga tggccctgtc cttttaccag acaaccatta    780

cctgtcgaca caatctgccc tttcgaaaga tcccaacgaa aagcgtgacc acatggtcct    840

tcttgagttt gtaactgctg ctgggattac acatggcatg gatgagctct acaaataatg    900

aggatccccg gcttatcggt cagtttcacc tgatttacgt aaaaacccgc ttcggcgggt    960

ttttgctttt ggaggggcag aaagatgaat gactgtccac gacgctatac ccaaaagaaa   1020

gacgaattct ctagatatcg ctcaatactg accatttaaa tcatacctga cctccatagc   1080

agaaagtcaa aagcctccga ccggaggctt ttgacttgat cggcacgtaa gaggttccaa   1140

ctttcaccat aatgaaataa gatcactacc gggcgtattt tttgagttat cgagattttc   1200

aggagctaag gaagctaaaa tgagccatat tcaacgggaa acgtcttgct cgaggccgcg   1260

attaaattcc aacatggatg ctgatttata tgggtataaa tgggctcgcg ataatgtcgg   1320

gcaatcaggt gcgacaatct atcgattgta tgggaagccc gatgcgccag agttgtttct   1380

gaaacatggc aaaggtagcg ttgccaatga tgttacagat gagatggtca ggctaaactg   1440

gctgacggaa tttatgcctc ttccgaccat caagcatttt atccgtactc ctgatgatgc   1500

atggttactc accactgcga tcccagggaa aacagcattc caggtattag aagaatatcc   1560

tgattcaggt gaaaatattg ttgatgcgct ggcagtgttc ctgcgccggt tgcattcgat   1620

tcctgtttgt aattgtcctt ttaacggcga tcgcgtattt cgtctcgctc aggcgcaatc   1680

acgaatgaat aacggtttgg ttggtgcgag tgattttgat gacgagcgta atggctggcc   1740

tgttgaacaa gtctggaaag aaatgcataa gcttttgcca ttctcaccgg attcagtcgt   1800

cactcatggt gatttctcac ttgataacct tatttttgac gaggggaaat taataggttg   1860

tattgatgtt ggacgagtcg gaatcgcaga ccgataccag gatcttgcca tcctatggaa   1920

ctgcctcggt gagttttctc cttcattaca gaaacggctt tttcaaaaat atggtattga   1980
```

```
taatcctgat atgaataaat tgcagtttca cttgatgctc gatgagtttt tctaatgagg   2040
gcccaaatgt aatcacctgg ctcaccttcg ggtgggcctt tctgcgttgc tggcgttttt   2100
ccataggctc cgcccccctg acgagcatca caaaaatcga tgctcaagtc agaggtggcg   2160
aaacccgaca ggactataaa gataccaggc gtttccccct ggaagctccc tcgtgcgctc   2220
tcctgttccg accctgccgc ttaccggata cctgtccgcc tttctccctt cgggaagcgt   2280
ggcgctttct catagctcac gctgtaggta tctcagttcg gtgtaggtcg ttcgctccaa   2340
gctgggctgt gtgcacgaac cccccgttca gcccgaccgc tgcgccttat ccggtaacta   2400
tcgtcttgag tccaacccgg taagacacga cttatcgcca ctggcagcag ccactggtaa   2460
caggattagc agagcgaggt atgtaggcgg tgctacagag ttcttgaagt ggtggcctaa   2520
ctacggctac actagaagaa cagtatttgg tatctgcgct ctgctgaagc cagttacctc   2580
ggaaaaagag ttggtagctc ttgatccggc aaacaaacca ccgctggtag cggtggtttt   2640
tttgtttgca agcagcagat tacgcgcaga aaaaaaggat ctcaagaaga tcctttgatt   2700
ttctaccgaa gaaaggccca cccgtgaagg tgagccagtg agttgattgc agtccagtta   2760
cgctggagtc tgaggctcgt cctgaatgat atcaagcttg aattcgtt               2808
```

<210> SEQ ID NO 45
<211> LENGTH: 2819
<212> TYPE: DNA
<213> ORGANISM: Artificial Sequence
<220> FEATURE:
<223> OTHER INFORMATION: Plasmid pSMART-ydfHp-GFPuv

<400> SEQUENCE: 45

```
tgaggctcgt cctgaatgat atcaagcttg aattcgttgc tatgccggac tgaatgtcca     60
ccgtcagtaa tttttatacc cggcgtaact gccgggttat tgcttgtcac aaaaaagtgg    120
tagactcatg cagttaactc actgtgtagg aggataatct atggctagca aaggagaaga    180
acttttcaca tggctagcaa aggagaagaa cttttcactg gagttgtccc aattcttgtt    240
gaattagatg gtgatgttaa tgggcacaaa ttttctgtca gtggagaggg tgaaggtgat    300
gctacatacg gaaagcttac ccttaaattt atttgcacta ctggaaaact acctgttcca    360
tggccaacac ttgtcactac tttctcttat ggtgttcaat gcttttcccg ttatccggat    420
catatgaaac ggcatgactt tttcaagagt gccatgcccg aaggttatgt acaggaacgc    480
actatatctt tcaaagatga cgggaactac aagacgcgtg ctgaagtcaa gtttgaaggt    540
gataccettg ttaatcgtat cgagttaaaa ggtattgatt ttaaagaaga tggaaacatt    600
ctcggacaca aactcgagta caactataac tcacacaatg tatacatcac ggcagacaaa    660
caaaagaatg gaatcaaagc taacttcaaa attcgccaca acattgaaga tggatccgtt    720
caactagcag accattatca acaaaatact ccaattggcg atggccctgt ccttttacca    780
gacaaccatt acctgtcgac acaatctgcc ctttcgaaag atcccaacga aaagcgtgac    840
cacatggtcc ttcttgagtt tgtaactgct gctgggatta cacatggcat ggatgagctc    900
tacaaataat gaggatcccc ggcttatcgg tcagtttcac ctgatttacg taaaaacccg    960
cttcggcggg tttttgcttt tggaggggca gaaagatgaa tgactgtcca cgacgctata   1020
cccaaaagaa agacgaattc tctagatatc gctcaatact gaccatttaa atcatacctg   1080
acctccatag cagaaagtca aaagcctccg accggaggct tttgacttga tcggcacgta   1140
agaggttcca actttcacca taatgaaata agatcactac cgggcgtatt ttttgagtta   1200
tcgagatttt caggagctaa ggaagctaaa atgagccata ttcaacggga aacgtcttgc   1260
```

```
tcgaggccgc gattaaattc caacatggat gctgatttat atgggtataa atgggctcgc   1320
gataatgtcg ggcaatcagg tgcgacaatc tatcgattgt atgggaagcc cgatgcgcca   1380
gagttgtttc tgaaacatgg caaaggtagc gttgccaatg atgttacaga tgagatggtc   1440
aggctaaact ggctgacgga atttatgcct cttccgacca tcaagcattt tatccgtact   1500
cctgatgatg catggttact caccactgcg atccccagga aaacagcatt ccaggtatta   1560
gaagaatatc ctgattcagg tgaaaatatt gttgatgcgc tggcagtgtt cctgcgccgg   1620
ttgcattcga ttcctgtttg taattgtcct tttaacggcg atcgcgtatt tcgtctcgct   1680
caggcgcaat cacgaatgaa taacggtttg gttggtgcga gtgattttga tgacgagcgt   1740
aatggctggc ctgttgaaca agtctggaaa gaaatgcata agcttttgcc attctcaccg   1800
gattcagtcg tcactcatgg tgatttctca cttgataacc ttatttttga cgaggggaaa   1860
ttaataggtt gtattgatgt tggacgagtc ggaatcgcag accgatacca ggatcttgcc   1920
atcctatgga actgcctcgg tgagttttct ccttcattac agaaacggct ttttcaaaaa   1980
tatggtattg ataatcctga tatgaataaa ttgcagtttc acttgatgct cgatgagttt   2040
ttctaatgag ggcccaaatg taatcacctg gctcaccttc gggtgggcct ttctgcgttg   2100
ctggcgtttt tccataggct ccgcccccct gacgagcatc acaaaaatcg atgctcaagt   2160
cagaggtggc gaaacccgac aggactataa agataccagg cgtttccccc tggaagctcc   2220
ctcgtgcgct ctcctgttcc gaccctgccg cttaccggat acctgtccgc ctttctccct   2280
tcgggaagcg tggcgctttc tcatagctca cgctgtaggt atctcagttc ggtgtaggtc   2340
gttcgctcca agctgggctg tgtgcacgaa ccccccgttc agcccgaccg ctgcgcctta   2400
tccggtaact atcgtcttga gtccaacccg gtaagacacg acttatcgcc actggcagca   2460
gccactggta acaggattag cagagcgagg tatgtaggcg gtgctacaga gttcttgaag   2520
tggtggccta actacggcta cactagaaga acagtatttg gtatctgcgc tctgctgaag   2580
ccagttacct cggaaaaaga gttggtagct cttgatccgg caaacaaacc accgctggta   2640
gcggtggttt ttttgtttgc aagcagcaga ttacgcgcag aaaaaaagga tctcaagaag   2700
atcctttgat tttctaccga agaaaggccc acccgtgaag gtgagccagt gagttgattg   2760
cagtccagtt acgctggagt ctgaggctcg tcctgaatga tatcaagctt gaattcgtt    2819
```

<210> SEQ ID NO 46
<211> LENGTH: 3424
<212> TYPE: DNA
<213> ORGANISM: Artificial Sequence
<220> FEATURE:
<223> OTHER INFORMATION: Plasmid pSMART-Ala2

<400> SEQUENCE: 46

```
ccaggcatca aataaaacga aaggctcagt cgaaagactg ggcctttcgt tttatctgtt     60
gtttgtcggt gaacgctctc tactagagtc acactggctc accttcgggt gggcctttct    120
gcgtttatac acagctaaca ccacgtcgtc cctatctgct gccctaggtc tatgagtggt    180
tgctggataa ctctttctga caccttacta tcttacaaat gtaacaaaaa agttattttt    240
ctgtaattcg agcatgtcat gttaccccgc gagcataaaa cgcgtatatt cagggagacc    300
acaacggttt ccctctacaa ataattttgt ttaactttgg aaaaaggaga tataccatga    360
tcattggggt gccgaaggag atcaaaaata atgagaaccg cgtcgcgttg accccgggag    420
gtgtcagcca gctgatctct aatggccatc gtgtcttagt tgaaacaggc gctggcctgg    480
```

```
gttctggctt cgaaaacgag gcctacgaat ctgcaggtgc ggaaattatt gctgatccaa    540
aacaggtctg ggatgcagag atggtcatga aagtgaaaga accgctcccg gaagaatatg    600
tctattttcg taaaggtctg gtgctgttta catatctgca tctggcagct gaaccggagc    660
tcgcacaagc ccttaaagat aaaggtgtca cggccatcgc atacgaaact gtcagcgaag    720
ggcgcacgct gccattactg accccgatgt cagaagtggc aggccgtatg gctgcgcaga    780
tcggcgcaca gtttcttgaa aaaccaaagg gcgggaaggg tattctctta gcaggagtgc    840
cgggcgtcag tcgtgggaaa gtaactatta ttggtggcgg cgtggtagga acaaatgctg    900
ccaaaatggc cgtcggtttg gggggccgacg taacaatcat tgcgcgtaat gccgatcgcc    960
ttcgtcaatt agacgatatc tttggccacc aaatcaaaac cctgatttcg aacccagtca   1020
atatcgcgga tgcggtggcg gaagctgatt tgttgatctg cgccgtgtta attccgggag   1080
cgaaagcacc tacattggtg acggaagaaa tggtgaaaca aatgaaaccg ggttcagtca   1140
ttgttgatgt ggctattgat cagggtggca tcgtggaaac ggtggaccat attaccactc   1200
acgaccagcc gacgtatgaa aaacatggtg tcgtacacta tgcggtggcg aatatgcctg   1260
gtgcggtccc acgtacgagt acaatcgcac tgacaaatgt caccgtgccg tatgcgttgc   1320
aaatcgcgaa caaaggtgcc gtgaaagcgc tggccgacaa tacggcgtta cgtgccggtc   1380
tgaacaccgc taacggtcac gtgacatatg aagcggtcgc gcgtgatttg gggtacgaat   1440
atgtaccggc ggaaaaagcc ttacaagacg aatcgagtgt cgctggtgca tagtaagctc   1500
ttctaatacg actcactata gggccggctt atcggtcagt ttcacctgat ttacgtaaaa   1560
acccgcttcg gcgggttttt gcttttggag gggcagaaag atgaatgact gtccacgacg   1620
ctatacccaa aagaaagacg aattctctag atatcgctca atactgacca tttaaatcat   1680
acctgacctc catagcagaa agtcaaaagc ctccgaccgg aggcttttga cttgatcggc   1740
acgtaagagg ttccaacttt caccataatg aaataagatc actaccgggc gtattttttg   1800
agttatcgag attttcagga gctaaggaag ctaaaatgag ccatattcaa cgggaaacgt   1860
cttgctcgag gccgcgatta aattccaaca tggatgctga tttatatggg tataaatggg   1920
ctcgcgataa tgtcgggcaa tcaggtgcga caatctatcg attgtatggg aagcccgatg   1980
cgccagagtt gtttctgaaa catggcaaag gtagcgttgc caatgatgtt acagatgaga   2040
tggtcaggct aaactggctg acggaattta tgcctcttcc gaccatcaag cattttatcc   2100
gtactcctga tgatgcatgg ttactcacca ctgcgatccc agggaaaaca gcattccagg   2160
tattagaaga atatcctgat tcaggtgaaa atattgttga tgcgctggca gtgttcctgc   2220
gccggttgca ttcgattcct gtttgtaatt gtccttttaa cggcgatcgc gtatttcgtc   2280
tcgctcaggc gcaatcacga atgaataacg gtttggttgg tgcgagtgat tttgatgacg   2340
agcgtaatgg ctggcctgtt gaacaagtct ggaaagaaat gcataagctt ttgccattct   2400
caccggattc agtcgtcact catggtgatt tctcacttga taaccttatt tttgacgagg   2460
ggaaattaat aggttgtatt gatgttggac gagtcggaat cgcagaccga taccaggatc   2520
ttgccatcct atggaactgc ctcggtgagt tttctccttc attacagaaa cggctttttc   2580
aaaaatatgg tattgataat cctgatatga ataaattgca gtttcacttg atgctcgatg   2640
agtttttcta atgagggccc aaatgtaatc acctggctca ccttcgggtg ggcctttctg   2700
cgttgctggc gtttttccat aggctccgcc cccctgacga gcatcacaaa aatcgatgct   2760
caagtcagag gtggcgaaac ccgacaggac tataaagata ccaggcgttt ccccctggaa   2820
gctccctcgt gcgctctcct gttccgaccc tgccgcttac cggatacctg tccgcctttc   2880
```

tcccttcggg aagcgtggcg ctttctcata gctcacgctg taggtatctc agttcggtgt 2940
aggtcgttcg ctccaagctg ggctgtgtgc acgaaccccc cgttcagccc gaccgctgcg 3000
ccttatccgg taactatcgt cttgagtcca acccggtaag acacgactta tcgccactgg 3060
cagcagccac tggtaacagg attagcagag cgaggtatgt aggcggtgct acagagttct 3120
tgaagtggtg gcctaactac ggctacacta gaagaacagt atttggtatc tgcgctctgc 3180
tgaagccagt tacctcggaa aaagagttgg tagctcttga tccggcaaac aaaccaccgc 3240
tggtagcggt ggtttttttg tttgcaagca gcagattacg cgcagaaaaa aaggatctca 3300
agaagatcct ttgatttttct accgaagaaa ggcccacccg tgaaggtgag ccagtgagtt 3360
gattgcagtc cagttacgct ggagtctgag gctcgtcctg aatgatatca agcttgaatt 3420
cgtt 3424

<210> SEQ ID NO 47
<211> LENGTH: 21
<212> TYPE: DNA
<213> ORGANISM: Artificial Sequence
<220> FEATURE:
<223> OTHER INFORMATION: fabI T2 targeting sequence

<400> SEQUENCE: 47
cagcctgctc cggtcggacc g 21

<210> SEQ ID NO 48
<211> LENGTH: 45
<212> TYPE: DNA
<213> ORGANISM: Artificial Sequence
<220> FEATURE:
<223> OTHER INFORMATION: C-terminal DAS+4 tag

<400> SEQUENCE: 48
gcggccaacg atgaaaacta ttctgaaaac tatgcggatg cgtct 45

<210> SEQ ID NO 49
<211> LENGTH: 59
<212> TYPE: DNA
<213> ORGANISM: Artificial Sequence
<220> FEATURE:
<223> OTHER INFORMATION: Primer gltA2-FOR

<400> SEQUENCE: 49
gggacagtta ttagttcgag ttccccgcgc cagcggggat aaaccgaaaa aaaaaacccc 59

<210> SEQ ID NO 50
<211> LENGTH: 63
<212> TYPE: DNA
<213> ORGANISM: Artificial Sequence
<220> FEATURE:
<223> OTHER INFORMATION: Primer gltA2-REV

<400> SEQUENCE: 50
gaatgaattg gtcaatacgg tttatccccg ctggcgcggg gaactcgagg tggtaccaga 60
tct 63

<210> SEQ ID NO 51
<211> LENGTH: 28
<212> TYPE: DNA
<213> ORGANISM: Artificial Sequence
<220> FEATURE:
<223> OTHER INFORMATION: Primer G2U-FOR1

```
<400> SEQUENCE: 51

ccggatgagc attcatcagg cgggcaag                                        28


<210> SEQ ID NO 52
<211> LENGTH: 47
<212> TYPE: DNA
<213> ORGANISM: Artificial Sequence
<220> FEATURE:
<223> OTHER INFORMATION: Primer G2U-REV1

<400> SEQUENCE: 52

cggtttatcc ccgctggcgc ggggaactcg aacttcataa cttttac                   47


<210> SEQ ID NO 53
<211> LENGTH: 34
<212> TYPE: DNA
<213> ORGANISM: Artificial Sequence
<220> FEATURE:
<223> OTHER INFORMATION: Primer G2U-FOR2

<400> SEQUENCE: 53

gcgccagcgg ggataaaccg ttaccattct gttg                                 34


<210> SEQ ID NO 54
<211> LENGTH: 28
<212> TYPE: DNA
<213> ORGANISM: Artificial Sequence
<220> FEATURE:
<223> OTHER INFORMATION: Primer G2U-REV2

<400> SEQUENCE: 54

cttgcccgcc tgatgaatgc tcatccgg                                        28
```